United States Patent
Davalos et al.

(10) Patent No.: US 11,311,329 B2
(45) Date of Patent: Apr. 26, 2022

(54) TREATMENT PLANNING FOR IMMUNOTHERAPY BASED TREATMENTS USING NON-THERMAL ABLATION TECHNIQUES

(71) Applicant: VIRGINIA TECH INTELLECTUAL PROPERTIES, INC., Blacksburg, VA (US)

(72) Inventors: Rafael V. Davalos, Blacksburg, VA (US); Natalie Beitel White, Christianburg, VA (US); Nikolaos Dervisis, Blacksburg, VA (US); Irving Coy Allen, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 337 days.

(21) Appl. No.: 16/352,759

(22) Filed: Mar. 13, 2019

(65) Prior Publication Data
US 2019/0282294 A1    Sep. 19, 2019

Related U.S. Application Data

(60) Provisional application No. 62/642,276, filed on Mar. 13, 2018, provisional application No. 62/642,298, (Continued)

(51) Int. Cl.
*A61B 18/14* (2006.01)
*A61K 31/282* (2006.01)
(Continued)

(52) U.S. Cl.
CPC .......... *A61B 18/14* (2013.01); *A61K 31/282* (2013.01); *A61K 31/4745* (2013.01);
(Continued)

(58) Field of Classification Search
CPC .......... A61B 18/14; A61B 2018/00577; A61B 2018/00613; A61B 2018/00827;
(Continued)

(56) References Cited

U.S. PATENT DOCUMENTS

| | | | |
|---|---|---|---|
| 1,653,819 | A | 12/1927 | Northcott |
| 3,730,238 | A | 5/1973 | Butler |

(Continued)

FOREIGN PATENT DOCUMENTS

| | | | |
|---|---|---|---|
| AU | 7656800 | A | 4/2001 |
| AU | 2002315095 | A1 | 12/2002 |

(Continued)

OTHER PUBLICATIONS

SAI Infusion Technologies, "Rabbit Ear Vein Catheters", https://www.sai-infusion.com/products/rabbit-ear-catheters, Aug. 10, 2017 webpage printout, 5 pages.

(Continued)

*Primary Examiner* — Michael F Peffley
(74) *Attorney, Agent, or Firm* — New River Valley IP Law, P.C.; Michele L. Mayberry

(57) ABSTRACT

Described herein are methods of performing immunotherapy on a subject and/or determining if a subject will be responsive to ablation immunotherapy.

19 Claims, 48 Drawing Sheets

Related U.S. Application Data filed on Mar. 13, 2018, provisional application No. 62/732,703, filed on Sep. 18, 2018.

(51) Int. Cl.
  *A61K 31/4745* (2006.01)
  *A61K 31/513* (2006.01)
  *A61K 31/519* (2006.01)
  *A61B 18/00* (2006.01)

(52) U.S. Cl.
  CPC .......... *A61K 31/513* (2013.01); *A61K 31/519* (2013.01); *A61B 2018/00577* (2013.01); *A61B 2018/00613* (2013.01); *A61B 2018/00827* (2013.01); *A61B 2018/00875* (2013.01)

(58) Field of Classification Search
  CPC .... A61B 2018/00875; A61B 2018/143; A61K 31/282; A61K 31/4745; A61K 31/513; A61K 31/519; A61K 45/06
  See application file for complete search history.

(56) References Cited

U.S. PATENT DOCUMENTS

| | | |
|---|---|---|
| 3,746,004 A | 7/1973 | Jankelson |
| 3,871,359 A | 3/1975 | Pacela |
| 4,016,886 A | 4/1977 | Doss et al. |
| 4,037,341 A | 7/1977 | Odle et al. |
| 4,216,860 A | 8/1980 | Heimann |
| 4,226,246 A | 10/1980 | Fragnet |
| 4,262,672 A | 4/1981 | Kief |
| 4,267,047 A | 5/1981 | Henne et al. |
| 4,278,092 A | 7/1981 | Borsanyi et al. |
| 4,299,217 A | 11/1981 | Sagae et al. |
| 4,311,148 A | 1/1982 | Courtney et al. |
| 4,336,881 A | 6/1982 | Babb et al. |
| 4,344,436 A | 8/1982 | Kubota |
| 4,392,855 A | 7/1983 | Oreopoulos et al. |
| 4,406,827 A | 9/1983 | Carim |
| 4,407,943 A | 10/1983 | Cole et al. |
| 4,416,276 A | 11/1983 | Newton et al. |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek et al. |
| 4,636,199 A | 1/1987 | Victor |
| 4,672,969 A | 6/1987 | Dew |
| 4,676,258 A | 6/1987 | Inokuchi et al. |
| 4,676,782 A | 6/1987 | Yamamoto et al. |
| 4,687,471 A | 8/1987 | Twardowski et al. |
| 4,716,896 A | 1/1988 | Ackerman |
| 4,723,549 A | 2/1988 | Wholey et al. |
| D294,519 S | 3/1988 | Hardy |
| 4,756,838 A | 7/1988 | Veltman |
| 4,772,269 A | 9/1988 | Twardowski et al. |
| 4,798,585 A | 1/1989 | Inoue et al. |
| 4,810,963 A | 3/1989 | Blake-Coleman et al. |
| 4,813,929 A | 3/1989 | Semrad |
| 4,819,637 A | 4/1989 | Dormandy et al. |
| 4,822,470 A | 4/1989 | Chang |
| 4,836,204 A | 6/1989 | Landymore et al. |
| 4,840,172 A | 6/1989 | Augustine et al. |
| 4,863,426 A | 9/1989 | Ferragamo et al. |
| 4,885,003 A | 12/1989 | Hillstead |
| 4,886,496 A | 12/1989 | Conoscenti et al. |
| 4,886,502 A | 12/1989 | Poirier et al. |
| 4,889,634 A | 12/1989 | El-Rashidy |
| 4,903,707 A | 2/1990 | Knute et al. |
| 4,907,601 A | 3/1990 | Frick |
| 4,919,148 A | 4/1990 | Muccio |
| 4,920,978 A | 5/1990 | Colvin |
| 4,921,484 A | 5/1990 | Hillstead |
| 4,946,793 A | 8/1990 | Marshall, III |
| 4,976,709 A | 12/1990 | Sand |
| 4,981,477 A | 1/1991 | Schon et al. |
| 4,986,810 A | 1/1991 | Semrad |
| 4,987,895 A | 1/1991 | Heimlich |
| 5,019,034 A | 5/1991 | Weaver et al. |
| 5,031,775 A | 7/1991 | Kane |
| 5,052,391 A | 10/1991 | Silberstone et al. |
| 5,053,013 A | 10/1991 | Ensminger et al. |
| 5,058,605 A | 10/1991 | Slovak |
| 5,071,558 A | 12/1991 | Itoh |
| 5,098,843 A | 3/1992 | Calvin |
| 5,122,137 A | 6/1992 | Lennox |
| 5,134,070 A | 7/1992 | Casnig |
| 5,137,517 A | 8/1992 | Loney et al. |
| 5,141,499 A | 8/1992 | Zappacosta |
| D329,496 S | 9/1992 | Wotton |
| 5,156,597 A | 10/1992 | Verreet et al. |
| 5,173,158 A | 12/1992 | Schmukler |
| 5,186,715 A | 2/1993 | Phillips et al. |
| 5,186,800 A | 2/1993 | Dower |
| 5,188,592 A | 2/1993 | Hakki |
| 5,190,541 A | 3/1993 | Abele et al. |
| 5,192,312 A | 3/1993 | Orton |
| 5,193,537 A | 3/1993 | Freeman |
| 5,209,723 A | 5/1993 | Twardowski et al. |
| 5,215,530 A | 6/1993 | Hogan |
| 5,224,933 A | 7/1993 | Bromander |
| 5,227,730 A | 7/1993 | King et al. |
| 5,242,415 A | 9/1993 | Kantrowitz et al. |
| 5,273,525 A | 12/1993 | Hofmann |
| D343,687 S | 1/1994 | Houghton et al. |
| 5,277,201 A | 1/1994 | Stern |
| 5,279,564 A | 1/1994 | Taylor |
| 5,281,213 A | 1/1994 | Milder |
| 5,283,194 A | 2/1994 | Schmukler |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross et al. |
| 5,318,563 A | 6/1994 | Malis et al. |
| 5,328,451 A | 7/1994 | Davis et al. |
| 5,334,167 A | 8/1994 | Cocanower |
| 5,348,554 A | 9/1994 | Imran et al. |
| D351,661 S | 10/1994 | Fischer |
| 5,383,917 A | 1/1995 | Desai et al. |
| 5,389,069 A | 2/1995 | Weaver |
| 5,391,158 A | 2/1995 | Peters |
| 5,403,311 A | 4/1995 | Abele et al. |
| 5,405,320 A | 4/1995 | Twardowski et al. |
| 5,425,752 A | 6/1995 | Vu Nguyen |
| 5,439,440 A | 8/1995 | Hofmann |
| 5,458,625 A | 10/1995 | Kendall |
| 5,484,400 A | 1/1996 | Edwards et al. |
| 5,484,401 A | 1/1996 | Rodriguez et al. |
| 5,533,999 A | 7/1996 | Hood et al. |
| 5,536,240 A | 7/1996 | Edwards et al. |
| 5,536,267 A | 7/1996 | Edwards et al. |
| 5,540,737 A | 7/1996 | Fenn |
| 5,546,940 A | 8/1996 | Panescu et al. |
| 5,562,720 A | 10/1996 | Stern et al. |
| 5,575,811 A | 11/1996 | Reid et al. |
| D376,652 S | 12/1996 | Hunt et al. |
| 5,582,588 A | 12/1996 | Sakurai et al. |
| 5,586,982 A | 12/1996 | Abela |
| 5,588,424 A | 12/1996 | Insler et al. |
| 5,588,960 A | 12/1996 | Edwards et al. |
| 5,599,294 A | 2/1997 | Edwards et al. |
| 5,599,311 A | 2/1997 | Raulerson |
| 5,616,126 A | 4/1997 | Malekmehr et al. |
| 5,620,479 A | 4/1997 | Diederich |
| 5,626,146 A | 5/1997 | Barber et al. |
| D380,272 S | 6/1997 | Partika et al. |
| 5,634,899 A | 6/1997 | Shapland et al. |
| 5,643,197 A | 7/1997 | Brucker et al. |
| 5,645,855 A | 7/1997 | Lorenz |
| 5,672,173 A | 9/1997 | Gough et al. |
| 5,674,267 A | 10/1997 | Mir et al. |
| 5,683,384 A | 11/1997 | Gough et al. |
| 5,687,723 A | 11/1997 | Avitall |

(56) References Cited

U.S. PATENT DOCUMENTS

| | | |
|---|---|---|
| 5,690,620 A | 11/1997 | Knott |
| 5,697,905 A | 12/1997 | d'Ambrosio |
| 5,700,252 A | 12/1997 | Klingenstein |
| 5,702,359 A | 12/1997 | Hofmann et al. |
| 5,718,246 A | 2/1998 | Vona |
| 5,720,921 A | 2/1998 | Meserol |
| 5,735,847 A | 4/1998 | Gough et al. |
| 5,752,939 A | 5/1998 | Makoto |
| 5,778,894 A | 7/1998 | Dorogi et al. |
| 5,782,882 A | 7/1998 | Lerman et al. |
| 5,800,378 A | 9/1998 | Edwards et al. |
| 5,800,484 A | 9/1998 | Gough et al. |
| 5,807,272 A | 9/1998 | Kun et al. |
| 5,807,306 A | 9/1998 | Shapland et al. |
| 5,807,395 A | 9/1998 | Mulier et al. |
| 5,810,742 A | 9/1998 | Peariman |
| 5,810,762 A | 9/1998 | Hofmann |
| 5,830,184 A | 11/1998 | Basta |
| 5,836,897 A | 11/1998 | Sakurai et al. |
| 5,836,905 A | 11/1998 | Lemelson et al. |
| 5,843,026 A | 12/1998 | Edwards et al. |
| 5,843,182 A | 12/1998 | Goldstein |
| 5,865,787 A | 2/1999 | Shapland et al. |
| 5,868,708 A | 2/1999 | Hart et al. |
| 5,873,849 A | 2/1999 | Bernard |
| 5,904,648 A | 5/1999 | Arndt et al. |
| 5,919,142 A | 7/1999 | Boone et al. |
| 5,919,191 A | 7/1999 | Lennox et al. |
| 5,921,982 A | 7/1999 | Lesh et al. |
| 5,944,710 A | 8/1999 | Dev et al. |
| 5,947,284 A | 9/1999 | Foster |
| 5,947,889 A | 9/1999 | Hehrlein |
| 5,951,546 A | 9/1999 | Lorentzen |
| 5,954,745 A | 9/1999 | Gertler et al. |
| 5,957,919 A | 9/1999 | Laufer |
| 5,957,963 A | 9/1999 | Dobak, III |
| 5,968,006 A | 10/1999 | Hofmann |
| 5,983,131 A | 11/1999 | Weaver et al. |
| 5,984,896 A | 11/1999 | Boyd |
| 5,991,697 A | 11/1999 | Nelson et al. |
| 5,999,847 A | 12/1999 | Elstrom |
| 6,004,339 A | 12/1999 | Wijay |
| 6,009,347 A | 12/1999 | Hofmann |
| 6,009,877 A | 1/2000 | Edwards |
| 6,010,613 A | 1/2000 | Walters et al. |
| 6,016,452 A | 1/2000 | Kasevich |
| 6,029,090 A | 2/2000 | Herbst |
| 6,041,252 A | 3/2000 | Walker et al. |
| 6,043,066 A | 3/2000 | Mangano et al. |
| 6,050,994 A | 4/2000 | Sherman |
| 6,055,453 A | 4/2000 | Hofmann et al. |
| 6,059,780 A | 5/2000 | Gough et al. |
| 6,066,134 A | 5/2000 | Eggers et al. |
| 6,068,121 A | 5/2000 | McGlinch |
| 6,068,650 A | 5/2000 | Hofmann et al. |
| 6,071,281 A | 6/2000 | Burnside et al. |
| 6,074,374 A | 6/2000 | Fulton |
| 6,074,389 A | 6/2000 | Levine et al. |
| 6,085,115 A | 7/2000 | Weaver et al. |
| 6,090,016 A | 7/2000 | Kuo |
| 6,090,105 A | 7/2000 | Zepeda et al. |
| 6,090,106 A | 7/2000 | Goble et al. |
| D430,015 S | 8/2000 | Himbert et al. |
| 6,096,035 A | 8/2000 | Sodhi et al. |
| 6,102,885 A | 8/2000 | Bass |
| 6,106,521 A | 8/2000 | Blewett et al. |
| 6,109,270 A | 8/2000 | Mah et al. |
| 6,110,192 A | 8/2000 | Ravenscroft et al. |
| 6,113,593 A | 9/2000 | Tu et al. |
| 6,116,330 A | 9/2000 | Salyer |
| 6,120,493 A | 9/2000 | Hofmann |
| 6,122,599 A | 9/2000 | Mehta |
| 6,123,701 A | 9/2000 | Nezhat |
| 6,132,397 A | 10/2000 | Davis et al. |
| 6,132,419 A | 10/2000 | Hofmann |
| 6,134,460 A | 10/2000 | Chance |
| 6,139,545 A | 10/2000 | Utley et al. |
| 6,150,148 A | 11/2000 | Nanda et al. |
| 6,159,163 A | 12/2000 | Strauss et al. |
| 6,178,354 B1 | 1/2001 | Gibson |
| D437,941 S | 2/2001 | Frattini |
| 6,193,715 B1 | 2/2001 | Wrublewski et al. |
| 6,198,970 B1 | 3/2001 | Freed et al. |
| 6,200,314 B1 | 3/2001 | Sherman |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann et al. |
| 6,219,577 B1 | 4/2001 | Brown, III et al. |
| D442,697 S | 5/2001 | Hajianpour |
| 6,233,490 B1 | 5/2001 | Kasevich |
| 6,235,023 B1 | 5/2001 | Lee et al. |
| D443,360 S | 6/2001 | Haberland |
| 6,241,702 B1 | 6/2001 | Lundquist et al. |
| 6,241,725 B1 | 6/2001 | Cosman |
| D445,198 S | 7/2001 | Frattini |
| 6,258,100 B1 | 7/2001 | Alferness et al. |
| 6,261,831 B1 | 7/2001 | Agee |
| 6,277,114 B1 | 8/2001 | Bullivant et al. |
| 6,278,895 B1 | 8/2001 | Bernard |
| 6,280,441 B1 | 8/2001 | Ryan |
| 6,283,988 B1 | 9/2001 | Laufer et al. |
| 6,283,989 B1 | 9/2001 | Laufer et al. |
| 6,284,140 B1 | 9/2001 | Sommermeyer et al. |
| 6,287,293 B1 | 9/2001 | Jones et al. |
| 6,287,304 B1 | 9/2001 | Eggers et al. |
| 6,296,636 B1 | 10/2001 | Cheng et al. |
| 6,298,726 B1 | 10/2001 | Machi et al. |
| 6,299,633 B1 | 10/2001 | Laufer |
| 6,300,108 B1 | 10/2001 | Rubinsky et al. |
| D450,391 S | 11/2001 | Hunt et al. |
| 6,312,428 B1 | 11/2001 | Eggers et al. |
| 6,326,177 B1 | 12/2001 | Schoenbach et al. |
| 6,327,505 B1 | 12/2001 | Medhkour et al. |
| 6,328,689 B1 | 12/2001 | Gonzalez et al. |
| 6,347,247 B1 | 2/2002 | Dev et al. |
| 6,349,233 B1 | 2/2002 | Adams |
| 6,351,674 B2 | 2/2002 | Silverstone |
| 6,375,634 B1 | 4/2002 | Carroll |
| 6,387,671 B1 | 5/2002 | Rubinsky et al. |
| 6,398,779 B1 | 6/2002 | Buysse et al. |
| 6,403,348 B1 | 6/2002 | Rubinsky et al. |
| 6,405,732 B1 | 6/2002 | Edwards et al. |
| 6,411,852 B1 | 6/2002 | Danek et al. |
| 6,419,674 B1 | 7/2002 | Bowser et al. |
| 6,428,802 B1 | 8/2002 | Atala |
| 6,443,952 B1 | 9/2002 | Mulier et al. |
| 6,463,331 B1 | 10/2002 | Edwards |
| 6,470,211 B1 | 10/2002 | Ideker et al. |
| 6,482,221 B1 | 11/2002 | Hebert et al. |
| 6,482,619 B1 | 11/2002 | Rubinsky et al. |
| 6,485,487 B1 | 11/2002 | Sherman |
| 6,488,673 B1 | 12/2002 | Laufer et al. |
| 6,488,678 B2 | 12/2002 | Sherman |
| 6,488,680 B1 | 12/2002 | Francischelli et al. |
| 6,491,706 B1 | 12/2002 | Alferness et al. |
| 6,493,589 B1 | 12/2002 | Medhkour et al. |
| 6,493,592 B1 | 12/2002 | Leonard et al. |
| 6,500,173 B2 | 12/2002 | Underwood et al. |
| 6,503,248 B1 | 1/2003 | Levine |
| 6,506,189 B1 | 1/2003 | Rittman et al. |
| 6,514,248 B1 | 2/2003 | Eggers et al. |
| 6,520,183 B2 | 2/2003 | Amar |
| 6,526,320 B2 | 2/2003 | Mitchell |
| D471,640 S | 3/2003 | McMichael et al. |
| D471,641 S | 3/2003 | McMichael et al. |
| 6,530,922 B2 | 3/2003 | Cosman et al. |
| 6,533,784 B2 | 3/2003 | Truckai et al. |
| 6,537,976 B1 | 3/2003 | Gupta |
| 6,540,695 B1 | 4/2003 | Burbank et al. |
| 6,558,378 B2 | 5/2003 | Sherman et al. |
| 6,562,604 B2 | 5/2003 | Rubinsky et al. |
| 6,569,162 B2 | 5/2003 | He |
| 6,575,969 B1 | 6/2003 | Rittman et al. |

(56) References Cited

U.S. PATENT DOCUMENTS

| | | |
|---|---|---|
| 6,589,161 B2 | 7/2003 | Corcoran |
| 6,592,594 B2 | 7/2003 | Rimbaugh et al. |
| 6,607,529 B1 | 8/2003 | Jones et al. |
| 6,610,054 B1 | 8/2003 | Edwards et al. |
| 6,611,706 B2 | 8/2003 | Avrahami et al. |
| 6,613,211 B1 | 9/2003 | Mccormick et al. |
| 6,616,657 B2 | 9/2003 | Simpson et al. |
| 6,627,421 B1 | 9/2003 | Unger et al. |
| D480,816 S | 10/2003 | McMichael et al. |
| 6,634,363 B1 | 10/2003 | Danek et al. |
| 6,638,253 B2 | 10/2003 | Breznock |
| 6,653,091 B1 | 11/2003 | Dunn et al. |
| 6,666,858 B2 | 12/2003 | Lafontaine |
| 6,669,691 B1 | 12/2003 | Taimisto |
| 6,673,070 B2 | 1/2004 | Edwards et al. |
| 6,678,558 B1 | 1/2004 | Dimmer et al. |
| 6,689,096 B1 | 2/2004 | Loubens et al. |
| 6,692,493 B2 | 2/2004 | Mcgovern et al. |
| 6,694,979 B2 | 2/2004 | Deem et al. |
| 6,694,984 B2 | 2/2004 | Habib |
| 6,695,861 B1 | 2/2004 | Rosenberg et al. |
| 6,697,669 B2 | 2/2004 | Dev et al. |
| 6,697,670 B2 | 2/2004 | Chomenky et al. |
| 6,702,808 B1 | 3/2004 | Kreindel |
| 6,712,811 B2 | 3/2004 | Underwood et al. |
| D489,973 S | 5/2004 | Root et al. |
| 6,733,516 B2 | 5/2004 | Simons et al. |
| 6,753,171 B2 | 6/2004 | Karube et al. |
| 6,761,716 B2 | 7/2004 | Kadhiresan et al. |
| D495,807 S | 9/2004 | Agbodoe et al. |
| 6,795,728 B2 | 9/2004 | Chornenky et al. |
| 6,801,804 B2 | 10/2004 | Miller et al. |
| 6,812,204 B1 | 11/2004 | McHale et al. |
| 6,837,886 B2 | 1/2005 | Collins et al. |
| 6,847,848 B2 | 1/2005 | Sterzer et al. |
| 6,860,847 B2 | 3/2005 | Alferness et al. |
| 6,865,416 B2 | 3/2005 | Dev et al. |
| 6,881,213 B2 | 4/2005 | Ryan et al. |
| 6,892,099 B2 | 5/2005 | Jaafar et al. |
| 6,895,267 B2 | 5/2005 | Panescu et al. |
| 6,905,480 B2 | 6/2005 | McGuckin et al. |
| 6,912,417 B1 | 6/2005 | Bernard et al. |
| 6,927,049 B2 | 8/2005 | Rubinsky et al. |
| 6,941,950 B2 | 9/2005 | Wilson et al. |
| 6,942,681 B2 | 9/2005 | Johnson |
| 6,958,062 B1 | 10/2005 | Gough et al. |
| 6,960,189 B2 | 11/2005 | Bates et al. |
| 6,962,587 B2 | 11/2005 | Johnson et al. |
| 6,972,013 B1 | 12/2005 | Zhang et al. |
| 6,972,014 B2 | 12/2005 | Eum et al. |
| 6,989,010 B2 | 1/2006 | Francischelli et al. |
| 6,994,689 B1 | 2/2006 | Zadno-Azizi et al. |
| 6,994,706 B2 | 2/2006 | Chornenky et al. |
| 7,011,094 B2 | 3/2006 | Rapacki et al. |
| 7,012,061 B1 | 3/2006 | Reiss et al. |
| 7,027,869 B2 | 4/2006 | Danek et al. |
| 7,036,510 B2 | 5/2006 | Zgoda et al. |
| 7,053,063 B2 | 5/2006 | Rubinsky et al. |
| 7,054,685 B2 | 5/2006 | Dimmer et al. |
| 7,063,698 B2 | 6/2006 | Whayne et al. |
| 7,087,040 B2 | 8/2006 | McGuckin et al. |
| 7,097,612 B2 | 8/2006 | Bertolero et al. |
| 7,100,616 B2 | 9/2006 | Springmeyer |
| 7,113,821 B1 | 9/2006 | Sun et al. |
| 7,130,697 B2 | 10/2006 | Chornenky et al. |
| 7,211,083 B2 | 5/2007 | Chornenky et al. |
| 7,232,437 B2 | 6/2007 | Berman et al. |
| 7,250,048 B2 | 7/2007 | Francischelli et al. |
| D549,332 S | 8/2007 | Matsumoto et al. |
| 7,257,450 B2 | 8/2007 | Auth et al. |
| 7,264,002 B2 | 9/2007 | Danek et al. |
| 7,267,676 B2 | 9/2007 | Chornenky et al. |
| 7,273,055 B2 | 9/2007 | Danek et al. |
| 7,291,146 B2 | 11/2007 | Steinke et al. |
| 7,331,940 B2 | 2/2008 | Sommerich |
| 7,331,949 B2 | 2/2008 | Marisi |
| 7,341,558 B2 | 3/2008 | Torre et al. |
| 7,344,533 B2 | 3/2008 | Pearson et al. |
| D565,743 S | 4/2008 | Phillips et al. |
| D571,478 S | 6/2008 | Horacek |
| 7,387,626 B2 | 6/2008 | Edwards et al. |
| 7,399,747 B1 | 7/2008 | Clair et al. |
| D575,399 S | 8/2008 | Matsumoto et al. |
| D575,402 S | 8/2008 | Sandor |
| 7,419,487 B2 | 9/2008 | Johnson et al. |
| 7,434,578 B2 | 10/2008 | Dillard et al. |
| 7,449,019 B2 | 11/2008 | Uchida et al. |
| 7,451,765 B2 | 11/2008 | Adler |
| 7,455,675 B2 | 11/2008 | Schur et al. |
| 7,476,203 B2 | 1/2009 | DeVore et al. |
| 7,520,877 B2 | 4/2009 | Lee et al. |
| 7,533,671 B2 | 5/2009 | Gonzalez et al. |
| D595,422 S | 6/2009 | Mustapha |
| 7,544,301 B2 | 6/2009 | Shah et al. |
| 7,549,984 B2 | 6/2009 | Mathis |
| 7,565,208 B2 | 7/2009 | Harris et al. |
| 7,571,729 B2 | 8/2009 | Saadat et al. |
| 7,632,291 B2 | 12/2009 | Stephens et al. |
| 7,655,004 B2 | 2/2010 | Long |
| 7,674,249 B2 | 3/2010 | Ivorra et al. |
| 7,680,543 B2 | 3/2010 | Azure |
| D613,418 S | 4/2010 | Ryan et al. |
| 7,718,409 B2 | 5/2010 | Rubinsky et al. |
| 7,722,606 B2 | 5/2010 | Azure |
| 7,742,795 B2 | 6/2010 | Stone et al. |
| 7,765,010 B2 | 7/2010 | Chornenky et al. |
| 7,771,401 B2 | 8/2010 | Hekmat et al. |
| RE42,016 E | 12/2010 | Chornenky et al. |
| D630,321 S | 1/2011 | Hamilton |
| D631,154 S | 1/2011 | Hamilton |
| RE42,277 E | 4/2011 | Jaafar et al. |
| 7,918,852 B2 | 4/2011 | Tullis et al. |
| 7,937,143 B2 | 5/2011 | Demarais et al. |
| 7,938,824 B2 | 5/2011 | Chornenky et al. |
| 7,951,582 B2 | 5/2011 | Gazit et al. |
| 7,955,827 B2 | 6/2011 | Rubinsky et al. |
| RE42,835 E | 10/2011 | Chornenky et al. |
| D647,628 S | 10/2011 | Helfteren |
| 8,048,067 B2 | 11/2011 | Davalos et al. |
| RE43,009 E | 12/2011 | Chornenky et al. |
| 8,109,926 B2 | 2/2012 | Azure |
| 8,114,070 B2 | 2/2012 | Rubinsky et al. |
| 8,162,918 B2 | 4/2012 | Ivorra et al. |
| 8,187,269 B2 | 5/2012 | Shadduck et al. |
| 8,221,411 B2 | 7/2012 | Francischelli et al. |
| 8,231,603 B2 | 7/2012 | Hobbs et al. |
| 8,240,468 B2 | 8/2012 | Wilkinson et al. |
| 8,251,986 B2 | 8/2012 | Chornenky et al. |
| 8,267,927 B2 | 9/2012 | Dalal et al. |
| 8,267,936 B2 | 9/2012 | Hushka et al. |
| 8,282,631 B2 | 10/2012 | Davalos et al. |
| 8,298,222 B2 | 10/2012 | Rubinsky et al. |
| 8,348,921 B2 | 1/2013 | Ivorra et al. |
| 8,361,066 B2 | 1/2013 | Long et al. |
| D677,798 S | 3/2013 | Hart et al. |
| 8,425,455 B2 | 4/2013 | Nentwick |
| 8,425,505 B2 | 4/2013 | Long |
| 8,454,594 B2 | 6/2013 | Demarais et al. |
| 8,465,464 B2 | 6/2013 | Travis et al. |
| 8,465,484 B2 | 6/2013 | Davalos et al. |
| 8,506,564 B2 | 8/2013 | Long et al. |
| 8,511,317 B2 | 8/2013 | Thapliyal et al. |
| 8,518,031 B2 | 8/2013 | Boyden et al. |
| 8,562,588 B2 | 10/2013 | Hobbs et al. |
| 8,603,087 B2 | 12/2013 | Rubinsky et al. |
| 8,632,534 B2 | 1/2014 | Pearson et al. |
| 8,634,929 B2 | 1/2014 | Chornenky et al. |
| 8,647,338 B2 | 2/2014 | Chornenky et al. |
| 8,715,276 B2 | 5/2014 | Thompson et al. |
| 8,753,335 B2 | 6/2014 | Moshe et al. |
| 8,814,860 B2 | 8/2014 | Davalos et al. |
| 8,835,166 B2 | 9/2014 | Phillips et al. |
| 8,845,635 B2 | 9/2014 | Daniel et al. |
| 8,880,195 B2 | 11/2014 | Azure |

(56) References Cited

U.S. PATENT DOCUMENTS

| | | |
|---|---|---|
| 8,903,488 B2 | 12/2014 | Callas et al. |
| 8,906,006 B2 | 12/2014 | Chornenky et al. |
| 8,926,606 B2 | 1/2015 | Davalos et al. |
| 8,958,888 B2 | 2/2015 | Chornenky et al. |
| 8,968,542 B2 | 3/2015 | Davalos et al. |
| 8,992,517 B2 | 3/2015 | Davalos et al. |
| 9,005,189 B2 | 4/2015 | Davalos et al. |
| 9,078,665 B2 | 7/2015 | Moss et al. |
| 9,149,331 B2 | 10/2015 | Deem et al. |
| 9,173,704 B2 | 11/2015 | Hobbs et al. |
| 9,198,733 B2 | 12/2015 | Neal, II et al. |
| 9,283,051 B2 | 3/2016 | Garcia et al. |
| 9,414,881 B2 | 8/2016 | Callas et al. |
| 9,598,691 B2 | 3/2017 | Davalos |
| 9,764,145 B2 | 9/2017 | Callas et al. |
| 9,867,652 B2 | 1/2018 | Sano et al. |
| 9,943,599 B2 | 4/2018 | Gehl et al. |
| 10,117,701 B2 | 11/2018 | Davalos et al. |
| 10,117,707 B2 | 11/2018 | Garcia et al. |
| 10,154,874 B2 | 12/2018 | Davalos et al. |
| 10,238,447 B2 | 3/2019 | Neal et al. |
| 10,245,098 B2 | 4/2019 | Davalos et al. |
| 10,245,105 B2 | 4/2019 | Davalos et al. |
| 10,272,178 B2 | 4/2019 | Davalos et al. |
| 10,286,108 B2 | 5/2019 | Davalos et al. |
| 10,292,755 B2 | 5/2019 | Davalos et al. |
| 10,448,989 B2 | 10/2019 | Arena et al. |
| 10,470,822 B2 | 11/2019 | Garcia et al. |
| 10,471,254 B2 | 11/2019 | Sano et al. |
| 10,537,379 B2 | 1/2020 | Sano et al. |
| 10,694,972 B2 | 6/2020 | Davalos et al. |
| 10,702,326 B2 | 7/2020 | Neal et al. |
| 10,828,085 B2 | 11/2020 | Davalos et al. |
| 10,828,086 B2 | 11/2020 | Davalos et al. |
| 10,959,772 B2 | 3/2021 | Davalos et al. |
| 2001/0039393 A1 | 11/2001 | Mori et al. |
| 2001/0044596 A1 | 11/2001 | Jaafar |
| 2001/0046706 A1 | 11/2001 | Rubinsky et al. |
| 2001/0047167 A1 | 11/2001 | Heggeness |
| 2001/0051366 A1 | 12/2001 | Rubinsky et al. |
| 2002/0002393 A1 | 1/2002 | Mitchell |
| 2002/0010491 A1 | 1/2002 | Schoenbach et al. |
| 2002/0022864 A1 | 2/2002 | Mahvi et al. |
| 2002/0040204 A1 | 4/2002 | Dev et al. |
| 2002/0049370 A1 | 4/2002 | Laufer et al. |
| 2002/0052601 A1 | 5/2002 | Goldberg et al. |
| 2002/0055731 A1 | 5/2002 | Atala et al. |
| 2002/0065541 A1 | 5/2002 | Fredricks et al. |
| 2002/0072742 A1 | 6/2002 | Schaefer et al. |
| 2002/0077314 A1 | 6/2002 | Falk et al. |
| 2002/0077676 A1 | 6/2002 | Schroeppel et al. |
| 2002/0082543 A1 | 6/2002 | Park et al. |
| 2002/0099323 A1 | 7/2002 | Dev et al. |
| 2002/0104318 A1 | 8/2002 | Jaafar et al. |
| 2002/0111615 A1 | 8/2002 | Cosman et al. |
| 2002/0112729 A1 | 8/2002 | DeVore et al. |
| 2002/0115208 A1 | 8/2002 | Mitchell et al. |
| 2002/0119437 A1 | 8/2002 | Grooms et al. |
| 2002/0133324 A1 | 9/2002 | Weaver et al. |
| 2002/0137121 A1 | 9/2002 | Rubinsky et al. |
| 2002/0138075 A1 | 9/2002 | Edwards et al. |
| 2002/0138117 A1 | 9/2002 | Son |
| 2002/0143365 A1 | 10/2002 | Herbst |
| 2002/0147462 A1 | 10/2002 | Mair et al. |
| 2002/0156472 A1 | 10/2002 | Lee et al. |
| 2002/0161361 A1 | 10/2002 | Sherman et al. |
| 2002/0183684 A1 | 12/2002 | Dev et al. |
| 2002/0183735 A1 | 12/2002 | Edwards et al. |
| 2002/0183740 A1 | 12/2002 | Edwards et al. |
| 2002/0188242 A1 | 12/2002 | Wu |
| 2002/0193784 A1 | 12/2002 | McHale et al. |
| 2002/0193831 A1 | 12/2002 | Edward |
| 2003/0009110 A1 | 1/2003 | Tu et al. |
| 2003/0016168 A1 | 1/2003 | Jandrell |
| 2003/0055220 A1 | 3/2003 | Legrain |
| 2003/0055420 A1 | 3/2003 | Kadhiresan et al. |
| 2003/0059945 A1 | 3/2003 | Dzekunov et al. |
| 2003/0060856 A1 | 3/2003 | Chornenky et al. |
| 2003/0078490 A1 | 4/2003 | Damasco et al. |
| 2003/0088189 A1 | 5/2003 | Tu et al. |
| 2003/0088199 A1 | 5/2003 | Kawaji |
| 2003/0096407 A1 | 5/2003 | Atala et al. |
| 2003/0105454 A1 | 6/2003 | Cucin |
| 2003/0109871 A1 | 6/2003 | Johnson et al. |
| 2003/0127090 A1 | 7/2003 | Gifford et al. |
| 2003/0130711 A1 | 7/2003 | Pearson et al. |
| 2003/0135242 A1 | 7/2003 | Mongeon et al. |
| 2003/0149451 A1 | 8/2003 | Chomenky et al. |
| 2003/0153960 A1 | 8/2003 | Chornenky et al. |
| 2003/0154988 A1 | 8/2003 | DeVore et al. |
| 2003/0159700 A1 | 8/2003 | Laufer et al. |
| 2003/0166181 A1 | 9/2003 | Rubinsky et al. |
| 2003/0170898 A1 | 9/2003 | Gundersen et al. |
| 2003/0194808 A1 | 10/2003 | Rubinsky et al. |
| 2003/0195385 A1 | 10/2003 | DeVore |
| 2003/0195406 A1 | 10/2003 | Jenkins et al. |
| 2003/0199050 A1 | 10/2003 | Mangano et al. |
| 2003/0208200 A1 | 11/2003 | Palanker et al. |
| 2003/0208236 A1 | 11/2003 | Heil et al. |
| 2003/0212394 A1 | 11/2003 | Pearson et al. |
| 2003/0212412 A1 | 11/2003 | Dillard et al. |
| 2003/0225360 A1 | 12/2003 | Eppstein et al. |
| 2003/0228344 A1 | 12/2003 | Fields et al. |
| 2004/0009459 A1 | 1/2004 | Anderson et al. |
| 2004/0019371 A1 | 1/2004 | Jaafar et al. |
| 2004/0055606 A1 | 3/2004 | Hendricksen et al. |
| 2004/0059328 A1 | 3/2004 | Daniel et al. |
| 2004/0059389 A1 | 3/2004 | Chornenky et al. |
| 2004/0068228 A1 | 4/2004 | Cunningham |
| 2004/0116965 A1 | 6/2004 | Falkenberg |
| 2004/0133194 A1 | 7/2004 | Eum et al. |
| 2004/0138715 A1 | 7/2004 | Groeningen et al. |
| 2004/0146877 A1 | 7/2004 | Diss et al. |
| 2004/0153057 A1 | 8/2004 | Davison |
| 2004/0176855 A1 | 9/2004 | Badylak |
| 2004/0193042 A1 | 9/2004 | Scampini et al. |
| 2004/0193097 A1 | 9/2004 | Hofmann et al. |
| 2004/0199159 A1 | 10/2004 | Lee et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0230187 A1 | 11/2004 | Lee et al. |
| 2004/0236376 A1 | 11/2004 | Miklavcic et al. |
| 2004/0243107 A1 | 12/2004 | Macoviak et al. |
| 2004/0267189 A1 | 12/2004 | Mavor et al. |
| 2004/0267340 A1 | 12/2004 | Cioanta et al. |
| 2005/0004507 A1 | 1/2005 | Schroeppel et al. |
| 2005/0010209 A1 | 1/2005 | Lee et al. |
| 2005/0010259 A1 | 1/2005 | Gerber |
| 2005/0013870 A1 | 1/2005 | Freyman et al. |
| 2005/0020965 A1 | 1/2005 | Rioux et al. |
| 2005/0043726 A1 | 2/2005 | Mchale et al. |
| 2005/0048651 A1 | 3/2005 | Ryttsen et al. |
| 2005/0049541 A1 | 3/2005 | Behar et al. |
| 2005/0061322 A1 | 3/2005 | Freitag |
| 2005/0066974 A1 | 3/2005 | Fields et al. |
| 2005/0112141 A1 | 5/2005 | Terman |
| 2005/0143817 A1 | 6/2005 | Hunter et al. |
| 2005/0165393 A1 | 7/2005 | Eppstein |
| 2005/0171522 A1 | 8/2005 | Christopherson |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |
| 2005/0197619 A1 | 9/2005 | Rule et al. |
| 2005/0261672 A1* | 11/2005 | Deem ............... A61B 18/1492 606/41 |
| 2005/0267407 A1 | 12/2005 | Goldman |
| 2005/0282284 A1 | 12/2005 | Rubinsky et al. |
| 2005/0283149 A1 | 12/2005 | Thorne et al. |
| 2005/0288684 A1 | 12/2005 | Aronson et al. |
| 2005/0288702 A1 | 12/2005 | McGurk et al. |
| 2005/0288730 A1 | 12/2005 | Deem et al. |
| 2006/0004356 A1 | 1/2006 | Bilski et al. |
| 2006/0004400 A1 | 1/2006 | McGurk et al. |

(56) References Cited

U.S. PATENT DOCUMENTS

| | | |
|---|---|---|
| 2006/0009748 A1 | 1/2006 | Mathis |
| 2006/0015147 A1 | 1/2006 | Persson et al. |
| 2006/0020347 A1 | 1/2006 | Barrett |
| 2006/0024359 A1 | 2/2006 | Walker et al. |
| 2006/0025760 A1 | 2/2006 | Podhajsky |
| 2006/0074413 A1 | 4/2006 | Behzadian |
| 2006/0079838 A1 | 4/2006 | Walker et al. |
| 2006/0079845 A1 | 4/2006 | Howard et al. |
| 2006/0079883 A1 | 4/2006 | Elmouelhi et al. |
| 2006/0085054 A1 | 4/2006 | Zikorus et al. |
| 2006/0089635 A1 | 4/2006 | Young et al. |
| 2006/0121610 A1 | 6/2006 | Rubinsky et al. |
| 2006/0142801 A1 | 6/2006 | Demarais et al. |
| 2006/0149123 A1 | 7/2006 | Vidlund et al. |
| 2006/0173490 A1 | 8/2006 | Lafontaine et al. |
| 2006/0182684 A1 | 8/2006 | Beliveau |
| 2006/0195146 A1 | 8/2006 | Tracey et al. |
| 2006/0212032 A1 | 9/2006 | Daniel et al. |
| 2006/0212078 A1 | 9/2006 | Demarais et al. |
| 2006/0217703 A1 | 9/2006 | Chornenky et al. |
| 2006/0224188 A1 | 10/2006 | Libbus et al. |
| 2006/0235474 A1 | 10/2006 | Demarais |
| 2006/0247619 A1 | 11/2006 | Kaplan et al. |
| 2006/0264752 A1 | 11/2006 | Rubinsky et al. |
| 2006/0264807 A1 | 11/2006 | Westersten et al. |
| 2006/0269531 A1 | 11/2006 | Beebe et al. |
| 2006/0276710 A1 | 12/2006 | Krishnan |
| 2006/0278241 A1 | 12/2006 | Ruano |
| 2006/0283462 A1 | 12/2006 | Fields et al. |
| 2006/0293713 A1 | 12/2006 | Rubinsky et al. |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2006/0293734 A1 | 12/2006 | Scott et al. |
| 2007/0010805 A1 | 1/2007 | Fedewa et al. |
| 2007/0016183 A1 | 1/2007 | Lee et al. |
| 2007/0016185 A1 | 1/2007 | Tullis et al. |
| 2007/0021803 A1 | 1/2007 | Deem et al. |
| 2007/0025919 A1 | 2/2007 | Deem et al. |
| 2007/0043345 A1 | 2/2007 | Davalos et al. |
| 2007/0060989 A1 | 3/2007 | Deem et al. |
| 2007/0078391 A1 | 4/2007 | Wortley et al. |
| 2007/0088347 A1 | 4/2007 | Young et al. |
| 2007/0093789 A1 | 4/2007 | Smith |
| 2007/0096048 A1 | 5/2007 | Clerc |
| 2007/0118069 A1 | 5/2007 | Persson et al. |
| 2007/0129711 A1 | 6/2007 | Altshuler et al. |
| 2007/0129760 A1 | 6/2007 | Demarais et al. |
| 2007/0151848 A1 | 7/2007 | Novak et al. |
| 2007/0156135 A1 | 7/2007 | Rubinsky et al. |
| 2007/0191889 A1 | 8/2007 | Lang |
| 2007/0203486 A1 | 8/2007 | Young |
| 2007/0230757 A1 | 10/2007 | Trachtenberg et al. |
| 2007/0239099 A1 | 10/2007 | Goldfarb et al. |
| 2007/0244521 A1 | 10/2007 | Bornzin et al. |
| 2007/0287950 A1 | 12/2007 | Kjeken et al. |
| 2007/0295336 A1 | 12/2007 | Nelson et al. |
| 2007/0295337 A1 | 12/2007 | Nelson et al. |
| 2008/0015571 A1 | 1/2008 | Rubinsky et al. |
| 2008/0021371 A1 | 1/2008 | Rubinsky et al. |
| 2008/0027314 A1 | 1/2008 | Miyazaki et al. |
| 2008/0027343 A1 | 1/2008 | Fields et al. |
| 2008/0033340 A1 | 2/2008 | Heller et al. |
| 2008/0033417 A1 | 2/2008 | Nields et al. |
| 2008/0045880 A1 | 2/2008 | Kjeken et al. |
| 2008/0052786 A1 | 2/2008 | Lin et al. |
| 2008/0065062 A1 | 3/2008 | Leung et al. |
| 2008/0071262 A1 | 3/2008 | Azure |
| 2008/0097139 A1 | 4/2008 | Clerc et al. |
| 2008/0097422 A1 | 4/2008 | Edwards et al. |
| 2008/0103529 A1 | 5/2008 | Schoenbach et al. |
| 2008/0121375 A1 | 5/2008 | Richason et al. |
| 2008/0125772 A1 | 5/2008 | Stone et al. |
| 2008/0132826 A1 | 6/2008 | Shadduck et al. |
| 2008/0132884 A1 | 6/2008 | Rubinsky et al. |
| 2008/0132885 A1 | 6/2008 | Rubinsky et al. |
| 2008/0140064 A1 | 6/2008 | Vegesna |
| 2008/0146934 A1 | 6/2008 | Czygan et al. |
| 2008/0154259 A1 | 6/2008 | Gough et al. |
| 2008/0167649 A1 | 7/2008 | Edwards et al. |
| 2008/0171985 A1 | 7/2008 | Karakoca |
| 2008/0190434 A1 | 8/2008 | Wai |
| 2008/0200911 A1 | 8/2008 | Long |
| 2008/0200912 A1 | 8/2008 | Long |
| 2008/0208052 A1 | 8/2008 | LePivert et al. |
| 2008/0210243 A1 | 9/2008 | Clayton et al. |
| 2008/0214986 A1 | 9/2008 | Ivorra et al. |
| 2008/0236593 A1 | 10/2008 | Nelson et al. |
| 2008/0249503 A1 | 10/2008 | Fields et al. |
| 2008/0262489 A1 | 10/2008 | Steinke |
| 2008/0269586 A1 | 10/2008 | Rubinsky et al. |
| 2008/0269838 A1 | 10/2008 | Brighton et al. |
| 2008/0275465 A1 | 11/2008 | Paul et al. |
| 2008/0281319 A1 | 11/2008 | Paul et al. |
| 2008/0283065 A1 | 11/2008 | Chang et al. |
| 2008/0288038 A1 | 11/2008 | Paul et al. |
| 2008/0300589 A1 | 12/2008 | Paul et al. |
| 2008/0306427 A1 | 12/2008 | Bailey |
| 2008/0312599 A1 | 12/2008 | Rosenberg |
| 2009/0018206 A1 | 1/2009 | Barkan et al. |
| 2009/0024075 A1 | 1/2009 | Schroeppel et al. |
| 2009/0029407 A1 | 1/2009 | Gazit et al. |
| 2009/0038752 A1 | 2/2009 | Weng et al. |
| 2009/0062788 A1 | 3/2009 | Long et al. |
| 2009/0062792 A1 | 3/2009 | Vakharia et al. |
| 2009/0081272 A1 | 3/2009 | Clarke et al. |
| 2009/0105703 A1 | 4/2009 | Shadduck |
| 2009/0114226 A1 | 5/2009 | Deem et al. |
| 2009/0125009 A1 | 5/2009 | Zikorus et al. |
| 2009/0138014 A1 | 5/2009 | Bonutti |
| 2009/0143705 A1 | 6/2009 | Danek et al. |
| 2009/0157166 A1 | 6/2009 | Singhal et al. |
| 2009/0163904 A1 | 6/2009 | Miller et al. |
| 2009/0171280 A1 | 7/2009 | Samuel et al. |
| 2009/0177111 A1 | 7/2009 | Miller et al. |
| 2009/0186850 A1 | 7/2009 | Kiribayashi et al. |
| 2009/0192508 A1 | 7/2009 | Laufer et al. |
| 2009/0198231 A1 | 8/2009 | Esser et al. |
| 2009/0228001 A1 | 9/2009 | Pacey |
| 2009/0247933 A1 | 10/2009 | Maor et al. |
| 2009/0248012 A1 | 10/2009 | Maor et al. |
| 2009/0269317 A1 | 10/2009 | Davalos |
| 2009/0275827 A1 | 11/2009 | Aiken et al. |
| 2009/0281477 A1 | 11/2009 | Mikus et al. |
| 2009/0292342 A1 | 11/2009 | Rubinsky et al. |
| 2009/0301480 A1 | 12/2009 | Elsakka et al. |
| 2009/0306544 A1 | 12/2009 | Ng et al. |
| 2009/0306545 A1 | 12/2009 | Elsakka et al. |
| 2009/0318905 A1 | 12/2009 | Bhargav et al. |
| 2009/0326366 A1 | 12/2009 | Krieg |
| 2009/0326436 A1 | 12/2009 | Rubinsky et al. |
| 2009/0326570 A1 | 12/2009 | Brown |
| 2010/0004623 A1 | 1/2010 | Hamilton, Jr. et al. |
| 2010/0006441 A1 | 1/2010 | Renaud et al. |
| 2010/0023004 A1 | 1/2010 | Francischelli et al. |
| 2010/0030211 A1 | 2/2010 | Davalos et al. |
| 2010/0049190 A1 | 2/2010 | Long et al. |
| 2010/0057074 A1 | 3/2010 | Roman et al. |
| 2010/0069921 A1 | 3/2010 | Miller et al. |
| 2010/0087813 A1 | 4/2010 | Long |
| 2010/0130975 A1 | 5/2010 | Long |
| 2010/0147701 A1 | 6/2010 | Field |
| 2010/0152725 A1 | 6/2010 | Pearson et al. |
| 2010/0160850 A1 | 6/2010 | Ivorra et al. |
| 2010/0168735 A1 | 7/2010 | Deno et al. |
| 2010/0174282 A1 | 7/2010 | Demarais et al. |
| 2010/0179530 A1 | 7/2010 | Long et al. |
| 2010/0196984 A1 | 8/2010 | Rubinsky et al. |
| 2010/0204560 A1 | 8/2010 | Salahieh et al. |
| 2010/0204638 A1 | 8/2010 | Hobbs et al. |
| 2010/0222677 A1 | 9/2010 | Placek et al. |
| 2010/0228234 A1 | 9/2010 | Hyde et al. |
| 2010/0228247 A1 | 9/2010 | Paul et al. |
| 2010/0241117 A1 | 9/2010 | Paul et al. |

(56) References Cited

U.S. PATENT DOCUMENTS

| | | |
|---|---|---|
| 2010/0249771 A1 | 9/2010 | Pearson et al. |
| 2010/0250209 A1 | 9/2010 | Pearson et al. |
| 2010/0255795 A1 | 10/2010 | Rubinsky et al. |
| 2010/0256628 A1 | 10/2010 | Pearson et al. |
| 2010/0256630 A1 | 10/2010 | Hamilton, Jr. et al. |
| 2010/0261994 A1 | 10/2010 | Davalos et al. |
| 2010/0286690 A1 | 11/2010 | Paul et al. |
| 2010/0298823 A1 | 11/2010 | Cao et al. |
| 2010/0331758 A1 | 12/2010 | Davalos et al. |
| 2011/0017207 A1 | 1/2011 | Hendricksen et al. |
| 2011/0034209 A1 | 2/2011 | Rubinsky et al. |
| 2011/0064671 A1 | 3/2011 | Bynoe |
| 2011/0092973 A1* | 4/2011 | Nuccitelli .............. A61N 1/205 606/49 |
| 2011/0106221 A1 | 5/2011 | Robert et al. |
| 2011/0112531 A1 | 5/2011 | Landis et al. |
| 2011/0118727 A1 | 5/2011 | Fish et al. |
| 2011/0118732 A1 | 5/2011 | Rubinsky et al. |
| 2011/0130834 A1 | 6/2011 | Wilson et al. |
| 2011/0144524 A1 | 6/2011 | Fish et al. |
| 2011/0144635 A1 | 6/2011 | Harper et al. |
| 2011/0144657 A1 | 6/2011 | Fish et al. |
| 2011/0152678 A1 | 6/2011 | Aljuri et al. |
| 2011/0166499 A1 | 7/2011 | Demarais et al. |
| 2011/0176037 A1 | 7/2011 | Benkley, I |
| 2011/0202053 A1 | 8/2011 | Moss et al. |
| 2011/0217730 A1 | 9/2011 | Gazit et al. |
| 2011/0251607 A1 | 10/2011 | Kruecker et al. |
| 2011/0301587 A1 | 12/2011 | Deem et al. |
| 2012/0034131 A1 | 2/2012 | Rubinsky et al. |
| 2012/0059255 A1 | 3/2012 | Paul et al. |
| 2012/0071872 A1 | 3/2012 | Rubinsky et al. |
| 2012/0071874 A1 | 3/2012 | Davalos et al. |
| 2012/0085649 A1 | 4/2012 | Sano et al. |
| 2012/0089009 A1 | 4/2012 | Omary et al. |
| 2012/0090646 A1 | 4/2012 | Tanaka et al. |
| 2012/0095459 A1 | 4/2012 | Callas et al. |
| 2012/0109122 A1 | 5/2012 | Arena et al. |
| 2012/0130289 A1 | 5/2012 | Demarais et al. |
| 2012/0150172 A1 | 6/2012 | Ortiz et al. |
| 2012/0165813 A1 | 6/2012 | Lee et al. |
| 2012/0179091 A1 | 7/2012 | Ivorra et al. |
| 2012/0226218 A1 | 9/2012 | Phillips et al. |
| 2012/0226271 A1 | 9/2012 | Callas et al. |
| 2012/0265186 A1 | 10/2012 | Burger et al. |
| 2012/0277741 A1 | 11/2012 | Davalos et al. |
| 2012/0303020 A1 | 11/2012 | Chornenky et al. |
| 2012/0310236 A1 | 12/2012 | Placek et al. |
| 2013/0030239 A1 | 1/2013 | Weyh et al. |
| 2013/0090646 A1 | 4/2013 | Moss et al. |
| 2013/0108667 A1 | 5/2013 | Soikum et al. |
| 2013/0110106 A1 | 5/2013 | Richardson |
| 2013/0184702 A1 | 7/2013 | Neal, II et al. |
| 2013/0196441 A1 | 8/2013 | Rubinsky et al. |
| 2013/0197425 A1 | 8/2013 | Golberg et al. |
| 2013/0202766 A1 | 8/2013 | Rubinsky et al. |
| 2013/0218157 A1 | 8/2013 | Callas et al. |
| 2013/0253415 A1 | 9/2013 | Sano et al. |
| 2013/0281968 A1 | 10/2013 | Davalos et al. |
| 2013/0345697 A1 | 12/2013 | Garcia et al. |
| 2013/0345779 A1 | 12/2013 | Maor et al. |
| 2014/0017218 A1 | 1/2014 | Scott et al. |
| 2014/0039489 A1 | 2/2014 | Davalos et al. |
| 2014/0046322 A1 | 2/2014 | Callas et al. |
| 2014/0066913 A1 | 3/2014 | Sherman |
| 2014/0081255 A1 | 3/2014 | Johnson et al. |
| 2014/0088578 A1 | 3/2014 | Rubinsky et al. |
| 2014/0121663 A1 | 5/2014 | Pearson et al. |
| 2014/0121728 A1 | 5/2014 | Dhillon et al. |
| 2014/0163551 A1 | 6/2014 | Maor et al. |
| 2014/0207133 A1 | 7/2014 | Model et al. |
| 2014/0296844 A1 | 10/2014 | Kevin et al. |
| 2014/0309579 A1 | 10/2014 | Rubinsky et al. |
| 2014/0378964 A1 | 12/2014 | Pearson |
| 2015/0088120 A1 | 3/2015 | Garcia et al. |
| 2015/0088220 A1 | 3/2015 | Callas et al. |
| 2015/0112333 A1 | 4/2015 | Chorenky et al. |
| 2015/0126922 A1 | 5/2015 | Willis |
| 2015/0152504 A1 | 6/2015 | Lin |
| 2015/0164584 A1 | 6/2015 | Davalos et al. |
| 2015/0173824 A1 | 6/2015 | Davalos et al. |
| 2015/0201996 A1 | 7/2015 | Rubinsky et al. |
| 2015/0265349 A1 | 9/2015 | Moss et al. |
| 2015/0289923 A1 | 10/2015 | Davalos et al. |
| 2015/0320478 A1 | 11/2015 | Cosman, Jr. et al. |
| 2015/0320488 A1 | 11/2015 | Moshe et al. |
| 2015/0320999 A1 | 11/2015 | Nuccitelli et al. |
| 2015/0327944 A1 | 11/2015 | Robert et al. |
| 2016/0022957 A1 | 1/2016 | Hobbs et al. |
| 2016/0066977 A1* | 3/2016 | Neal, II .............. A61B 18/18 606/34 |
| 2016/0074114 A1 | 3/2016 | Pearson et al. |
| 2016/0113708 A1 | 4/2016 | Moss et al. |
| 2016/0143698 A1 | 5/2016 | Garcia et al. |
| 2016/0235470 A1 | 8/2016 | Callas et al. |
| 2016/0287313 A1 | 10/2016 | Rubinsky et al. |
| 2016/0287314 A1 | 10/2016 | Arena et al. |
| 2016/0338758 A9 | 11/2016 | Davalos et al. |
| 2016/0338761 A1 | 11/2016 | Chornenky et al. |
| 2016/0354142 A1 | 12/2016 | Pearson et al. |
| 2016/0367310 A1 | 12/2016 | Dnik et al. |
| 2017/0035501 A1 | 2/2017 | Chornenky et al. |
| 2017/0189579 A1 | 7/2017 | Davalos |
| 2017/0209620 A1 | 7/2017 | Davalos et al. |
| 2017/0266438 A1 | 9/2017 | Sano |
| 2017/0360326 A1 | 12/2017 | Davalos |
| 2018/0071014 A1 | 3/2018 | Neal et al. |
| 2018/0125565 A1 | 5/2018 | Sano et al. |
| 2018/0161086 A1 | 6/2018 | Davalos et al. |
| 2019/0029749 A1 | 1/2019 | Garcia |
| 2019/0046255 A1 | 2/2019 | Davalos et al. |
| 2019/0069945 A1 | 3/2019 | Davalos et al. |
| 2019/0076528 A1 | 3/2019 | Soden et al. |
| 2019/0083169 A1 | 3/2019 | Single et al. |
| 2019/0133671 A1 | 5/2019 | Davalos et al. |
| 2019/0175248 A1 | 6/2019 | Neal, II |
| 2019/0175260 A1 | 6/2019 | Davalos |
| 2019/0223938 A1 | 7/2019 | Arena et al. |
| 2019/0232048 A1 | 8/2019 | Latouche et al. |
| 2019/0233809 A1 | 8/2019 | Neal et al. |
| 2019/0256839 A1 | 8/2019 | Neal et al. |
| 2019/0282294 A1 | 9/2019 | Davalos et al. |
| 2019/0328445 A1 | 10/2019 | Sano et al. |
| 2019/0351224 A1 | 11/2019 | Sano et al. |
| 2019/0376055 A1 | 12/2019 | Davalos et al. |
| 2020/0046432 A1 | 2/2020 | Garcia et al. |
| 2020/0046967 A1 | 2/2020 | Ivey et al. |
| 2020/0093541 A9 | 3/2020 | Neal et al. |
| 2020/0197073 A1 | 6/2020 | Sano et al. |
| 2020/0260987 A1 | 8/2020 | Davalos et al. |
| 2020/0323576 A1 | 10/2020 | Neal et al. |
| 2020/0405373 A1 | 12/2020 | O'Brien et al. |
| 2021/0022795 A1 | 1/2021 | Davalos et al. |
| 2021/0023362 A1 | 1/2021 | Lorenzo et al. |
| 2021/0052882 A1 | 2/2021 | Wasson et al. |
| 2021/0113265 A1* | 4/2021 | D'Agostino ....... A61B 18/1492 |
| 2021/0137410 A1 | 5/2021 | O'Brien et al. |
| 2021/0186600 A1 | 6/2021 | Davalos et al. |
| 2021/0361341 A1 | 11/2021 | Neal et al. |
| 2021/0393312 A1 | 12/2021 | Davalos et al. |

FOREIGN PATENT DOCUMENTS

| | | |
|---|---|---|
| AU | 2003227960 A1 | 12/2003 |
| AU | 2005271471 A2 | 2/2006 |
| AU | 2006321570 A1 | 6/2007 |
| AU | 2006321574 A1 | 6/2007 |
| AU | 2006321918 A1 | 6/2007 |
| AU | 2009243079 A2 | 1/2011 |
| CA | 2297846 A1 | 2/1999 |
| CA | 2378110 A1 | 2/2001 |
| CA | 2445392 A1 | 11/2002 |
| CA | 2458676 A1 | 3/2003 |
| CA | 2487284 A1 | 12/2003 |

(56) References Cited

FOREIGN PATENT DOCUMENTS

| | | |
|---|---|---|
| CA | 2575792 A1 | 2/2006 |
| CA | 2631940 A1 | 6/2007 |
| CA | 2631946 A1 | 6/2007 |
| CA | 2632604 A1 | 6/2007 |
| CA | 2722296 A1 | 11/2009 |
| CA | 2751462 A1 | 11/2010 |
| CN | 1525839 A | 9/2004 |
| CN | 101534736 A | 9/2009 |
| CN | 102238921 A | 11/2011 |
| CN | 102421386 A | 4/2012 |
| CN | 106715682 A | 5/2017 |
| DE | 863111 | 1/1953 |
| DE | 4000893 | 7/1991 |
| DE | 60038026 | 2/2009 |
| EP | 0218275 A1 | 4/1987 |
| EP | 0339501 A2 | 11/1989 |
| EP | 0378132 A | 7/1990 |
| EP | 0533511 A1 | 3/1993 |
| EP | 0998235 A1 | 5/2000 |
| EP | 0528891 B1 | 7/2000 |
| EP | 1196550 A2 | 4/2002 |
| EP | 1439792 A1 | 7/2004 |
| EP | 1442765 A1 | 8/2004 |
| EP | 1462065 A2 | 9/2004 |
| EP | 1061983 B1 | 11/2004 |
| EP | 1493397 A1 | 1/2005 |
| EP | 1506039 A1 | 2/2005 |
| EP | 0935482 B1 | 5/2005 |
| EP | 1011495 B1 | 11/2005 |
| EP | 1796568 A1 | 6/2007 |
| EP | 1207797 B1 | 2/2008 |
| EP | 1406685 B1 | 6/2008 |
| EP | 1424970 B1 | 12/2008 |
| EP | 2280741 A1 | 2/2011 |
| EP | 2381829 A1 | 11/2011 |
| EP | 2413833 A1 | 2/2012 |
| EP | 2488251 A2 | 8/2012 |
| EP | 2642937 A2 | 10/2013 |
| EP | 1791485 B1 | 12/2014 |
| EP | 2373241 B1 | 1/2015 |
| EP | 1962710 B1 | 8/2015 |
| EP | 1962708 B1 | 9/2015 |
| EP | 1962945 B1 | 4/2016 |
| EP | 3143124 A1 | 3/2017 |
| EP | 3852868 A1 | 7/2021 |
| ES | 2300272 | 6/2008 |
| ES | 2315493 | 4/2009 |
| JP | 2001510702 A | 8/2001 |
| JP | 2003505072 A | 2/2003 |
| JP | 2003506064 A | 2/2003 |
| JP | 2004203224 A | 7/2004 |
| JP | 2004525726 A | 8/2004 |
| JP | 2004303590 A | 10/2004 |
| JP | 2005501596 A | 1/2005 |
| JP | 2005526579 A | 9/2005 |
| JP | 2008508946 A | 3/2008 |
| JP | 452316 B2 | 4/2009 |
| JP | 2009518130 A | 5/2009 |
| JP | 2009518150 A | 5/2009 |
| JP | 2009518151 A | 5/2009 |
| JP | 2009532077 A | 9/2009 |
| JP | 2010503496 A | 2/2010 |
| JP | 2011137025 | 7/2011 |
| JP | 2011137025 A | 7/2011 |
| JP | 2012510332 A | 5/2012 |
| JP | 2012515018 A | 7/2012 |
| JP | 2012521863 A | 9/2012 |
| JP | 2014501574 A | 1/2014 |
| JP | 6594901 B2 | 10/2019 |
| KR | 101034682 A | 5/2011 |
| WO | 9104014 | 4/1991 |
| WO | 9634571 | 11/1996 |
| WO | 9639531 A | 12/1996 |
| WO | 9810745 | 3/1998 |
| WO | 9814238 A | 4/1998 |
| WO | 9901076 | 1/1999 |
| WO | 9904710 | 2/1999 |
| WO | 0020554 A | 4/2000 |
| WO | 0107583 A | 2/2001 |
| WO | 0107584 A | 2/2001 |
| WO | 0107585 A | 2/2001 |
| WO | 0110319 A | 2/2001 |
| WO | 0148153 A | 7/2001 |
| WO | 2001048153 A1 | 7/2001 |
| WO | 0170114 A1 | 9/2001 |
| WO | 0181533 A | 11/2001 |
| WO | 02078527 A | 10/2002 |
| WO | 02089686 A | 11/2002 |
| WO | 02100459 A | 12/2002 |
| WO | 2003020144 A1 | 3/2003 |
| WO | 2003047684 A2 | 6/2003 |
| WO | 03099382 A | 12/2003 |
| WO | 2004037341 A2 | 5/2004 |
| WO | 2004080347 A2 | 9/2004 |
| WO | 2005065284 A | 7/2005 |
| WO | 2006017666 A2 | 2/2006 |
| WO | 2006031541 A1 | 3/2006 |
| WO | 2006130194 A2 | 12/2006 |
| WO | 2007067628 A1 | 6/2007 |
| WO | 2007067937 A2 | 6/2007 |
| WO | 2007067938 A2 | 6/2007 |
| WO | 2007067939 A2 | 6/2007 |
| WO | 2007067940 A2 | 6/2007 |
| WO | 2007067941 A2 | 6/2007 |
| WO | 2007067943 A2 | 6/2007 |
| WO | 2007070361 A2 | 6/2007 |
| WO | 2007100727 A2 | 9/2007 |
| WO | 2007123690 A2 | 11/2007 |
| WO | 2008063195 A1 | 5/2008 |
| WO | 2008034103 A3 | 11/2008 |
| WO | 2009046176 A1 | 4/2009 |
| WO | 2007137303 | 7/2009 |
| WO | 2009134876 A | 11/2009 |
| WO | 2009135070 A1 | 11/2009 |
| WO | 2009137800 A2 | 11/2009 |
| WO | 2010064154 A1 | 6/2010 |
| WO | 2010080974 A1 | 7/2010 |
| WO | 2010117806 A1 | 10/2010 |
| WO | 2010118387 A | 10/2010 |
| WO | 2010132472 A1 | 11/2010 |
| WO | 2010151277 A | 12/2010 |
| WO | 2011047387 A | 4/2011 |
| WO | 2011062653 A1 | 5/2011 |
| WO | 2011072221 A1 | 6/2011 |
| WO | 2012051433 A2 | 4/2012 |
| WO | 2012071526 A | 5/2012 |
| WO | 2012071526 A2 | 5/2012 |
| WO | 2012088149 A | 6/2012 |
| WO | 2015175570 A1 | 11/2015 |
| WO | 2016100325 A1 | 6/2016 |
| WO | 2016164930 A1 | 10/2016 |
| WO | 2017117418 A1 | 7/2017 |
| WO | 2020061192 A1 | 3/2020 |

OTHER PUBLICATIONS

Sanchez, B., G. Vandersteen, R. Bragos, and J. Schoukens, "Basics of broadband impedance spectroscopy measurements using periodic excitations," Measurement Science and Technology, vol. 23, No. 10, p. 105501, 2012.

Sanchez, B., G. Vandersteen, R. Bragos, and J. Schoukens, "Optimal multisine excitation design for broadband electrical impedance spec-troscopy," Measurement Science and Technology, vol. 22, No. 11, p. 115601, 2011.

Shao, Qi et al. Engineering T cell response to cancer antigens by choice of focal therapeutic conditions, International Journal of Hyperthermia, 2019, DOI: 10.1080/02656736.2018.1539253.

Thomson et al., "Investigation of the safety of irreversible electroporation in humans," J Vasc Interv Radiol, 22, pp. 611-621, 2011.

U.S. Appl. No. 12/491,151 (U.S. Pat. No. 8,992,517), file history through Feb. 2015, 113 pages.

U.S. Appl. No. 12/609,779 (U.S. Pat. No. 8,465,484), file history through May 2013, 100 pages.

(56) References Cited

OTHER PUBLICATIONS

U.S. Appl. No. 12/757,901 (U.S. Pat. No. 8,926,606), file history through Jan. 2015, 165 pages.
U.S. Appl. No. 12/906,923 (U.S. Pat. No. 9,198,733), file history through Nov. 2015, 55 pages.
U.S. Appl. No. 13/332,133 (U.S. Pat. No. 10,448,989), file history through Sep. 2019, 226 pages.
U.S. Appl. No. 13/550,307 (U.S. Pat. No. 10,702,326), file history through May 2020, 224 pages.
U.S. Appl. No. 13/919,640 (U.S. Pat. No. 8,814,860), file history filed Jul. 2014, 41 pages.
U.S. Appl. No. 13/958,152, file history through Dec. 2019, 391 pages.
U.S. Appl. No. 13/989,175 (U.S. Pat. No. 9,867,652), file history through Dec. 2017, 200 pages.
U.S. Appl. No. 14/012,832 (U.S. Pat. No. 9,283,051), file history through Nov. 2015, 17 pages.
U.S. Appl. No. 14/017,210 (U.S. Pat. No. 10,245,098), file history through Jan. 2019, 294 pages.
U.S. Appl. No. 14/558,631 (U.S. Pat. No. 10,117,707), file history through Jul. 2018, 58 pages.
U.S. Appl. No. 14/627,046 (U.S. Pat. No. 10,245,105), file history through Feb. 2019, 77 pages.
U.S. Appl. No. 14/940,863 (U.S. Pat. No. 10,238,447), file history through Oct. 2019, 23 pages.
U.S. Appl. No. 15/011,752 (U.S. Pat. No. 10,470,822), file history through Jul. 2019, 54 pages.
U.S. Appl. No. 15/186,653 (U.S. Pat. No. 10,292,755), file history through Mar. 2019, 21 pages.
U.S. Appl. No. 15/310,114 (U.S. Pat. No. 10,471,254), file history through Aug. 2019, 44 pages.
U.S. Appl. No. 15/423,986 (U.S. Pat. No. 10,286,108), file history through Jan. 2019, 124 pages.
U.S. Appl. No. 15/424,335 (U.S. Pat. No. 10,272,178), file history through Feb. 2019, 57 pages.
U.S. Appl. No. 15/536,333 (U.S. Pat. No. 10,694,972), file history through Apr. 2020, 78 pages.
U.S. Appl. No. 15/843,888 (U.S. Pat. No. 10,537,379), file history through Sep. 2019, 33 pages.
U.S. Appl. No. 15/881,414 (U.S. Pat. No. 10,154,874), file history through Nov. 2018, 43 pages.
U.S. Appl. No. 16/177,745 (Patented), file history through Jun. 2020, 57 pages.
U.S. Appl. No. 16/232,962 (Patented), file history through Jun. 2020, 44 pages.
Van Den Bos, W. et al., "MRI and contrast-enhanced ultrasound imaging for evaluation of focal irreversible electroporation treatment: results from a phase i-ii study in patients undergoing ire followed by radical prostatectomy," European radiology, vol. 26, No. 7, pp. 2252-2260, 2016.
Voyer, D., A. Silve, L. M. Mir, R. Scorretti, and C. Poignard, "Dynamical modeling of tissue electroporation," Bioelectrochemistry, vol. 119, pp. 98-110, 2018.
Zhao, Y., S. Bhonsle, S. Dong, Y. Lv, H. Liu, A. Safaai-Jazi, R. V. Davalos, and C. Yao, "Characterization of conductivity changes during high-frequency irreversible electroporation for treatment planning," IEEE Transactions on Biomedical Engineering, vol. 65, No. 8, pp. 1810-1819, 2017.
Hughes, et al., An Analysis of Studies Comparing Electrical Impedance Tomography with X-Ray Videofluoroscopy in the Assessment of Swallowing, Physiol. Meas. 15, 1994, pp. A199-A209.
Ibey et al., "Selective cytotoxicity of intense nanosecond-duration electric pulses in mammalian cells." Biochimica Et Biophysica Acta-General Subjects, vol. 1800, pp. 1210-1219 (2010).
Issa, et al., The TUNA Procedure for BPH: Review of the Technology: The TUNA Procedure for BPH: Basic Procedure and Clinical Results, Reprinted from Infections in Urology, Jul./Aug. 1998 and Sep./Oct. 1998.
Ianuša, et al., MRI Macromolecular Contrast Agents as Indicators of Changed Tumor Blood Flow, Radiol. Oncol. 2001; 35(2): 139-47.

Ivorra et al., "In vivo electric impedance measurements during and after electroporation of rat live." Bioelectrochemistry, vol. 70, pp. 287-295 (2007).
Ivorra et al., "In vivo electrical conductivity measurements during and after tumor electroporation: conductivity changes reflect the treatment outcome." Physics in Medicine and Biology, vol. 54, pp. 5949-5963 (2009).
Ivorra,"Bioimpedance monitoring for physicians: an overview." Biomedical Applications Group, 35 pages (2002).
Ivorra, A., ed. "Tissue Electroporation as a Bioelectric Phenomenon: Basic Concepts. Irreversible Electroporation", ed. B. Rubinsky., Springer Berlin Heidelberg. 23-61 (2010).
Jarm et al., "Antivascular effects of electrochemotherapy: implications in treatment of bleeding metastases." Expert Rev Anticancer Ther. vol. 10, pp. 729-746 (2010).
Jaroszeski, et al., In Vivo Gene Delivery by Electroporation, Advanced Drug Delivery Review, vol. 35, pp. 131-137, 1999.
Jensen et al., "Tumor volume in subcutaneous mouse xenografts measured by microCT is more accurate and reproducible than determined by 18FFDG-microPET or external caliper." BMC medical Imaging vol. 8:16, 9 Pages (2008).
Jordan, D.W., et al., "Effect of pulsed, high-power radiofrequency radiation on electroporation of mammalian cells". Ieee Transactions on Plasma Science, 32(4): p. 1573-1578 (2004).
Jossinet et al., Electrical Impedance Endo-Tomography: Imaging Tissue From Inside, IEEE Transactions on Medical Imaging, vol. 21, No. 6, Jun. 2002, pp. 560-565.
Katsuki, S., et al., "Biological effects of narrow band pulsed electric fields", Ieee Transactions on Dielectrics and Electrical Insulation, 14(3): p. 663-668 (2007).
Kingham et al., "Ablation of perivascular hepatic malignant tumors with irreversible electroporation." Journal of the American College of Surgeons, 2012. 215(3), p. 379-387.
Kinosita and Tsong, "Formation and resealing of pores of controlled sizes in human erythrocyte membrane." Nature, vol. 268 (1977) pp. 438-441.
Kinosita and Tsong, "Voltage-induced pore formation and hemolysis of human erythrocytes." Biochimica et Biophysica Acta (BBA)—Biomembranes, 471 (1977) pp. 227-242.
Kinosita et al., "Electroporation of cell membrane visualized under a pulsed-laser fluorescence microscope." Biophysical Journal, vol. 53, pp. 1015-1019 (1988).
Kinosita, et al., Hemolysis of Human Erythrocytes by a Transient Electric Field, Proc. Natl. Acad. Sci. USA, vol. 74, No. 5, pp. 1923-1927, 1977.
Kirson et al., "Alternating electric fields arrest cell proliferation in animal tumor models and human brain tumors." Proceedings of the National Academy of Sciences vol. 104, pp. 10152-10157 (2007).
Kolb, J.F., et al., "Nanosecond pulsed electric field generators for the study of subcellular effects", Bioelectromagnetics, 27(3): p. 172-187 (2006).
Kotnik and Miklavcic, "Theoretical evaluation of voltage inducement on internal membranes of biological cells exposed to electric fields." Biophysical Journal, vol. 90(2), pp. 480-491 (2006).
Kotnik et al., "Sensitivity of transmembrane voltage induced by applied electric fields—A theoretical analysis", Bioelectrochemistry and Bioenergetics,vol. 43, Issue 2, 1997, pp. 285-291.
Kotnik, T. and D. Miklavcic, "Theoretical evaluation of the distributed power dissipation in biological cells exposed to electric fields", Bioelectromagnetics, 21(5): p. 385-394 (2000).
Kotnik, T., et al., "Cell membrane electropermeabilization by symmetrical bipolar rectangular pulses. Part II. Reduced electrolytic contamination", Bioelectrochemistry, 54(1): p. 91-5 (2001).
Kotnik, T., et al., "Role of pulse shape in cell membrane electropermeabilization", Biochimica Et Biophysica Acta—Biomembranes, 1614(2): p. 193-200 (2003).
Labeed et al., "Differences in the biophysical properties of membrane and cytoplasm of apoptotic cells revealed using dielectrophoresis." Biochimica et Biophysica Acta (BBA)—General Subjects, vol. 1760, pp. 922-929 (2006).

(56) References Cited

OTHER PUBLICATIONS

Lackovic, I., et al., "Three-dimensional Finite-element Analysis of Joule Heating in Electrochemotherapy and in vivo Gene Electrotransfer", Ieee Transactions on Dielectricsand Electrical Insulation, 16(5): p. 1338-1347 (2009).
Laufer et al., "Electrical impedance characterization of normal and cancerous human hepatic tissue." Physiological Measurement, vol. 31, pp. 995-1009 (2010).
Lebar et al., "Inter-pulse interval between rectangular voltage pulses affects electroporation threshold of artificial lipid bilayers." IEEE Transactions on NanoBioscience, vol. 1 (2002) pp. 116-120.
Lee, E. W. et al. Advanced Hepatic Ablation Technique for Creating Complete Cell Death: Irreversible Electroporation. Radiology 255, 426-433, doi:10.1148/radiol.10090337 (2010).
Lee, E.W., et al., "Imaging guided percutaneous irreversible electroporation: ultrasound and immunohistological correlation", Technol Cancer Res Treat 6: 287-294 (2007).
Li, W., et al., "The Effects of Irreversible Electroporation (IRE) on Nerves" PloS One, Apr. 2011, 6(4), e18831.
Liu, et al., Measurement of Pharyngeal Transit Time by Electrical Impedance Tomography, Clin. Phys. Physiol. Meas., 1992, vol. 13, Suppl. A, pp. 197-200.
Long, G., et al., "Targeted Tissue Ablation With Nanosecond Pulses", Ieee Transactions on Biomedical Engineering, 58(8) (2011).
Lundqvist, et al., Altering the Biochemical State of Individual Cultured Cells and Organelles with Ultramicroelectrodes, Proc Natl Acad. Sci USA, vol. 95, pp. 10356-10360, Sep. 1998.
Lurquin, Gene Transfer by Electroporation, Molecular Biotechnology, vol. 7, 1997.
Lynn, et al., A New Method for the Generation and Use of Focused Ultrasound in Experimental Biology, The Journal of General Physiology, vol. 26, 179-193, 1942.
Maček Lebar and Miklavčič, "Cell electropermeabilization to small molecules in vitro: control by pulse parameters." Radiology and Oncology, vol. 35(3), pp. 193-202 (2001).
Mahmood, F., et al., "Diffusion-Weighted MRI for Verification of Electroporation-Based Treatments", Journal of Membrane Biology 240: 131-138 (2011).
Mahnic-Kalamiza, S., et al., "Educational application for visualization and analysis of electric field strength in multiple electrode electroporation," BMC Med Educ, vol. 12, p. 102, 2012.
Malpica et al., "Grading ovarian serous carcinoma using a two-tier system." The American Journal of Surgical Pathology, vol. 28, pp. 496-504 (2004).
Maor et al., The Effect of Irreversible Electroporation on Blood Vessels, Tech, in Cancer Res. and Treatment, vol. 6, No. 4, Aug. 2007, pp. 307-312.
Maor, E., A. Ivorra, and B. Rubinsky, Non Thermal Irreversible Electroporation: Novel Technology for Vascular Smooth Muscle Cells Ablation, PLoS ONE, 2009, 4(3): p. e4757.
Maor, E., A. Ivorra, J. Leor, and B. Rubinsky, Irreversible electroporation attenuates neointimal formation after angioplasty, IEEE Trans Biomed Eng, Sep. 2008, 55(9): p. 2268-74.
Marszalek et al., "Schwan equation and transmembrane potential induced by alternating electric field." Biophysical Journal, vol. 58, pp. 1053-1058 (1990).
Martin, n.R.C.G., et al., "Irreversible electroporation therapy in the management of locally advanced pancreatic adenocarcinoma." Journal of the American College of Surgeons, 2012. 215(3): p. 361-369.
Marty, M., et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, 3-13, 2006.
Miklavčič, et al., A Validated Model of an in Vivo Electric Field Distribution in Tissues for Electrochemotherapy and for DNA Electrotransfer for Gene Therapy, Biochimica et Biophysica Acta 1523 (2000), pp. 73-83.
Miklavčič, et al., The Importance of Electric Field Distribution for Effective in Vivo Electroporation of Tissues, Biophysical Journal, vol. 74, May 1998, pp. 2152-2158.
Miller, L., et al.. Cancer cells ablation with irreversible electroporation, Technology in Cancer Research and Treatment 4 (2005) 699-706.
Mir et al., "Mechanisms of Electrochemotherapy" Advanced Drug Delivery Reviews 35:107-118 (1999).
Mir, et al., Effective Treatment of Cutaneous and Subcutaneous Malignant Tumours by Electrochemotherapy, British Journal of Cancer, vol. 77, No. 12, pp. 2336-2342, 1998.
Mir, et al., Electrochemotherapy Potentiation of Antitumour Effect of Bleomycin by Local Electric Pulses, European Journal of Cancer, vol. 27, No. 1, pp. 68-72, 1991.
Mir, et al., Electrochemotherapy, a Novel Antitumor Treatment: First Clinical Trial, C.R. Acad. Sci. Paris, Ser. III, vol. 313, pp. 613-618, 1991.
Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.
Mir, L.M., et al., Electric Pulse-Mediated Gene Delivery to Various Animal Tissues, in Advances in Genetics, Academic Press, 2005, p. 83-114.
Mir, Therapeutic Perspectives of In Vivo Cell Electropermeabilization, Bioelectrochemistry, vol. 53, pp. 1-10, 2000.
Mulhall et al., "Cancer, pre-cancer and normal oral cells distinguished by dielectrophoresis." Analytical and Bioanalytical Chemistry, vol. 401, pp. 2455-2463 (2011).
Narayan, et al., Establishment and Characterization of a Human Primary Prostatic Adenocarcinoma Cell Line (ND-1), The Journal of Urology, vol. 148, 1600-1604, Nov. 1992.
Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.
Naslund, Michael J., Transurethral Needle Ablation of the Prostate, Urology, vol. 50, No. 2, Aug. 1997.
Neal II et al., "A Case Report on the Successful Treatment of a Large Soft-Tissue Sarcoma with Irreversible Electroporation," Journal of Clinical Oncology, 29, pp. 1-6, 2011.
Neal II, R. E., et al., "Experimental characterization and numerical modeling of tissue electrical conductivity during pulsed electric fields for irreversible electroporation treatment planning," IEEE Trans Biomed Eng., vol. 59:4, pp. 1076-1085. Epub 2012 Jan. 6, 2012.
Neal II, R. E., et al., "Successful Treatment of a Large Soft Tissue Sarcoma with Irreversible Electroporation", Journal of Clinical Oncology, 29:13, e372-e377 (2011).
Neal II, R.E., et al., "Treatment of breast cancer through the application of irreversible electroporation using a novel minimally invasive single needle electrode." Breast Cancer Research and Treatment, 2010 123(1): p. 295-301.
Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.
Neal RE II, et al. (2013) Improved Local and Systemic Anti-Tumor Efficacy for Irreversible Electroporation in Immunocompetent versus Immunodeficient Mice. PLoS ONE 8(5): e64559. https://doi.org/10.1371/journal.pone.0064559.
Nesin et al., "Manipulation of cell volume and membrane pore comparison following single cell permeabilization with 60- and 600-ns electric pulses." Biochimica et Biophysica Acta (BBA)—Biomembranes, vol. 1808, pp. 792-801 (2011).
Neumann, et al., Gene Transfer into Mouse Lyoma Cells by Electroporation in High Electric Fields, J. EMBO., vol. 1, No. 7, pp. 841-845, 1982.
Neumann, et al., Permeability Changes Induced by Electric Impulses in Vesicular Membranes, J. Membrane Biol., vol. 10, pp. 279-290, 1972.

(56) References Cited

OTHER PUBLICATIONS

Nikolova, B., et al., "Treatment of Melanoma by Electroporation of Bacillus Calmette-Guerin". Biotechnology & Biotechnological Equipment, 25(3): p. 2522-2524 (2011).

Nuccitelli, R., et al., "A new pulsed electric field therapy for melanoma disrupts the tumor's blood supply and causes complete remission without recurrence", Int J Cancer, 125(2): p. 438-45 (2009).

O'Brien et al., "Investigation of the Alamar Blue (resazurin) fluorescent dye for the assessment of mammalian cell cytotoxicity." European Journal of Biochemistry, vol. 267, pp. 5421-5426 (2000).

Okino, et al., Effects of High-Voltage Electrical Impulse and an Anticancer Drug on In Vivo Growing Tumors, Japanese Journal of Cancer Research, vol. 78, pp. 1319-1321, 1987.

Onik, et al., Sonographic Monitoring of Hepatic Cryosurgery in an Experimental Animal Model, AJR American J. of Roentgenology, vol. 144, pp. 1043-1047, May 1985.

Onik, et al., Ultrasonic Characteristics of Frozen Liver, Cryobiology, vol. 21, pp. 321-328, 1984.

Onik, G. and B. Rubinsky, eds. "Irreversible Electroporation: First Patient Experience Focal Therapy of Prostate Cancer. Irreversible Electroporation", ed. B. Rubinsky 2010, Springer Berlin Heidelberg, pp. 235-247.

Dnik, G., P. Mikus, and B. Rubinsky, "Irreversible electroporation: implications for prostate ablation." Technol Cancer Res Treat, 2007. 6(4): p. 295-300.

Organ, L.W., Electrophysiological principles of radiofrequency lesion making, Appl. Neurophysiol., 1976. 39: p. 69-76.

Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.

Paszek et al., "Tensional homeostasis and the malignant phenotype." Cancer Cell, vol. 8, pp. 241-254 (2005).

Pavselj, N. et al. The course of tissue permeabilization studied on a mathematical model of a subcutaneous tumor in small animals. IEEE Trans Biomed Eng 52, 1373-1381 (2005).

Pavselj, N., et al., "A numerical model of skin electroporation as a method to enhance gene transfection in skin. 11th Mediterranean Conference on Medical and Biological Engineering and Computing", vols. 1 and 2, 16(1-2): p. 597-601 (2007).

PCT International Preliminary Report on Patentability of Corresponding International Application No. PCT/2011/062067, dated May 28, 2013.

PCT International Preliminary Report on Patentability of Corresponding International Application No. PCT/2011/066239, dated Jun. 25, 2013.

PCT International Search Report (dated Aug. 2, 2011), Written Opinion (dated Aug. 2, 2011), and International Preliminary Report an Patentability (dated Apr. 17, 2012) of PCT/US10/53077.

PCT International Search Report (dated Aug. 22, 2012), and Written Opinion (dated Aug. 22, 2012) of PCT/US11/66239.

PCT International Search Report (dated Aug. 26, 2005), Written Opinion (dated Aug. 26, 2005), and International Preliminary Report on Patentability (dated Jun. 26, 2006) of PCT/US2004/043477.

PCT International Search Report (dated Jan. 19, 2010), Written Opinion (dated Jan. 19, 2010), and International Preliminary Report an Patentability (dated Jan. 4, 2010) of PCT/US09/62806, 15 pgs.

PCT International Search Report (dated Jul. 15, 2010), Written Opinion (dated Jul. 15, 2010), and International Preliminary Report an Patentability (dated Oct. 11, 2011) from PCT/US2010/030629.

PCT International Search Report (dated Jul. 9, 2009), Written Opinion (dated Jul. 9, 2009), and International Preliminary Report or Patentability (dated Nov. 2, 2010) of PCT/US2009/042100.

PCT International Search Report and Written Opinion (dated Jul. 25, 2012) of PCT/US2011/062067.

PCT International Search Report, 4 pgs, (dated Jul. 30, 2010), Written Opinion, 7 pgs, (dated Jul. 30, 2010), and International Preliminary Report on Patentability, 8 pgs, (dated Oct. 4, 2011) from PCT/US2010/029243.

PCT IPRP for PCT/US15/30429 (WO2015175570), dated Nov. 15, 2016.

Phillips, M., Maor, E. & Rubinsky, B. Non-Thermal Irreversible Electroporation for Tissue Decellularization. J. Biomech. Eng, doi:10.1115/1.4001882 (2010).

Piñero, et al., Apoptotic and Necrotic Cell Death Are Both Induced by Electroporation in HL60 Human Promyeloid Leukaemia Cells, Apoptosis, vol. 2, No. 3, 330-336, Aug. 1997.

Polak et al., "On the Electroporation Thresholds of Lipid Bilayers: Molecular Dynamics Simulation Investigations." The Journal of Membrane Biology, vol. 246, pp. 843-850 (2013).

Precision Office Tuna System, When Patient Satisfaction is Your Goal, VidaMed 2001.

Pucihar et al., "Numerical determination of transmembrane voltage induced on irregularly shaped cells." Annals of Biomedical Engineering, vol. 34, pp. 642-652 (2006).

(Arena, Christopher B. et al.) Co-pending U.S. Appl. No. 15/186,653, filed Jun. 20, 2016, and published as U.S. Publication No. 2016/0287314 on Oct. 6, 2016, Specification, Claims, Figures.

(Arena, Christopher B. et al.) Co-pending U.S. Appl. No. 16/372,520, filed Apr. 2, 2019, which published as 20190223938 on Jul. 25, 2019, Specification, Claims, Figures.

(Arena, Christopher B. et al.) Co-Pending Application No. PCT/US11/66239, filed Dec. 20, 2011, Specification, Claims, Figures.

(Arena, Christopher B et al.) Co-Pending U.S. Appl. No. 13/332,133, filed Dec. 20, 2011 and published as U.S. Publication No. 2012/0109122 on May 3, 2012, Specification, Claims, Figures.

(Davalos, Rafael et al.) Co-pending U.S. Appl. No. 10/571,162, filed Oct. 18, 2006 (published as 2007/0043345 on Feb. 22, 2007), Specification, Figures, Claims.

(Davalos, Rafael et al.) Co-Pending U.S. Appl. No. 12/757,901, filed Apr. 9, 2010, Specification, Claims, Figures.

(Davalos, Rafael et al.) Co-Pending Application No. PCT/US04/43477, filed Dec. 21, 2004, Specification, Claims, Figures.

(Davalos, Rafael V. et al.) Co-Pending Application No. PCT/US10/53077, filed Oct. 18, 2010, Specification, Claims, Figures.

(Davalos, Rafael V. et al.) Co-Pending U.S. Appl. No. 12/491,151, filed Jun. 24, 2009, and published as U.S. Publication No. 2010/0030211 on Feb. 4, 2010, Specification, Claims, Figures.

(Davalos, Rafael V. et al.) Co-Pending U.S. Appl. No. 12/609,779, filed Oct. 30, 2009, and published as U.S. Publication No. 2010/0331758 on Dec. 30, 2010, Specification, Claims, Figures.

(Davalos, Rafael V. et al.) Co-Pending U.S. Appl. No. 13/919,640, filed Jun. 17, 2013, and published as U.S Publication No. 2013/0281968 on Oct. 24, 2013, Specification, Claims, Figures.

(Davalos, Rafael V. et al.) Co-pending U.S. Appl. No. 15/424,335, filed Feb. 3, 2017, and published as U.S Publication No. 2017/0189579 on Jul. 6, 2017, Specification, Claims, Figures.

(Davalos, Rafael V. et al.) Co-pending U.S. Appl. No. 15/536,333, filed Jun. 15, 2017, and published as U.S. Publication No. 2017/0360326 on Dec. 21, 2017, Specification, Claims, Figures.

(Davalos, Rafael V. et al.) Co-pending U.S. Appl. No. 15/881,414, filed Jan. 26, 2018, and published as U.S. Publication No. 2018/0161086 on Jun. 14, 2018, Specification, Claims, Figures.

(Davalos, Rafael V. et al.) Co-pending U.S. Appl. No. 16/177,745, filed Nov. 1, 2018, and published as U.S Publication No. 2019/0069945 on Mar. 7, 2019, Specification, Claims, Figures.

(Davalos, Rafael V. et al.) Co-pending U.S. Appl. No. 16/232,962, filed Dec. 26, 2018, and published as U.S Publication No. 2019/0133671 on May 9, 2019, Specification, Claims, Figures.

(Davalos, Rafael V. et al.) Co-pending U.S. Appl. No. 16/275,429, filed Feb. 14, 2019, which published as 2019/0175260 on Jun. 13, 2019, Specification, Claims, Figures.

(Davalos, Rafael V. et al.) Co-pending U.S. Appl. No. 16/535,451, filed Aug. 8, 2019, and Published as U.S. Publication No. 2019/0376055 on Dec. 12, 2019, Specification, Claims, Figures.

(Davalos, Rafael V. et al.) Co-Pending Application No. PCT/US09/62806, filed Oct. 30, 2009, Specification, Claims, Figures.

(Davalos, Rafael V. et al.) Co-Pending Application No. PCT/US10/30629, filed Apr. 9, 2010, Specification, Claims, Figures.

(Davalos, Rafael V. et al.) Co-pending application No. PCT/US19/51731, filed Sep. 18, 2019, Specification, Claims, Figures.

(56) References Cited

OTHER PUBLICATIONS (Davalos, Rafael V. et al.) Co-Pending U.S. Appl. No. 14/017,210, filed Sep. 3, 2013, and published as U.S. Publication No. 2014/0039489 on Feb. 6, 2014, Specification, Claims, Figures.
(Davalos, Rafael V. et al.) Co-Pending U.S. Appl. No. 14/627,046, filed Feb. 20, 2015, and published as U.S. Publication No. 2015/0164584 on Jun. 18, 2015, Specification, Claims, Figures.
(Davalos, Rafael V. et al.) Co-Pending U.S. Appl. No. 14/686,380, filed Apr. 14, 2015, and published on U.S. Publication No. 2015/0289923 on Oct. 15, 2015, Specification, Claims, Figures.
(Davalos, Rafael V. et al.) Co-Pending U.S. Appl. No. 12/432,295, filed Apr. 29, 2009, and published as U.S. Publication No. 2009/0269317-A1 on Oct. 29, 2009, Specification, Figures, Claims.
(Davalos, Rafael V. et al.) Co-pending U.S. Appl. No. 15/423,986, filed Feb. 3, 2017, and published as U.S. Publication No. 2017/0209620 on Jul. 27, 2017, Specification, Claims, Figures.
(Davalos, Rafael V. et al.) Co-Pending Application No. PCT/US09/42100, filed Apr. 29, 2009, Specification, Claims, Figures.
(Garcia, Paulo A. et al.) Co-Pending U.S. Appl. No. 14/012,832, filed Aug. 28, 2013, and published as U.S. Publication No. 2013/0345697 on Dec. 26, 2013, Specification, Claims, Figures.
(Garcia, Paulo A. et al.) Co-Pending U.S. Appl. No. 14/558,631, filed Dec. 2, 2014, and published as U.S. Publication No. 2015/0088120 on Mar. 26, 2015, Specification, Claims, Figures.
(Garcia, Paulo A. et al.) Co-Pending U.S. Appl. No. 15/011,752, filed Feb. 1, 2016, and published as U.S Publication No. 2016/0143698 on May 26, 2016, Specification, Claims, Figures.
(Garcia, Paulo A. et al.) Co-Pending U.S. Appl. No. 16/655,845, filed Oct. 17, 2019, Specification, Claims, Figures.
(Garcia, Paulo A. et al.) Co-pending U.S. Appl. No. 16/152,743, filed Oct. 5, 2018, Specification, Claims, Figures.
(Latouche, Eduardo et al.) Co-pending U.S. Appl. No. 16/210,771, filed Dec. 5, 2018, and which published as US Patent Publication No. 2019/0232048 on Aug. 1, 2019, Specification, Claims, Figures.
(Mahajan, Roop L. et al.) Co-Pending U.S. Appl. No. 13/958,152, filed Aug. 2, 2013, Specification, Claims, Figures.
(Neal, Robert E. et al.) Co-Pending U.S. Appl. No. 12/906,92, filed Oct. 18, 2010, Specification, Claims, Figures.
(Neal, Robert E. et al.) Co-Pending U.S. Appl. No. 14/808,679, filed Jul. 24, 2015 and Published as U.S. Publication No. 2015/0327944 on Nov. 19, 2015, Specification, Claims, Figures.
(Neal, Robert E. et al.) Co-pending U.S. Appl. No. 16/375,878, filed Apr. 5, 2019, which published on Aug. 1, 2019 as US 2019-0233809 A1, Specification, Claims, Figures.
(Neal, Robert E. et al.) Co-pending U.S. Appl. No. 16/404,392, filed May 6, 2019, and published as U.S. Publication No. 2019/0256839 on Aug. 22, 2019, Specification, Claims, Figures.
(Neal, Robert E. et al.) Co-Pending U.S. Appl. No. 13/550,307, filed Jul. 16, 2012, and published as U.S. Publication No. 2013/0184702 on Jul. 18, 2013, Specification, Claims, Figures.
(Neal, Robert E. et al.) Co-pending U.S. Appl. No. 14/940,863, filed Nov. 13, 2015 and Published as US 2016/0066977 on Mar. 10, 2016, Specification, Claims, Figures.
(Neal, Robert E. et al.) Co-pending U.S. Appl. No. 16/280,511, filed Feb. 20, 2019, and published as U.S. Publication No. 2019/0175248 on Jun. 13, 2019, Specification, Claims, Figures.
(Pearson, Robert M. et al.) Co-pending Application No. PCT/US2010/029243, filed Mar. 30, 2010, published as WO 2010/117806 on Oct. 14, 2010, Specification, Claims, Figures.
(Pearson, Robert M. et al.) Co-pending U.S. Appl. No. 12/751,826, filed Mar. 31, 2010 (published as 2010/0250209 on Sep. 30, 2010), Specification, Claims, Figures.
(Pearson, Robert M. et al.) Co-pending U.S. Appl. No. 12/751,854, filed Mar. 31, 2010 (published as 2010/0249771 on Sep. 30, 2010), Specification, Claims, Figures.
(Sano, Michael B. et al.) Co-Pending Application No. PCT/US2015/030429, Filed May 12, 2015, Published on Nov. 19, 2015 as WO 2015/175570, Specification, Claims, Figures.
(Sano, Michael B. et al.) Co-Pending U.S. Appl. No. 13/989,175, filed May 23, 2013, and published as U.S. Publication No. 2013/0253415 on Sep. 26, 2013, Specification, Claims, Figures.
(Sano, Michael B. et al.) Co-Pending U.S. Appl. No. 15/310,114, filed Nov. 10, 2016, and published as U.S. Publication No. 2017/0266438 on Sep. 21, 2017, Specification, Claims, Figures.
(Sano, Michael B. et al.) Co-pending U.S. Appl. No. 15/843,888, filed Dec. 15, 2017, and published as U.S Publication No. 2018/0125565 on May 10, 2018, Specification, Claims, Figures.
(Sano, Michael B. et al.) Co-pending U.S. Appl. No. 16/443,351, filed Jun. 17, 2019 (published as 20190328445 on Oct. 31, 2019), Specification, Claims, Figures.
(Sano, Michael B. et al.) Co-pending U.S. Appl. No. 16/520,901, filed Jul. 24, 2019, and published as U.S. Publication No. 2019/0351224 on Nov. 21, 2019, Specification, Claims, Figures.
Co-Pending U.S. Appl. No. 12/491,151, Official Notice of Allowance dated Nov. 6, 2014, 15 pages.
Co-Pending U.S. Appl. No. 12/491,151, Official Notice of Allowance dated Oct. 15, 2014, 5 pages.
Co-Pending U.S. Appl. No. 12/491,151, Requirement for Restriction/Election dated Dec. 2, 2011, 6 pages.
Co-Pending U.S. Appl. No. 12/491,151, Response to Apr. 4, 2014 Non-Final Rejection dated Aug. 22, 2014, 12 pages.
Co-Pending U.S. Appl. No. 12/491,151, Response to Non-Final Rejection dated Mar. 28, 2012, 10 pages.
Co-Pending U.S. Appl. No. 12/491,151, Response to Requirement for Restriction/Election dated Dec. 13, 2011, 2 pages.
Co-Pending U.S. Appl. No. 12/491,151, Response with RCE to Final Rejection dated Aug. 20, 2012, 14 pages.
Co-Pending U.S. Appl. No. 12/491,151, Supplemental Amendment dated Dec. 17, 2012, 6 pages.
Co-Pending U.S. Appl. No. 12/757,901, Certificate of Correction, Aug. 2016, 3 pages.
Co-Pending U.S. Appl. No. 12/906,923, Office Actions and Responses dated Jul. 2017, 55 pages.
Co-Pending U.S. Appl. No. 12/906,923, Official Notice of Allowance and Examiner's Amendment, dated May 26, 2015, 21 pages.
Co-Pending U.S. Appl. No. 12/906,923, Response dated Oct. 24, 2014 Office Action, filed Jan. 26, 2015, 11 pages.
Co-Pending U.S. Appl. No. 12/906,923, Non-Final Office Action dated Oct. 24, 2014, 11 pages.
Co-Pending U.S. Appl. No. 12/906,923, Requirement for Restriction/Election, dated Jan. 29, 2014, 9 pages.
Co-Pending U.S. Appl. No. 12/906,923, Response to Restriction Requirement, dated Mar. 19, 2014, 3 pages.
Co-Pending U.S. Appl. No. 13/332,133, Amendment with ROE after Board Decision, dated Mar. 29, 2019, 16 pages.
Co-Pending U.S. Appl. No. 13/332,133, Board Decision dated Jan. 29, 2019, 13 pages.
Co-Pending U.S. Appl. No. 13/332,133, Notice of Allowance, dated May 31, 2019, 5 pages.
Co-Pending U.S. Appl. No. 13/332,133, Office Actions and Responses through Mar. 2018, 221 pages.
Co-Pending U.S. Appl. No. 13/550,307, filed Aug. 13, 2018 Applicant-Initiated Interview Summary, 3 pages.
Co-Pending U.S. Appl. No. 13/550,307, Final Office Action dated Dec. 5, 2018, 17 pages.
Co-Pending U.S. Appl. No. 13/550,307, Office Actions and Responses through Mar. 2018, 133 pages.
Co-Pending U.S. Appl. No. 13/550,307, Response to Mar. 14, 2018 Non-Final Office Action dated Jul. 16, 2018, 12 pages.
Co-Pending U.S. Appl. No. 13/550,307 Interview Request and Summary, Dec. 13, 19, 2019, 4 pages.
Co-Pending U.S. Appl. No. 13/550,307 Non-final office action dated Aug. 22, 2019, 19 pages.
Co-Pending U.S. Appl. No. 13/550,307 Notice of panel decision from pre-appeal brief review dated May 16, 2019, 2 pages.
Co-Pending U.S. Appl. No. 13/550,307 Pre-appeal brief request for review dated Apr. 4, 2019, 7 pages.
Co-Pending U.S. Appl. No. 13/550,307 Response to Aug. 22, 2019 Non-final office action dated Dec. 23, 2019, 10 pages.
Co-Pending U.S. Appl. No. 14/012,832, Ex Parte Quayle Office Action dated Aug. 28, 2015, 6 pages.

(56) References Cited

OTHER PUBLICATIONS

Co-Pending U.S. Appl. No. 14/012,832, Notice of Allowance dated Nov. 4, 2015, 5 pages.
Co-Pending U.S. Appl. No. 14/012,832, Response to Ex Parte Quayle Office Action dated Aug. 28, 2015, filed with RCE on Oct. 28, 2015, 9 pages.
Co-Pending U.S. Appl. No. 14/558,631, Final Office Action dated Sep. 1, 2017, 9 pages.
Co-Pending U.S. Appl. No. 14/558,631, Non-Final Office Action dated Jan. 8, 2018, 5 pages.
Co-Pending U.S. Appl. No. 14/558,631, Non-Final Office Action dated Mar. 13, 2017, 10 pages.
Co-Pending U.S. Appl. No. 14/558,631, Notice of Allowance dated Jul. 17, 2018, 2 pages.
Co-Pending U.S. Appl. No. 14/558,631, Notice of Allowance dated Jun. 21, 2018, 7 pages.
Co-Pending U.S. Appl. No. 14/558,631, Response to Jan. 8, 2018 Non-Final Office Action dated Apr. 9, 2018, 8 pages.
Co-Pending U.S. Appl. No. 14/558,631, Response to Mar. 13, 2017 Non-Final Office Action dated Jul. 13, 2017, 10 pages.
Co-Pending U.S. Appl. No. 14/558,631, Response to Sep. 1, 2017 Final Office Action dated Dec. 1, 2017, 7 pages.
Co-Pending U.S. Appl. No. 14/686,380, Final Office Action dated May 9, 2018, 14 pages.
Co-Pending U.S. Appl. No. 14/686,380, Final Office Action dated Sep. 3, 2019, 28 pages.
Co-Pending U.S. Appl. No. 14/686,380, Non-Final Office Action dated Feb. 13, 2020, 11 pages.
Co-Pending U.S. Appl. No. 14/686,380, Non-Final Office Action dated May 1, 2019, 18 pages.
Co-Pending U.S. Appl. No. 14/686,380, Non-Final Office Action dated Nov. 22, 2017, 11 pages.
Co-Pending U.S. Appl. No. 14/686,380, Response to Jul. 19, 2017 Restriction Requirement, dated Sep. 15, 2017, 2 pages.
Co-Pending U.S. Appl. No. 14/686,380, Response to May 9, 2018 Final Office Action with RCE, dated Aug. 30, 2018, 14 pages.
Co-Pending U.S. Appl. No. 14/686,380, Response to Non-Final Office Action Filed Aug. 1, 2019, 11 pages.
Co-Pending U.S. Appl. No. 14/686,380, Response dated Nov. 22, 2017 Non-Final Office Action dated Mar. 28, 2018, 11 pages.
Co-Pending U.S. Appl. No. 14/686,380, Restriction Requirement dated Jul. 19, 2017, 7 pages.
Co-Pending U.S. Appl. No. 14/940,863, Notice of Allowance dated Jan. 25, 2019, 5 pages.
Edd, J.F, et al., 2007, "Mathematical modeling of irreversible electroporation for treatment planning.", Technology in Cancer Research and Treatment, 6:275-286.
Ellis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).
Eppich et al., "Pulsed electric fields for selection of hematopoietic cells and depletion of tumor cell contaminants." Nature Biotechnology 18, pp. 882-887 (2000).
Erez, et al., Controlled Destruction and Temperature Distributions in Biological Tissues Subjected to Monoactive Electrocoagulation, Transactions of the ASME: Journal of Mechanical Design, vol. 102, Feb. 1980.
Ermolina et al., "Study of normal and malignant white blood cells by time domain dielectric spectroscopy." IEEE Transactions on Dielectrics and Electrical Insulation, 8 (2001) pp. 253-261.
Esser, A.T., et al., "Towards solid tumor treatment by irreversible electroporation: intrinsic redistribution of fields and currents in tissue" Technol Cancer Res Treat, 6(4): p. 261-74 (2007).
Esser, A.T., et al., "Towards Solid Tumor Treatment by Nanosecond Pulsed Electric Fields", Technology in Cancer Research & Treatment, 8(4): p. 289-306 (2009).
Faroja, M., et al., "Irreversible Electroporation Ablation: Is the entire Damage Nonthermal?", Radiology, 266(2), 462-470 (2013).

Fischbach et al., "Engineering tumors with 3D scaffolds." Nat Meth 4, pp. 855-860 (2007).
Flanagan et al., "Unique dielectric properties distinguish stem cells and their differentiated progeny." Stem Cells, vol. 26, pp. 656-665 (2008).
Fong et al., "Modeling Ewing sarcoma tumors in vitro with 3D scaffolds." Proceedings of the National Academy of Sciences vol. 110, pp. 6500-6505 (2013).
Foster RS, "High-intensity focused ultrasound in the treatment of prostatic disease", European Urology, 1993, vol. 23 Suppl 1, pp. 29-33.
Foster, R.S., et al., Production of Prostatic Lesions in Canines Using Transrectally Administered High-Intensity Focused Ultrasound. Eur. Urol., 1993; 23: 330-336.
Fox, et al., Sampling Conductivity Images via MCMC, Mathematics Department, Auckland University, New Zealand, May 1997.
Freeman, S.A., et al., Theory of Electroporation of Planar Bilayer-Membranes—Predictions of the Aqueous Area, Change in Capacitance, and Pore-Pore Separation. Biophysical Journal, 67(1): p. 42-56 (1994).
Garcia et al., "Irreversible electroporation (IRE) to treat brain cancer." ASME Summer Bioengineering Conference, Marco Island, FL, Jun. 25-29, 2008.
Garcia P.A., et al., "7.0-T Magnetic Resonance Imaging Characterization of Acute Blood-Brain-Barrier Disruption Achieved with Intracranial Irreversible Electroporation", Plos One, Nov. 2012, 7:11, e50482.
Garcia P.A., et al., "Pilot study of irreversible electroporation for intracranial surgery", Conf Proc IEEE Eng Med Biol Soc, 2009:6513-6516, 2009.
Garcia PA, Rossmeisl JH, Jr., Neal RE, 2nd, Ellis TL, Davalos RV, "A Parametric Study Delineating Irreversible Electroporation from Thermal Damage Based on a Minimally Invasive Intracranial Procedure", Biomed Eng Online 10:34(2011).
Garcia, P. A., et al., "Towards a predictive model of electroporation-based therapies using pre-pulse electrical measurements," Conf Proc IEEE Eng Med Biol Soc, vol. 2012, pp. 2575-2578, 2012.
Garcia, P. A., et al., "Non-thermal Irreversible Electroporation (N-TIRE) and Adjuvant Fractioned Radiotherapeutic Multimodal Therapy for Intracranial Malignant Glioma in a Canine Patient" TechnoL Cancer Res. Treatment 10(1), 73-83 (2011).
Garcia, P. et al. Intracranial nonthermal irreversible electroporation: in vivo analysis. J Membr Biol 236, 127-136 (2010).
Garcia, Paulo A., Robert E. Neal II and Rafael V. Davalos, Chapter 3, Non-Thermal Irreversible Electroporation for Tissue Ablation, In: Electroporation in Laboratory and Clinical Investigations ISBN 978-1-61668-327-6 Editors: Enrico P. Spugnini and Alfonso Baldi, 2010, 22 pages.
Gascoyne et al., "Membrane changes accompanying the induced differentiation of Friend murine erythroleukemia cells studied by dielectrophoresis." Biochimica et Biophysica Acta (BBA)—Biomembranes, vol. 1149, pp. 119-126 (1993).
Gauger, et al., A Study of Dielectric Membrane Breakdown in the Fucus Egg, J. Membrane Biol., vol. 48, No. 3, pp. 249-264, 1979.
Gehl, et al., In Vivo Electroporation of Skeletal Muscle: Threshold, Efficacy and Relation to Electric Field Distribution, Biochimica et Biphysica Acta 1428, 1999, pp. 233-240.
Gençer, et al., Electrical Impedance Tomography: Induced-Current Imaging Achieved with a Multiple Coil System, IEEE Transactions on Biomedical Engineering, vol. 43, No. 2, Feb. 1996.
Gilbert, et al., Novel Electrode Designs for Electrochemotherapy, Biochimica et Biophysica Acta 1334, 1997, pp. 9-14.
Gilbert, et al., The Use of Ultrasound Imaging for Monitoring Cryosurgery, Proceedings 6th Annual Conference, IEEE Engineering in Medicine and Biology, 107-111, 1984.
Gilbert, T. W., et al., "Decellularization of tissues and organs", Biomaterials, Elsevier Science Publishers, Barking, GB, vol. 27, No. 19, Jul. 1, 2006, pp. 3675-3683.
Gimsa et al., "Dielectric spectroscopy of single human erythrocytes at physiological ionic strength: dispersion of the cytoplasm." Biophysical Journal, vol. 71, pp. 495-506 (1996).

(56) References Cited

OTHER PUBLICATIONS

Glidewell, et al., The Use of Magnetic Resonance Imaging Data and the Inclusion of Anisotropic Regions in Electrical Impedance Tomography, Biomed, Sci. Instrum. 1993; 29: 251-7.
Solberg, A. and Rubinsky, B., "A statistical model for multidimensional irreversible electroporation cell death in tissue." Biomed Eng Online, 9, 13 pages, 2010.
Gothelf, et al., Electrochemotherapy: Results of Cancer Treatment Using Enhanced Delivery of Bleomycin by Electroporation, Cancer Treatment Reviews 2003: 29: 371-387.
Gowrishankar T.R., et al., "Microdosimetry for conventional and supra-electroporation in cells with organelles". Biochem Biophys Res Commun, 341(4): p. 1266-76 (2006).
Griffiths, et al., A Dual-Frequency Electrical Impedance Tomography System, Phys. Med. Biol., 1989, vol. 34, No. 10, pp. 1465-1476.
Griffiths, The Importance of Phase Measurement in Electrical Impedance Tomography, Phys. Med. Biol., 1987, vol. 32, No. 11, pp. 1435-1444.
Griffiths, Tissue Spectroscopy with Electrical Impedance Tomography: Computer Simulations, IEEE Transactions an Biomedical Engineering, vol. 42, No. 9, Sep. 1995.
Gumerov, et al., The Dipole Approximation Method and Its Coupling with the Regular Boundary Element Method for Efficient Electrical Impedance Tomography, Boundary Element Technology XIII, 1999.
Hapala, Breaking the Barrier: Methods for Reversible Permeabilization of Cellular Membranes, Critical Reviews in Biotechnology, 17(2): 105-122, 1997.
Helczynska et al., "Hypoxia promotes a dedifferentiated phenotype in ductal breast carcinoma in situ." Cancer Research, vol. 63, pp. 1441-1444 (2003).
Heller, et al., Clinical Applications of Electrochemotherapy, Advanced Drug Delivery Reviews, vol. 35, pp. 119-129, 1999.
Hjouj, M., et al., "Electroporation-Induced BBB Disruption and Tissue Damage Depicted by MRI", Neuro-Oncology 13 Issue suppl 3, abstract ET-32 (2011).
Hjouj, M., et al., "MRI Study on Reversible and Irreversible Electroporation Induced Blood Brain Barrier Disruption", PLOS ONE, Aug. 2012, 7:8, e42817.
Hjouj, Mohammad et al., "Electroporation-Induced BBB Disruption and Tissue Damage Depicted by MRI," Abstracts from 16th Annual Scientific Meeting of the Society for Neuro-Oncology in Conjunction with the AANS/CNS Section on Tumors, Nov. 17-20, 2011, Orange County California, Neuro-Oncology Supplement, vol. 13, Supplement 3, page iii114.
Ho, et al., Electroporation of Cell Membranes: A Review, Critical Reviews in Biotechnology, 16(4): 349-362, 1996.
Holder, et al., Assessment and Calibration of a Low-Frequency System for Electrical Impedance Tomography (EIT), Optimized for Use in Imaging Brain Function in Ambulant Human Subjects, Annals of the New York Academy of Science, vol. 873, Issue 1, ELECTRICAL BI, pp. 512-519, 1999.
Hu, Q., et al., "Simulations of transient membrane behavior in cells subjected to a high-intensity ultrashort electric pulse", Physical Review E, 71(3) (2005).
Huang, et al., Micro-Electroporation: Improving the Efficiency and Understanding of Electricla Permeabilization of Cells, Biomedical Microdevices, vol. 2, pp. 145-150, 1999.
(Davalos, Rafael V. et al.) Co-pending U.S. Appl. No. 16/865,031, filed May 1, 2020, Specification, Claims, Figures.
(Davalos, Rafael V. et al.) Co-pending U.S. Appl. No. 17/069,359, filed Oct. 13, 2020, Specification, Claims, Drawings.
(Davalos, Rafael V. et al.) Co-Pending Application No. AU 2009243079, filed Apr. 29, 2009 see PCT/US2009/042100 for documents as filed), Specification, Claims, Figures.
(Davalos, Rafael V. et al.) Co-Pending International Application No. PCT/US15/65792, filed Dec. 15, 2015, Specification, Claims, Drawings.
(Davalos, Rafael V. et al.) Co-Pending Application No. CA 2,722,296, filed Apr. 29, 2009, Amended Claims (7 pages), Specification, Figures (See PCT/US2009/042100 for Specification and figures as filed).
(Davalos, Rafael V. et al.) Co-Pending Application No. EP 09739678.2 filed Apr. 29, 2009, Amended Claims (3 pages), Specification and Figures (See PCT/US2009/042100).
(Lorenzo, Melvin F. et al.) Co-pending U.S. Appl. No. 16/938,778, filed Jul. 24, 2020, Specification, Claims, Figures.
(Neal, Robert E. et al.) Co-pending U.S. Appl. No. 16/865,772, filed May 4, 2020, Specification, Claims, Figures.
(Neal, Robert et al.) Co-Pending Application No. EP 10824248.8, filed May 9, 2012, Amended Claims 3 pages), Specification and Figures (See PCT/US10/53077).
(O'Brien, Timothy J. et al.) Co-Pending U.S. Appl. No. 16/915,760, filed Jun. 29, 2020, Specification, Claims, Figures.
(O'Brien, Timothy J. et al.) Co-Pending U.S. Appl. No. 17/152,379, filed Jan. 19, 2021, Specification, Claims, Figures.
(Sano, Michael B. et al.) Co-Pending Application No. AU 2015259303, filed Oct. 24, 2016, Specification, Figures, Claims.
(Sano, Michael B. et al.) Co-Pending Application No. CN 201580025135.6, filed Nov. 14, 2016, Specification, Claims, Figures (Chinese language and english language versions).
(Sano, Michael B. et al.) Co-Pending Application No. CN 202011281572.3, filed Nov. 16, 2020, Specification, Claims, Figures (Chinese version, 129 pages (see also WO 2015/175570), English Version of claims, 2 pages).
(Sano, Michael B. et al.) Co-Pending Application No. EP 11842994.3, filed Jun. 24, 2013, Amended Claims (18 pages), Specification and Figures (See PCT/US11/62067).
(Sano, Michael B. et al.) Co-Pending Application No. EP 15793361.5, filed Dec. 12, 2016, Specification, Claims, Figures.
(Sano, Michael B. et al.) Co-pending application No. HK 17112121.8, filed Nov. 20, 2017 and published as Publication No. HK1238288 on Apr. 27, 2018, Specification, Claims, Figures (See PCT/US15/30429 for English Version of documents as filed).
(Sano, Michael B. et al.) Co-Pending Application No. JP 2013-541050, filed May 22, 2013, Claims, Specification, and Figures (See PCT/US11/62067 for English Version).
(Sano, Michael B. et al.) Co-Pending Application No. JP 2016-567747, filed Nov. 10, 2016, Specification, Claims, Figures (see PCT/US15/30429 for English Version of documents as filed).
(Sano, Michael B. et al.) Co-pending Application No. JP 2019-133057 filed Jul. 18, 2019, 155 pgs, Specification, Claims, Figures (See PCT/US15/30429 for English Version of documents as filed).
(Wasson, Elisa M. et al.) Co-pending U.S. Appl. No. 17/000,049, filed Aug. 21, 2020, Specification, Claims, Figures.
Al-Sakere et al., "Tumor ablation with irreversible electroporation," PLoS ONE, 2, e1135, 2007, 8 pages.
Beitel-White, N., S. Bhonsle, R. Martin, and R. V. Davalos, "Electrical characterization of human biological tissue for irreversible electroporation treatments," in 2018 40th Annual International Conference of the IEEE Engineering in Medicine and Biology Society (EMBC). IEEE, 2018, pp. 4170-4173.
Ben-David, E. et al., "Irreversible Electroporation: Treatment Effect Is Susceptible to Local Environment and Tissue Properties," Radiology, vol. 269, No. 3, 2013, 738-747.
Bhonsle, S. et al., "Characterization of Irreversible Electroporation Ablation with a Validated Perfused Organ Model," J. Vasc. Interv. Radiol., vol. 27, No. 12, pp. 1913-1922.e2, 2016.
Bhonsle, S., M. F. Lorenzo, A. Safaai-Jazi, and R. V. Davalos, "Characterization of nonlinearity and dispersion in tissue impedance during high-frequency electroporation," IEEE Transactions on Biomedical Engineering, vol. 65, No. 10, pp. 2190-2201, 2018.
Bonakdar, M., E. L. Latouche, R. L. Mahajan, and R. V. Davalos, "The feasibility of a smart surgical probe for verification of IRE treatments using electrical impedance spectroscopy," IEEE Trans. Biomed. Eng., vol. 62, No. 11, pp. 2674 2684, 2015.
Bondarenko, A. and G. Ragoisha, Eis spectrum analyser (the program is available online at http://www.abc.chemistry.bsu.by/vi/analyser/.

(56) References Cited

OTHER PUBLICATIONS

Boussetta, N., N. Grimi, N. I. Lebovka, and E. Vorobiev, "Cold" electroporation in potato tissue induced by pulsed electric field, Journal of food engineering, vol. 115, No. 2, pp. 232-236, 2013.
Bulvik, B. E. et al. "Irreversible Electroporation versus Radiofrequency Ablation☐: A Comparison of Local and Systemic Effects in a Small Animal Model," Radiology, vol. 280, No. 2, 2016, 413-424.
Castellvi, Q., B. Mercadal, and A. Ivorra, "Assessment of electroporation by electrical impedance methods," in Handbook of electroporation. Springer-Verlag, 2016, pp. 671-690.
Creason, S. C., J. W. Hayes, and D. E. Smith, "Fourier transform faradaic admittance measurements iii. comparison of measurement efficiency for various test signal waveforms," Journal of Electroanalytical chemistry and interfacial electrochemistry, vol. 47, No. 1, pp. 9-46, 1973.
Davalos et al., "Electrical impedance tomography for imaging tissue electroporation," IEEE Transactions on Biomedical Engineering, 51, pp. 761-767, 2004.
De Senneville, B. D et al., "MR thermometry for monitoring tumor ablation," European radiology, vol. 17, No. 9, pp. 2401-2410, 2007.
Frandsen, S. K., H. Gissel, P. Hojman, T. Tramm, J. Eriksen, and J. Gehl. Direct therapeutic applications of calcium electroporation to effectively induce tumor necrosis. Cancer Res 72:1336-41, 2012.
Sarcla-Sánchez, T., A. Azan, I. Leray, J. Rosell-Ferrer, R. Bragos, and L. M. Mir, "Interpulse multifrequency electrical mpedance measurements during electroporation of adherent differentiated myotubes," Bioelectrochemistry, vol. 105, pp. 123-135, 2015.
Gawad, S., T. Sun, N. G. Green, and H. Morgan, "Impedance spectroscopy using maximum length sequences: Application to single cell analysis," Review of Scientific Instruments, vol. 78, No. 5, p. 054301, 2007.
Granot, Y., A. Ivorra, E. Maor, and B. Rubinsky, "In vivo imaging of irreversible electroporation by means of electrical impedance tomography," Physics in Medicine & Biology, vol. 54, No. 16, p. 4927, 2009.
Hoejholt, K. L et al. Calcium electroporation and electrochemotherapy for cancer treatment: Importance of cell membrane composition investigated by lipidomics, calorimetry and in vitro efficacy. Scientific Reports (Mar. 18, 2019) 9:4758, p. 1-12.
Ivey, J. W., E. L. Latouche, M. B. Sano, J. H. Rossmeisl, R. V. Davalos, and S. S. Verbridge, "Targeted cellular ablation based on the morphology of malignant cells," Sci. Rep., vol. 5, pp. 1-17, 2015.
Kranjc, M., S. Kranjc, F. Bajd, G. Sersa, I. Sersa, and D. Miklavcic, "Predicting irreversible electroporation-induced tissue damage by means of magnetic resonance electrical impedance tomography," Scientific reports, vol. 7, No. 1, pp. 1-10, 2017.
Latouche, E. L., M. B. Sano, M. F. Lorenzo, R. V. Davalos, and R. C. G. Martin, "Irreversible electroporation for the ablation of pancreatic malignancies: A patient-specific methodology," J. Surg. Oncol., vol. 115, No. 6, pp. 711-717, 2017.
Lee, R. C., D. J. Canaday, and S. M. Hammer. Transient and stable ionic permeabilization of isolated skeletal muscle cells after electrical shock. J. Burn Care Rehabil. 14:528-540,1993.
Martinsen, O. G. and Grimnes, S., Bioimpedance and bioelectricity basics. Academic press, 2011.
Min, M., A. Giannitsis, R. Land, B. Cahill, U. Pliquett, T. Nacke, D. Frense, G. Gastrock, and D. Beckmann, "Comparison of rectangular wave excitations in broad band impedance spectroscopy for microfluidic applications," in World Congress on Medical Physics and Biomedical Engineering, Sep. 7-12, 2009, Munich, Germany. Springer, 2009, pp. 85-88.
Min, M., U. Pliquett, T. Nacke, A. Barthel, P. Annus, and R. Land, "Broadband excitation for short-time impedance spectroscopy," Physiological measurement, vol. 29, No. 6, p. S185, 2008.
Neal II et al., "Experimental Characterization and Numerical Modeling of Tissue Electrical Conductivity during Pulsed Electric Fields for Irreversible Electroporation Treatment Planning," Biomedical Engineering, IEEE Transactions on Biomedical Engineering, vol. 59, pp. 1076-1085, 2012.

Neal II, R. E. et al. In Vitro and Numerical Support for Combinatorial Irreversible Electroporation and Electrochemotherapy Glioma Treatment. Annals of Biomedical Engineering, Oct. 29, 2013, 13 pages.
O'Brien, T. J et al., "Effects of internal electrode cooling on irreversible electroporation using a perfused organ model," Int. J Hyperth., vol. 35, No. 1, pp. 44-55, 2018.
Pakhomova, O. N., Gregory, B., Semenov I., and Pakhomov, A. G., BBA—Biomembr., 2014, 1838, 2547-2554.
Pending U.S. Appl. No. 16/404,392, Preliminary Amendment, filed Jun. 4, 2019, 9 pages.
Pending U.S. Appl. No. 16/404,392, Preliminary Amendment, filed Jun. 6, 2019, 5 pages.
Pending U.S. Appl. No. 16/404,392, Response to Final Office action dated Mar. 20, 2020, filed Sep. 18, 2020, 7 pages.
Pending U.S. Appl. No. 16/404,392, Response to Non-Final Office action dated Sep. 6, 2019, filed Dec. 6, 2019, 8 pages.
Pending U.S. Appl. No. 16/443,351, Preliminary amendment filed Feb. 3, 2020.
Pending U.S. Appl. No. 16/520,901, Preliminary Amendment filed Aug. 14, 2019.
Pending U.S. Appl. No. 16/520,901, Second Preliminary Amendment filed Feb. 4, 2020.
Pending U.S. Appl. No. 16/535,451 Preliminary Amendment filed Aug. 8, 2019, 3 pages.
Pending U.S. Appl. No. 16/535,451 Second Preliminary Amendment filed Oct. 9, 2019, 15 pages.
Pending U.S. Appl. No. 16/535,451 Third Preliminary Amendment filed Nov. 5, 2019, 4 pages.
Pending U.S. Appl. No. 16/655,845, Preliminary Amendment filed Oct. 16, 2020, 6 pages.
Pending U.S. Appl. No. 16/747,219, Preliminary Amendment filed Jan. 20, 2020, 5 pages.
Pending U.S. Appl. No. 16/747,219, Preliminary Amendment filed Jan. 4, 2021, 5 pages.
Pending U.S. Appl. No. 16/865,031, Preliminary Amendment filed May 1, 2020, 7 pages.
Pending U.S. Appl. No. 16/865,772, Preliminary Amendment filed May 4, 2020, 6 pages.
Pending U.S. Appl. No. 16/915,760, Preliminary Amendment filed Jul. 6, 2020, 5 pages.
Pending Application No. AU 2009243079, First Examination Report, Jan. 24, 2014, 4 pages.
Pending Application No. AU 2009243079, Voluntary Amendment filed Dec. 6, 2010, 35 pages.
Pending Application No. AU 2015259303, First Examination Report dated Oct. 26, 2020, 6 pages.
Pending Application No. CA 2,722,296 Examination Report dated Apr. 2, 2015, 6 pages.
Pending Application No. CN 201580025135.6 English translation of Apr. 29, 2020 Office action, 7 pages.
Pending Application No. CN 201580025135.6 English translation of Sep. 25, 2019 Office action.
Pending Application No. CN 201580025135.6 Preliminary Amendment filed with application dated Nov. 14, 2016.
Pending Application No. CN 201580025135.6 Response to Sep. 25, 2019 Office action, filed Feb. 10, 2020, English language version and original document.
Pending Application No. CN 201580025135.6, First Office Action, dated Sep. 25, 2019 (Chinese and English Versions, each 6 pages).
Pending Application No. CN 201580025135.6, Response to First Office Action, dated Feb. 7, 2020, (Chinese Vrsion, 13 pages, and English Version, 10 pages).
Pending Application No. CN 201580025135.6, Second Office Action, dated Apr. 29, 2020 (Chinese Version, 4 pages, and English Version, 7 pages).
Pending Application No. EP 09739678.2 Extended European Search Report dated May 11, 2012, 7 pages.
Pending Application No. EP 09739678.2, Communication pursuant to Rule 94.3, dated Apr. 16, 2014, 3 pages.
Pending Application No. EP 09739678.2, Office Action dated Apr. 16, 2014, 3 pages.

(56) References Cited

OTHER PUBLICATIONS

Pending Application No. EP 09739678.2, Response to Extended European Search Report and Communication pursuant to Rules 70(2) and 70a(2) EPC, dated Dec. 10, 2012.
Pending Application No. EP 10824248.8, Extended Search Report (dated Jan. 20, 2014), 6 pages.
Pending Application No. EP 10824248.8, Invitation Pursuant to rule 62a(1) EPC (Sep. 25, 2013), 2 pages.
Pending Application No. EP 10824248.8, Communication Pursuant to Rule 70(2) dated Feb. 6, 2014, 1 page.
Pending Application No. EP 10824248.8, Response to Invitation Pursuant to rule 62a(1) EPC (Sep. 25, 2013), Response filed Nov. 18, 2013.
Pending Application No. EP 11842994.3, Communication Pursuant to Rules 70(2) and 70a(2) EPC dated Apr. 28, 2014, 1 page.
Pending Application No. EP 11842994.3, Extended European Search Report dated Apr. 9, 2014, 34 pages.
Pending Application No. EP 15793361.5, Claim amendment filed Jul. 18, 2018, 13 pages.
Pending Application No. EP 15793361.5, European Search Report dated Dec. 4, 2017, 9 pages.
Pending Application No. JP 2013-541050, Voluntary Amendment filed Oct. 29, 2013, 4 pages (with English Version of the Claims, 2 pages).
Pending Application No. JP 2016-567747 Amendment filed Jul. 18, 2019, 7 pgs.
Pending Application No. JP 2016-567747 English translation of amended claims filed Jul. 18, 2019, 6 pgs.
Pending Application No. JP 2016-567747, First Office Action (Translation) dated Feb. 21, 2019, 5 pages.
Pending Application No. JP 2016-567747, First Office Action dated Feb. 21, 2019, 4 pages.
Pending Application No. JP 2016-567747, Decision to Grant with English Version of allowed claims, 9 pages.
Pending Application No. JP 2019-133057, amended claims (English language version) filed Aug. 14, 2019, 5 pages.
Pending Application No. JP 2019-133057, Office Action dated Sep. 14, 2020, 5 pages (and English translation, 6 pages).
Qiao et al. Electrical properties of breast cancer cells from impedance measurement of cell suspensions, 2010, Journal of Physics, 224, 1-4 (2010).
Ringel-Scaia, V. M. et al., High-frequency irreversible electroporation is an effective tumor ablation strategy that induces immunologic cell death and promotes systemic anti-tumor immunity. EBioMedicine, 2019, 44, 112-125.
Rossmeisl, John H. et al. Safety and feasibility of the NanoKnife system for irreversible electroporation ablative treatment of canine spontaneous intracranial gliomas J. Neurosurgery 123.4 (2015): 1008-1025.
(Sano, Michael B. et al.) Co-Pending U.S. Appl. No. 16/747,219, filed Jan. 20, 2020, Specification, Claims, Figures.
(Sano, Michael B. et al.) Co-Pending Application No. PCT/US11/62067, filed Nov. 23, 2011, Specification, Claims, Figures.
(Sano, Michael B. et al.) Co-Pending Application No. PCT/US15/30429, filed May 12, 2015, Specification, Claims, Figures.
Abiror, I.G., et al., "Electric Breakdown of Bilayer Lipid-Membranes .1. Main Experimental Facts and Their Qualitative Discussion", Bioelectrochemistry and Bioenergetics, 6(1):p. 37-52 (1979).
Agerholm-Larsen, B., et al., "Preclinical Validation of Electrochemotherapy as an Effective Treatment for Brain Tumors", Cancer Research 71: 3753-3762 (2011).
Alberts et al., "Molecular Biology of the Cell," 3rd edition, Garland Science, New York, 1994, 1 page.
Al-Sakere, B. et al., 2007, "Tumor ablation with irreversible electroporation." PLoS ONE 2.
Amasha, et al., Quantitative Assessment of Impedance Tomography for Temperature Measurements in Microwave Hyperthermia, Clin. Phys. Physiol. Meas., 1998, Suppl. A, 49-53.
Andreason, Electroporation as a Technique for the Transfer of Macromolecules into Mammalian Cell Lines, J. Tiss. Cult. Meth., 15:56-62, 1993.
Appelbaum, L., et al., "US Findings after Irreversible Electroporation Ablation: Radiologic-Pathologic Correlation" Radiology 262(1), 117-125 (2012).
Arena et al. "High-Frequency Irreversible Electroporation (H-FIRE) for Non-thermal Ablation without Muscle Contraction." Biomed. Eng. Online, vol. 10, 20 pages (2011).
Arena, C.B., et al., "A three-dimensional in vitro tumor platform for modeling therapeutic irreversible electroporation." Biophysical Journal, 2012.103(9): p. 2033-2042.
Arena, Christopher B., et al., "Towards the development of latent heat storage electrodes for electroporation-based therapies", Applied Physics Letters, 101, 083902 (2012).
Arena, Christopher B., et al.,"PHASE Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.
Asami et al., "Dielectric properties of mouse lymphocytes and erythrocytes." Biochimica et Biophysica Acta (BBA)—Molecular Cell Research, 1010 (1989) pp. 49-55.
Bagla, S. and Papadouris, D., "Percutaneous Irreversible Electroporation of Surgically Unresectable Pancreatic Cancer: A Case Report" J. Vascular Int. Radiol. 23(1), 142-145 (2012).
Baker, et al., Calcium-Dependent Exocytosis in Bovine Adrenal Medullary Cells with Leaky Plasma Membranes, Nature, vol. 276, pp. 620-622, 1978.
Ball, C., K.R. Thomson, and H. Kavnoudias, "Irreversible electroporation: a new challenge in "out of-operating theater" anesthesia." Anesth Analg, 2010. 110(5): p. 1305-9.
Bancroft, et al., Design of a Flow Perfusion Bioreactor System for Bone Tissue-Engineering Applications, Tissue Engineering, vol. 9, No. 3, 2003, p. 549-554.
Baptista et al., "The Use of Whole Organ Decellularization for the Generation of a Vascularized Liver Organoid," Heptatology, vol. 53, No. 2, pp. 604-617 (2011).
Barber, Electrical Impedance Tomography Applied Potential Tomography, Advances in Biomedical Engineering, Beneken and Thevenin, eds., IOS Press, pp. 165-173, 1993.
Beebe, S.J., et al., "Diverse effects of nanosecond pulsed electric fields on cells and tissues", DNA and Cell Biology, 22(12): 785-796 (2003).
Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No 01CH37251). IEEE, Part vol. 1, 2001, pp. 211-215, vol. I, Piscataway, NJ, USA.
Beebe, S.J., et al.,, "Nanosecond, high-intensity pulsed electric fields induce apoptosis in human cells", FASEB J, 17(9): p. 1493-5 (2003).
Belehradek, J., et al., "Electropermeabilization of Cells in Tissues Assessed by the Qualitative and Quantitative Electroloading of Bleomycin", Biochimica Et Biophysica Acta—Biomembranes, 1190(1): p. 155-163 (1994).
Ben-David, E.,et al, "Characterization of Irreversible Electroporation Ablation in In Vivo Procine Liver" Am. J. Roentgenol. 198(1), W62-W68 (2012).
Benz, R., et al. "Reversible electrical breakdown of lipid bilayer membranes: a charge-pulse relaxation study". J Membr Biol, 48(2): p. 181-204 (1979).
Blad, et al., Impedance Spectra of Tumour Tissue in Comparison with Normal Tissue; a Possible Clinical Application for Electrical Impedance Tomography, Physiol. Meas. 17 (1996) A105-A115.
Bolland, F., et al., "Development and characterisation of a full-thickness acellular porcine bladder matrix for tissue engineering", Biomaterials, Elsevier Science Publishers, Barking, GB, vol. 28, No. 6, Nov. 28, 2006, pp. 1061-1070.
Boone, K., Barber, D. & Brown, B. Review—Imaging with electricity: report of the European Concerted Action on Impedance Tomography. J Med. Eng. Technol. 21, 201-232 (1997).

(56) References Cited

OTHER PUBLICATIONS

Bower et al., "Irreversible electroporation of the pancreas: definitive local therapy without systemic effects." Journal of surgical oncology, 2011. 104(1): p. 22-28.
BPH Management Strategies: Improving Patient Satisfaction, Urology Times, May 2001, vol. 29, Supplement 1.
Brown, et al., Blood Flow Imaging Using Electrical Impedance Tomography, Clin. Phys. Physiol. Meas., 1992, vol. 13, Suppl. A, 175-179.
Brown, S.G., Phototherapy of tumors. World J. Surgery, 1983. 7: p. 700-9.
Cannon et al., "Safety and early efficacy of irreversible electroporation for hepatic tumors in proximity to vital structures " Journal of Surgical Oncology, 6 pages (2012).
Carpenter A.E. et al., "CellProfiler: image analysis software for identifying and quantifying cell phenotypes." Genome Biol. 2006; 7(10): R100. Published online Oct. 31, 2006, 11 pages.
Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).
Chandrasekar, et al., Transurethral Needle Ablation of the Prostate (TUNA)—a Propsective Study, Six Year Follow up, (Abstract), Presented at 2001 National Meeting, Anaheim, CA, Jun. 5, 2001.
Chang, D.C., "Cell Poration and Cell-Fusion Using an Oscillating Electric-Field". Biophysical Journal, 56(4): p. 641-652 (1989).
Charpentier, K.P., et al., "Irreversible electroporation of the pancreas in swine: a pilot study." HPB: the official journal of the International Hepato Pancreato Biliary Association, 2010. 12(5): p. 348-351.
Chen et al., "Classification of cell types using a microfluidic device for mechanical and electrical measurement on single cells" Lab on a Chip, vol. 11, pp. 3174-3181 (2011).
Chen, M.T., et al., "Two-dimensional nanosecond electric field mapping based on cell electropermeabilization", PMC Biophys, 2(1):9 (2009).
Clark et al., "The electrical properties of resting and secreting pancreas." The Journal of Physiology, vol. 189, pp. 247-260 (1967).
Coates, C.W.,et al, "The Electrical Discharge of the Electric Eel, Electrophorous Electricus," Zoologica, 1937, 22(1), pp. 1-32.
Cook, et al., ACT3: A High-Speed, High-Precision Electrical Impedance Tomograph, IEEE Transactions on Biomedical Engineering, vol. 41, No. 8, Aug. 1994.
Co-Pending U.S. Appl. No. 12/491,151, Final Rejection dated Apr. 20, 2012, 8 pages.
Co-Pending U.S. Appl. No. 12/491,151, (Non-Final Rejection dated Apr. 4, 2014, 12 pages.
Co-Pending U.S. Appl. No. 12/491,151, Non-Final Rejection dated Dec. 28, 2011, 7 pages.
Co-Pending U.S. Appl. No. 12/491,151, Official Notice of Allowance dated Feb. 12, 2015, 2 pages.
Rajagopal, V. and S.G. Rockson, Coronary restenosis: a review of mechanisms and management, The American Journal of Medicine, 2003, 115(7): p. 547-553.
Reberšek, M. and D. Miklavčič, "Advantages and Disadvantages of Different Concepts of Electroporation Pulse Generation," AUTOMATIKA 52(2011) 1, 12-19.
Rols, M.P., et al., Highly Efficient Transfection of Mammalian Cells by Electric Field Pulses: Application to Large Volumes of Cell Culture by Using a Flow System, Eur. J. Biochem. 1992, 206, pp. 115-121.
Ron et al., "Cell-based screening for membranal and cytoplasmatic markers using dielectric spectroscopy." Biophysical chemistry, 135 (2008) pp. 59-68.
Rossmeisl et al., "Pathology of non-thermal irreversible electroporation (N-TIRE)-induced ablation of the canine brain." Journal of Veterinary Science vol. 14, pp. 433-440 (2013).
Rossmeisl, "New Treatment Modalities for Brain Tumors in Dogs and Cats." Veterinary Clinics of North America: Small Animal Practice 44, pp. 1013-1038 (2014).
Rubinsky et al., "Optimal Parameters for the Destruction of Prostate Cancer Using Irreversible Electroporation." The Journal of Urology, 180 (2008) pp. 2668-2674.
Rubinsky, B., "Irreversible Electroporation in Medicine", Technology in Cancer Research and Treatment, vol. 6, No. 4, Aug. 1, 2007, pp. 255-259.
Rubinsky, B., ed, Cryosurgery. Annu Rev. Biomed. Eng. vol. 2 2000. 157-187.
Rubinsky, B., et al., "Irreversible Electroporation: A New Ablation Modality—Clinical Implications" Technol. Cancer Res. Treatment 6(1), 37-48 (2007).
Sabuncu et al., "Dielectrophoretic separation of mouse melanoma clones." Biomicrofluidics, vol. 4, 7 pages (2010).
Salford, L.G., et al., "A new brain tumour therapy combining bleomycin with in vivo electropermeabilization", Biochem. Biophys Res Commun., 194(2): 938-943 (1993).
Salmanzadeh et al., "Investigating dielectric properties of different stages of syngeneic murine ovarian cancer cells" Biomicrofiuidics 7, 011809 (2013), 12 pages.
Salmanzadeh et al., "Dielectrophoretic differentiation of mouse ovarian surface epithelial cells, macrophages, and fibroblasts using contactless dielectrophoresis." Biomicrofiuidics, vol. 6, 13 Pages (2012).
Salmanzadeh et al., "Sphingolipid Metabolites Modulate Dielectric Characteristics of Cells in a Mouse Ovarian Cancer Progression Model." Integr. Biol., 5(6), pp. 843-852 (2013).
Sano et al., "Contactless Dielectrophoretic Spectroscopy: Examination of the Dielectric Properties of Cells Found in Blood " Electrophoresis, 32, pp. 3164-3171, 2011.
Sano et al., "In-vitro bipolar nano- and microsecond electro-pulse bursts for irreversible electroporation therapies." Bioelectrochemistry vol. 100, pp. 69-79 (2014).
Sano et al., "Modeling and Development of a Low Frequency Contactless Dielectrophoresis (cDEP) Platform to Sort Cancer Cells from Dilute Whole Blood Samples." Biosensors & Bioelectronics, 8 pages (2011).
Sano, M. B., et al., "Towards the creation of decellularized organ constructs using irreversible electroporation and active mechanical perfusion", Biomedical Engineering Online, Biomed Central LTD, London, GB, vol. 9, No. 1, Dec. 10, 2010, p. 83.
Saur et al., "CXCR4 expression increases liver and lung metastasis in a mouse model of pancreatic cancer." Gastroenterology, vol. 129, pp. 1237-1250 (2005).
Schmukler, Impedance Spectroscopy of Biological Cells, Engineering in Medicine and Biology Society, Engineering Advances: New Opportunities for Biomedical Engineers, Proceedings of the 16th Annual Internal Conference of the IEEE, vol. 1, p. A74, downloaded from IEEE Xplore website, 1994.
Schoenbach et al., "Intracellular effect of ultrashort electrical pulses." Bioelectromagnetics, 22 (2001) pp. 440-448.
Seibert et al., "Clonal variation of MCF-7 breast cancer cells in vitro and in athymic nude mice." Cancer Research, vol. 43, pp. 2223-2239 (1983).
Seidler et al., "A Cre-IoxP-based mouse model for conditional somatic gene expression and knockdown in vivo by using avian retroviral vectors." Proceedings of the National Academy of Sciences, vol. 105, pp. 10137-10142 (2008).
Sel, D. et al. Sequential finite element model of tissue electropermeabilization. IEEE Transactions on Biomedical Engineering 52, 816-827, doi:10 1109/tbme.2005.845212 (2005).
Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).
Sersa, et al., Reduced Blood Flow and Oxygenation in SA-1 Tumours after Electrochemotherapy with Cisplatin, British Journal of Cancer, 87, 1047-1054, 2002.
Sersa, et al., Tumour Blood Flow Modifying Effects of Electrochemotherapy: a Potential Vascular Targeted Mechanism, Radiol. Oncol, 37(1): 43-8, 2003.
Sharma, A., et al., "Review on Thermal Energy Storage with Phase Change Materials and Applications", Renewable Sustainable Energy Rev. 13(2), 318-345 (2009).

(56) References Cited

OTHER PUBLICATIONS

Sharma, et al., Poloxamer 188 Decreases Susceptibility of Artificial Lipid Membranes to Electroporation, Biophysical Journal, vol. 71, No. 6, pp. 3229-3241, Dec. 1996.

Shiina, S., et al., Percutaneous ethanol injection therapy for hepatocellular carcinoma: results in 146 patients. AJR, 1993, 160: p. 1023-8.

Szot et al., "3D in vitro bioengineered tumors based on collagen I hydrogels." Biomaterials vol. 32, pp. 7905-7912 (2011).

Falele, S. and P. Gaynor, "Non-linear time domain model of electropermeabilization: Effect of extracellular conductivity and applied electric field parameters", Journal of Electrostatics,66(5-6): p. 328-334 (2008).

Talele, S. and P. Gaynor, "Non-linear time domain model of electropermeabilization: Response of a single cell to an arbitrary applied electric field", Journal of Electrostatics, 65(12): p. 775-784 (2007).

Talele, S., et al., "Modelling single cell electroporation with bipolar pulse parameters and dynamic pore radii". Journal of Electrostatics, 68(3): p. 261-274 (2010).

Teissie, J. and T.Y. Tsong, "Electric-Field Induced Transient Pores in Phospholipid-Bilayer Vesicles". Biochemistry, 20(6): p. 1548-1554 (1981).

Tekle, Ephrem, R. Dean Astumian, and P. Boon Chock, Electroporation by using bipolar oscillating electric field: An improved method for DNA transfection of NIH 3T3 cells, Proc. Natl. Acad. Sci., vol. 88, pp. 4230-4234, May 1991, Biochemistry.

Thompson, et al., To determine whether the temperature of 2% lignocaine gel affects the initial discomfort which may be associated with its instillation into the male urethra, BJU International (1999), 84, 1035-1037.

Thomson, K. R., et al., "Investigation of the Safety of Irreversible Electroporation in Humans" J. Vascular Int. Radiol. 22(5), 611-621 (2011).

Tibbitt et al., "Hydrogels as Extracellular Matrix Mimics for 3D Cell Culture", Jul. 2009, Biotechnol Bioeng, 103(4),655-663.

TUNA—Suggested Local Anesthesia Guidelines, no date available.

Verbridge et al., "Oxygen-Controlled Three-Dimensional Cultures to Analyze Tumor Angiogenesis." Tissue Engineering, Part A vol. 16, pp. 2133-2141 (2010).

Vernier, P.T., et al., "Nanoelectropulse-driven membrane perturbation and small molecule permeabilization", Bmc Cell Biology, 7 (2006).

VIDAMED, Inc., Transurethral Needle Ablation (TUNA): Highlights from Worldwide Clinical Studies, Vidamed's Office TUNA System, 2001.

Wasson, Elisa M. et al. The Feasibility of Enhancing Susceptibility of Glioblastoma Cells to IRE Using a Calcium Adjuvant. Annals of Biomedical Engineering, vol. 45, No. 11, Nov. 2017 pp. 2535-2547.

Weaver et al., "A brief overview of electroporation pulse strength-duration space: A region where additional intracellular effects are expected." Bioelectrochemistry vol. 87, pp. 236-243 (2012).

Weaver, Electroporation: A General Phenomenon for Manipulating Cells and Tissues, Journal of Cellular Biochemistry, 51: 426-435, 1993.

Weaver, et al., Theory of Electroporation: A Review, Bioelectrochemistry and Bioenergetics, vol. 41, pp. 136-160, 1996.

Weaver, J. C., Electroporation of biological membranes from multicellular to nano scales, IEEE Trns. Dielectr. Electr. Insul. 10, 754-768 (2003).

Weaver, J.C., "Electroporation of cells and tissues", IEEE Transactions on Plasma Science, 28(1): p. 24-33 (2000).

Weisstein: Cassini Ovals. From MathWorld—A. Wolfram Web Resource; Apr. 30, 2010; http://mathworld.wolfram.com/ (updated May 18, 2011).

Wimmer, Thomas, et al., "Planning Irreversible Electroporation (IRE) in the Porcine Kidney: Are Numerical Simulations Reliable for Predicting Empiric Ablation Outcomes?", Cardiovasc Intervent Radiol. Feb. 2015; 38(1): 182-190. doi:10.1007/s00270-014-0905-2.

Yang et al., "Dielectric properties of human leukocyte subpopulations determined by electrorotation as a cell separation criterion." Biophysical Journal, vol. 76, pp. 3307-3314 (1999).

Yao et al., "Study of transmembrane potentials of inner and outer membranes induced by pulsed-electric-field model and simulation." IEEE Trans Plasma Sci, 2007. 35(5): p. 1541-1549.

Zhang, Y., et al., MR imaging to assess immediate response to irreversible electroporation for targeted ablation of liver tissues: preclinical feasibility studies in a rodent model. Radiology, 2010. 256(2): p. 424-32.

Zimmermann, et al., Dielectric Breakdown of Cell Membranes, Biophysical Journal, vol. 14, No. 11, pp. 881-899, 1974.

Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.

Zlotta, et al., Possible Mechanisms of Action of Transurethral Needle Ablation of the Prostate on Benign Prostatic Hyperplasia Symptoms: a Neurohistochemical Study, Reprinted from Journal of Urology, vol. 157, No. 3, Mar. 1997, pp. 894-899.

Co-Pending U.S. Appl. No. 14/940,863, Notice of Allowance dated May 25, 2018, 9 pages.

Co-Pending U.S. Appl. No. 14/940,863, Notice of Allowance dated Sep. 19, 2018, 5 pages.

Co-Pending U.S. Appl. No. 15/011,752 Final Office Action dated Dec. 19, 2018, 6 pages.

Co-Pending U.S. Appl. No. 15/011,752 Non-Final Office Action dated May 11, 2018, 11 pages.

Co-Pending U.S. Appl. No. 15/011,752 Notice of Allowance dated Mar. 22, 2019, 6 pages.

Co-Pending U.S. Appl. No. 15/011,752 Preliminary Amendment, filed Feb. 2, 2016, 6 pages.

Co-Pending U.S. Appl. No. 15/011,752 Response to Dec. 19, 2018 Final Office Action dated Mar. 5, 2019, 6 pages.

Co-Pending U.S. Appl. No. 15/011,752 Response to May 11, 2018 Non-Final Office Action dated Oct. 11, 2018, 11 pages.

Co-Pending U.S. Appl. No. 15/536,333, Office Actions and Responses dated Jan. 2, 2020, 69 pages.

Co-Pending U.S. Appl. No. 15/881,414 Amendment and Petition for Priority Claim dated Jul. 26, 2018, 26 pages.

Co-Pending U.S. Appl. No. 15/881,414, filed Apr. 26, 2018 Non-Final Office Action, 8 pages.

Co-Pending U.S. Appl. No. 15/881,414 Corrected Notice of Allowability dated Nov. 13, 2018, 2 pages.

Co-Pending U.S. Appl. No. 15/881,414 Notice of Allowance dated Oct. 24, 2018, 7 pages.

Co-Pending U.S. Appl. No. 15/881,414 Petition Decision dated Oct. 9, 2018, 9 pages.

Co-Pending U.S. Appl. No. 15/881,414 Response to Apr. 26, 2018 Non-Final Office Action, dated Jul. 26, 2018, 15 pages.

Co-Pending U.S. Appl. No. 16/152,743 Preliminary Amendment filed Oct. 5, 2018, 7 pages.

Co-Pending U.S. Appl. No. 16/177,745, Applicant-initiated interview summary dated Dec. 16, 2019, 3 pages.

Co-Pending U.S. Appl. No. 16/177,745, Final office action dated Jan. 9, 2020, 8 pages.

Co-Pending U.S. Appl. No. 16/177,745, Non-final office action dated Aug. 20, 2019, 10 pages.

Co-Pending U.S. Appl. No. 16/177,745, Preliminary Amendment dated Dec. 19, 2018, 7 pages.

Co-Pending U.S. Appl. No. 16/177,745, Response to Aug. 20, 2019 Non-final office action dated Nov. 20, 2019, 10 pages.

Co-Pending U.S. Appl. No. 16/232,962 Applicant-initiated interview Summary dated Dec. 16, 2019, 3 pages.

Co-Pending U.S. Appl. No. 16/232,962 Final office action dated Jan. 9, 2020, 7 pages.

Co-Pending U.S. Appl. No. 16/232,962 Non-Final office action dated Aug. 20, 2019, 9 pages.

Co-Pending U.S. Appl. No. 16/232,962 Response to Aug. 20, 2019 Non-final office action dated Nov. 20, 2019, 10 pages.

Co-Pending U.S. Appl. No. 16/275,429 Preliminary Amendment Filed Mar. 28, 2019, 6 pages.

(56) References Cited

OTHER PUBLICATIONS

Co-Pending application No. PCT/US19/51731 International Search Report and Written Opinion dated Feb. 20, 2020, 19 pgs.
Co-Pending application No. PCT/US19/51731 Invitation to Pay Additional Search Fees dated Oct. 28, 2019, 2 pgs.
Corovic, S., et al., "Analytical and numerical quantification and comparison of the local electric field in the tissue for different electrode configurations," Biomed Eng Online, 6, 2007.
Cowley, Good News for Boomers, Newsweek, Dec. 30, 1996/Jan. 6, 1997.
Cox, et al., Surgical Treatment of Atrial Fibrillation: A Review, Europace (2004) 5, S20-S-29.
Crowley, Electrical Breakdown of Biomolecular Lipid Membranes as an Electromechanical Instability, Biophysical Journal, vol. 13, pp. 711-724, 1973.
Dahl et al., "Nuclear shape, mechanics, and mechanotransduction." Circulation Research vol. 102, pp. 1307-1318 (2008).
Daskalov, I., et al., "Exploring new instrumentation parameters for electrochemotherapy—Attacking tumors with bursts of biphasic pulses instead of single pulses", IEEE Eng Med Biol Mag, 18(1): p. 62-66 (1999).
Daud, A.I., et al., "Phase I Trial of Interleukin-12 Plasmid Electroporation in Patients With Metastatic Melanoma," Journal of Clinical Oncology, 26, 5896-5903, Dec. 20, 2008.
Davalos, et al., Theoretical Analysis of the Thermal Effects During In Vivo Tissue Electroporation, Bioelectrochemistry, vol. 61, pp. 99-107, 2003.
Davalos, et al., A Feasibility Study for Electrical Impedance Tomography as a Means to Monitor Tissue Electroporation for Molecular Medicine, IEEE Transactions on Biomedical Engineering, vol. 49, No. 4, Apr. 2002.
Davalos, et al., Tissue Ablation with Irreversible Electroporation, Annals of Biomedical Engineering, vol. 33, No. 2, p. 223-231, Feb. 2005.
Davalos, R. V. & Rubinsky, B. Temperature considerations during irreversible electroporation. International Journal of Heat and Mass Transfer 51, 5617-5622, doi:10.1016/j.ijheatmasstransfer.2008.04.046 (2008).
Davalos, R.V., et al., "Electrical impedance tomography for imaging tissue electroporation," IEEE Transactions on Biomedical Engineering, 51, 761-767, 2004.
Davalos, Real-Time Imaging for Molecular Medicine through Electrical Impedance Tomography of Electroporation, Dissertation for Ph.D. in Engineering—Mechanical Engineering, Graduate Division of University of California, Berkeley, 2002.
De Vuyst, E., et al., "In situ bipolar Electroporation for localized cell loading with reporter dyes and investigating gap junctional coupling", Biophysical Journal, 94(2): p. 469-479 (2008).
Dean, Nonviral Gene Transfer to Skeletal, Smooth, and Cardiac Muscle in Living Animals, Am J. Physiol Cell Physiol 289: 233-245, 2005.
Demirbas, M. F., "Thermal Energy Storage and Phase Change Materials: An Overview" Energy Sources Part B 1(1), 85-95 (2006).
Dev, et al., Medical Applications of Electroporation, IEEE Transactions of Plasma Science, vol. 28, No. 1, pp. 206-223, Feb. 2000.
Dev, et al., Sustained Local Delivery of Heparin to the Rabbit Arterial Wall with an Electroporation Catheter, Catheterization and Cardiovascular Diagnosis, Nov. 1998, vol. 45, No. 3, pp. 337-343.
Duraiswami, et al., Boundary Element Techniques for Efficient 2-D and 3-D Electrical Impedance Tomography, Chemical Engineering Science, vol. 52, No. 13, pp. 2185-2196, 1997.
Duraiswami, et al., Efficient 2D and 3D Electrical Impedance Tomography Using Dual Reciprocity Boundary Element Techniques, Engineering Analysis with Boundary Elements 22, (1998) 13-31.
Duraiswami, et al., Solution of Electrical Impedance Tomography Equations Using Boundary Element Methods, Boundary Element Technology XII, 1997, pp. 226-237.
Edd, J., et al., In-Vivo Results of a New Focal Tissue Ablation Technique: Irreversible Electroporaton, IEEE Trans. Biomed Eng. 53 (2006) p. 1409-1415.
PCT Application No. PCT/US15/30429, International Search Report and Written Opinion dated Oct. 16, 2015, 19 pages.
PCT Application No. PCT/US15/65792, International Search Report (dated Feb. 9, 2016), Written Opinion (dated Feb. 9, 2016), and International Preliminary Report on Patentability (dated Jun. 20, 2017), 15 pages.
Pending U.S. Appl. No. 14/686,380, Final Office Action dated Oct. 6, 2020, 14 pages.
Pending U.S. Appl. No. 14/686,380, Response dated Feb. 13, 2020 Non-Final Office Action, filed Jul. 1, 2020, 8 pages.
Pending U.S. Appl. No. 14/686,380, Response dated Oct. 6, 2020 Final Office Action with RCE, dated Jan. 6, 2020, 11 pages.
Pending U.S. Appl. No. 14/686,380, Response dated Sep. 3, 2019 Final Office Action, filed Jan. 3, 2020, 10 pages.
Pending U.S. Appl. No. 14/808,679, Interview Summary, dated Apr. 26, 2019, 3 pages.
Pending U.S. Appl. No. 14/808,679, Preliminary Amendment dated Jul. 24, 2015, 6 pages.
Pending U.S. Appl. No. 14/808,679, Restriction Requirement dated Mar. 19, 2018, 7 pages.
Pending U.S. Appl. No. 14/808,679, 3rd Renewed Petition, filed Dec. 9, 2019 and Petition Decision Dec. 18, 2019, 11 pages.
Pending U.S. Appl. No. 14/808,679, Final Office Action dated Dec. 28, 2020, 11 pages.
Pending U.S. Appl. No. 14/808,679, Final Office Action dated Jan. 11, 2019, 12 pages.
Pending U.S. Appl. No. 14/808,679, Non-Final Office Action dated Jun. 12, 2020, 10 pages.
Pending U.S. Appl. No. 14/808,679, Non-Final Office Action dated Sep. 10, 2018, 12 pages.
Pending U.S. Appl. No. 14/808,679, Petition Decision, dated Oct. 1, 2019, 5 pages.
Pending U.S. Appl. No. 14/808,679, Petition Decision, dated Oct. 23, 2019, 6 pages.
Pending U.S. Appl. No. 14/808,679, Petition Decision, dated Dec. 3, 2019, 5 pages.
Pending U.S. Appl. No. 14/808,679, Petition for Priority and Supplemental Response, filed May 8, 2019, 25 pages.
Pending U.S. Appl. No. 14/808,679, Petition Supplement, filed Sep. 25, 2019, 10 pages.
Pending U.S. Appl. No. 14/808,679, Petition, filed May 8, 2019, 2 pages.
Pending U.S. Appl. No. 14/808,679, Preliminary Amendment, filed Jul. 27, 2015, 9 pages.
Pending U.S. Appl. No. 14/808,679, RCE filed Apr. 11, 2019, 8 pages.
Pending U.S. Appl. No. 14/808,679, Renewed Petition, filed Oct. 9, 2019, 1 pages.
Pending U.S. Appl. No. 14/808,679, Response dated Mar. 19, 2018 Restriction Requirement dated May 21, 2018, 2 pages.
Pending U.S. Appl. No. 14/808,679, Response to Non-Final Office Action dated Jun. 12, 2020, filed Sep. 14, 2020, 9 pages.
Pending U.S. Appl. No. 14/808,679, Response dated Sep. 10, 2018 Non-Final Office Action dated Dec. 10, 2018, 9 pages.
Pending U.S. Appl. No. 14/808,679, Second Renewed Petition, filed Oct. 31, 2019, 3 pages.
Pending U.S. Appl. No. 14/808,679, Supplemental Response, dated May 8, 2019, 16 pages.
Pending U.S. Appl. No. 16/152,743, Non-Final Office Action dated Sep. 25, 2020, 10 pages.
Pending U.S. Appl. No. 16/152,743, Petition for Delayed Claim for Priority dated Dec. 28, 2020, 2 pages.
Pending U.S. Appl. No. 16/152,743, Response dated Sep. 25, 2020 Non-Final Office Action dated Dec. 28, 2020, 9 pages.
Pending U.S. Appl. No. 16/152,743, Second Preliminary Amendment filed May 2, 2019, 6 pages.
Pending U.S. Appl. No. 16/210,771, Non-Final Office Action dated Sep. 3, 2020, 9 pages.
Pending U.S. Appl. No. 16/210,771, Preliminary Amendment filed Dec. 5, 2018, 8 pages.

(56) References Cited

OTHER PUBLICATIONS

Pending U.S. Appl. No. 16/210,771, Response to Restriction Requirement, filed Jul. 8, 2020, 7 pages.
Pending U.S. Appl. No. 16/210,771, Response to Sept. 3, 2020 Non-Final Office Action filed Jan. 4, 2021, 11 pages.
Pending U.S. Appl. No. 16/210,771, Restriction Requirement, dated Jun. 9, 2020, 7 pages.
Pending U.S. Appl. No. 16/210,771, Second Preliminary Amendment filed Oct. 14, 2019, 7 pages.
Pending U.S. Appl. No. 16/275,429 Notice of Allowance dated Nov. 10, 2020, 9 pages.
Pending U.S. Appl. No. 16/280,511, Non-final Office Action dated Dec. 4, 2020, 10 pgs.
Pending U.S. Appl. No. 16/280,511, Preliminary Amendment filed Nov. 2, 2020, 6 pages.
Pending U.S. Appl. No. 16/372,520 Preliminary Amendment filed Apr. 9, 2019, 7 pages.
Pending U.S. Appl. No. 16/375,878, Preliminary Amendment, filed Apr. 9, 2019, 9 pages.
Pending U.S. Appl. No. 16/375,878, Second Preliminary Amendment, filed Feb. 5, 2020, 3 pages.
Pending U.S. Appl. No. 16/404,392, Final Office Action dated Mar. 20, 2020, 8pgs.
Pending U.S. Appl. No. 16/404,392, Interview Summary dated Sep. 6, 2019, 8pgs.
Pending U.S. Appl. No. 16/404,392, Non-Final Office Action dated Nov. 13, 2020, 8pgs.
Pending U.S. Appl. No. 16/404,392, Non-Final Office Action dated Sep. 6, 2019, 8pgs.
Pending U.S. Appl. No. 16/404,392, Petition for Priority, filed Jun. 4, 2019, 2 pages.
(Davalos, Rafael V. et al.) Co-pending U.S. Appl. No. 17/172,731, filed Feb. 10, 2021, Specification, Claims, Figures.
(Davalos, Rafael V. et al.) Co-pending U.S. Appl. No. 17/277,662, filed Mar. 18, 2021, Specification, Claims, Figures.
(Davalos, Rafael V. et al.) Co-pending Application No. 19861489.3 filed Apr. 16, 2021, Specification, figures (See PCT/US19/51731), and claims (3 pages).
(Neal, Robert et al.) Co-pending U.S. Appl. No. 17/338,960, filed Jun. 4, 2021, Specification, Claims, Figures.
Alinezhadbalalami, N. et al., "Generation of Tumor-activated T cells Using Electroporation", Bioelectrochemistry 142 (2021) 107886, Jul. 13, 2021, 11 pages.
PCT Application No. PCT/US19/51731, International Preliminary Reporton Patentability dated Mar. 23, 2021, 13 pages.
Pending U.S. Appl. No. 14/686,380, Applicant Initiated Interview Summary dated Feb. 9, 2021, 3 pages.
Pending U.S. Appl. No. 14/686,380, Applicant Initiated Interview Summary dated Mar. 8, 2021, 2 pages.
Pending U.S. Appl. No. 14/686,380, Non-Final Office Action dated May 7, 2021, 17 pages.
Pending U.S. Appl. No. 14/808,679, Appeal Brief, filed Jun. 3, 2021, 25 pages.
Pending U.S. Appl. No. 14/808,679, Examiner's Answer to Appeal Brief, dated Sep. 15, 2021, 6 pages.
Pending U.S. Appl. No. 14/808,679, Panel Decision from Pre-Appeal Brief Review, dated Apr. 26, 2021, 2 pages.
Pending U.S. Appl. No. 14/808,679, Pre-Appeal Brief Reasons for Request for Review, dated Mar. 29, 2021, 5 pages.
Pending U.S. Appl. No. 16/152,743, Final Office Action dated Jul. 15, 2021, 8 pages.
Pending U.S. Appl. No. 16/210,771, Applicant-Initiated Interview Summary dated Aug. 13, 2021, 4 pages.
Pending U.S. Appl. No. 16/210,771, Final Office Action dated May 14, 2021, 13 pages.
Pending U.S. Appl. No. 16/210,771, Response to May 14, 2021 Final Office Action, filed Aug. 16, 2021, 6 pages.
Pending U.S. Appl. No. 16/280,511, Notice of Allowance dated Aug. 2, 2021, 7 pgs.
Pending U.S. Appl. No. 16/280,511, Response to Dec. 4, 2020 Non-final Office Action dated Jun. 4, 2021, 8 pgs.
Pending U.S. Appl. No. 16/375,878, Non-Final Office Action dated Jun. 24, 2021, 8 pages.
Pending U.S. Appl. No. 16/404,392, Non-Final Office Action dated May 28, 2021, 8 pages.
Pending U.S. Appl. No. 16/404,392, Response dated May 28, 2021 Non-Final Office Action, filed Sep. 23, 2021, 13 pages.
Pending U.S. Appl. No. 16/404,392, Response dated Nov. 13, 2020 Non-Final Office action, filed Feb. 16, 2021, 8 pages.
Pending U.S. Appl. No. 16/535,451 Non-Final Office Action, dated Jun. 24, 2021, 12 pages.
Pending U.S. Appl. No. 16/865,031, Second Preliminary Amendment, filed Sep. 17, 2021, 10 pages.
Pending U.S. Appl. No. 16/865,772, Second Preliminary Amendment filed Jun. 30, 2020, 4 pages.
Pending U.S. Appl. No. 16/865,772, Third Preliminary Amendment, filed Sep. 17, 2021, 6 pages.
Pending U.S. Appl. No. 17/069,359, Preliminary Amendment, filed Sep. 17, 2021, 6 pages.
Pending U.S. Appl. No. 17/172,731, Preliminary Amendment, filed Sep. 17, 2021, 7 pages.
Pending U.S. Appl. No. 17/277,662 Preliminary Amendment filed Mar. 18, 2021, 8 pages.
Pending U.S. Appl. No. 17/338,960, Response to Notice to File Missing Parts and Amendment, filed Aug. 16, 2021, 7 pages.
Pending Application No. CN 202011281572.3, Amendment filed Sep. 8, 2021 (16 pages) with English Version of the Amended Claims (7 pages).
Pending Application No. EP 15793361.5, Communication Pursuant to Article 94(3) EPC, dated May 3, 2021, 4 pages.
Pending Application No. JP 2019-133057, Response dated Sep. 14, 2020 Office Action filed Mar. 18, 2021 (6 pages) with English Version of claims and response (5 pages).
U.S. Appl. No. 16/275,429 (U.S. Pat. No. 10,959,772), file history through Feb. 2021, 18 pages.
(Davalos, Rafael et al.) Co-Pending Application No. PCT/US21/51551, filed Sep. 22, 2021, Specification, Claims, Figures.
Pending U.S. Appl. No. 14/686,380, Advisory Action dated Oct. 20, 2021, 3 pages.
Pending U.S. Appl. No. 14/686,380, Appeal Brief filed Nov. 5, 2021, 21 pages.
Pending U.S. Appl. No. 14/686,380, Amendment after Notice of Appeal, dated Oct. 12, 2021, 6 pages.
Pending U.S. Appl. No. 16/152,743, Notice of Allowance, dated Oct. 27, 2021, 8 pages.
Pending U.S. Appl. No. 16/152,743, Response to Jul. 15, 2021 Final Office Action, filed Oct. 13, 2021, 6 pages.
Pending U.S. Appl. No. 16/210,771, Non-Final Office Action dated Oct. 7, 2021, 10 pages.
Pending U.S. Appl. No. 16/404,392, Notice of Allowance, dated Oct. 27, 2021, 7 pages.
Pending U.S. Appl. No. 16/520,901, Non-Final Office Action, dated Oct. 13, 2021, 9 pages.
Pending U.S. Appl. No. 16/535,451 Response to Jun. 24, 2021 Non-Final Office Action, dated Oct. 26, 2021, 10 pages.
Pending U.S. Appl. No. 16/655,845, Restriction Requirement, dated Oct. 21, 2021, 6 pages.
Pending Application No. AU 2015259303, Notice of Acceptance and Allowed Claims, dated Oct. 15, 2021, 7 pages.
Pending Application No. AU 2015259303, Response to First Examination Report dated Sep. 20, 2021, 126 pages.
Pending Application No. JP 2019-133057, Office Action dated Sep. 1, 2021, 3 pages (and English translation, 4 pages).
Pending Application No. PCT/US21/51551, International Search Report and Written Opinion dated Dec. 29, 2021, 14 pages.
Zhao, J. et al. "Irreversible electroporation reverses resistance to immune checkpoint blockade in pancreatic cancer", Nature Communications (2019) 10:899, 14 pages.
(Aycock, Kenneth N. et al.) Co-pending U.S. Appl. No. 17/535,742, filed Nov. 26, 2021, Specification, Claims, and Figures.
Pending U.S. Appl. No. 14/808,679, Reply Brief, dated Nov. 15, 2021, 5 pages.

(56) References Cited

OTHER PUBLICATIONS

Pending U.S. Appl. No. 16/210,771, Response to Oct. 7, 2021 Non-Final Office Action, dated Jan. 7, 2022, 7 pages.
Pending U.S. Appl. No. 16/210,771, Rule 1.132 Declaration dated Jan. 7, 2022, 3 pages.
Pending U.S. Appl. No. 16/375,878, Response to Jun. 24, 2021 Non-Final Office Action, dated Dec. 22, 2021, 8 pages.
Pending U.S. Appl. No. 16/535,451 Final Office Action, dated Feb. 4, 2022, 7 pages.
Pending U.S. Appl. No. 16/655,845, Response to Oct. 21, 2021 Restriction Requirement, dated Dec. 21, 2021, 7 pages.
Pending Application No. 19861489.3 Response to Communication pursuant to Rules 161(2) and 162 EPC, filed Nov. 16, 2021, 7 pages.
Pending Application No. EP 15793361.5, Response to May 3, 2021 Communication Pursuant to Article 94(3) EPC, dated Nov. 12, 2021, 12 pages.
Pending Application No. JP 2019-133057, Request for Amendment and Appeal filed Dec. 23, 2021 (8 pages) with English Translation of the Amended Claims (2 pages).

\* cited by examiner

FIGS. 2A-D

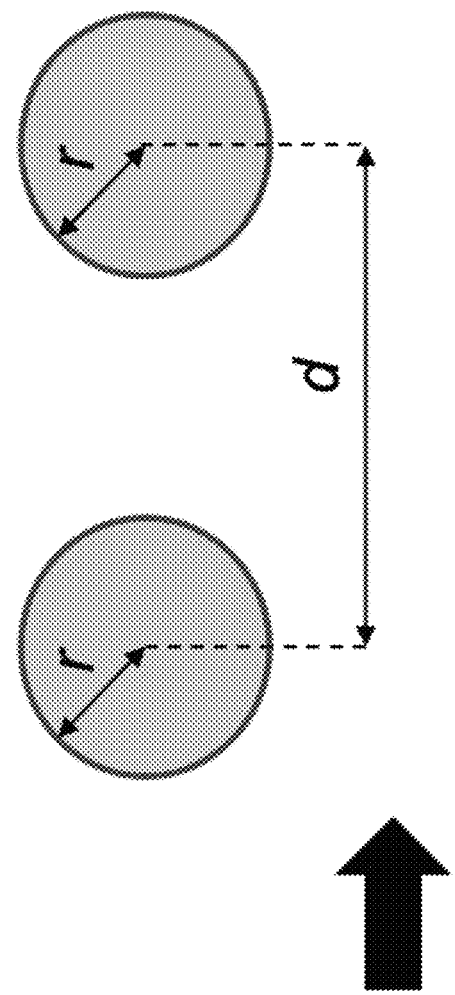
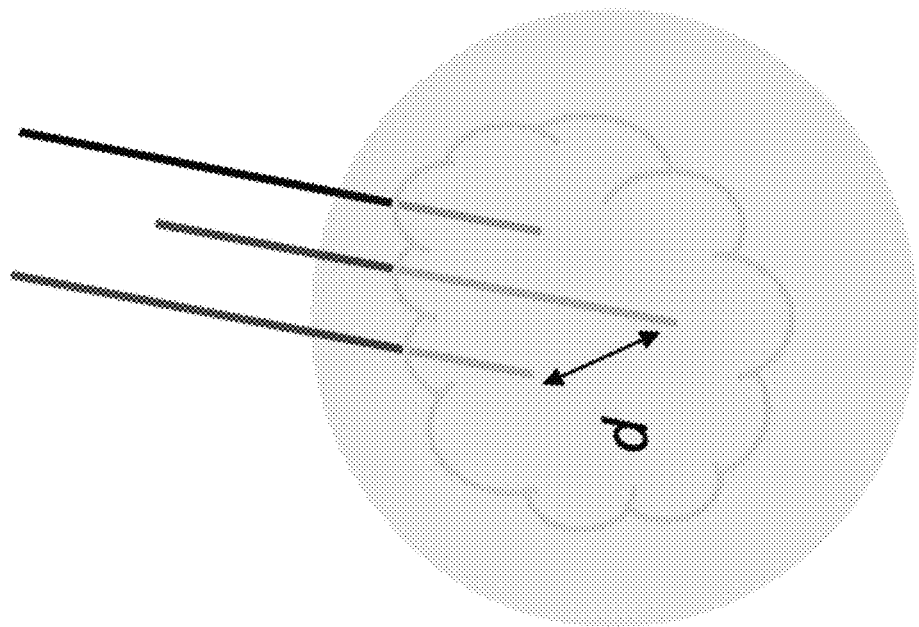
$$K = \frac{2\pi d}{\cosh^{-1}\frac{2d^2 - 4r^2}{r^2}}$$
FIG. 20

| | V (V) | σ (S/m) | d (cm) | r (mm) | K | I (A) |
|---|---|---|---|---|---|---|
| 1 | 3000 | 0.2 | 1 | 0.5 | 0.0085 | 5.11 |
| 2 | 3000 | 0.2 | 2 | 0.5 | 0.0143 | 8.60 |
| 3 | 3000 | 0.3 | 3 | 0.5 | 0.0197 | 17.7 |
| 4 | 3000 | 1 | 1 | 0.5 | 0.0085 | 25.5 |
| 5 | 3000 | 1 | 3 | 0.5 | 0.0197 | 59.1 |

FIG. 21

Patient 1

| Canonical Pathway | Observation 8 | Observation 11 |
|---|---|---|
| HMGB1 Signaling | | |
| Neuroinflammation Signaling Pa | | |
| IL-6 Signaling | | |
| TREM1 Signaling | | |
| IL-17A Signaling in Airway Cells | | |
| STAT3 Pathway | | |
| Acute Phase Response Signalin | | |
| LXR/RXR Activation | | ■ |
| Tec Kinase Signaling | | |
| Role of IL-17F in Allergic Inflam | | |
| JAK/Stat Signaling | | |
| Colorectal Cancer Metastasis Si | | |
| Renin-Angiotensin Signaling | | |
| Th1 Pathway | | |
| Pancreatic Adenocarcinoma Sig | | |
| Production of Nitric Oxide and F | | |
| NF-κB Signaling | | |
| PPARα/RXRα Activation | | ■ |
| IGF-1 Signaling | | |
| Dendritic Cell Maturation | | |
| OX40 Signaling Pathway | | |
| VEGF Signaling | | |
| Type I Diabetes Mellitus Signalir | | |
| Th2 Pathway | | |
| Sirtuin Signaling Pathway | | ■ |
| IL-9 Signaling | | |
| GM-CSF Signaling | | |
| ILK Signaling | | |
| PI3K/AKT Signaling | | |
| VDR/RXR Activation | | |
| Role of NFAT in Cardiac Hypert | | |
| Antioxidant Action of Vitamin C | | |
| IL-2 Signaling | | |
| Role of NANOG in Mammalian E | | |

Patient 2

| Canonical Pathway | Observation 9 | Observation 12 |
|---|---|---|
| IL-6 Signaling | | |
| HMGB1 Signaling | | |
| Acute Phase Response Signalin | | |
| Th1 Pathway | | |
| TREM1 Signaling | | |
| LXR/RXR Activation | | ■ |
| PPAR Signaling | | |
| JAK/Stat Signaling | | |
| Pancreatic Adenocarcinoma Sig | | |
| Neuroinflammation Signaling Pa | | |
| Dendritic Cell Maturation | | |
| IL-17A Signaling in Airway Cells | | |
| PPARα/RXRα Activation | | ■ |
| NF-κB Signaling | | |
| p38 MAPK Signaling | | |
| Osteoarthritis Pathway | | |
| Type I Diabetes Mellitus Signalir | | |
| Tec Kinase Signaling | | |
| Role of IL-17F in Allergic Inflam | | |
| iNOS Signaling | | |
| IL-9 Signaling | | |
| GM-CSF Signaling | | |
| LPS/IL-1 Mediated Inhibition of | | |
| PI3K/AKT Signaling | | |
| Production of Nitric Oxide and F | | |
| CNTF Signaling | | |
| IGF-1 Signaling | | |
| IL-3 Signaling | | |
| Small Cell Lung Cancer Signalinc | | |
| Inflammasome pathway | | |
| OX40 Signaling Pathway | | |
| Colorectal Cancer Metastasis Si | | |
| Adrenomedullin signaling pathw | | |
| Th2 Pathway | | |
| Renin-Angiotensin Signaling | | |
| Cholecystokinin/Gastrin-mediat | | |
| Role of NFAT in Cardiac Hypert | | |
| Antioxidant Action of Vitamin C | | ■ |

Patient 3

| Canonical Pathway | Observation 10 | Observation 13 |
|---|---|---|
| IL-8 Signaling | | ■ |
| Dendritic Cell Maturation | | |
| Toll-like Receptor Signaling | | |
| NF-κB Signaling | | |
| HMGB1 Signaling | | |
| TREM1 Signaling | | |
| Colorectal Cancer Metastasis Si | | |
| Cholecystokinin/Gastrin-mediat | | |
| Endothelin-1 Signaling | | |
| LXR/RXR Activation | | |
| Neuroinflammation Signaling Pa | | |
| Glioblastoma Multiforme Signalir | | |
| IL-6 Signaling | | |
| Osteoarthritis Pathway | | |
| LPS/IL-1 Mediated Inhibition of | | |
| Telomerase Signaling | | |
| VDR/RXR Activation | | |
| p38 MAPK Signaling | | ■ |
| STAT3 Pathway | | |
| IL-17A Signaling in Gastric Cells | | |
| Glioma Signaling | | |
| Ceramide Signaling | | |
| PPAR Signaling | | |
| Role of IL-17F in Allergic Inflam | | |
| Role of Pattern Recognition Re | | |
| Role of PI3K/AKT Signaling in th | | |
| Huntington's Disease Signaling | | |
| Inflammasome pathway | | |
| Activation of IRF by Cytosolic F | | |
| Acute Phase Response Signalin | | |
| Prolactin Signaling | | |
| Production of Nitric Oxide and F | | |
| iNOS Signaling | | |
| Aryl Hydrocarbon Receptor Sig | | |

FIG. 23

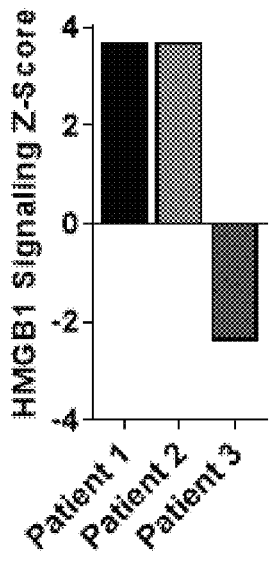 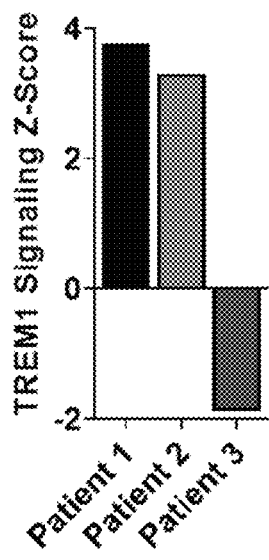 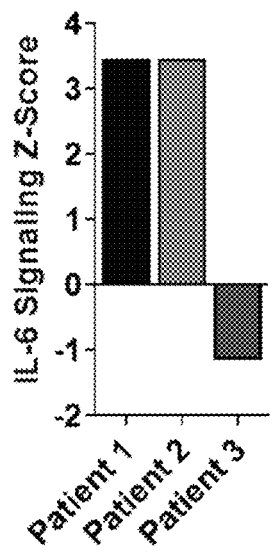
FIG. 24A        FIG. 24B        FIG. 24C
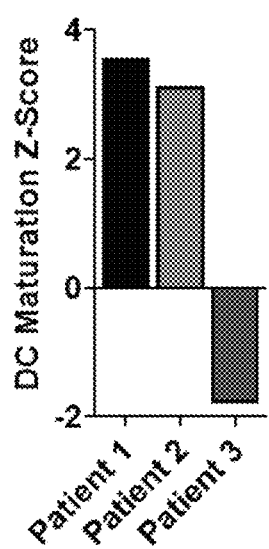 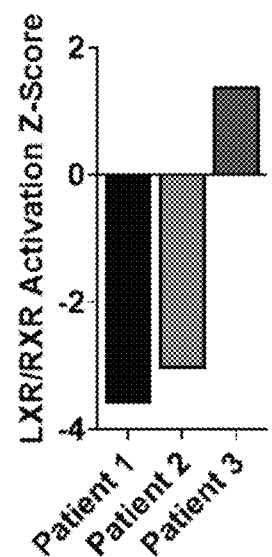 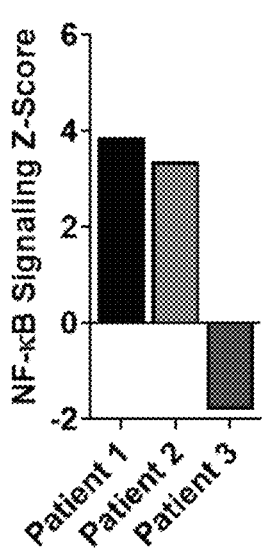
FIG. 24D        FIG. 24E        FIG. 24F

| Material | Parameter | Value | Units |
|---|---|---|---|
| Liver | $\rho$, Density | 1079 | $[kg/m^3]$ |
| | $c_p$, Heat Capacity | 3540 | $[J/kg/K]$ |
| | $k$, Thermal Conductivity | 0.52 | $[W/m/K]$ |
| | $\alpha$, Thermal Coefficient of Conductivity | 2 | $[\%/°C]$ |
| | $\omega_b$, Perfusion | $7.15e^{-3}$ | $[1/s]$ |
| Insulation | $\rho$, Density | 2329 | $[kg/m^3]$ |
| | $c_p$, Heat Capacity | 700 | $[J/kg/K]$ |
| | $k$, Thermal Conductivity | 130 | $[W/m/K]$ |
| | $\sigma$, Electrical Conductivity | $1.0e^{-12}$ | $[S/m]$ |
| Electrode | $\rho$, Density | 7900 | $[kg/m^3]$ |
| | $c_p$, Heat Capacity | 500 | $[J/kg/K]$ |
| | $k$, Thermal Conductivity | 15 | $[W/m/K]$ |
| | $\sigma$, Electrical Conductivity | $2.22e^{-6}$ | $[S/m]$ |

FIG. 34

| Gene name | Avg ΔCt | ΔΔCt | Fold Regulation |
|---|---|---|---|
| CXCL10 | 2.25 | 0.210061 | 381.67 |
| HIF1A | 2.22 | 0.2152 | 51.9 |
| SPP1 | 8.46 | 0.002831 | -87.14 |
| MYC | 3.37 | 0.096867 | -3.94 |
| TLR2 | 10.77 | 0.000572 | -15.97 |

FIG. 35

TREATMENT PLANNING FOR IMMUNOTHERAPY BASED TREATMENTS USING NON-THERMAL ABLATION TECHNIQUES

CROSS-REFERENCE TO RELATED APPLICATIONS

This application claims the benefit of and priority to U.S. Provisional Patent Application No. 62/642,276, filed on Mar. 13, 2018, entitled "Irreversible electroporation for liver cancer immunotherapy," the contents of which is incorporated by reference herein in its entirety.

This application claims the benefit of and priority to U.S. Provisional Patent Application No. 62/642,298, filed on Mar. 13, 2018, entitled "Novel Approaches for Stimulating the Immune System," the contents of which is incorporated by reference herein in its entirety.

This application claims the benefit of and priority to U.S. Provisional Patent Application No. 62/732,703, filed on Sep. 18, 2018, entitled "Real-Time Patient Screening for Immunotherapy," the contents of which is incorporated by reference herein in its entirety.

BACKGROUND

Some types of cancers come with the most dismal prognoses, particularly after metastasis has already occurred. Although several immunotherapies for cancers exists, there still is a great need for techniques to allow treatment customization to improve treatment outcomes on the individual patient level.

SUMMARY

Described herein are aspects of a method of treating a tissue in a patient that can include ablating the tissue using a non-thermal ablation technique; measuring a change in a treatment parameter in real-time during the step of ablating; and administering an additional treatment to the subject in response to the measured change in the treatment parameter. The step of administering the additional treatment can occur 4-30 days post ablating. The additional treatment can be selected from the group of: tissue resection, thermal ablation, non-thermal ablation, chemotherapy, radiation therapy, immunotherapy, biologic therapy, genetic therapy, and combinations thereof. The additional treatment can be measuring the amount of a proinflammatory immune molecule or cell, a suppressive immune molecule or cell, or both in a bodily fluid or a biopsied tissue of the patient. The non-thermal ablation technique can be irreversible electroporation. The non-thermal ablation technique, can be high-frequency irreversible electroporation. The treatment parameter can be bulk tissue conductivity. The change in bulk tissue conductivity can be measured by measuring current during the step of ablating. The step of administering the additional treatment can occur 4-30 days post ablating when the current measured is between 25 A and 100 A. The treatment parameter can be measured by measuring current during the step of ablating. The step of administering the additional treatment can occur 4-30 days post ablating when the current measured is between 25 A and 100 A.

Also described herein are aspects of a method that can include a method of treating a tissue in a patient comprising: inserting first electrode and a second electrode into the tissue applying a plurality of electrical pulses through the first electrode and the second electrode, wherein the electrical pulses are configured to cause non-thermal irreversible electroporation of the tissue; measuring a current of the applied electrical pulses; and administering an additional treatment to the subject in response to the subject, wherein the step of administering occurs 0 to 5 days after non-thermal irreversible electroporation when the current is less than 25 A, and wherein the step of administering occurs 4-30 days after non-thermal irreversible electroporation when the current is between 25 A and 100 A. The additional treatment can be selected from the group consisting of: tissue resection, thermal ablation, non-thermal ablation, chemotherapy, radiation therapy, immunotherapy, biologic therapy, genetic therapy, and combinations thereof. The additional treatment can be measuring the amount of a pro-inflammatory immune molecule or cell, a suppressive immune molecule or cell, or both in a bodily fluid or a biopsied tissue of the patient. The electrical pulses can be configured to cause non-thermal high-frequency irreversible electroporation of the tissue.

Also described herein are aspects of a method of treating a tissue in a patient that can include the step of applying a plurality of electrical pulses to the tissue, wherein the electrical pulses are configured to cause non-thermal irreversible electroporation of the tissue; measuring a current of the applied electrical pulses; administering an additional treatment to the subject in response to the subject, wherein the step of administering occurs 0 to 5 days after non-thermal irreversible electroporation when the current is less than 25 A, and wherein the step of administering occurs 4-30 days after non-thermal irreversible electroporation when the current is between 25 A and 100 A. The additional treatment is selected from the group consisting of: tissue resection, thermal ablation, non-thermal ablation, chemotherapy, radiation therapy, immunotherapy, biologic therapy, genetic therapy, and combinations thereof. The additional treatment can be measuring the amount of a pro-inflammatory immune molecule or cell, a suppressive immune molecule or cell, or both in a bodily fluid or a biopsied tissue of the patient. The electrical pulses can be configured to cause non-thermal high-frequency irreversible electroporation of the tissue. The plurality of electrical pulses can be applied through a plurality of electrodes inserted into the tissue.

BRIEF DESCRIPTION OF THE DRAWINGS

Further aspects of the present disclosure will be readily appreciated upon review of the detailed description of its various embodiments, described below, when taken in conjunction with the accompanying drawings.

(FIG. 12A) Mice were injected with 1.26×106 4T1 cells directly into mammary tissue. On day 11, H-FIRE was administered. Clinical and tumor progression were monitored daily through day 27 where the tumors reached about 1.6 cm in diameter in the untreated mice. n=10 mice per treatment group. *p<0.05. (FIG. 12B) Mice were injected with 1.26× 106 Pan02 cells subcutaneously (s.c.) and tumors were allowed to progress for 10 days. On day 11 (0.5 cm), H-FIRE was administered. Clinical and tumor progression were monitored daily through day 35 where the tumors reached about 1.35 cm in diameter in the untreated mice. n=3 mice per treatment group. *p<0.05.

FIG. 18A) Experimental setup with electrodes inserted into tissue mimic. FIGS. 18B-18E) Live/dead staining reveals regions of the tissue impacted following 80 bursts containing (FIG. 18B) 2, (FIG. 18C) 24, and (FIG. 18D) 50 bipolar 2 µs pulses with a 2 µs delay between alternating pulses. (FIG. 18E) Diffuse treatment of 50 bipolar 2 µs pulses with 20 ms between alternating pulses. Scale bar=2 mm.

FIG. 19A) Viability of cells after overnight incubation measured using LDH following 99 pulses at increasing field strengths. FIGS. 19B-19D) Influence of electric pulse parameters on select gene expression in Pan02 cells measured with real time PCR (ddCt). (FIG. 19B) Il-6, (FIG. 19C) Tslp, (FIG. 19D) Ccl-2. (n=3 repetitions; *,**, +, #p<0.05 ANOVA with Tukeys post-test).

FIG. 20 shows the appropriate shape factor calculation for voltage applied across two needle electrodes. An example three needle configuration is shown. During IRE, pulses are delivered across probe pairs, therefore only two will act as source and sink at any given point. Bulk tissue conductivity is calculated using this shape factor and the resistance according to Ohm's Law (voltage equals current times resistance). The relationship is given by $R=1/(\sigma*K)$ where R is resistance ($\Omega$), $\sigma$ is the conductivity (S/m), and K is the shape factor given in FIG. 20 where I is the spacing between the electrodes and r is the electrode radius.

FIG. 21 shows a table that shows three example shape factor calculations assuming a static, bulk tissue conductivity of 0.2 S/m. The changes in this conductivity value result in changes in the output current. Additionally, changes in the electrode and/or voltage parameters affects the output current value as in the examples shown; V is applied voltage, is σ the bulk electrical conductivity, d is the spacing between the electrodes, r is the radius of the electrodes, K is the shape factor (dimensionless), and l is output current.

FIGS. 24A-24F show graphs show results from the top 6 canonical pathways impacted by H-FIRE, comparing pre-treatment to post-treatment, ranked by z-score. Patient 1 and 2 are highly consistent, with patient 3 demonstrating opposing results.

FIG. 25A. IPA network analysis identified 2 functional networks that fit the canonical pathways identified above, cell injury/death and cell mediated immunity. Both of these networks were significantly upregulated in all patients following H-FIRE treatment FIG. 25C. NF-κB signaling was one of the most dominate pathways impacted by H-FIRE treatment. Gene expression patterns revealed a significant global up-regulation in NF-κB signaling.

(FIG. 26B) A standard IRE voltage waveform pulse and (FIG. 26D) HFIRE 2-5-2 voltage waveform burst.

FIG. 34 shows Tissue and probe properties employed for numerical modeling.

FIG. 35 shows mean (n=3) fold change in gene expression following H-FIRE treatment compared to baseline. Only genes with significant changes in expression are shown.

DETAILED DESCRIPTION

Figure 1:
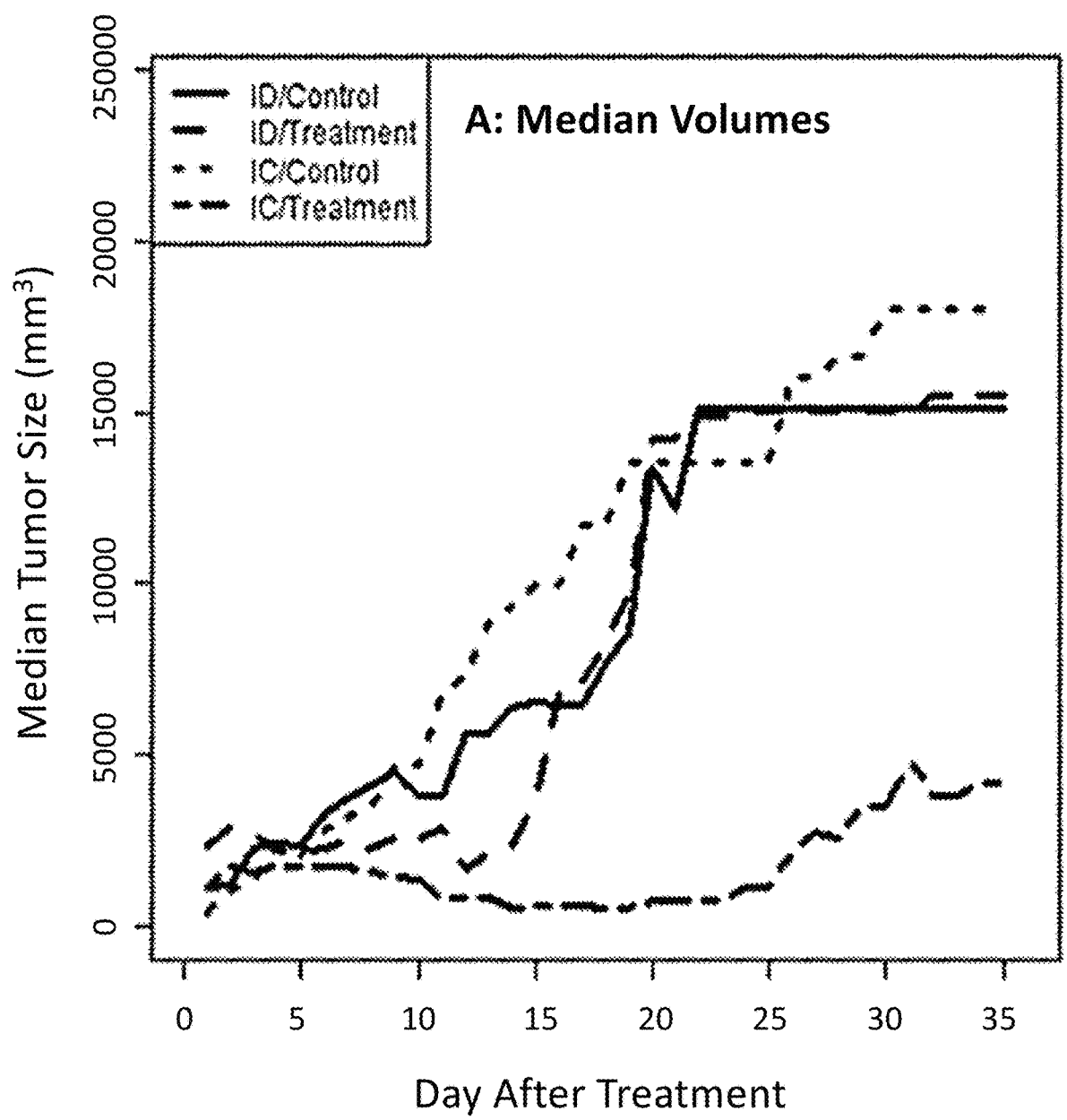
FIG. 1 shows a graph that can demonstrate imputed median primary tumor volumes (mm$^3$) for each group of mice, showing significantly smaller median tumor size in the treated immunocompetent (IC) BALB/c mice.
Figure 2:
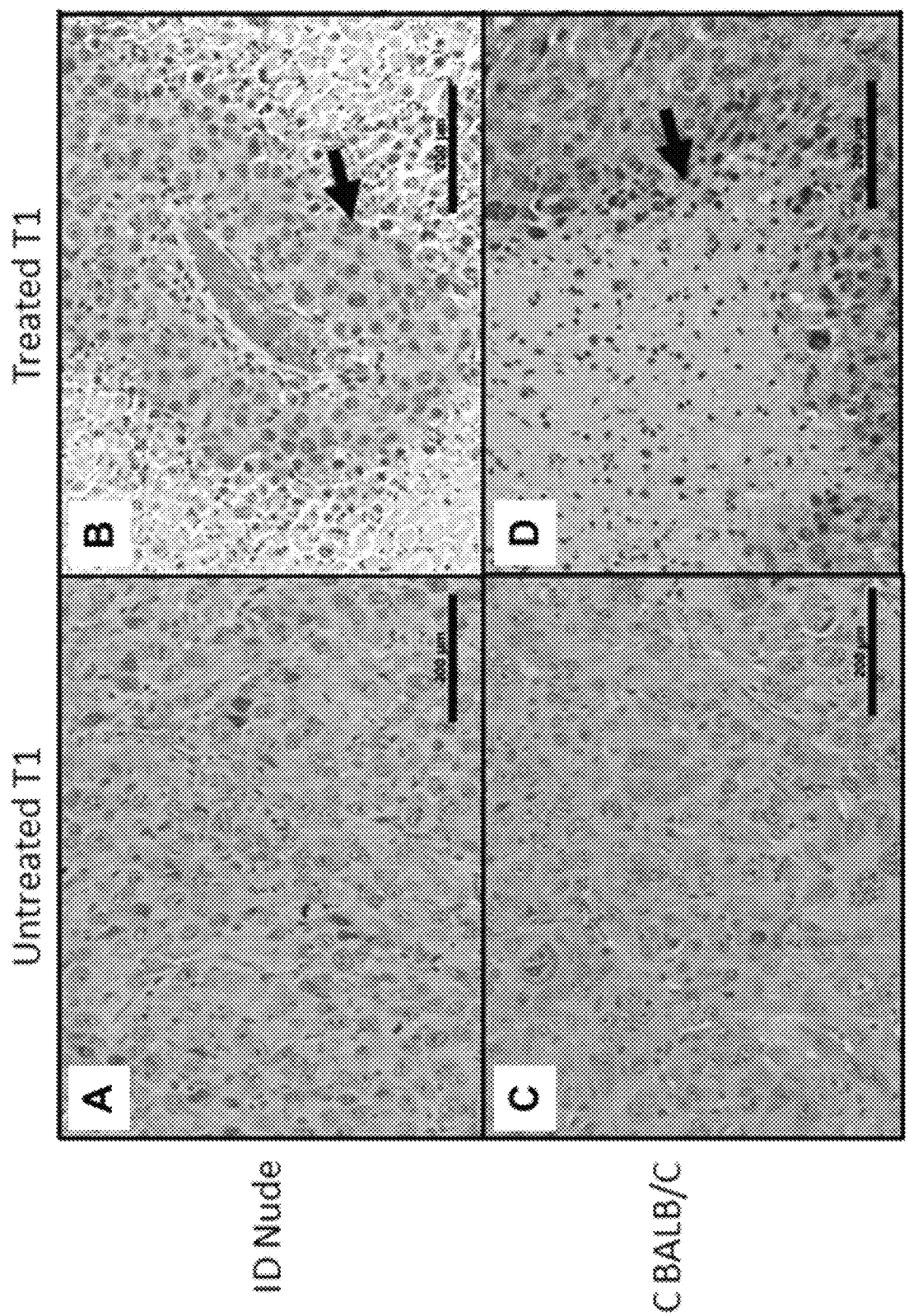
FIGS. 2A-2D show CD3+ staining, which is indicative for T-cell presences, performed for (FIGS. 2A and 2C) untreated and (FIGS. 2B and 2D) treated initial T1 tumors between (FIGS. 2A and 2B) ID nude and (FIGS. 2C and 2D) IC BALB/c mice. There was no notable difference observed in CD3+ infiltration for ID nude mice between (FIG. 2A) untreated and (FIG. 2B) treated tumors. For the IC BALB/c mice, a robust increase in CD3+ (T-cell) infiltration is observed in treated tumors (FIG. 2D) relative to untreated T1 controls (FIG. 2C). Increased T-cell presence in treated T1 IC mice was also more robust than for both groups for nude mice (FIGS. 2A and 2B). All scale bars 200 mm. Panels (FIGS. 2A, 2C, and 2D) 200×, panel (FIG. 2B) 400× magnification

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of immunology, molecular biology, electrophysiology, physiology, cell biology, cancer biology, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible unless the context clearly dictates otherwise.

Definitions

As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "administering" refers to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. In some embodiments, administering can be achieved by any suitable mechanism, technique, and/or device. In some embodiments, administering can be intravenous through a catheter and/or needle.

As used herein, "agent" refers to any substance, compound, molecule, and the like, which can be biologically active or otherwise can induce a biological and/or physiological effect on a subject to which it is administered to. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed As used herein "cancer" can refer to one or more types of cancer including, but not limited to, acute lymphoblastic leukemia, acute myeloid leukemia, adrenocortical carcinoma, Kaposi Sarcoma, AIDS-related lymphoma, primary central nervous system (CNS) lymphoma, anal cancer, appendix cancer, astrocytomas, atypical teratoid/Rhabdoid tumors, basa cell carcinoma of the skin, bile duct cancer, bladder cancer, bone cancer (including but not limited to Ewing Sarcoma, osteosarcomas, and malignant fibrous histiocytoma), brain tumors, breast cancer, bronchial tumors, Burkitt lymphoma, carcinoid tumor, cardiac tumors, germ cell tumors, embryonal tumors, cervical cancer, cholangiocarcinoma, chordoma, chronic lymphocytic leukemia, chronic myelogenous leukemia, chronic myeloproliferative neoplasms, colorectal cancer, craniopharyngioma, cutaneous T-Cell lymphoma, ductal carcinoma in situ, endometrial cancer, ependymoma, esophageal cancer, esthesioneuroblastoma, extracranial germ cell tumor, extragonadal germ cell tumor, eye cancer (including, but not limited to, intraocular melanoma and retinoblastoma), fallopian tube cancer, gallbladder cancer, gastric cancer, gastrointestinal carcinoid tumor, gastrointestinal stromal tumors, central nervous system germ cell tumors, extracranial germ cell tumors, extragonadal germ cell tumors, ovarian germ cell tumors, testicular cancer, gestational trophoblastic disease, hary cell leukemia, head and neck cancers, hepatocellular (liver) cancer, Langerhans cell histiocytosis, Hodgkin lymphoma, hypopharyngeal cancer, islet cell tumors, pancreatic neuroendocrine tumors, kidney (renal cell) cancer, laryngeal cancer, leukemia, lip cancer, oral cancer, lung cancer (non-small cell and small cell), lymphoma, melanoma, Merkel cell carcinoma, mesothelioma, metastatic squamous cell neck cancer, midline tract carcinoma with and without NUT gene changes, multiple endocrine neoplasia syndromes, multiple myeloma, plasma cell neoplasms, mycosis fungoides, myelodyspastic syndromes, myelodysplastic/myeloproliferative neoplasms, chronic myelogenous leukemia, nasal cancer, sinus cancer, non-Hodgkin lymphoma, pancreatic cancer, paraganglioma, paranasal sinus cancer, parathyroid cancer, penile cancer, pharyngeal cancer, pheochromocytoma, pituitary cancer, peritoneal cancer, prostate cancer, rectal cancer, Rhabdomyosarcoma, salivary gland cancer, uterine sarcoma, Sézary syndrome, skin cancer, small intestine cancer, large intestine cancer (colon cancer), soft tissue sarcoma, T-cell lymphoma, throat cancer, oropharyngeal cancer, nasopharyngeal cancer, hypoharyngeal cancer, thymoma, thymic carcinoma, thyroid cancer, transitional cell cancer of the renal pelvis and ureter, urethral cancer, uterine cancer, vaginal cancer, cervical cancer, vascular tumors and cancer, vulvar cancer, and Wilms Tumor.

As used herein, "chemotherapeutic agent" or "chemotherapeutic" refers to a therapeutic agent utilized to prevent or treat cancer.

As used herein, "control" can refer to an alternative subject or sample used in an experiment for comparison purpose and included to minimize or distinguish the effect of variables other than an independent variable.

As used herein, "differentially expressed," refers to the differential production of RNA, including but not limited to mRNA, tRNA, miRNA, siRNA, snRNA, and piRNA transcribed from a gene or regulatory region of a genome or the protein product encoded by a gene as compared to the level of production of RNA or protein by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "dose," "unit dose," or "dosage" can refer to physically discrete units suitable for use in a subject, each unit containing a predetermined quantity of a pharmaceutical formulation or immunotherapy thereof calculated to produce the desired response or responses in association with its administration.

As used herein, "immunomodulator," refers to an agent, such as a therapeutic agent, which is capable of modulating or regulating one or more immune function or response.

As used herein, "mammal," for the purposes of treatments, can refer to any animal classified as a mammal, including human, domestic and farm animals, nonhuman primates, and zoo, sports, or pet animals, such as, but not limited to, dogs, horses, cats, and cows.

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans).

As used herein, the terms "optional" or "optionally" means that the subsequently described event or circumstance can or cannot occur, and that the description includes instances where said event or circumstance occurs and instances where it does not.

As used herein, "patient" can refer to an organism, host, or subject in need of treatment.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "preventative" and "prevent" refers to hindering or stopping a disease or condition before it occurs, even if undiagnosed, or while the disease or condition is still in the sub-clinical phase.

As used interchangeably herein, the terms "sufficient" and "effective," can refer to an amount (e.g. mass, volume, dosage, concentration, and/or time period) needed to achieve one or more desired result(s). For example, a therapeutically effective amount refers to an amount needed to achieve one or more therapeutic effects.

A "suitable control" is a control that will be instantly appreciated by one of ordinary skill in the art as one that is included such that it can be determined if the variable being evaluated an effect, such as a desired effect or hypothesized effect. One of ordinary skill in the art will also instantly appreciate based on inter alia, the context, the variable(s), the desired or hypothesized effect, what is a suitable or an appropriate control needed.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be therapeutic in terms of a partial or complete cure of a disease, condition, symptom or adverse effect attributed to the disease, disorder, or condition. The term "treatment" as used herein covers any treatment of a tumor or a cancer in a subject, particularly a human, and can include any one or more of the following: (a) inhibiting the disease, i.e., arresting its development; and (b) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, "non-thermal ablation" refers to any technique that can result in the destruction and/or death of cells, cellular structures, cellular components, and/or tissue, including human tissue and non-human tissue, within and surrounding a target site, while preserving the extracellular matrix, nerves, major blood vessels, and other sensitive structures of the treated tissues, without raising the temperature of the cells or treated tissues local to and surrounding the target site of ablation to an overall temperature over about 65° C. at the conclusion of pulse delivery and those cells that do not die but are still affected by the treatment. In some aspects, "non-thermal ablation" includes techniques that involve stimulating, killing or altering cellular components of cells and/or tissue with pulsed electrical energy that does not raise the temperature of the cells and/or tissue over about 65° C. at the conclusion of pulse. Non-thermal ablation techniques include, but are not limited to irreversible electroporation (IRE), high frequency irreversible electroporation (HFIRE or H-FIRE) supraporation, reversible electroporation, histotripsy (focused ultrasound), shock wave therapies, high-intensity focused ultrasound (HIFU), and ultrasonic ablation. Techniques and parameters of operation of non-thermal ablation techniques, including HFIRE and IRE can be found in U.S. Pat. No. 8,926,606, U.S. Pat. Pub. 2012/0109122, and U.S. Pat. Pub.: 2014/0039489, which are herein incorporated by reference as if expressed in their entireties.

As used herein, "thermal ablation" refers to any technique that can result in the destruction and/or death of cells, cellular structures, cellular components, and/or tissue, including human tissue and non-human tissue, within and surrounding a target site, by transmitting energy, sufficient to increase the overall temperature of the tissue and/or cells within or surrounding a target site to above 65° C. Thermal ablation techniques can include but are not limited to electrical energy, microwave ablation, a radiofrequency (RF) ablation, dual thermal ablation, and laser ablation.

As used herein, "ablation" without further qualification refers to both thermal and non-thermal ablation.

As used herein, "immunosuppressive treatment" refers to any treatment modality, including, but not limited to, thermal ablation, resection, and/or chemotherapy, that do not allow for the innate and/or adaptive immune responses to active, peak, and/or come to completion.

As used herein, "non-immunosuppressive treatment" refers to any treatment modality, including, but not limited to, non-thermal ablation, such as IRE and/or HFIRE, that allows for the innate and/or adaptive immune responses to active, peak, and/or come to completion.

Discussion

Some types of cancers come with the most dismal prognoses, particularly after metastasis has already occurred. In some cases, tumor resection and/or thermal ablation is not a viable option for therapy. Further, while delivery of chemotherapeutics are often part of a standard cancer therapy regimen or protocol, they may also be immunosuppressive, and thus can reduce the patient's own immune system's ability to combat the cancer and mute or otherwise suppress the patient's biological immune defense mechanisms. Additionally, tumors in some areas, such as immunotolerant organs and systems (e.g. liver, gastrointestinal organs, respiratory system, genitourinary tract), are not affected as much by the patient's immune system because its immediate microenvironment is effectively immunosuppressed. The immunosuppressive microenvironment characteristic in immunotolerant organs are characterized by a balance between pro-inflammatory and anti-inflammatory mediators produced by specialized immune cells that reside in these organs and serve to protect the system from overzealous immune responses that can lead to diseases, such as those associated with autoimmunity. However, this immunosuppression can promote tumorigenesis and become a hindrance to certain therapeutics, such as checkpoint inhibitor therapies, that function through activating the immune system. This immunosuppression in both healthy immunotolerant organs and in tumors is, in part, mediated by groups of immunosuppressive cells, including regulatory T cells (Treg), tumor associated macrophages (TAM), tumor associated neutrophils (TAN), and myeloid derived suppressor cells (MDSC). Based on the location and type of tumor, in many cases, tumor resection is immediately considered as a viable treatment option followed by chemotherapy and other modalities, such as thermal ablation. As stated above, the use of resection, chemotherapy, and thermal ablation may reduce a subject's or patient's ability to capitalize on their own immune response.

Cancer immunotherapy, which involves eliciting a host immune response that can result in tumor regression has been an increasingly compelling field of interest. Much focus in this field has been on the vaccination against various cancer types by injecting cancer antigens and thus stimulating the host's immune system to target the cancer. A more recent area of investigation for inducing anti-tumor immunity is based on the direct destruction of cancerous tumors by ablative methods. By treating cancer using ablative approaches, the tumor may undergo a multi-agent anti-cancer treatment or vaccine through the production of tumor antigens resulting from the destructed tissue. Although some efficacy in some patients has been achieved, the invention described herein provides for the ability to optimize patient treatment planning and improve treatment outcome at the individual patient level. Most common cancer treatments, including, but not limited to, thermal ablation, resection, and delivery of chemotherapies limit or hinder the natural biological immune response and what is needed in the art is a primary treatment modality of non-thermal ablation, such as IRE or HFIRE, that targets the destruction of tumor cells and/or tissue at the target site and the surrounding area, while also supporting, maintaining, and enhancing the natural biological immune response.

After treatment of a target site, including, but not limited to, thermal ablation, non-thermal ablation, resection, chemotherapy, and other modalities, a human patient will have both an innate immune response and an adaptive immune response. While the innate immune response peaks a couple of days (up to 72 hours or more) post treatment e.g. IRE, the adaptive immune response takes longer to promote (about 10-21 days). The adaptive immune response can destroy circulating and/or metastatic cancer cells. This peak or total response time for both the innate and adaptive immune responses are important factors when considering an overall treatment plan for a patient. As disclosed herein, and described in greater detail below, one advantage of using non-thermal ablation, such as IRE or HFIRE, as a primary modality for treatment of tumors is to allow the patient's innate and adaptive immune responses sufficient time to peak or respond. In other words, non-thermal ablation, such as IRE and HFIRE, may be described herein as a form of non-immunosuppressive treatment modalities. A non-immunosuppressive treatment modality is a form of treatment that allows for the innate and adaptive immune response to active, peak, and/or come to completion, thereby providing the patient with the important immune response defense to the tumor. Conversely, common treatment modalities used in the art today, including, but not limited to, thermal ablation, resection, and/or chemotherapy are considered immunosuppressive treatments, meaning they do not allow for the innate and adaptive immune responses to active, peak, and/or come to completion, thereby depriving the patient of important immune response defense.

Depending on the tumor type and tissue location of the tumor, it is common practice for an overall treatment plan to include delivery of multiple forms of treatment modalities to a patient, including, but not limited to, thermal ablation, resection, and/or chemotherapy. If any of these treatment modalities, such as thermal ablation, resection, and/or chemotherapy, is completed before the innate immune response can peak and trigger the adaptive immune response, then the subject may not benefit from this overall immune response effect. As described above, these treatment modalities may be considered immunosuppressive. If any of these treatment modalities, such as thermal ablation, resection, and/or chemotherapy, is completed before the innate immune response can peak and trigger the adaptive immune response, then the subject may not benefit from this overall immune response effect. As described above, these treatment modalities may be considered immunosuppressive. Moreover, if a non-immunosuppressive treatment modality, such as non-thermal ablation using IRE or HFIRE, is followed by an immunosuppressive treatment modality, such as thermal ablation, resection, and/or chemotherapy, without waiting a sufficient amount of time this secondary immunosuppressive treatment modality may impede the innate and/or adaptive immune response. Therefore, there is a need in the art to confirm that a sufficient delay in time, which is described below in greater detail, may be measured in terms of days, has passed after the primary non-immunosuppressive treatment has been delivered before any secondary immunosuppressive treatment is delivered. Improved immune system activation/promotion is expected to improve local tumor ablation, increased tumor surveillance, and increased targeting of metastatic lesions at sites distal to the primary tumor. If the delivery of an immunosuppressive treatment modality is given to a patient before the innate and/or adaptive immune responses active, peak, and/or come to completion, the patient may lose these benefits.

Figure 9:
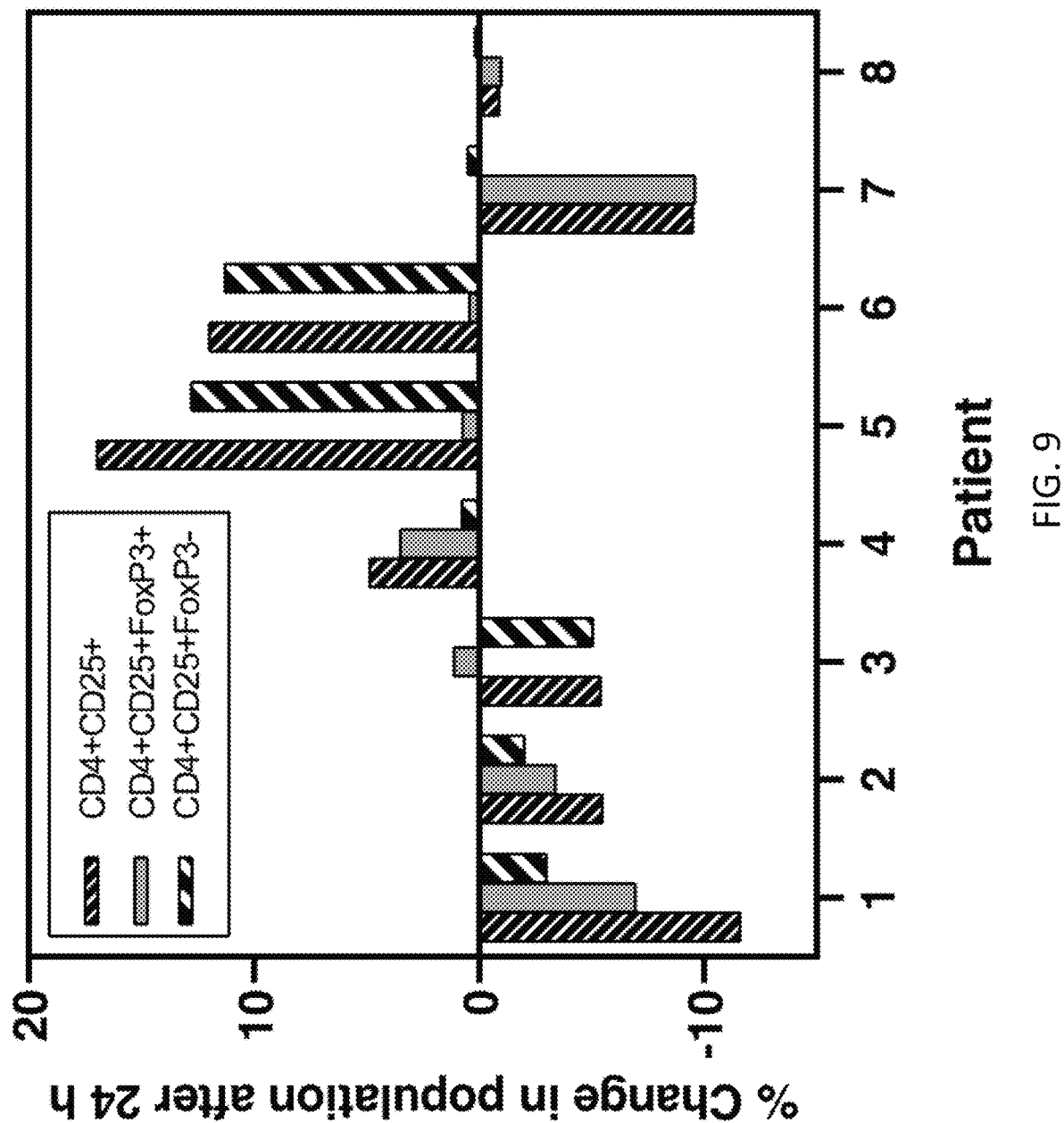
FIG. 9 shows a graph that can demonstrate the percent change in Regulatory T-cell subpopulations i.e. CD4+CD25+, CD4+CD25+FoxP3+, and CD4+CD25+FoxP3−, after 24 hours following IRE treatment. Populations were calculated as a subset of total CD4+ cells. n=7

Described herein are treatment devices, systems and methods of measuring, directly or indirectly, a treatment parameter, including, but not limited to, the bulk tissue conductivity using a suitable technique in real-time during a non-thermal ablation treatment and forming a treatment plan based on the measured the treatment parameter, such as the tumor bulk tissue conductivity of the tissue being treated. As shown in FIG. 9, the devices, systems, and methods described herein can result in patient stratification based on their ability to immunologically respond to non-thermal ablation treatment, which provides the opportunity for a clinician to prescribe customized precise care and improve treatment outcome. This treatment plan may include stopping the delivery of non-thermal ablation, such as stopping the delivery of electrical pulses used for IRE and/or HFIRE, before the non-thermal ablation is complete, and/or treating the subject with subsequent suitable treatment modalities, including, but not limited to, immunosuppressive treatment(s) and/or non-immunosuppressive treatment(s). The subsequent treatment(s) can be different than the current standard of care for that patient. In other words, the clinician can make different treatment decisions based on the real-time measurement a treatment parameter, such as bulk tissue conductivity of the tissue being treated, during a non-thermal ablation treatment. As is discussed elsewhere herein the different treatment regimens that can be prescribed and applied can aim to take advantage of an innate and/or adaptive immune response that can be activated by the non-immunosuppressive non-thermal ablation treatment. In some instances, non-thermal ablation techniques may be used after immunosuppressive treatment efforts are delivered. The devices, systems, and methods described herein can be a departure from that standard paradigm and instead be used prior to down-stream treatments and co-therapies to provide a more precise and individualize treatment approach. Even when non-thermal ablation is already a first form of treatment, the devices, systems, and method described herein can be used to adjust and customize the patient's overall treatment protocol, thereby increasing the overall efficacy of secondary or downstream treatments.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Described herein are aspects of a method of treating a target site comprising target tissue (e.g. tumor and/or cancer) and/or target cells in a subject, that can include the step of measuring, directly or indirectly, a treatment parameter, including, but not limited to, bulk tissue conductivity, in real-time during a non-thermal ablation treatment and determining a downstream and/or secondary treatment regimen for the patient based on the measured treatment parameter, such as the bulk tissue conductivity, or change thereof during non-thermal ablation therapy. In some aspects the non-thermal ablation treatment can be the delivery of electrical pulses capable of resulting in IRE and/or H-FIRE of the tissues and/or cells within and surrounding the target site. Other suitable non-thermal ablation treatments are described elsewhere herein. Moreover, the non-thermal ablation may also be a non-immunosuppressive treatment modality.

Using IRE as a model to discuss the specific treatment parameter of bulk tissue conductivity, attention is directed to FIG. 20 shows the appropriate shape factor calculation for voltage applied across two needle electrodes. An example three needle configuration is shown. During an IRE treatment, electrical pulses are delivered across at least a pair of electrodes, therefore only two electrodes may act as source and sink at any given point. Bulk tissue conductivity is calculated using this shape factor and the resistance according to Ohm's Law (voltage equals current times resistance). The relationship is given by $R=1/(\sigma*K)$ where R is resistance ($\Omega$), $\sigma$ is the conductivity (S/m), and K is the shape factor given in FIG. 20, where l is the spacing between the electrodes and r is the electrode radius. FIG. 21 shows a table that shows three example shape factor calculations assuming a static, bulk tissue conductivity of 0.2 S/m. The changes in this conductivity value result in changes in the output current. Additionally, changes in the electrode distance, size, and shape, and/or voltage and pulse parameters affects the output current value as in the output current value as in the examples shown; V is applied voltage, is tithe bulk electrical conductivity, d is the spacing between the electrodes, r is the radius of the electrodes, K is the shape factor (dimensionless), and l is output current. Although the change in amperage or absolute value in amperage that would indicate to a clinician to make a treatment decision, indicate that a patient would be a responder to immunotherapy, and/or apply a secondary treatment as described elsewhere herein, may change based on the specific device and treatment characteristics, based on those specific characteristics one of ordinary skill in the art will be able to calculate an equivalent change in amperage and/or threshold value to base a treatment decision, diagnosis, treatment application on.

In some aspects, the clinician can determine a treatment strategy for a patient in response to a positive change in the treatment parameter. The positive change can be an increase in the absolute value in current, a percentage increase in the current, and/or a percentage increase or change in the bulk conductivity of the tissue. In some aspects, the positive change can be an increase in the current to over 25 A. In some aspects, the positive change can be an increase in the absolute value in the current to about 25-100 A. The amperage that is considered a positive change can vary based on, for example, the tissue and the characteristics of the device used (e.g. electrode length, distance apart, etc.). Based on the exact parameters used for treatment, one of skill in the art can calculate the appropriate amperage values that would guide a clinician in further treatment of the patient as described herein. This is discussed in greater detail elsewhere herein. In some aspects, the positive change can be in increase in the percentage change in current. In some aspects, the percentage change can range from about 100% to about 400%. In some aspects, the percentage change can be about 175%. In some aspects, the positive change can be an increase or change in the tissue bulk conductivity such that tissue bulk conductivity ranges from about 0.7 S/m to about 1.5 S/m. In some aspects, a positive change can be reached when the tissue bulk conductivity reaches about 1 S/m. In some aspects, treatment is delayed for a period of time (e.g. 4-30 days) when a positive change in the treatment parameter occurs. In some times treatment that is different than the standard of care is taken when a positive change in the treatment parameter occurs. In some aspects, immediate treatment action is taken when a positive change in the treatment parameter occurs. In some aspects, patients that will respond to immunotherapy can be identified when a positive change in the treatment parameter occurs.

The downstream or secondary treatment regimen can be any suitable treatment modality and can include, but is not limited to, tumor resection, thermal ablation, a subsequent non-thermal ablation, chemotherapy, radiation therapy, immunotherapy, biologic therapy, genetic therapy (gene editing), and combinations thereof. In some aspects, the subsequent downstream treatment(s) is/are delayed a period of time that can be at least 4-30 days after the initial non-thermal ablation treatment. This can allow both the innate and the adaptive immune systems to be promoted. In some aspects, the period of time that downstream treatment can be delayed can be 4, 5, 6, 7, 8, 9, 10, 11, 12, 13, 14, 15, 16, 17, 18, 19, 20, 21, 22, 23, 24, 25, 26, 27, 28, 29, or 30 days.

The downstream treatment regimen can optionally be or include measuring an immune response in the subject at one or more time points post non-thermal ablation treatment. In some aspects, the activation/promotion of the immune response can be evaluated by monitoring the reduction in immunosuppressive immune molecules and/or increase in pro-inflammatory molecules on the local and systemic level. In some aspects, the population of Treg cells are monitored. Other suitable immune molecules and/or cell types that can be measured post non-thermal ablation can include, but are not limited to, interferon gamma (IFNg); TNF; IL-6; HMGB1; ATP; IL-21; IL-22; IL-23; IL-1B (which are all secreted proteins or damage associated molecular patterns that are associated with inflammatory conditions and whose increase is associated with an increase in the immune response) TGFB, IL-2, IL-10, Tregs, TAMs, TANs, and MDSCs (which are cell types and molecules whose decrease is associated with decreasing suppression of the immune response). These immune molecules and/or cells can be measured in biopsy or other tissue and/or a bodily fluid (e.g. blood, saliva, urine, breast milk). The local and/or systemic levels of one or more of these immune molecules and/or cells can be measured. Assays and techniques (e.g. flow cytometry, spectroscopy, immunoassays, and the like) for detecting and measuring these immune cells and/or molecules will be appreciated by those of ordinary skill in the art. Monitoring can occur for 1-30 days or more post non-thermal ablation treatment. In some aspects, the only additional treatment step taken is monitoring of the immune response.

Downstream or secondary treatment(s) can be delayed when the current increases above 25 A. Downstream or secondary treatment(s) can be delayed when the current increases to between 25 A and 100 A. Downstream or secondary treatment(s) can be delayed when the current increases about 100% to about 400% from the start of treatment. Downstream or secondary treatment(s) can be delayed when the tissue bulk conductivity reaches about 0.7 S/m to about 1.5 S/m.

In some aspects, a treatment parameter such as the bulk tissue conductivity can be measured during a non-thermal ablating treatment via measuring tissue impedance. Methods and techniques for measuring tumor tissue impedance can include measuring impedance using an impedance sensor during the initial non-thermal ablation treatment. In some aspects, the bulk tissue conductivity can be measured during a non-thermal ablation treatment by evaluating current output during a non-thermal ablation treatment or a change in current during non-thermal ablation treatment. It will be appreciated that the tissue can be modeled as an electric circuit. Non-thermal ablation and/or tissue impedance measurement technique that relies on delivery of a current to the tissue can result in pores in the membrane that can disrupt cell membrane capacitance and result in a lower cell resistance and an observed periprocedural current rise, which can be measured in real time. Current can be measured by a variety of techniques, including but not limited to impedance spectroscopy, MREIT, and impedance of tissue (previously discussed). In some aspects, when the current rises to above 25 A, rise to between 25 A and 100 A, or not rise above 25 A during treatment, this can indicate to a clinician that an immune response in the patient can be promoted, which can result in alteration to downstream or secondary treatment procedures. In some aspects, the non-thermal ablation treatment can be the delivery of electrical pulses that results in either IRE and/or H-FIRE of tissue and/or cells within the target site and surrounding the target site.

In some aspects, where the current is measured in real-time and rises to above 25 A, then the non-thermal tissue ablation procedure can be ceased and a subsequent treatment plan may be developed that includes, but not limited to, the delivery of downstream or secondary treatment(s) that can be delayed 4-30 days. In some aspects, when the current does not rise above 25 A, then a downstream or secondary treatment(s) can begin immediately or within 5 days post non-thermal ablation. In aspects where the patient's immune response is going to be monitored by detecting and/or measuring the levels of immunosuppressive and/or pro-inflammatory immune molecules and/or cells, screening can begin before, during, and/or after non-thermal ablation treatment and is not depending on any change in or threshold level of bulk tissue conductivity.

In some aspects, the method of treating a tissue (e.g. a tumor or a cancer) in a subject can include: administering non-thermal ablation to a treatment site, measuring bulk tissue conductivity of the tissue during the non-thermal ablation, detecting a change in the bulk tissue conductivity during the non-thermal ablation and performing an additional downstream treatment in response to the change in the bulk tissue conductivity. In some aspects, the bulk tissue conductivity can be measured by measuring tissue impedance (e.g. via an impedance sensor). In some aspects, the bulk tissue conductivity can be measured by measuring a change in current that can be applied to the treatment site. In some aspects, downstream treatment(s) can be delayed when the current increases above 25 A. Downstream treatment(s) can be delayed when the current increases to between 25 A and 100 A.

In some aspects, the method of treating a tissue and/or cells (e.g. a tumor or a cancer) within a target site in a subject can include: administering non-thermal ablation to a treatment site, measuring a treatment parameter, including, but not limited to the bulk tissue conductivity of the tissue during the non-thermal ablation, detecting a change in the treatment parameter, such as the bulk tissue conductivity during the non-thermal ablation and performing an additional downstream or secondary treatment in response to the change in the bulk tissue conductivity (the measured treatment parameter). In some aspects, the bulk tissue conductivity can be measured by measuring tissue impedance (e.g. via an impedance sensor). In some aspects, the bulk tissue conductivity can be measured by measuring a change in current that can be applied to the treatment site. In some aspects, downstream or secondary treatment(s) can be delayed when the measured current increases above 25 A. Downstream or secondary treatment(s) can be delayed when the measured current increases to between 25 A and 100 A.

In some aspects, the method of treating tissue and/or cells (e.g. a tumor or a cancer) within a target site in a subject can include: administering a specific set of a plurality of electrical pulses to the target site which can induce non-thermal irreversible electroporation (IRE) and/or non-thermal High Frequency irreversible electroporation (H-FIRE) of the treatment site; measuring a treatment parameter, including, but not limited to, current during the step of administering the plurality of electrical pulses to the tumor; detecting a change in the measured parameter such as current; and performing an additional downstream or secondary treatment as a result of the change in current (the measured treatment parameter), wherein the downstream or secondary treatment step can include, but is not limited to, tumor resection, thermal ablation, a secondary non-thermal ablation, chemotherapy, radiation therapy, immunotherapy, biologic therapy, genetic therapy (gene editing), and combinations thereof. In some aspects, if there is not a positive change in the current, then this can indicate that the immune system (local and/or systemic) of the subject will not be stimulated by the IRE and/or H-FIRE treatment and thus there is no reason to delay the downstream or secondary treatment.

In some aspects the current can increase during non-thermal IRE and/or H-FIRE. Downstream or secondary treatment(s) can be delayed when the current increases above 25 A. Downstream or secondary treatment(s) can be delayed when the current increases to between 25 A and 100 A. Downstream or secondary treatment(s) can be delayed when the current increases about 100% to about 400% from the start of treatment. Downstream or secondary treatment(s) can be delayed when the tissue bulk conductivity reaches about 0.7 S/m to about 1.5 S/m.

In some aspects, the immune response can be measured by detecting one or more immune molecules or cell types at a time point after the delivery of the non-thermal ablation such as IRE and/or H-FIRE. This is also discussed in greater detail elsewhere herein. The immune response stimulated by the non-thermal ablation, such as IRE and/or H-FIRE, can be pro-inflammatory and/or non-immunosuppressive.

In one example, insofar as the subject can be immunologically responsive to the IRE and/or H-FIRE where there is a positive change in current, for example a change of current between 25 A-100 A, the downstream or secondary treatment of a tissue resection can be delayed for a period of time in an effort to best engage the adaptive immune system, which peaks 10-21 days post-stimulation. This intentional and/or planned delay in time between the primary non-immunosuppressive treatment of non-thermal ablation and the downstream or secondary immunosuppressive treatment of a tissue resection is an example of a treatment plan specifically devised by the clinician to allow, in-part, for the subject's own immune response to respond and work to destroy the tumor or metastatic cells in circulation. In some cases, the subject's own immune response can respond to tumor antigens released as a result of the non-thermal ablation such as IRE and/or H-FIRE or already present. In some aspects, when a positive change in current, for example a change of current between 25 A-100 A, is detected, the downstream or secondary immunosuppressive treatment of a tissue resection of all or part of the tumor is delayed for a period of time to allow the subject's immune system to respond to the H-FIRE and/or IRE.

In yet another example, insofar as the subject can be immunologically responsive to the primary non-immunosuppressive treatment of non-thermal ablation and a positive change in current, for example a change of current between 25 A-100 A, is detected, the primary non-immunosuppressive treatment of non-thermal ablation may be intentionally stopped by the clinician mid-treatment and before all of the planned electrical pulses have been delivered. For example, if the primary non-immunosuppressive treatment of non-thermal ablation has an initial treatment plan of delivering at least 90 total electrical pulses over the entire non-thermal ablation procedure, and a treatment parameter, such as a positive change in current is monitored and detected to have a change of between 25 A-100 A, before all of the at least 90 total electrical pulses have been delivered, then the clinician may pause and/or stop the delivery of electrical pulses as this change in current may indicate that the subject's immune system is having a positive respond to the non-thermal ablation procedure and the treatment does not need to be completed as originally planned.

In some aspects, the patient is a subject that is eligible for tumor resection surgery as a current standard of care. Standards and guidelines for determining if a tumor and thus a subject is eligible for a resection procedure will be instantly appreciated by one of ordinary skill in the art. In some cases, the method can be performed on a subject that is ineligible for tumor resection to monitor the effect of other treatment modalities and/or determine when other treatment modalities should be administered as discussed in greater detail elsewhere herein.

In some aspects, the method described herein can be performed on the remaining tissue after a partial resection of tissue.

In some aspects, the method described herein can be used to screen patients to determine if their (or will not) immune response will be stimulated post-non-ablation treatment or not. In other words, the method described herein can be used to screen patients to determine if they will respond to this immunotherapy or not and thus be used by the clinician to determine and administer an appropriate treatment for the individual patient.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1

Patients with pancreatic cancer have one of the most dismal prognoses of all cancer types with an approximate five-year survival rate less than 5%. A primary cause of such discouraging statistics is that most cases of pancreatic cancer are diagnosed after metastasis has already occurred. Of all pancreatic cancer types, pancreatic ductal adenocarcinoma (PDAC) represents approximately 95% of cases. The only curative option for patients with PDAC is surgery, yet most patients present with unresectable tumors (due to the involvement of critical structures) and prognosis remains poor. Most patients with metastatic PDAC are given cytotoxic chemotherapy for palliative care. Recently, a combinatorial chemotherapy cocktail (FOLFIRINOX) consisting of oxaliplatin, irinotecan, fluorouracil, and leucovorin has been shown to incrementally improve survival rates for patients with metastatic pancreatic cancer, however, its associated toxicity profile limits its use to otherwise healthy patients.

To achieve an optimal clinical outcome (with destruction of both primary and metastatic cancer cells), it is important to consider how different therapeutic strategies affect the patients' immune systems. Most common chemotherapies may be considered immunosuppressive therapies and limit or hinder the natural biological immune response. What is needed in the art is a primary treatment modality, such as a non-immunosuppressive non-thermal ablation modality like IRE and/or HFIRE that targets the destruction of tumor cells while also supporting, maintaining, and enhancing the natural biological immune response. By attacking tumor and/or cancer cell using non-thermal ablative approaches, the tumor and/or cancel cell may actually act as its own multiagent anti-cancer vaccine through the production of tumor antigens resulting from the destructed tissue and/or cells. Likewise, this could potentially afford destruction of both primary and metastatic cancers and prevent the likelihood of cancer recurrence. Such alternative modalities either as supplement to chemotherapy or as stand-alone primary treatments to enhance immune response are needed. Clinicians are also in need of treatment planning methods and systems to determine an overall treatment regime that will be most effective for a given patient. The method described in this Example 1 can aid clinicians in deciding which secondary or downstream treatment(s), after non-thermal ablation has been delivered as a primary treatment, are optimal for a given patient. Additionally, non-thermal ablation such as IRE and/or HFIRE may lend itself as a preliminary or primary treatment modality as it is a non-immunosuppressive treatment, and a clinician may decide to deliver the non-thermal ablation prior to a downstream or secondary treatment(s), such as tumor resection.

Moreover, a clinician can be able to use real-time feedback of a treatment parameter, including, but not limited to, a change in current, during the preliminary or primary non-thermal ablation treatment such as IRE and/or HFIRE to create a patient specific treatment plan that is intended to maintain, support, and/or enhance the patient's immune response. If there is a positive change in current, clinicians can leave the tumor in situ while the immune response is promoted, and follow up after a period of time, such as 4-30 days, with administration of downstream treatment(s) such as tumor resection, thermal ablation, a subsequent non-thermal ablation, chemotherapy, radiation therapy, immunotherapy, biologic therapy, genetic therapy (gene editing), and/or combinations thereof. If there is no positive change in current, the clinician could immediately perform the downstream or secondary treatment(s), such an immediate tissue resection and put the patient on a standard of chemotherapy therapy. Such an approach could greatly increase the number of patients that would benefit from non-thermal ablation as a preliminary or primary treatment modality.

Background

Irreversible electroporation (IRE), which can include H-FIRE, is a non-thermal and non-immunosuppressive ablation technique used to kill cancerous tissue by delivering short electric pulses through electrodes inserted directly into a target site. The resulting electric field increases the transmembrane potential and disrupts cell homeostasis through irreversible membrane pore formation, leading to cell death. IRE can be used to treat unresectable tumors in close proximity to vital structures, such as PDAC surrounding the superior mesenteric artery (SMA). Thus, IRE can be used to treat tumors with intricate morphologies while preserving nerves and major blood vessels in the treatment zone, making it an excellent surgical candidate when resection or thermal ablations are limited by these critical structures. This modality is also particularly attractive for tumors with perineural invasion, which is related to pain and worsened prognosis. To date, IRE has been clinically used to treat human pancreatic, prostate, liver, and kidney tumors and is currently in clinical trials for the ablation of unresectable pancreatic cancer. IRE has been shown to be promising in treating locally advanced pancreatic cancer (LAPC). In a 200 patient clinical trial, IRE combined with resection doubled the median survival rate of LAPC patients. IRE can be modulated to enrich an anti-tumor microenvironment, surpassing traditional pancreatic cancer treatment paradigms. Additionally, it is disclosed herein that using real-time a treatment parameter, such as a change in measured current, can be used to create a patient specific treatment regime that enhances this modulation and enrichment that in turn may lead to regression of primary and metastatic disease through the production of an anti-tumor immune response. Initial results suggest a positive systemic immune response resulting from local ablation, making this technology potentially beneficial for metastatic diseases. This invention utilizes the now clinically available IRE treatment option to monitor the pro-immune response of a patient in real time.

A rapidly advancing field of research in energy-based ablation technologies is based on the concept of immunomodulation that is promoted as a result of a primary tumor ablation, which could contribute to yet another mechanism of tumor cell death and destruction. Combining non-thermal ablation procedures, such as IRE and/or HFIRE, with a downstream or secondary treatment(s) of delivering immunotherapies to a subject has been shown to induce an abscopal effect in which the local non-thermal ablation promotes systematic immune responses leading to regression of tumors and/or cancer cells distant from the target or treatment site. Conversely, high temperature based thermal ablation methods destroy tumors by disruptive necrosis which results in protein denaturation and reduces the amount of intact antitumor antigens while coagulating the tissue, preventing the spill of intracellular products into systemic circulation. Whereas the non-thermal ablation, such as IRE and/or HFIRE, maintains intact intracytoplasmic organelles and proteins, while opening up the plasma membrane, releasing intact, recognizable tumor antigens. In particular, supplying the patient's immune system with adjuvants has been shown to better promote a positive systemic immune response in patients.

The non-thermal mechanism of IRE promotes a more pro-inflammatory and non-immunosuppressive response when compared to thermal ablation techniques. This suggests that a non-thermal ablation such as IRE and/or HFIRE can be used in conjunction with immunotherapy to optimize patient survival. This also suggests that it may be possible to create a patient specific treatment protocol or regime using real-time feedback of a treatment parameter, such as a change in current of from about 25 A-100 A, from the IRE and/or HFIRE procedure. The immune response to IRE has been examined in osteosarcoma rat and renal carcinoma mouse models. Local anti-tumor response (FIG. 1) has been shown to be greater in immunocompetent BALB/c mice when compared with immunodeficient nude mice. IC mice also exhibited higher T-cell infiltration relative to control (FIGS. 2A-2D). In mice treated with IRE, the therapy also promoted a systemic immune response which protected the mice from tumor re-challenge.

This Example can describe the use of real-time current feedback from IRE treatment by the clinician to determine the optimal downstream or secondary treatment(s) to maximize patient outcome and maximize the patient's immune response. Depending on monitored and measured treatment parameter feedback, such as a change in current between 25 A-100 A, the clinician can determine if the patient is having a positive immune response and choose to continue treatment with either continuing the non-thermal ablation or select the downstream or secondary treatment and an optimal delay between these treatments if so desired. Non-thermal ablation such as IRE and/or HFIRE can create an inflammatory response and increases antigen presentation at the primary tumor, and this release of antigens and cellular content from the cells can be monitored in real time using the IRE pulse delivery device. This method can allows clinician to make real time decisions about adjuvant therapies during the IRE treatment itself. Thus, IRE lends itself as a preliminary therapy to determine the extent of a patient's immune response and inform clinicians as to which subsequent therapy to administer.

Method Summary

Seven patients with unresectable Pancreatic Ductal Adenocarcinoma (PDAC) were treated with IRE. Postoperative management of patients treated for pancreatic lesions with IRE is standard and follows guidelines for any type of pancreatic resection. Forkhead box P3 (FoxP3) expressing T-regulatory cells are a sign of immune tolerance. To identify T-regulatory cells and FoxP3 subsets, isolated peripheral blood mononuclear cells (PBMC) were labeled with anti-CD4–Pe-Cy-5, CD25–Pe and anti-FoxP3– AlexaFlour488. Concentrations of CD4+ and CD25+ cells and T-regulatory levels were measured using a flow cytometer assay for PBMC in CD4+ cells. FoxP3 subset T-regulatory cells were identified as those stained with antibodies against FoxP3/CD25 and identified according to the expression of CD4+, CD25hi and FoxP3+ by fluorescence-activated cell sorting (FACS). All PBMC samples were analyzed within 3 hours of collection to ensure cell viability.

Figure 3:
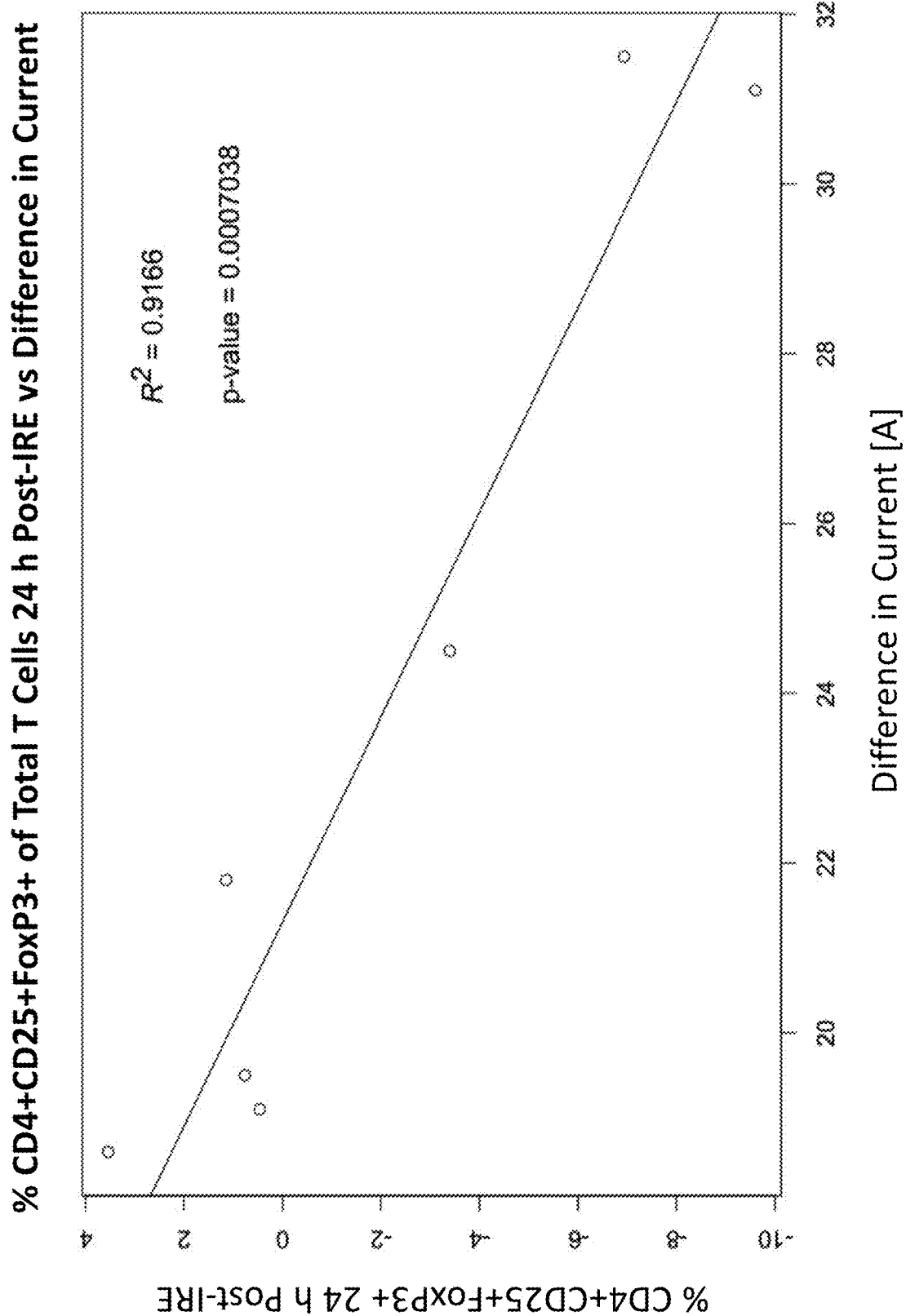
FIG. 3 shows a graph that can demonstrate percent CD4+CD25+FoxP3+ of total T cells 24 h post-IRE vs. difference in current (n=7).
Figure 4:
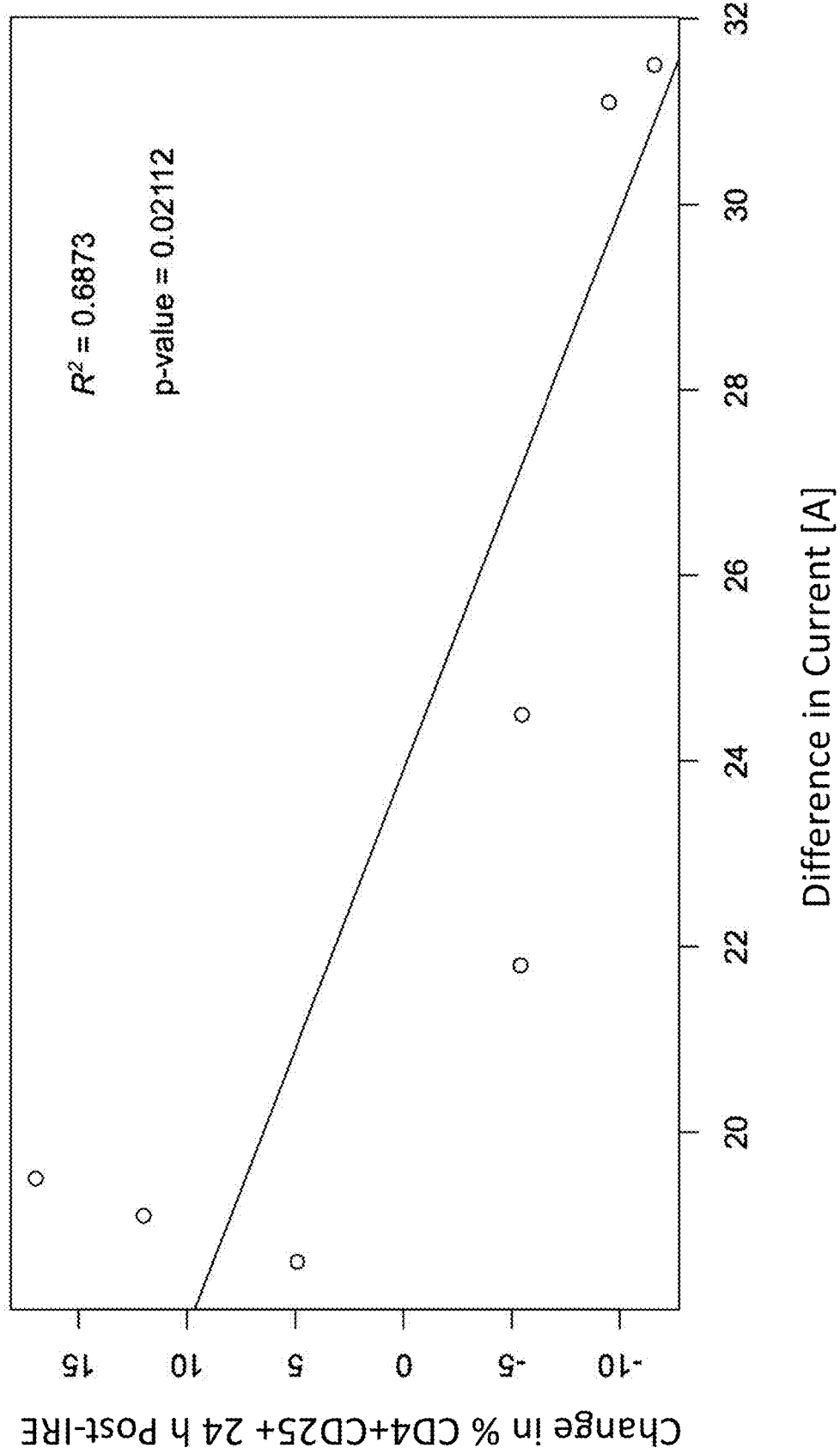
FIG. 4 shows a graph that can demonstrate percent CD4+CD25+ cells 24 h post-irreversible electroporation (IRE) vs. difference in current (n=7).
Figure 5:
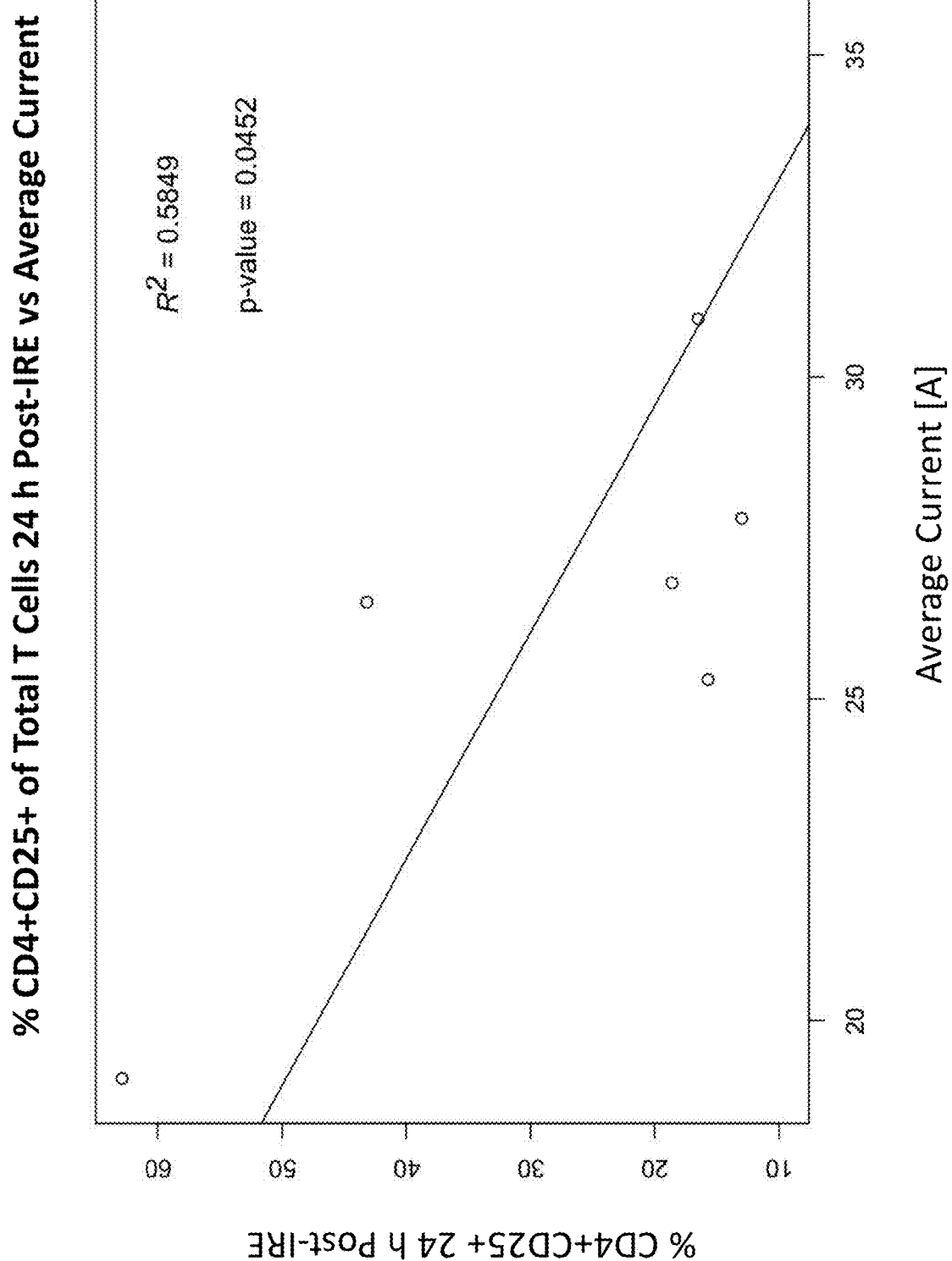
FIG. 5 shows a graph that can demonstrate percent CD4+CD25+ of total T cells 24 h post-IRE vs. average current.
Figure 6:
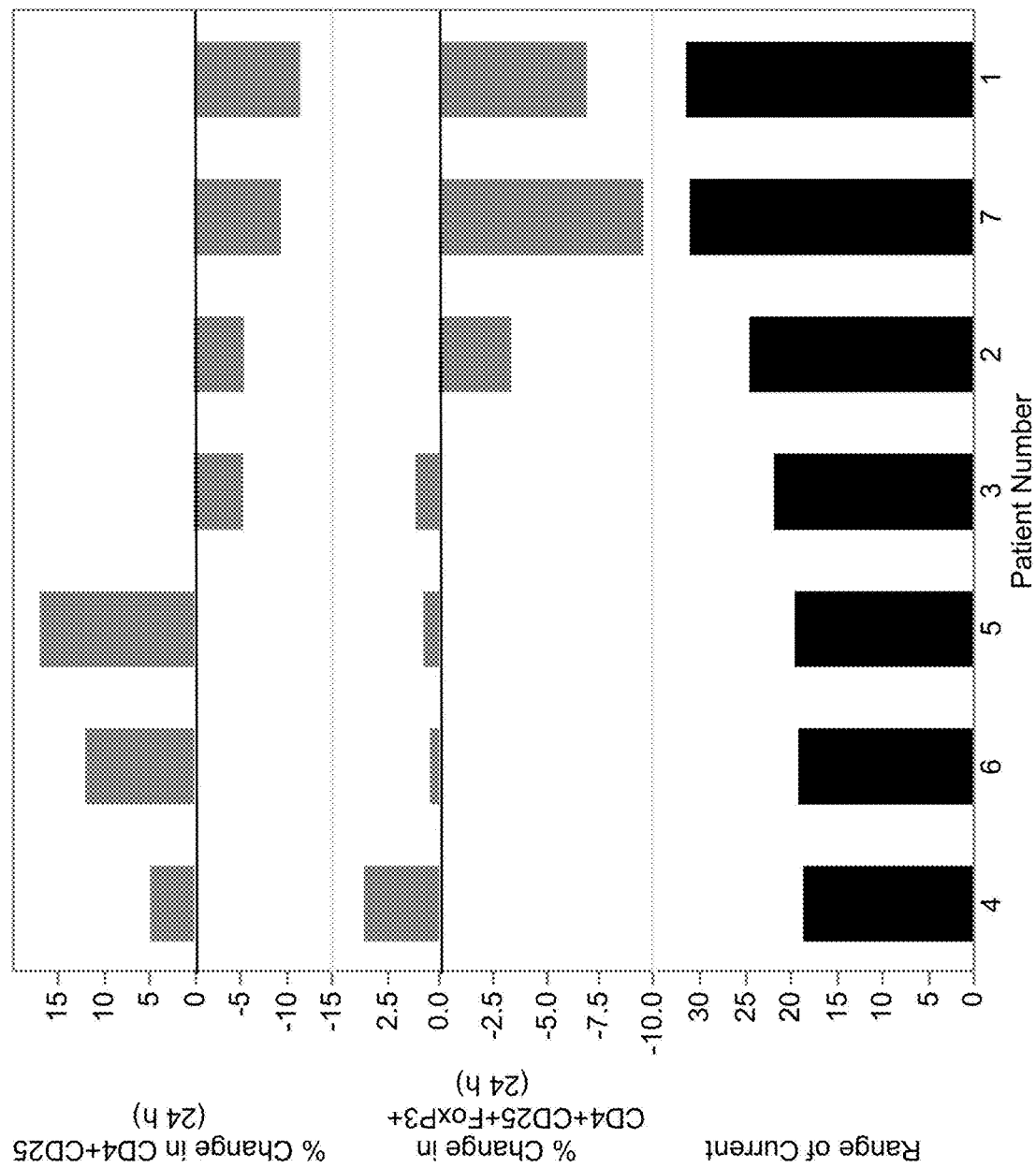
FIG. 6 shows a graph that can demonstrate the percent change in CD4+CD25+ and CD4+CD25+FoxP3+ 24 hours after IRE. The changes are shown in order of increasing overall change in output current (lower most panel) during the treatment in each patient. Populations were calculated as a subset of total CD4+ cells (n=7).
Figure 10A:
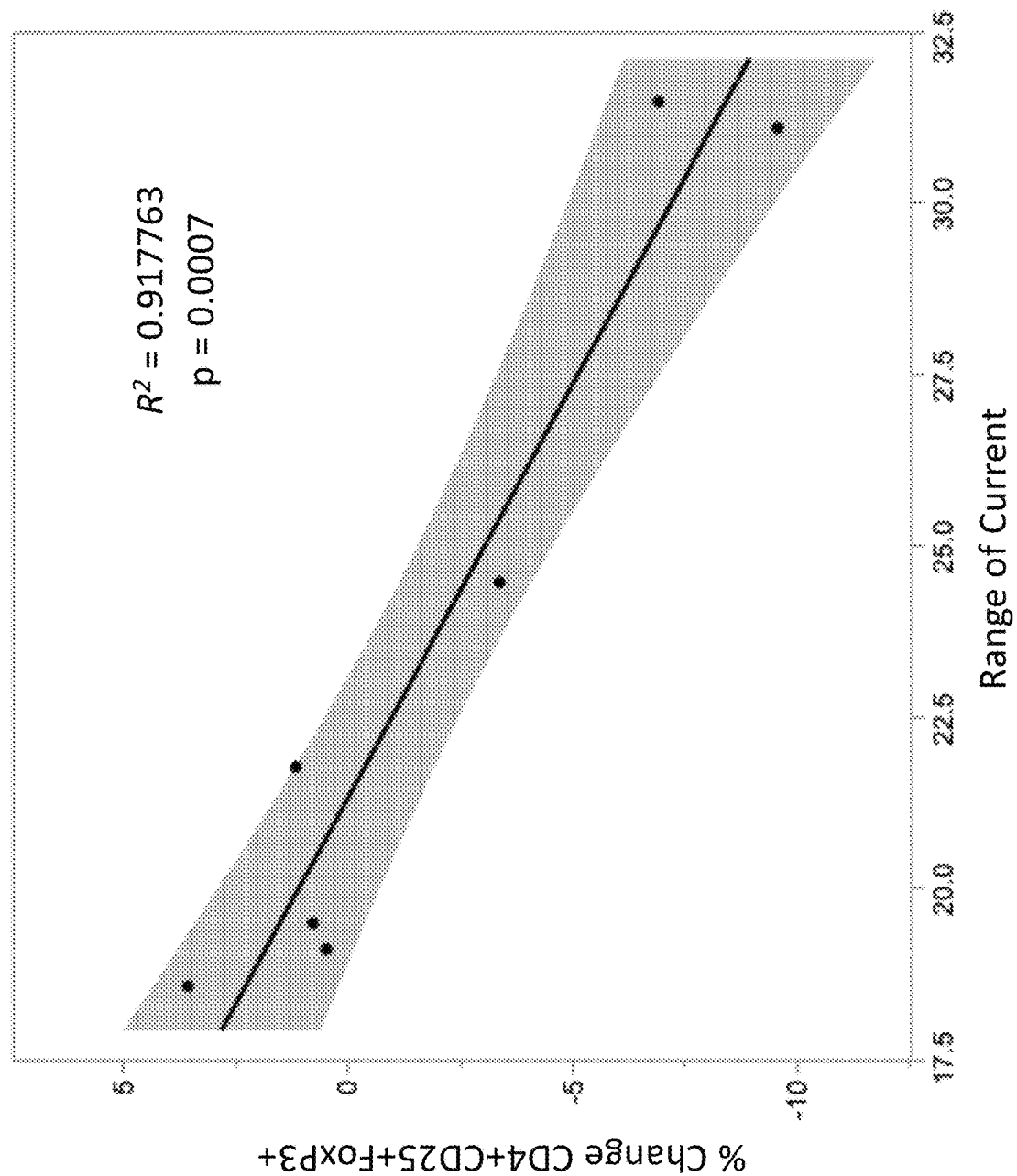
FIGS. 10A-10B shows graphs that can demonstrate the change in FIG. 10A) CD4+CD25+FoxP3+ and FIG. 10B) CD4+CD25+ after 24 hours following IRE decreases linearly with the range of current delivered during the IRE treatment for n=7 patients. A linear regression was performed using JMP Pro software.
Figure 10B:
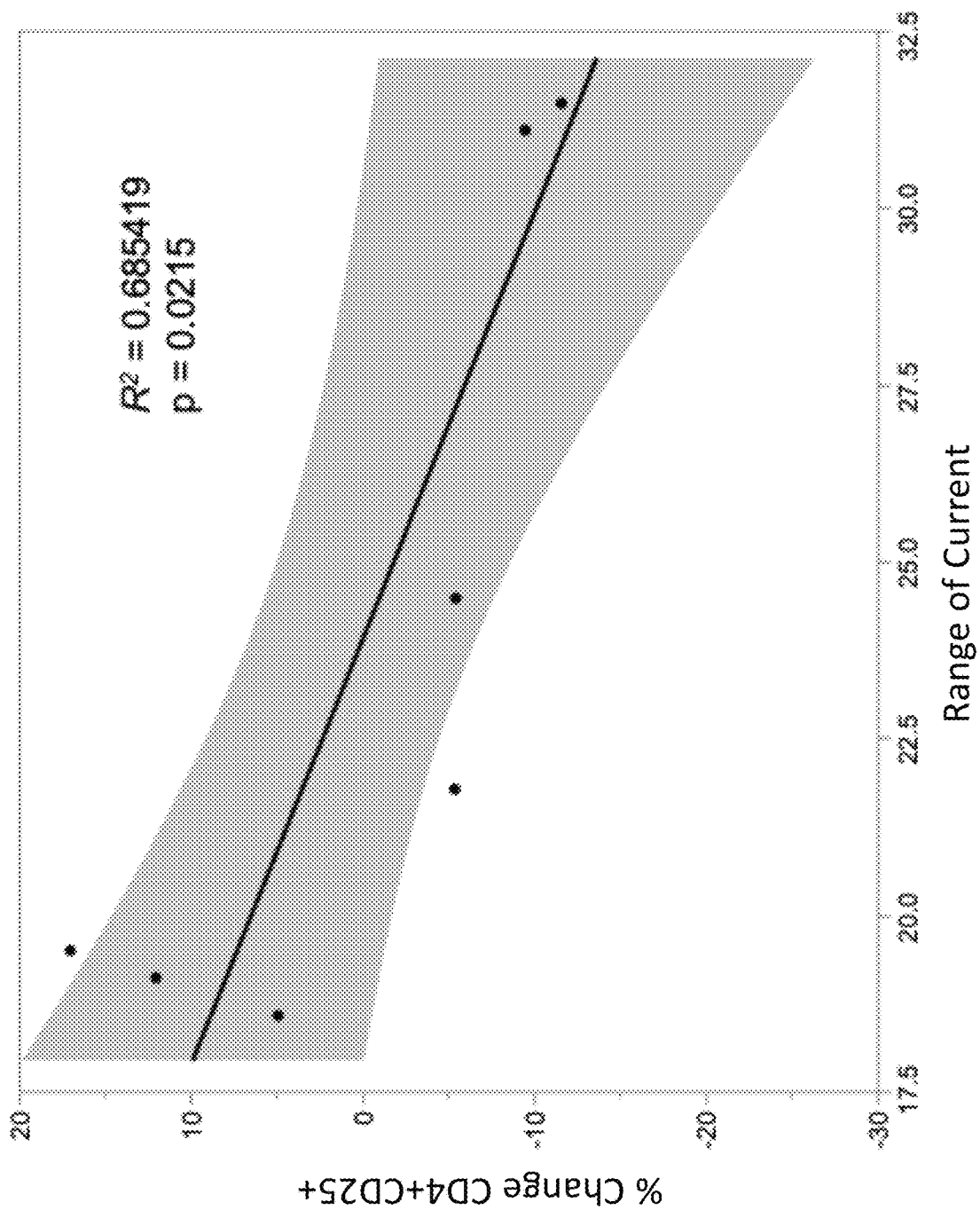

Current waveforms from the 7 performed IRE treatments were collected from the IRE pulse generator. The total change in current as well as average current delivered were calculated using a MATLAB script (vR2016a, Mathworks Inc., Natick, Mass., US). A linear regression was performed to examine the relationship between current and T-cell population changes using JMP Pro software (version 13.0.0, SAS Institute, Cary, N.C., USA). A statistical significance level of 0.05 was used for the analysis. T cell populations measured from blood samples before and 24 hours, but could be up to 5 days post IRE treatment, after treatment show an array of responses between the 7 different patients (FIG. 6). This indicates a response from the patient's immune system following IRE treatment. Of the 7 patients treated with IRE, some exhibited an increase in T-cell populations while others exhibited a decrease. The change in T cell levels was found to linearly correlate with changes in the delivered electrical current. In particular, a higher change in current values during treatment responded in a more negative change in CD4+CD25+ and CD4+CD25+FoxP3+ levels. Both linear relationships were found to be statistically significant (FIGS. 10A and 10B). Supporting data can be found in FIGS. 3-5. Both average current and change in current are linearly correlated with T cell populations (n=7 patients) measured 24 hours after IRE treatment. FIG. 6 shows a bar chart showing range of current and percent change in patient T-cell populations before and 24 hours after IRE.

Considering the dire need for new approaches for treating late-stage pancreatic cancers with curative intent, this method allows clinicians to make a real-time decision regarding a downstream or secondary treatment. The suggested predictive linear model can be implemented in the clinic during non-thermal ablation such as IRE and/or HFIRE treatments to correlate treatment feedback with a patient specific immune response. The relationship between current delivered and changes in the patient's immune response could position IRE as a preliminary or a primary therapy which clinicians can use to treat the underlying disease; screen patients for possible immunotherapy candidates; and help the clinician to formulate patient specific treatment regimens to increase the positive immune response and positive overall outcomes. This screening capability could prevent unnecessary rounds of ineffective treatments, and allows for a more personalized treatment plan.

Patients eligible for tumor resection surgery or another immunosuppressive therapy can first undergo a non-thermal IRE and/or HFIRE procedure. If there is a positive change in a selected treatment parameter, such as a change in current of from about 25 A-100 A, the clinician may decide to leave the tumor in situ and wait for an intentional delay in time, such as more than one day, for the optimal immune response to occur before resecting and delivering immunotherapy. If during the non-thermal procedural there is no positive change in the selected treatment parameter, such as current, the clinician could immediately resect and/or perform the immunosuppressive therapy. Such an approach could greatly increase the number of patients that would benefit from the IRE.

Example 2

Patients with pancreatic cancer have one of the most dismal prognoses of all cancer types with an approximate five-year survival rate of 9%. The only curative option for patients with pancreatic ductal adenocarcinoma (PDAC) is surgical resection, yet most patients present with unresectable tumors due to the proximity of the tumor to critical structures or with metastatic disease. Immune-based therapies have recently gained attention due to their early clinical success in altering the course of disease in patients with previously untreatable cancers. Unfortunately, the relatively immunosuppressive nature of pancreatic cancer hinders the systemic delivery of immunotherapies in PDAC as compared with other tumor types. This immunosuppressive phenotype of pancreatic cancer derives from specialized immune cells, such as T-regulatory ($T_{reg}$) cells, which ultimately mask the tumor from the immune system, resulting in a reduced anti-cancer immune response.

A local anti-tumor response has been shown to be greater in immunocompetent rats when compared with immunodeficient rats following a non-thermal IRE treatment. Also, non-thermal IRE has been shown to reduce resistance to an immune checkpoint blockade in a rat model. By using tumor disruptive approaches, the tumor can act as its own anti-cancer vaccine through the production of patient-specific tumor antigens associated with the ablated tissue. The production of neoantigens along with decreases in suppressive immune cell populations like $T_{reg}$ cells in the ablation zone can lead to increased pro-inflammatory immune system involvement. This could potentially facilitate the destruction of both primary and metastatic tumors and prevent the likelihood of cancer recurrence following treatment. Non-thermal ablation such as IRE and/or HFIRE has been used to treat human prostate, liver, and kidney tumors. In locally advanced pancreatic cancer (LAPC) patients, IRE has been shown to nearly double the median survival when combined with chemotherapy. However, since some types of chemotherapy have been shown to have a cytotoxic effect on immune cells, some patients demonstrating a decline in $T_{reg}$ cells may benefit from the synergistic effects of IRE and immunotherapy.

Recently, circulating $T_{reg}$ cell populations in the blood of unresectable pancreatic cancer patients undergoing chemotherapy were shown to be associated with improved overall survival rates. This Example 3 can demonstrate report that post-IRE $T_{reg}$ cell populations are correlated with the change in a treatment parameter, here such a treatment parameter was the current delivered to the local tumor. Specifically, a change of approximately 25 A resulted in a negative change in Tie cell populations 24 hours after IRE treatment. Since current changes can be monitored in real-time, future changes in $T_{reg}$ cell populations may be predicted during the IRE treatment. This ability to predict changes in the patient's systemic immune system may improve treatment applications and has the potential to maximize post-treatment options.

Methods.

Figure 7:
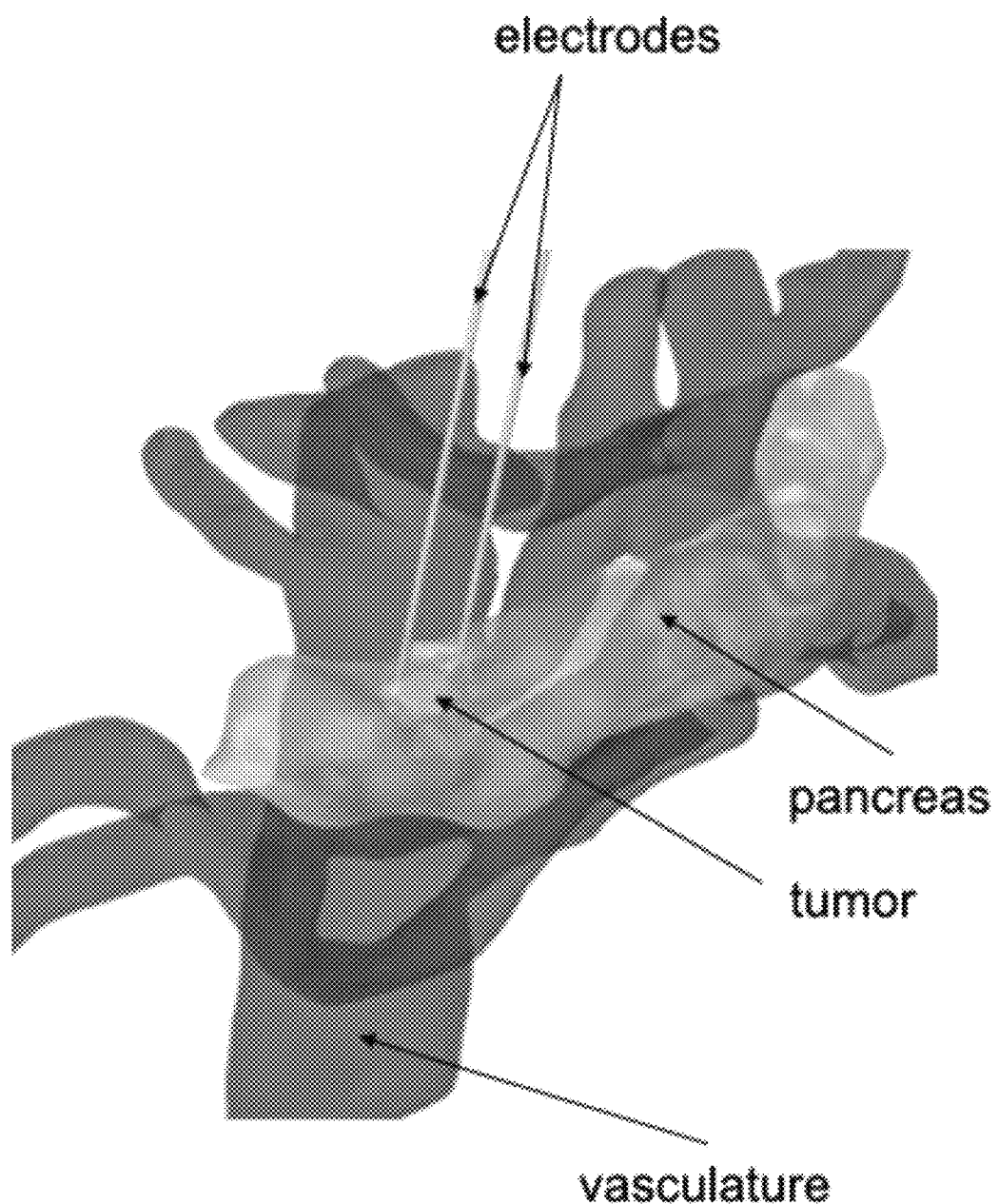
FIG. 7 shows a representative 3D reconstruction of a human pancreas, tumor, and vasculature used for treatment planning purposes. Two electrodes are inserted into the tumor in this example. Pancreas and vasculature reconstruction was prepared using 3matic and Gmsh software using a pre-operative CT scan; electrodes and tumor mimic placed using COMSOL software.

Seven patients with stage 3 pancreatic cancer were treated with IRE via laparotomy procedure. Prior to the electrode placement procedure, two-dimensional ultrasound imaging was used to check for metastatic disease and to confirm primary tumor size. Ultrasound was used during needle placement in order to bracket the primary tumor and safeguard proper needle placement (FIG. 7). Patients were under appropriate paralytic and narcotic protocol. The first set of pulses consisted of 20 pulses per pair of probes that were used to assess local fibrosis and tissue resistance. The remainder of the treatment consisted of 100-300 pulses per probe-pair contingent on changes in resistance measured across each probe-pair.

Postoperative management of patients treated for pancreatic lesions with IRE was standard and followed guidelines for any type of pancreatic resection.

Flow Cytometry Assay

Patient blood specimens were collected both before and 24 hours after the IRE procedure. Blood specimens were transported to the lab for immediate processing to isolate peripheral blood mononuclear cells (PBMCs). Briefly, red blood cells were lysed with hypotonic lysis buffer and total PBMCs were isolated and stored at −80° C. in RPMI media with 10% human serum albumin and 10% DMSO. Forkhead box P3 (FoxP3) expressing T-regulatory cells are a sign of immune tolerance. To identify Treg and FoxP3 subsets, isolated PBMCs were stained with FoxP3 staining buffer set (130-093-142, Miltenyi Biotec, Germany) per manufacturer instructions, and evaluated using FACSCalibur (BD Biosciences, San Jose, Calif.). Next, the CD4+ lymphocyte population was identified using BD FACSCalibur (BD Biosciences, San Jose, Calif.), then sub-populations were gated and recorded. For each patient, PBMC specimens obtained before IRE and 24 hours after IRE, were processed and analyzed simultaneously to avoid experimental variability due to the thawing and staining procedure. Data were recorded and analysis was performed using FlowJo software (Ashland, Oreg.).

Waveform Analysis

Figure 8:
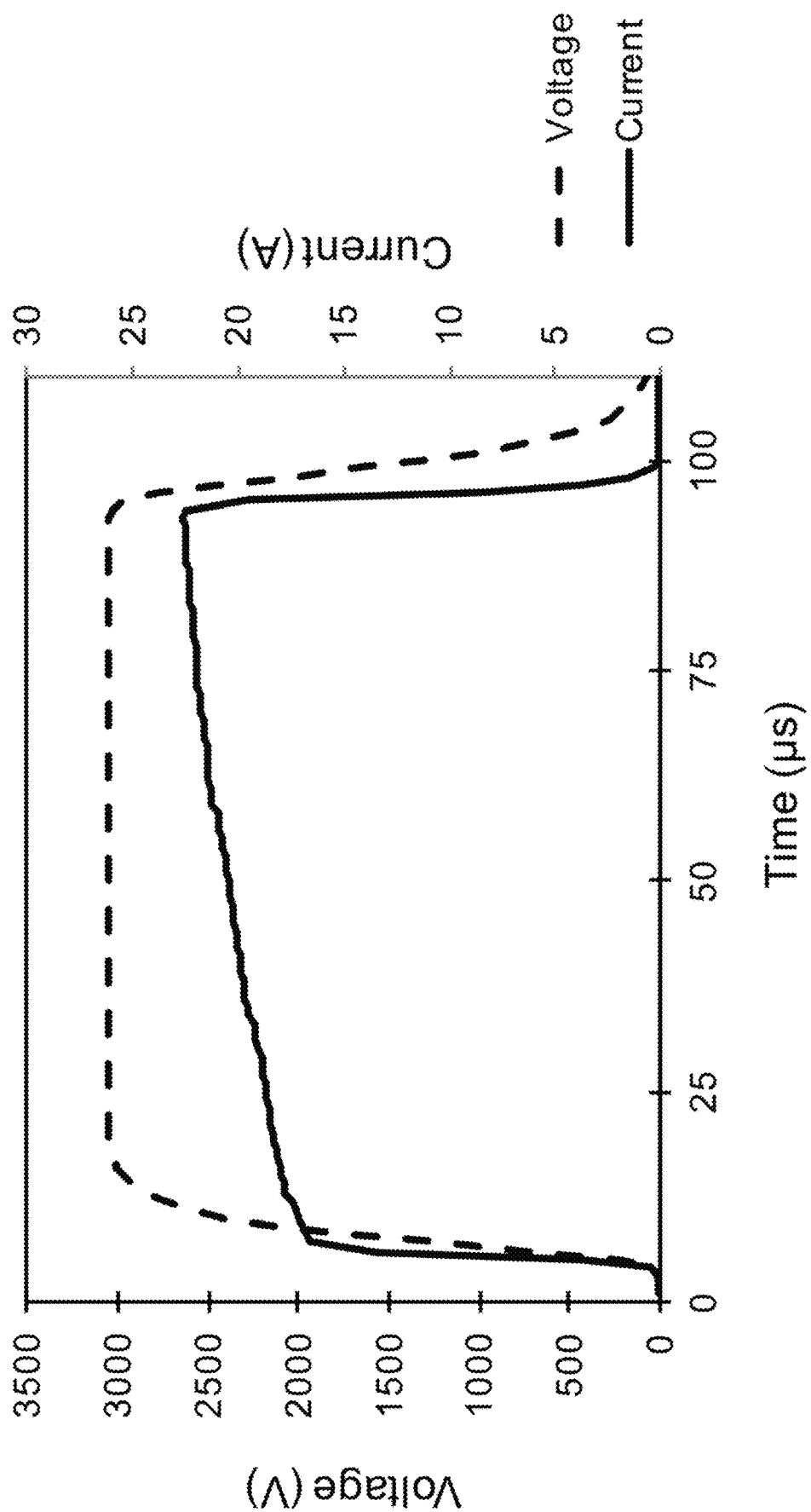
FIG. 8 shows a graph that can demonstrate a representative IRE pulse delivered using the Nanoknife® device. The resistance value resulting from the applied voltage and current is displayed to the user during treatment.

Current waveforms from the seven performed IRE treatments were collected from the IRE pulse generator (FIG. 8). The total change in current as well as average current delivered were calculated using a MATLAB script (vR2016a, Mathworks Inc., Natick, Mass., US). A linear regression was performed to examine the relationship between current and T-cell population changes using JMP Pro software (version 13.0.0, SAS Institute, Cary, N.C., USA). A statistical significance level of 0.05 was used for the analysis.

Results.

$T_{reg}$ cell populations measured from blood samples before and 24 hours after treatment show an array of responses between the seven different patients (FIG. 9). These $T_{reg}$ cell populations represent both natural and promoted $T_{reg}$ cells, which can attenuate anti-tumor immune responses. Of the patients treated with IRE, some exhibited an increase in T-cell populations, while others exhibited a decrease. The change in $T_{reg}$ cell levels were found to linearly correlate with changes in the delivered electrical current (FIG. 6). The range in current is defined as the difference between the maximum and minimum output current values reached during treatment. In particular, a higher change in current value during treatment responded in a more negative change in CD4+CD25+ and CD4+CD25+FoxP3+ levels. Both linear relationships were found to be statistically significant (FIGS. 10A-10B).

Discussion.

The seven patients had an array of responses in output current change, ranging from approximately 17 A to 30 A. This range indicates that the content of the treatment zone varies from patient to patient, and the electrical impedance changes differently in response to treatments with similar applied voltage and electrode spacing. These results indicate that the degree to which the target tissue undergoes impedance changes affects cell populations related to the immune response in the ablation zone and the surrounding area. Electroporation induces pores in the membranes of cells in the target zone, which may induce inflammation resulting in edema and the production of antigens. In turn, these changes reduce the impedance of the tissue resulting in an increased current output. Additionally, while IRE retains the stromal elements of vasculature, the treatment may interfere with endothelial cells, which further promotes inflammation in the treatment site.

The decrease of $T_{reg}$ cells in the ablation zone also creates an inflammatory response at the primary tumor site. Since systemic $T_{reg}$ cell reduction has been previously shown to improve the prognosis of pancreatic cancer patients, removal of these inhibitory cells could shift the tumor microenvironment from an anti-inflammatory state to one more favorable for anti-tumor immune system activation/promotion. During treatment, this shift may be predicted by monitoring the change in output current delivered through the electrodes. In practice, these results imply that the decline of the $T_{reg}$ population be predicted in real time using the IRE pulse delivery device. The relationship between current delivered and changes in the patient's immune cell populations, beyond just the $T_{reg}$ cell populations, could also position IRE as a preliminary therapy that clinicians could use to screen patients for immunotherapy.

Ultimately, this correlation can provide clinicians with a metric they can use to optimize an IRE treatment and subsequent therapy.

This Example can describe and at least demonstrate the use of real-time current feedback as a treatment parameter from the IRE treatment to be used by the clinician when determining the possibility of a follow-up downstream or secondary therapy to maximize patient outcomes and maximize the immune response. The suggested predictive linear model can be implemented in the clinic during IRE treatments to correlate treatment feedback with the patient's predicted Tie cell population, which is normally unknown until hours following treatment. This information provides clinicians with a much needed metric to monitor a facet of the patient's immune response. Considering the dire need for new approaches for treating late-stage pancreatic cancers, we believe that this approach could poise IRE as a potential preliminary or primary therapy which can be used to screen patients for the appropriate follow-up therapy. For example, a patient demonstrating a high predicted change in $T_{reg}$ cells would perhaps benefit more from downstream or secondary treatment of immunotherapy rather than chemotherapy, which has been shown to have a cytotoxic effect on immune cells. Additionally, the ability to predict an unchanging $T_{reg}$ cell population in some patients could prevent unnecessary rounds of ineffective treatment and provide a more personalized treatment plan. This screening capability can improve clinician decision making processes regarding follow-up treatment, and ultimately patient outcomes. As discussed elsewhere herein, the screening can confirm the increase in immune activity and/or a decrease in immunosuppressive activity and thus further optimize the downstream treatment strategy post non-thermal ablation.

Example 3

Canine hepatocellular carcinoma (HCC) is an uncommon primary liver tumor that can be presented in three forms: massive, nodular, and diffuse. The massive form represents about 60% of HCCs and carries an excellent prognosis when amendable to surgery, while there is no effective treatment for the nodular and diffuse forms. The prognosis for dogs diagnosed with non-resectable HCC has remained dismal for decades, with a median survival measured in weeks to months, despite chemotherapy, targeted therapies, and radiation. Immunotherapy is an attractive therapeutic option for primary liver tumors, because they arise in the background of an immune-tolerant microenvironment. Described in this Example is the effect of H-FIRE on local and systemic immunological stimulation.

High-frequency irreversible electroporation (H-FIRE) is a technique for the focal treatment of pathologic tissues that involves placing minimally invasive electrodes within the targeted tumor tissue. Based on the standard irreversible electroporation (IRE), H-FIRE induces a series of short (ranging from 1 nanosecond to 5 microseconds), bi-polar electric pulses electric pulses, which are applied to destabilize the cell membrane, by creating nanopores, and inducing cell death in a non-thermal fashion. H-FIRE preserves the extracellular matrix, major tissue vasculature, nerves, and other sensitive structures, while negating the need for paralytics during treatment. HFIRE treatments are thought to promote an antitumor immune response, are independent of local blood flow, can be delivered quickly, and can be visualized in real-time.

Figure 11A:
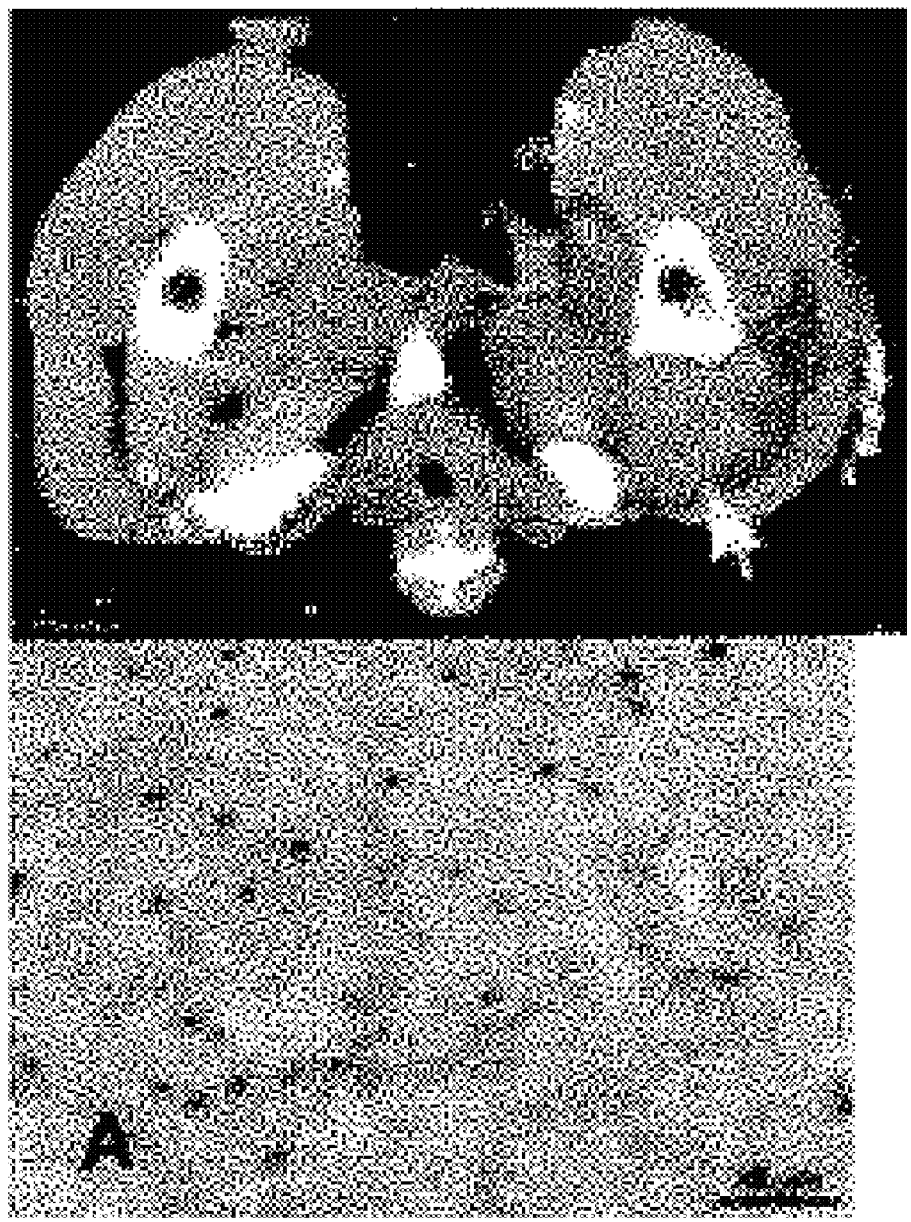
FIGS. 11A-11C shows CT scan images of the pelvis and hind limbs visualizing the target region, practically surrounding the femur and adjacent to the sciatic nerve and femoral arteries. IRE resulted in marked influx of mixed inflammatory cells into the treatment region (FIG. 11B), which was composed of primarily CD3+ lymphocytes, 24 hours post-treatment (FIG.11A→pretreatment, FIG. 11A→post treatment).
Figure 11B:
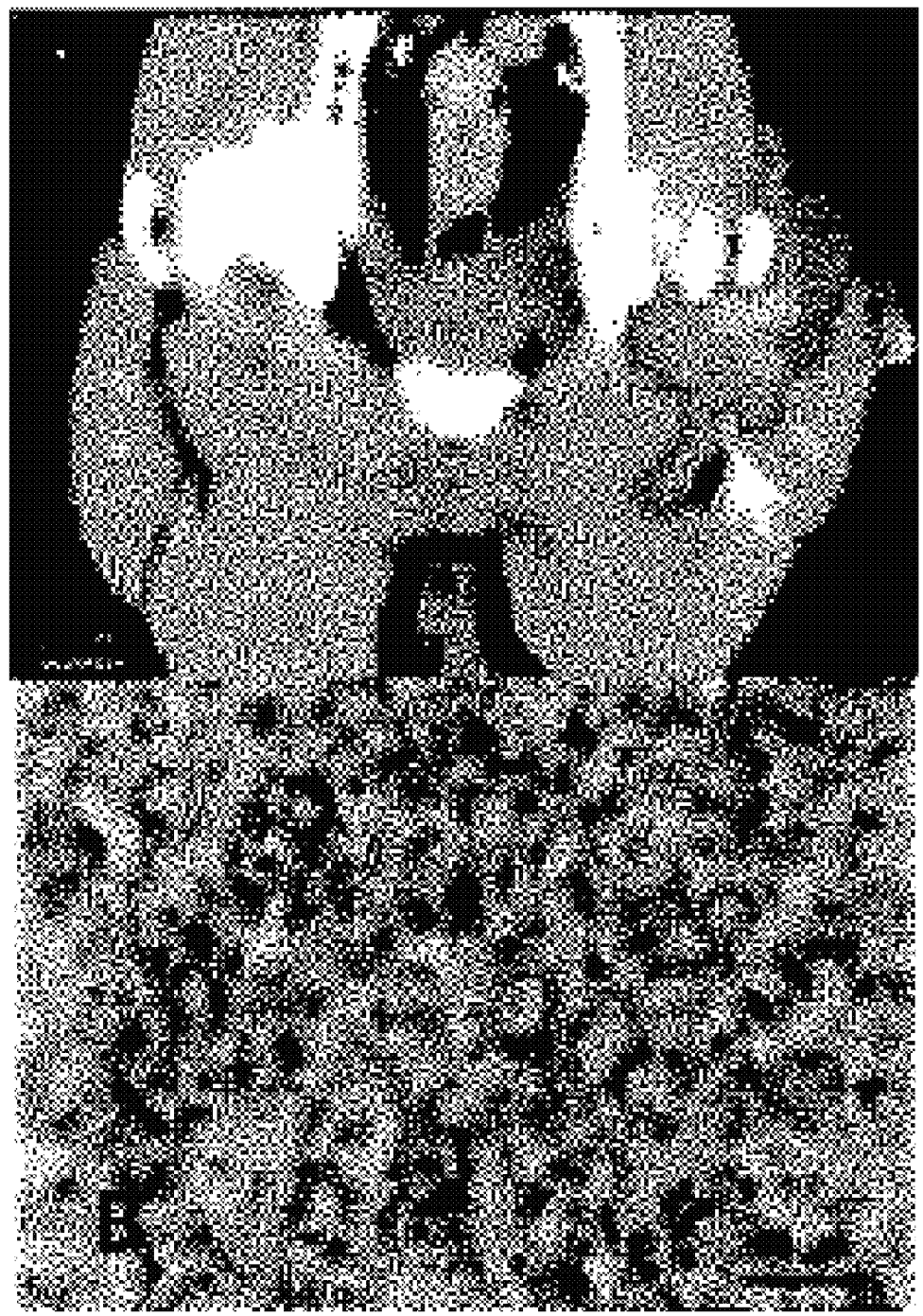
Figure 11C:
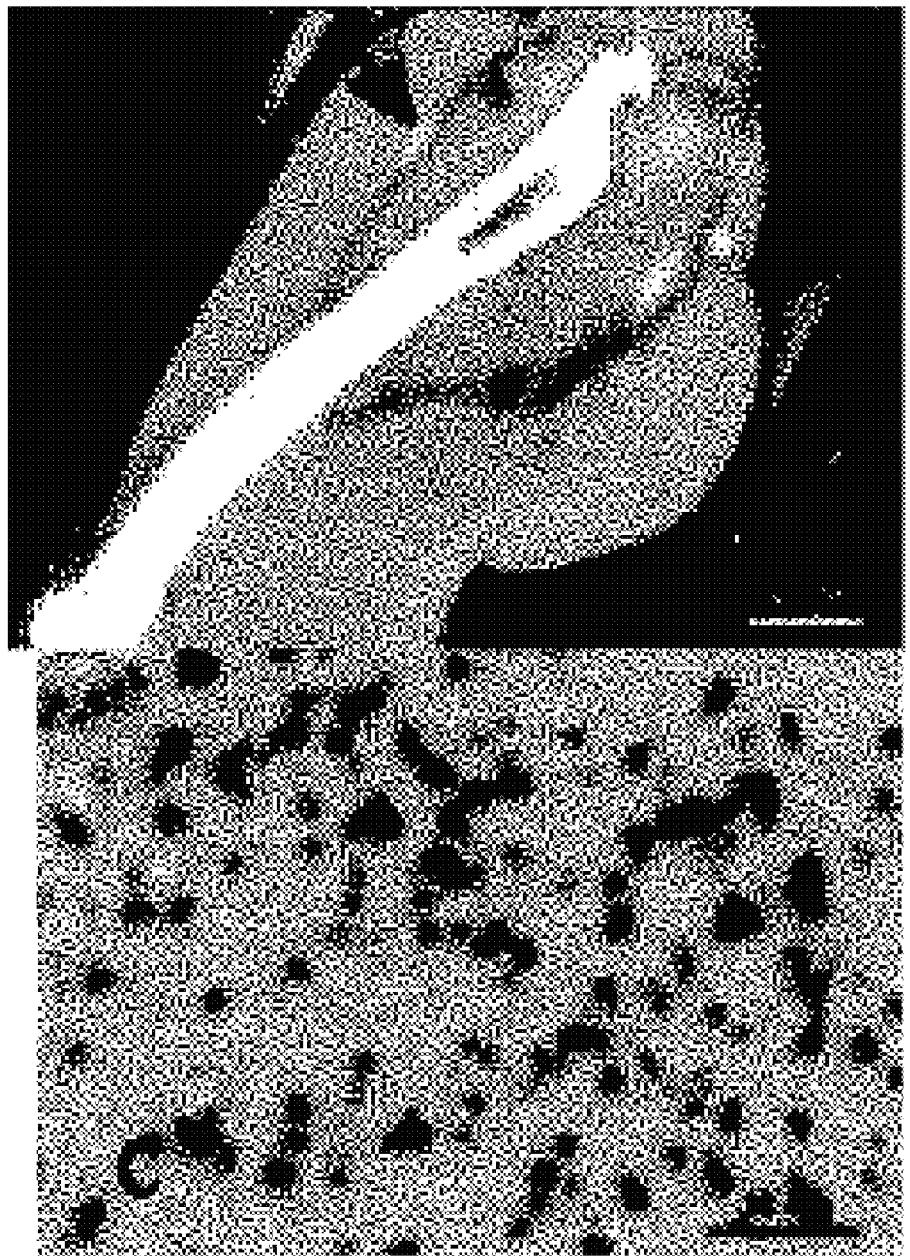
Figure 12A:
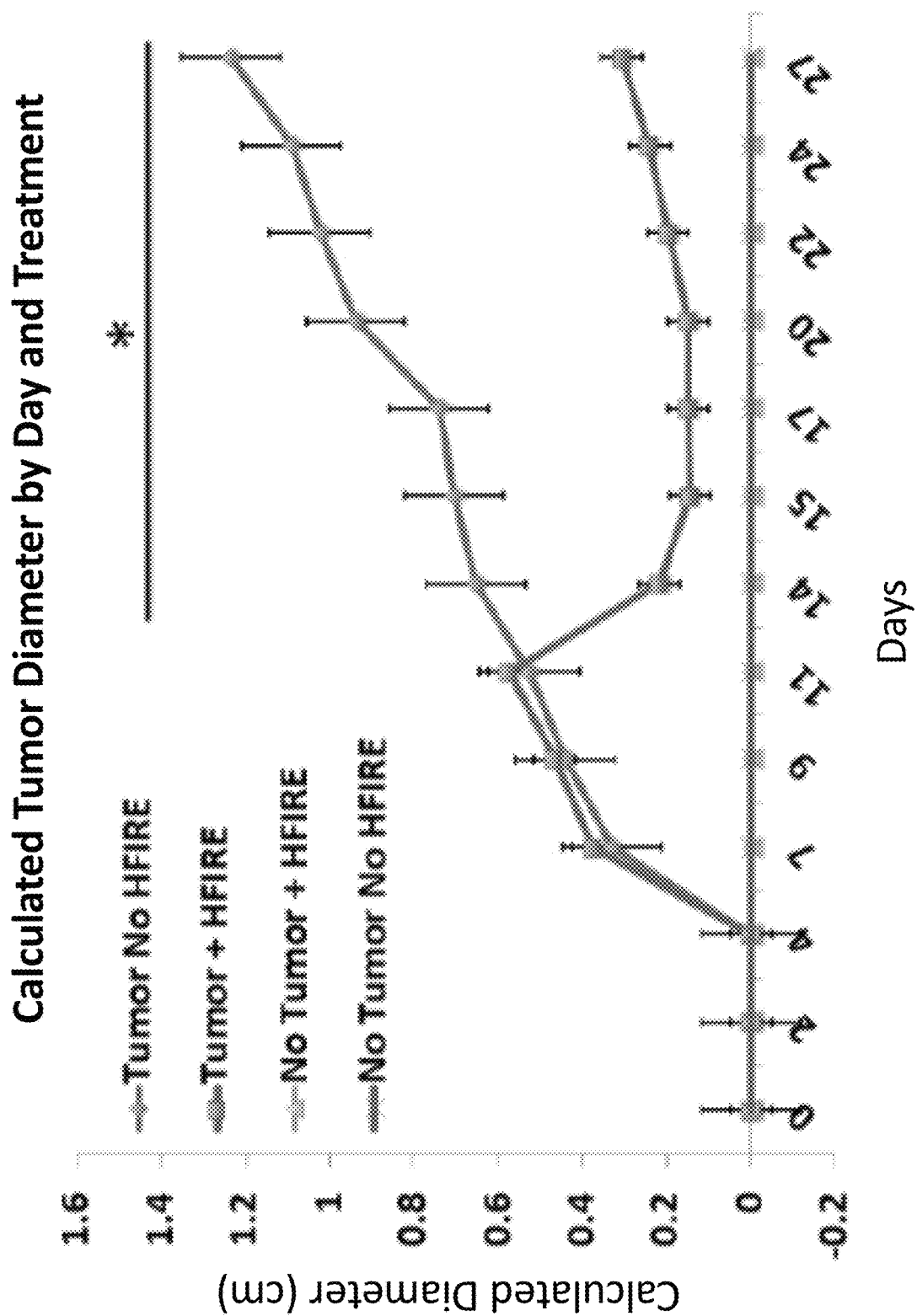
FIGS. 12A-12B show graphs that can demonstrate that H-FIRE treatment significantly reduces tumor progression and ablates the primary 4T1 mammary tumor.
Figure 12B:
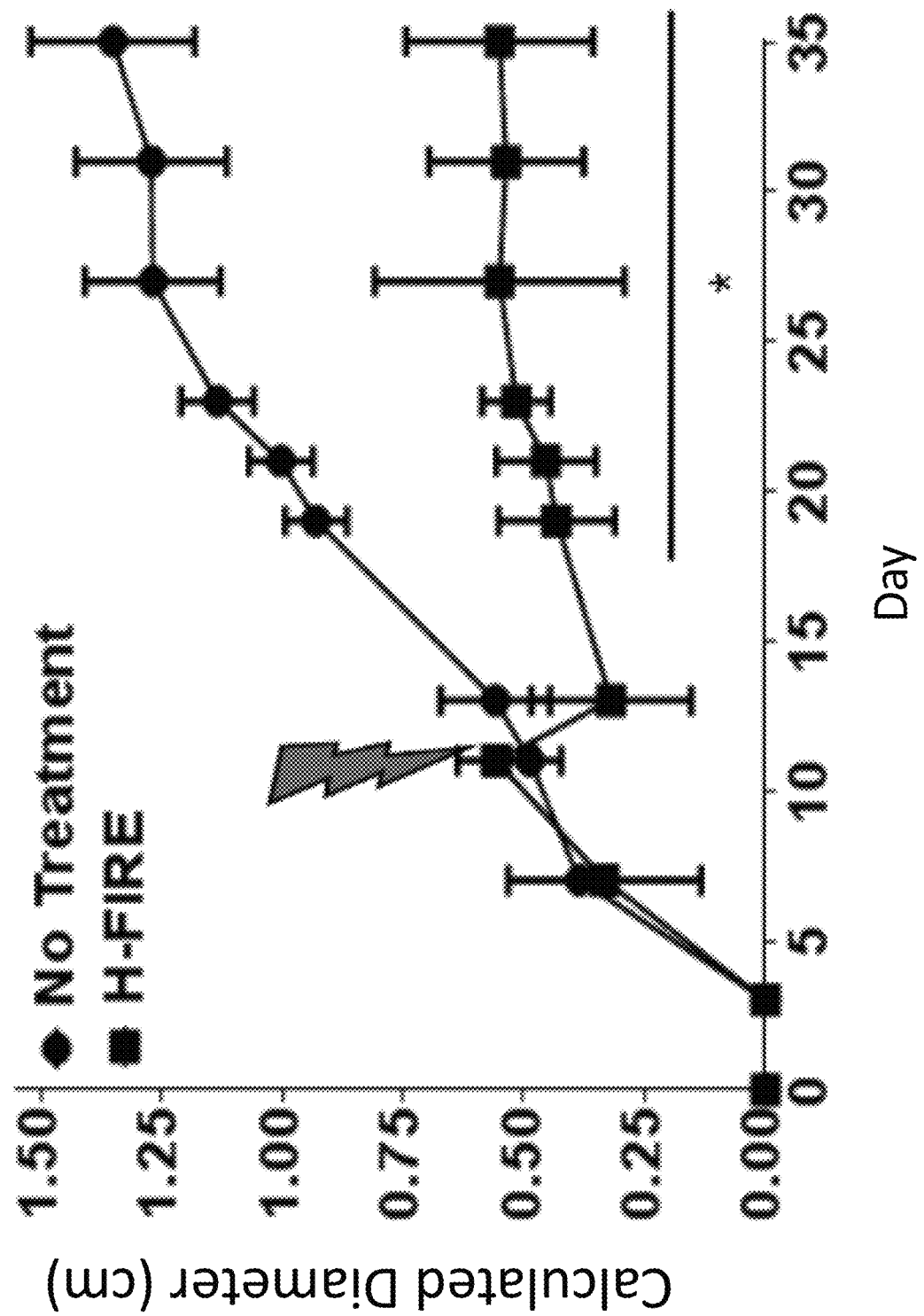
Figure 13A:
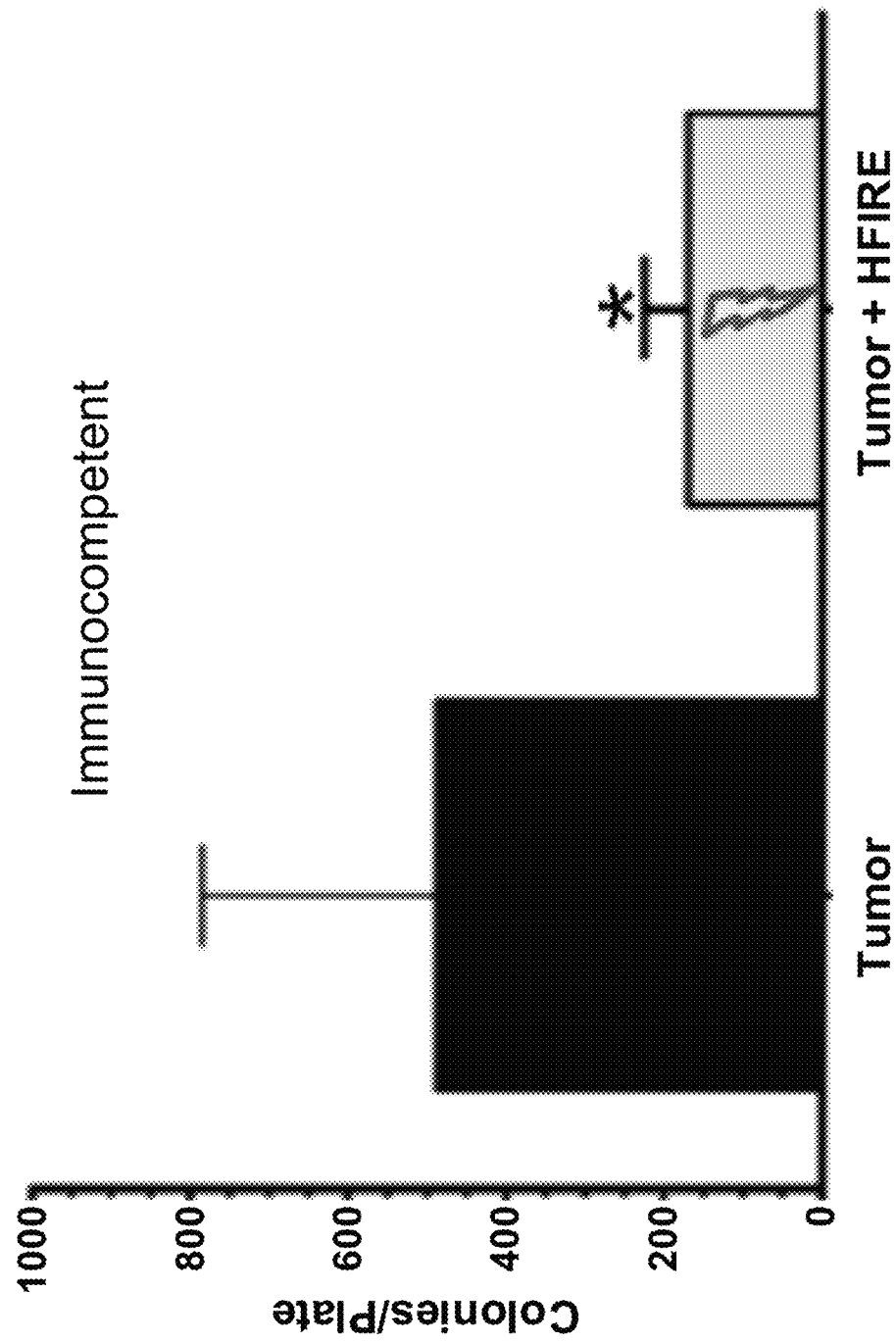
FIGS. 13A-13B show graphs that can demonstrate a decrease in circulating metastases following H-FIRE treatment of the primary tumor in immunocompetent mice. Circulating metastases were quantified in both (FIG. 13A) BALB/c and (FIG. 13B) NSG mice following treatment of the primary 4T1 (breast cancer) tumor with an ablation dose of H-FIRE. Following necropsy, blood samples were plated in media with 6 mM 6-thioguanine. After 10-14 days, formed colonies were counted. n=6-10 mice. *p=0.05.
Figure 13B:
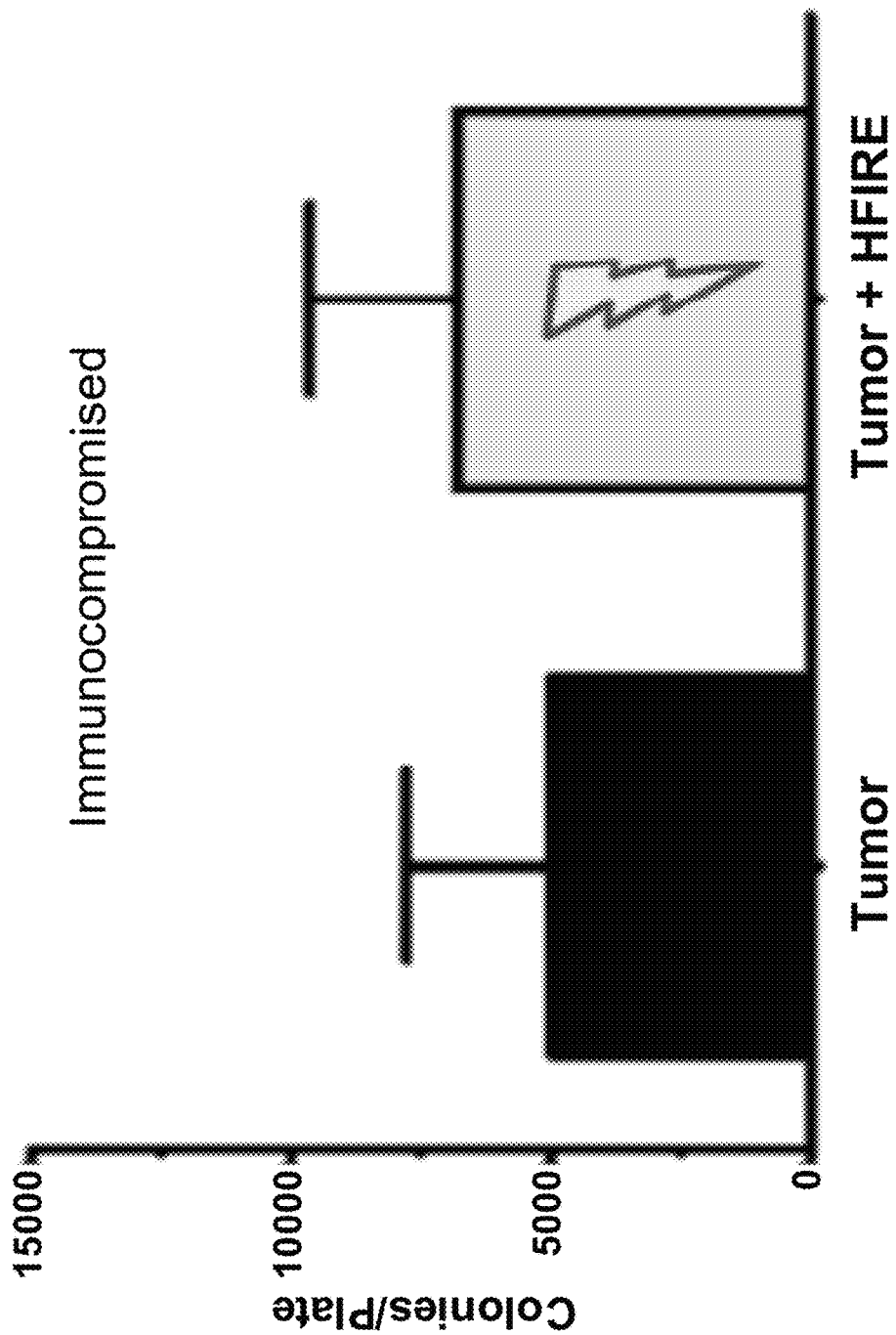
Figure 14:
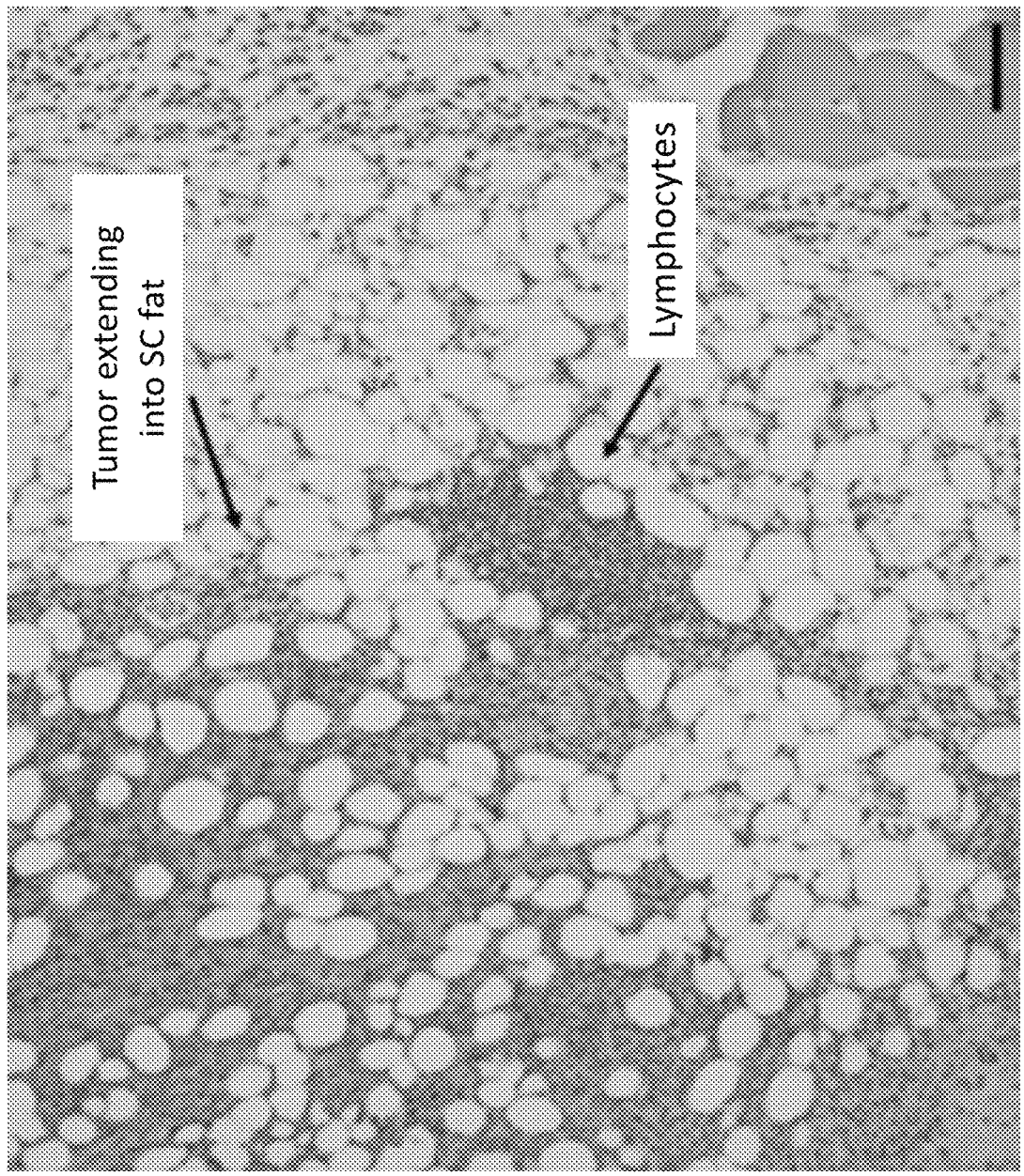
FIG. 14 shows a microscopic image that can demonstrate increased lymphocyte infiltration following H-FIRE in the local Pan02 tumor. Histopathology assessments revealed increased marginal and intra-tumor lymphocytes 14 days post-treatment with an ablation dose of H-FIRE.
Figure 15:
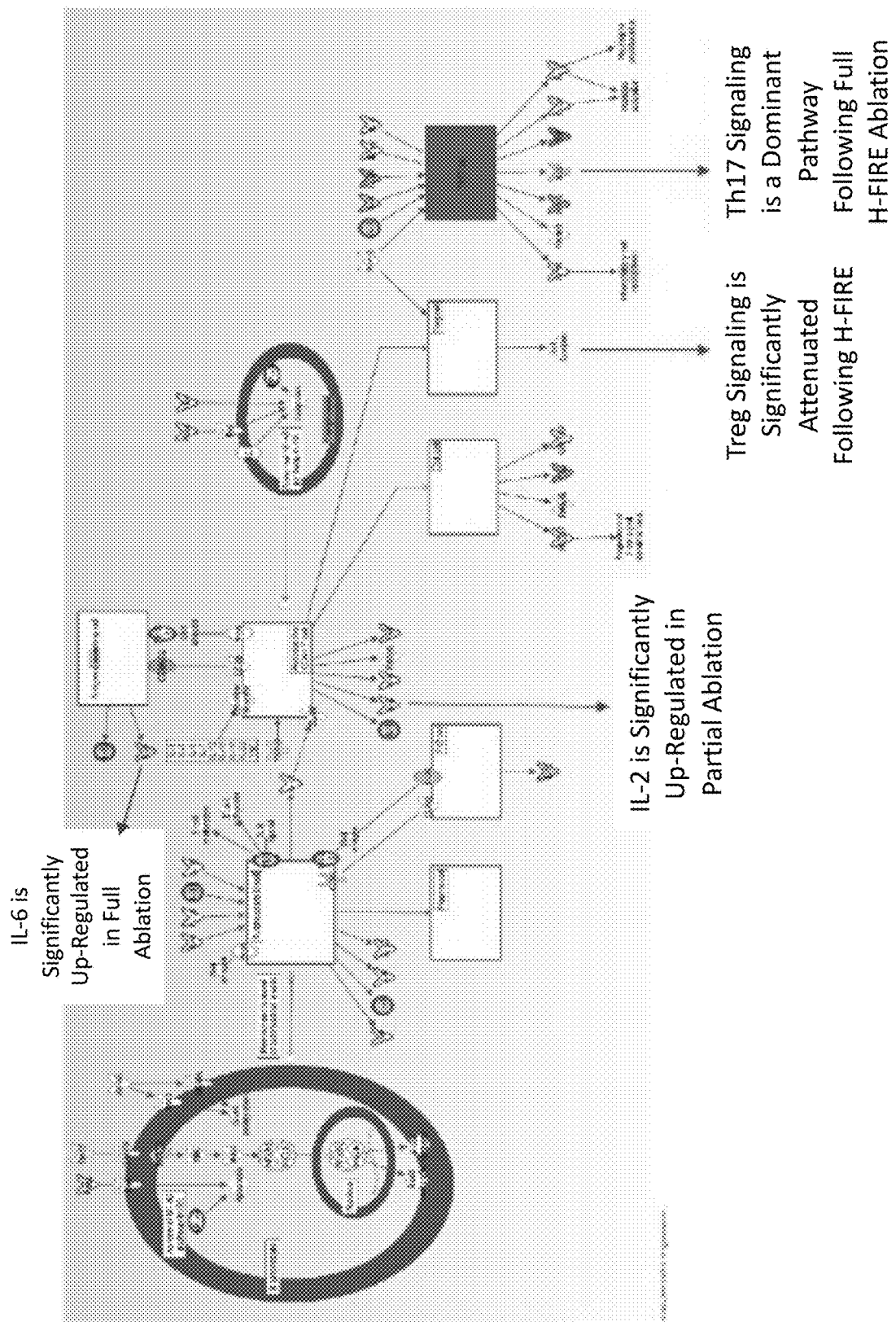
FIG. 15 shows a gene expression pathway analysis of tumor microenvironment following H-FIRE. Gene expression profiling revealed significant changes in inflammatory signaling in the 4T1 mammary tumor model. Data indicate a significant shift in the tumor microenvironment to a Th1/Th17 profile and high levels of IL-6 following full ablation. A significant increase in IL-2 signaling was found in tumors that received a sub-ablation dose of H-FIRE, consistent with increased lymphocyte expansion and recruitment.
Figure 16:
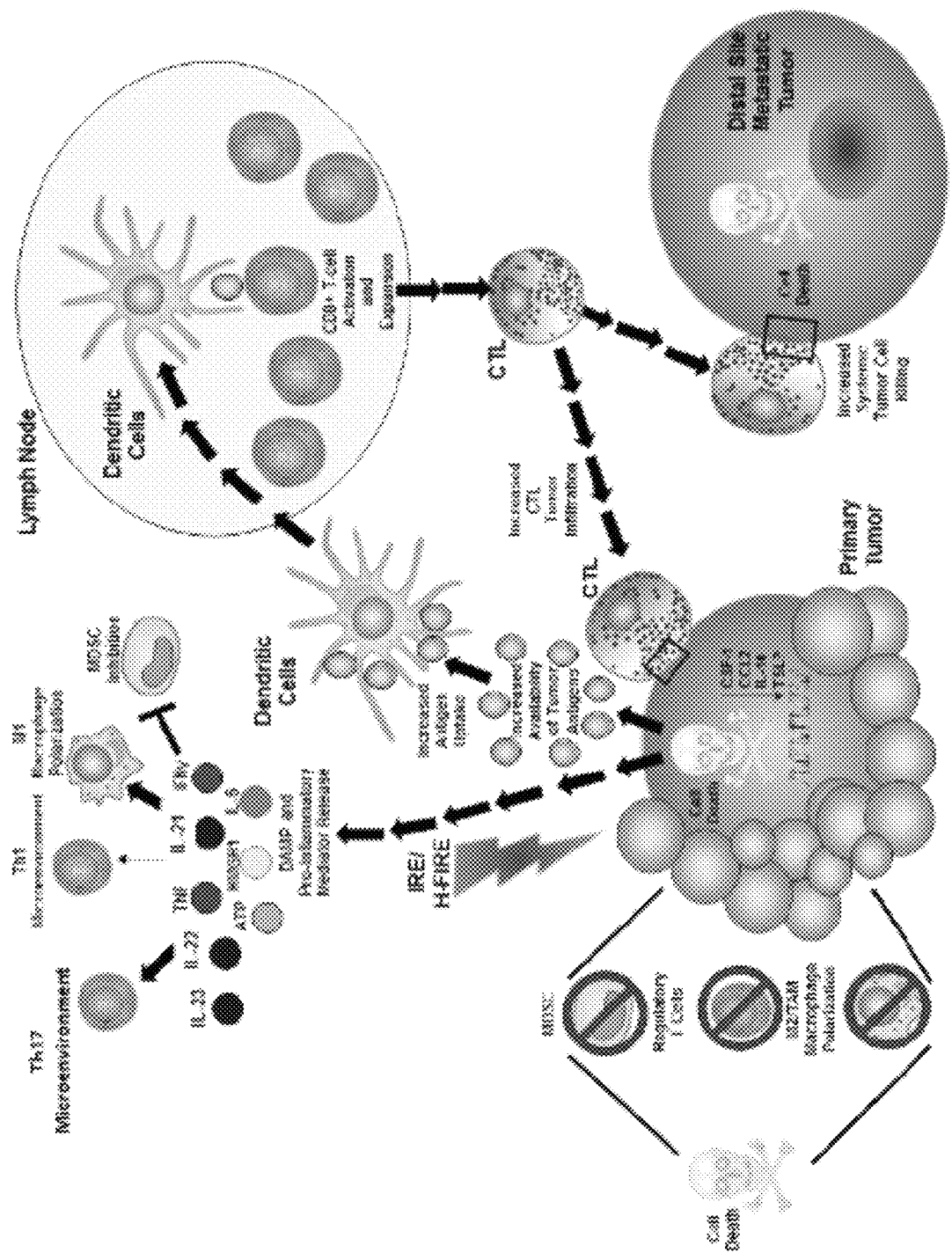
FIG. 16 shows a schematic of the local and systemic efficacy of IRE and H-FIRE ablation is associated with immune system activation/promotion. In this model, the cell death and tumor ablation driven by IRE/H-FIRE treatment promotes the innate immune system and promotes a shift in the tumor microenvironment from immunosuppressive to pro-inflammatory (Th1 and Th17), which serves to recruit increased numbers of antigen presenting cells to the local tumor. The cell death and damage associated with treatment increases antigen availability and presentation, further engaging the adaptive immune system. Increased tumor specific antigen presentation promotes T cell activation and increased CTL mediated cancer cell killing in the primary tumor and metastatic cells in distal locations. Increased activation/promotion of the adaptive immune system will also improve immunological memory, which should attenuate recurrence. IRE and H-FIRE would be excellent candidates for combination therapeutic approaches using new classes of checkpoint inhibitors and/or other immunomodulatory therapeutics.

A flat-coated retriever diagnosed with histiocytic sarcoma presented with a history of degenerative coxofemoral joint disease, postural reaction deficits associated with sciatic neuropathy and a large periarticular mass of the left coxofemoral joint. A single IRE treatment to the primary tumor followed by lomustine chemotherapy was curative, as the dog achieved complete response and was euthanized for unrelated reasons about 5 years post IRE/chemotherapeutic treatment. Post-treatment biopsies indicated significant T-cell infiltrates (FIGS. 11A-11C).

Following this response, the effect of IRE therapy on the immune system was examined. A murine model of renal cortical adenocarcinoma (RENCA) was used in 2 groups of mice: 1) immunodeficient mice and 2) immunocompetent mice. During these experiments, both groups of mice were implanted with RENCA cells, and upon tumor formation, treated with IRE.

Treatment resulted in significantly increased tumor response rate and overall survival in the immunocompetent mice when compared to the immunodeficient mice. A robust CD3+ lymphocytic tumor infiltration post-IRE was observed in the treated immunocompetent mice. Moreover, when re-challenged with the same cell line 18 days after the IRE treatment, tumor growth was significantly reduced or prevented entirely (FIGS. 2A-2D). These data can support that IRE can promote an immune response that can invoke a systemic immune reaction beyond the ablation region. As is discussed elsewhere herein, a non-immunosuppressive manner such that an initial and local innate immune response followed by promotion of the adaptive immune response, which can be effective to target and destroy circulating and/or metastatic cells.

Example 4

Figure 17:
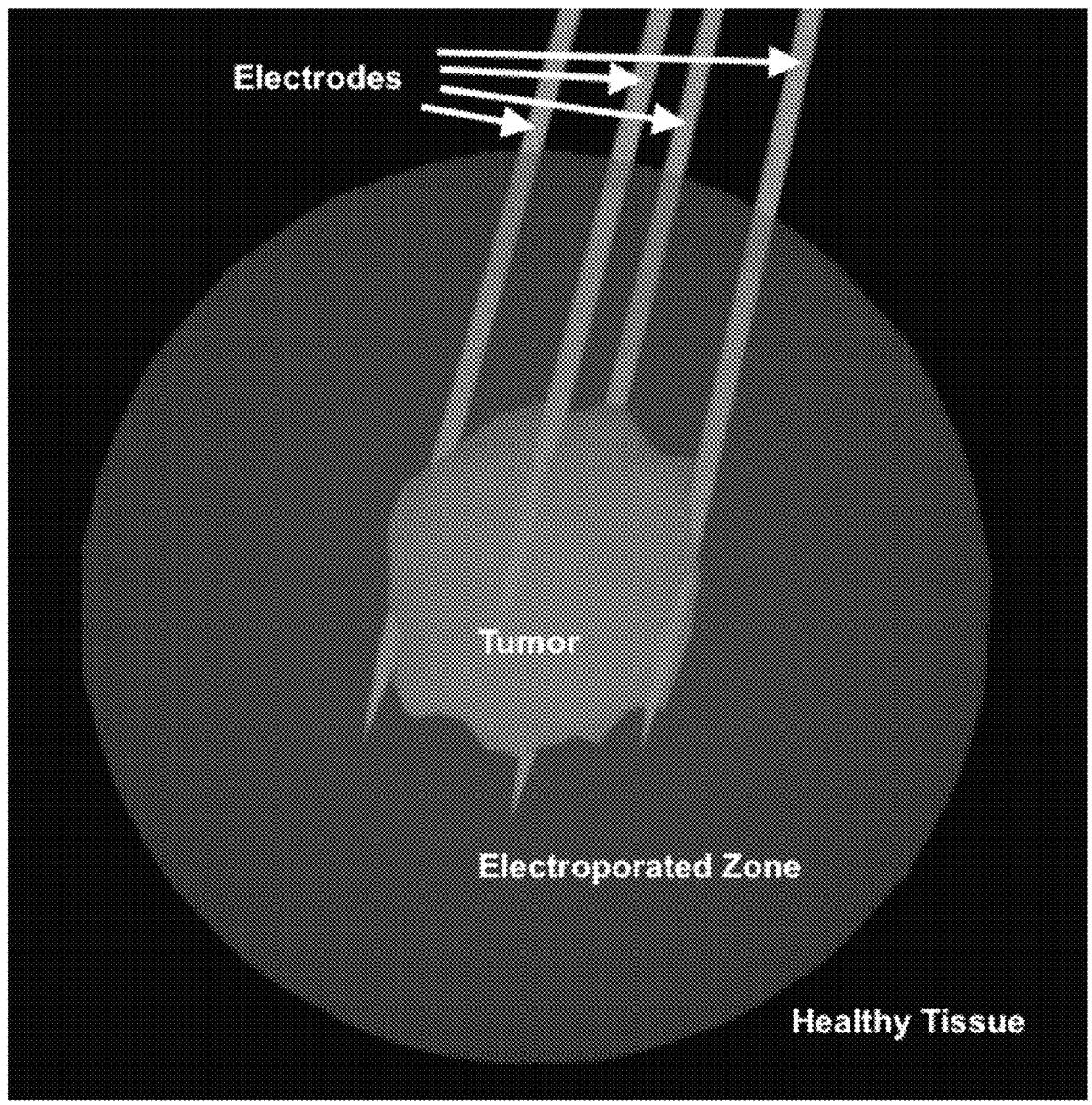
FIG. 17 shows a schematic of H-FIRE targeting within a tumor.

IRE is a technique designed to ablate cancerous tissue by delivering short electric pulses through electrodes inserted directly into targeted tumors (FIG. 17). IRE was originally developed for non-resectable tumors; however, as these techniques have evolved, the clinical applications that can benefit from the precision and non-thermal nature of the approach can now be extended, which are discussed at least in this Example.

Several in vitro models and tissue mimics were developed to evaluate the field effects of IRE and H-FIRE. These include cell monoculture, spheroid models, 3D tissue mimics and 3D organoids (FIGS. 18A-18E). Studies with these models have been validated in a variety of pre-clinical animal models including mouse, rate, pig, and dog, in both human and veterinary clinical trials.

Figure 18A:
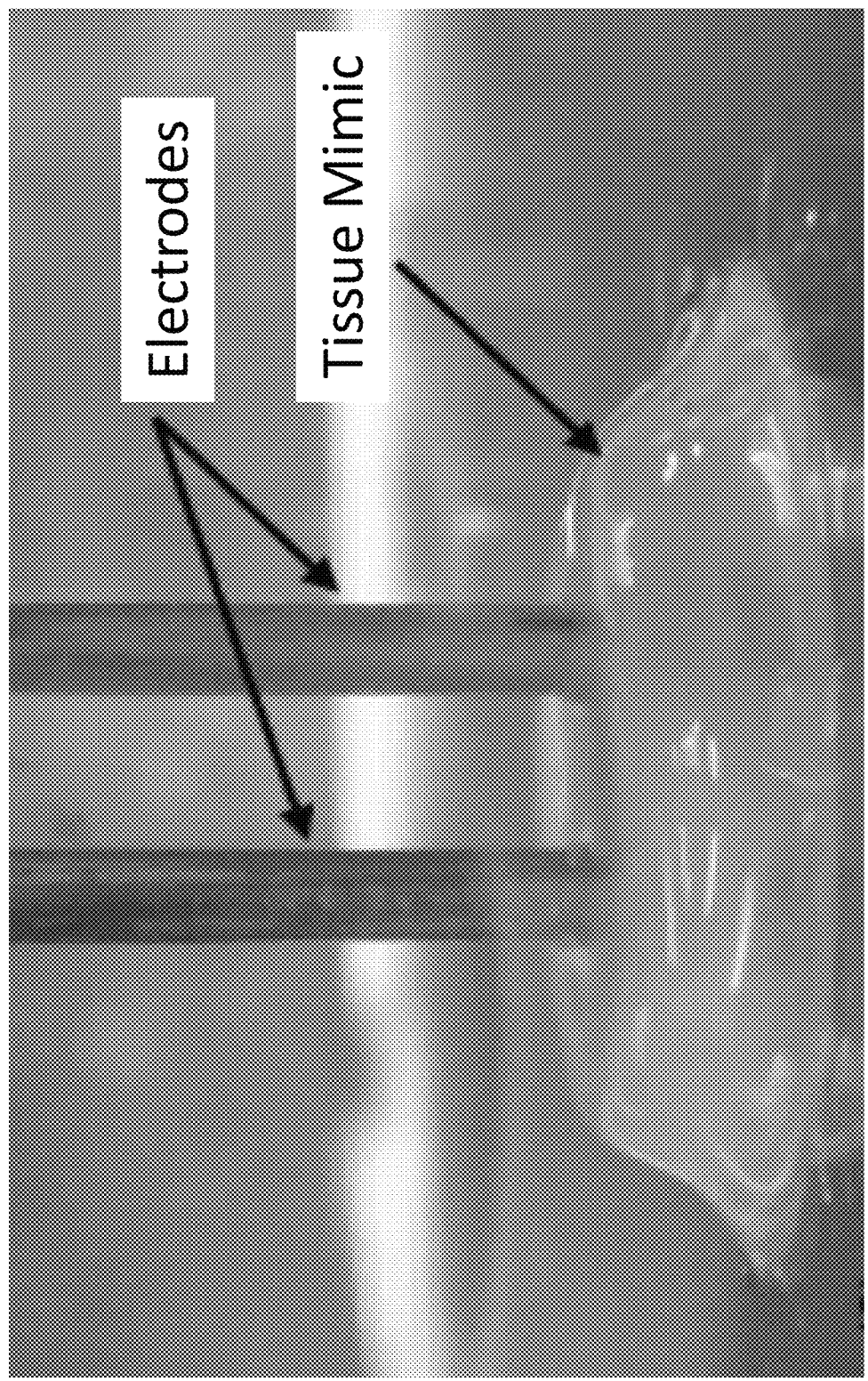
FIGS. 18A-18E can demonstrate H-FIRE treatment and modeling in a 3D tumor mimic.
Figures 18B, 18C, 18D, 18E:
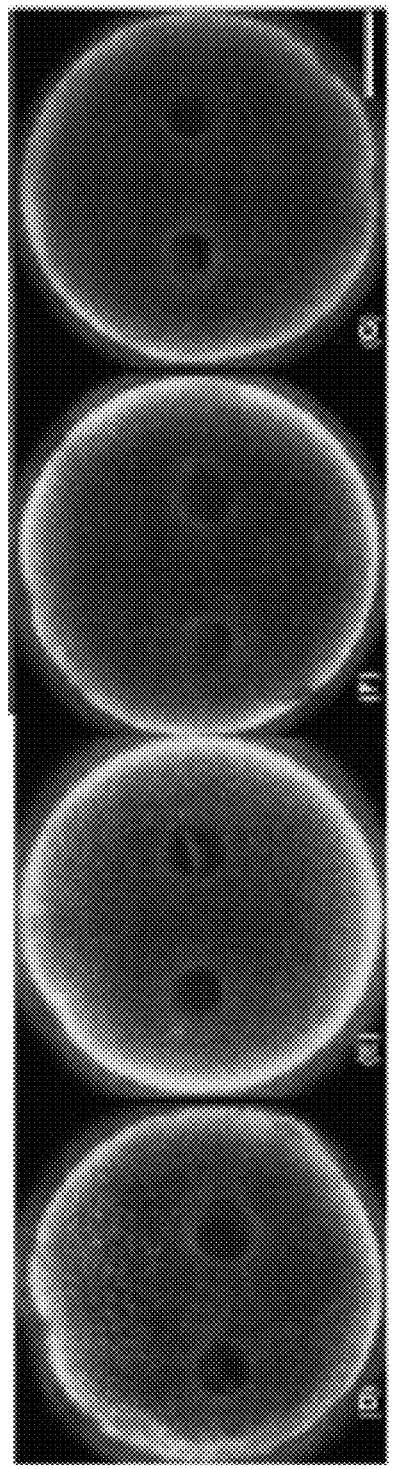
Figure 19A:
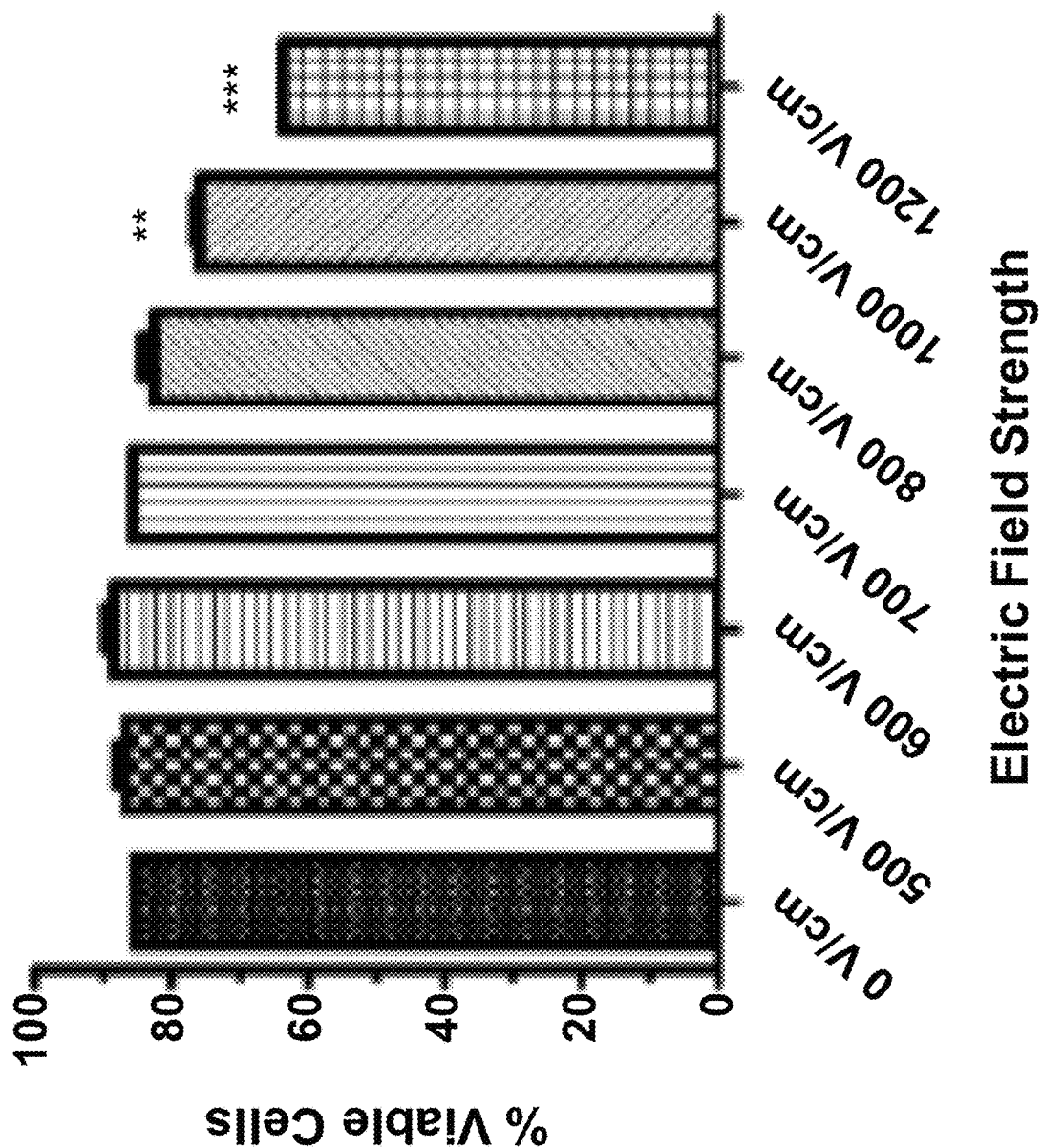
FIGS. 19A-19D shows graphs that can demonstrate that IRE enhances the pro-inflammatory tumor microenvironment in Pan02 cells.
Figure 19C:
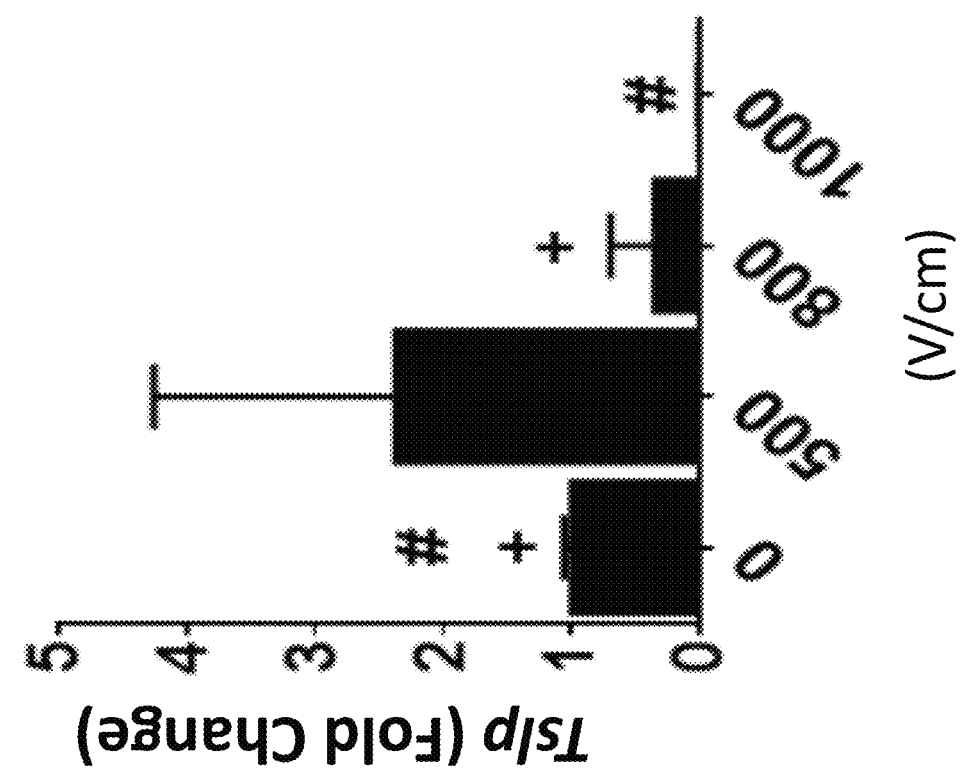
Figure 19B:
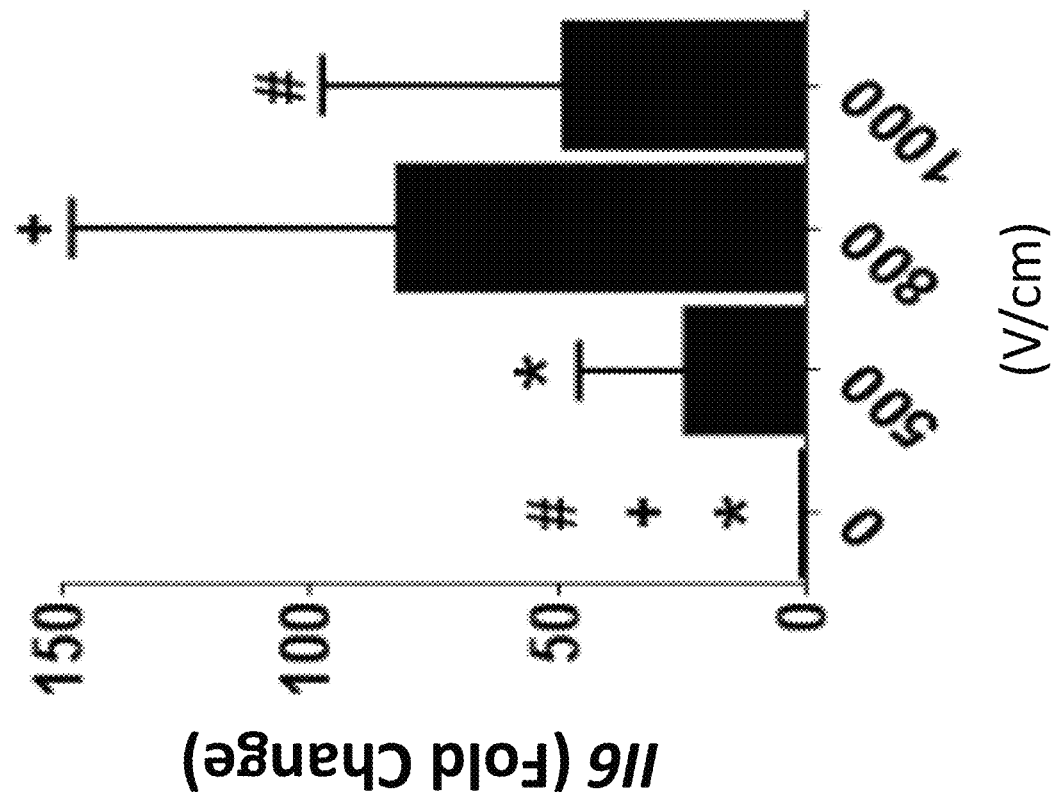
Figure 19D:
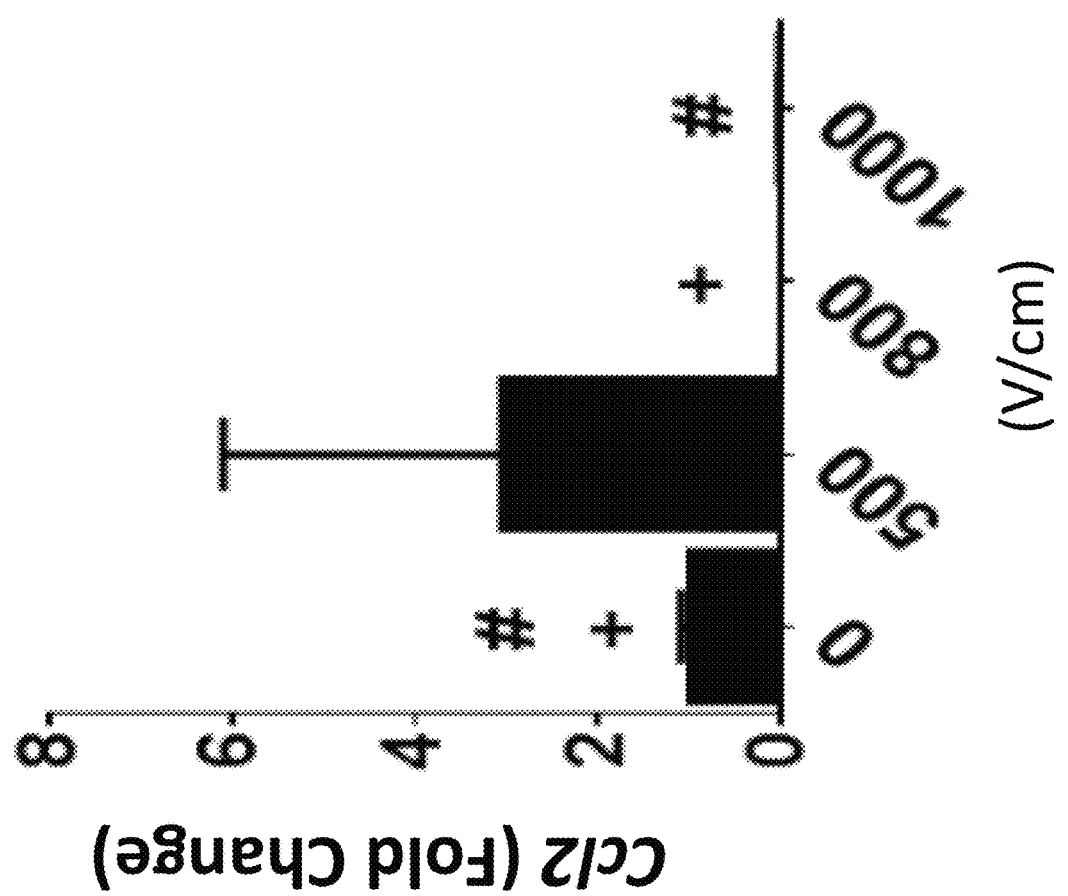

FIGS. 18A-18E can demonstrate H-FIRE treatment and modeling in a 3D tumor mimic. FIG. 18A) Experimental setup with electrodes inserted into tissue mimic. FIGS. 18B-18E) Live/dead staining reveals regions of the tissue impacted following 80 bursts containing (FIG. 18B) 2, (FIG. 18C) 24, and (FIG. 18D) 50 bipolar 2 μs pulses with a 2 μs delay between alternating pulses. (FIG. 18E) Diffuse treatment of 50 bipolar 2 μs pulses with 20 ms between alternating pulses. Scale bar=2 mm.

In these in vitro models, IRE treatment of mouse Pan02 pancreatic cancer cells was observed to promote a pro-inflammatory micro environment. IRE was observed to dose dependently induce cell death, while simultaneously increasing the production of pro-inflammatory mediators, such as IL-6 (FIGS. 19A-19D). Furthermore, IRE treatment was shown to dose dependently reduce the concentrations of genes associated with the immunosuppressive microenvironment, including thymic stromal lymphopoietin (Tslp) and Ccl2 (FIGS. 19A-19D). Epithelial derived cells are the primary producers of TSLP, which has been implicated in augmenting Th2 microenvironments and facilitating M1 macrophage polarization to M2/TAM phenotypes. Likewise, CCL2 has been shown to have multiple pro-tumorigenic roles, including promoting growth, facilitating angiogenesis, and recruiting host stromal cells to support progression.

FIGS. 19A-19D shows the results from gene expression pathway analysis of the tumor microenvironment following H-FIRE. To better define changes in the in situ 4T1 tumor microenvironment, we utilized gene expression profiling and commercial pathway analysis software to identify biological functions and gene networks impacted by treatment. In these studies, we observed significant down-regulation of breast cancer-associated genes in the ablated tumors compared to the untreated tumor groups. We also observed a significant shift in the balance between immunosuppressive and pro-inflammatory-associated gene transcription. Following treatment, genes associated with immunosuppression were significantly down-regulated, while genes associated with inflammation and pro-inflammatory immune responses were significantly up-regulated. Specifically, as shown here, we observed a significant shift in the tumor microenvironment to a Th1/Th17 profile and high levels of IL-6 following tumor ablation. A significant increase in IL-2 signaling was found in tumors that received a sub-ablation dose of H-FIRE, consistent with increased lymphocyte expansion and recruitment. Signaling networks associated with cytotoxicity were also significantly increased in responsive tumors, likely associated with increased cell death following treatment. Also shown here, gene networks associated with recruitment of leukocytes were significantly up-regulated in tumors following H-FIRE. IL-17 signaling and antigen presentation networks were also significantly up-regulated in some groups of animals. These data are consistent with the pro-inflammatory shift observed in the tumor microenvironment and may suggest that adaptive immune system signaling may benefit from this tumor ablation strategy. Together, these data indicate that H-FIRE treatment changes the tumor microenvironment, shifting it from one that is favorable for tumor progression to an anti-tumor, pro-inflammatory microenvironment driven by increased cellular immunity.

Example 5

Patient specific modeling and IRE treatment have beneficial therapeutic effects on the clinical progression of pancreatic cancer. An initial study of IRE on 200 patients with radiographic stage III LAPC and perioperative 90-day outcomes, local failure, and overall survival was completed and reported (NCT02041936) (Martin et al. Treatment of 200 locally advanced (stage III) pancreatic adenocarcinoma patients with irreversible electroporation: safety and efficacy. Annals of surgery. 2015; 123(4):1008-25. All patients underwent chemotherapy and 52% of patients received chemoradiation therapy for a median of 6 months prior to IRE. The initial results suggested that IRE reduced length of hospital stays, reduced local recurrence rates, and increased survival from 13 months to 28.3 months.

Beyond these benefits, further examination into immune system response revealed a decrease in $Tr_{ee}$ populations in the pancreas within the first 3 days after treatment. An apparent influx of inflammatory T cells 9 days following IRE occurred. Immune cell infiltration paralleled vascular re-epithelialization, and this population was expected to contain proportionately more cytotoxic CD8+ T cells, pro-inflammatory macrophages, and anti-tumor T helper cells (Th1), as well as, fewer regulatory T cells, anti-tumor macrophages, MDSCs, and Th17 cells.

Example 6

Despite promising treatments for cancer, metastatic disease and recurrence remain significant challenges. New therapeutic paradigms and treatment strategies are needed to eliminate mortality. Irreversible Electroporation (IRE) and High Frequency Irreversible Electroporation (H-FIRE) are emerging therapeutic approaches for tumor ablation. These techniques use a series of electric pulses applied through electrodes inserted directly into the targeted tumor to induce cancer cell death without the generation of significant thermal effects.

This Example can describe and demonstrate the effects of these treatment strategies on both tumor ablation and changes in the local tumor microenvironment. Both treatments were observed to be effective at improving survival outcomes and reducing tumor ablation in models of both breast and pancreatic cancer. Likewise, these treatments were both observed to improve innate and adaptive anti-tumor immunity by shifting the tumor microenvironment from an immunosuppressive environment that favors tumor growth and metastasis to a pro-inflammatory environment that restricts tumor progression. See e.g. FIGS. 12A-16. This can occur through the reduction of pro-tumor leukocytes in the field of treatment, the improved release of pro-inflammatory damage associated molecular patterns, and increased recruitment of antigen presenting cells and lymphocytes to the treated area. The non-thermal nature of the treatment can result in greater availability of tumor antigens in a non-denatured state, which can improve antigen presentation and engagement of the anti-tumor adaptive immune system.

Ultimately, promotion of the adaptive immune system improves detection and eradication of metastatic cells at sites distal to the primary tumor and treatment site. Together, these data can indicate that improved therapeutic outcomes can be achieved by a treat and resect approach, whereby resection occurs about 5-14 days post-IRE or post-HFIRE treatment after engagement of the adaptive immune system. The increased tumor antigen presentation and lymphocyte recruitment can improve conventional treatment strategies with chemotherapeutics and complement emerging immunomodulatory approaches targeting primary tumors, metastatic lesions, and preventing recurrence.

Example 7

This Example can describe HFIRE treatment on HCC in canines. Three dogs with resectable HCC were recruited. CT was performed for HFIRE treatment planning prior to delivery on day 0. Post-treatment CT and tumor resection were performed on day 4. Dogs were hospitalized following HFIRE until discharge. Pre- and post-HFIRE biopsy samples were processed with H&E and IHC for CD3, CD4, CD8, and CD79a. Blood was collected on days 0, 2 and 4 for CBC and chemistry.

HFIRE generally resulted in predictable ablation volumes assessed by post-treatment CT and gross specimens. No detectable cardiac interference and minimal muscle contraction occurred during HFIRE. No clinically significant adverse events occurred secondary to HFIRE. Microscopically, a well-defined ablation zone surrounded by a reactive zone was evident in the majority of samples. This zone was composed primarily of maturing collagen interspersed with few fibroblasts, macrophages, and CD3+/CD4−/CD8− lymphocytes not identified in the pre-treatment samples. FIGS. 26A-26D can show a voltage waveform that can illustrate the bipolar electrode, a schematic of the experimental set-up, and a comparison between a typical IRE voltage waveform and the HFIRE voltage waveform utilized in this assessment.

Methods

Dogs. Dogs diagnosed with HCC were screened for inclusion with a complete blood count, serum chemistry, urinalysis, prothrombin time, partial thromboplastin time, CT imaging of the thorax and abdomen with triple phase contrast enhancement and ultrasound-guided needle core biopsy of the liver mass prior to enrollment. Inclusion criteria included the presence of a surgically resectable primary liver tumor, a histologic diagnosis of HCC, and liver enzymes less than 4× the upper reference limit. Dogs were excluded if their tumor was non-resectable based on consultation with a board-certified surgeon or if survival was expected to be less than 6 weeks due to the presence of significant comorbidities.

Imaging. Dogs were imaged using a Toshiba Aquilion CT scanner. Dogs were anesthetized via inhalation anesthesia, breath hold during the scan. Precontrast and immediate, 1 minute delay and 3 minute delay scans of the thorax and abdomen were obtained using contrast agent and pressure injector. Images were analyzed in Horos image station. Dogs were imaged before H-FIRE treatment, and 4 days after treatment.

H-FIRE Treatment.

A custom built High Frequency Irreversible Electroporation (HFIRE) generator (EPULSUS®-FBM1-5, Energy Pulse Systems, Lisbon, Portugal) capable of producing sub-microsecond, bipolar pulses in rapid bursts was used to deliver HFIRE therapy via a single, 18-gauge bipolar electrode (AngioDynamics Inc., Latham, N.Y., USA) transcutaneously. The generator was set to deliver 300 bursts of a voltage amplitude of 2,250 V via a voltage waveform presenting pulse widths 2 µs with a 5 µs delay between each change in polarity (2-5-2; on-off-on [µs]) for a total on-time (energized-time) of 100 µs for each burst. An oscilloscope (DPO2002B, Tektronix Inc., Beaverton, Oreg., USA) was used to monitor the voltage and current waveforms subsequent of the signal being attenuated using a 1000×high voltage probe (P5210 A, Tektronix Inc., Beaverton, Oreg., USA) and passing through a current probe (2877, Pearson Electronics, Palo Alto, Calif., USA). A voltage waveform FIG. 1 illustrates the bipolar electrode, a schematic of the experimental set-up, and a comparison between a typical IRE voltage waveform and the HFIRE voltage waveform utilized within this assessment.

Numerical Modeling.

Numerical modeling can be employed predict electric field distributions, and determine electric field thresholds required prior to treatment of the patients. Abdominal computed tomography (CT) images from HCC patients were imported into 3D Slicer (an open source platform for medical image informatics), where relevant anatomical features (liver, hepatic artery, and tumor) were highlighted, labeled. Then a surface model maker tool was employed to interpolate between slices and re-construct the identified features in 3-dimensions. Each relevant geometry was transferred to 3-matic (Materialse, Leuven, Belgium), where the bipolar electrode was reconstructed and placed into the simulated tumor-tissue model. The entire assembly was meshed for import into a commercial finite element package (COMSOL Multiphysics, v.5.4; Stockholm, Sweden) for analysis using predefined boundary and initial conditions (FIG. 34). Dynamic electrical properties were then assigned to normal and malignant tissue within patient-specific hepatic geometries using tissue data normalized to hepatic tissue properties. The methods for predicting electric field distributions for HFIRE are similar to those described for IRE therapies. The governing equation for the electric potential, $\Phi$ at the end of a pulse was determined from equation 1 using the electro-quasistatic approximation and the electric field distribution, $\vec{E}$ by taking the gradient of the electric potential as shown in equation 2.

$$0 = -\nabla \cdot (\sigma \nabla \Phi) \quad (1)$$

$$\vec{E} = -\nabla \Phi \quad (2)$$

where $\sigma$ is the tissue conductivity. The electrical boundary conditions at the tissue-electrode interface were set to $\Phi=V$ (source) and $\Phi=0$ (sink). Boundaries not in contact with an electrode were treated as electrically insulating.

Figure 27:
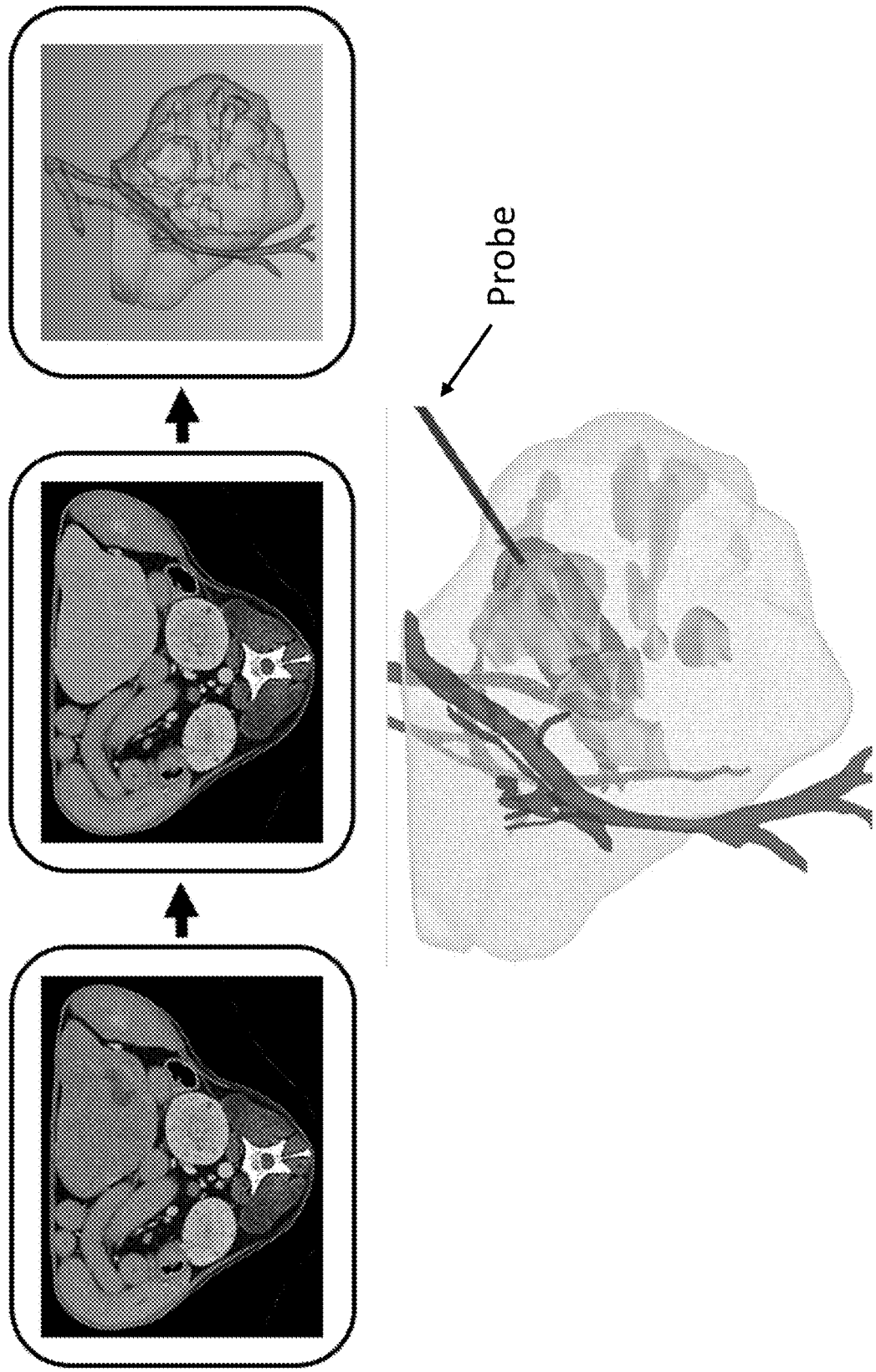
FIG. 27 shows a schematic of the 3D-reconstruction and numerical modeling process for patient 1.

A modified Pennes Bioheat equation, shown in equation 3, was applied to simulate the tissue temperature throughout treatment $$\rho c_p \frac{\partial T}{\partial t} = \nabla \cdot (k \nabla T) - \omega_b \rho_b c_b (T - T_b) + \sigma |\nabla \Phi|^2 \quad (3)$$

where $\rho$ is the density of the tissue, $c_p$ is the specific heat of the tissue, k is the thermal conductivity, $\omega_b$ is the blood perfusion, $\rho_b$ is the blood density, $c_b$ is the specific heat of the blood, and $T_b$ is the blood temperature. The tissue boundaries were defined as adiabatic at the edge of the domain to illustrate the maximum temperature increase within the tissue model. Further, a duty cycle approach was applied to the thermal simulation, averaging the thermal energy of a single pulse over a period of 1 s to significantly reduce the computation time. FIG. 27 provides a schematic describing each step of the 3D reconstruction process, including a patient specific finite element model.

Dog Hospitalization and Tumor Resection

Dogs were hospitalized post H-FIRE treatment in the Intensive Care Unit (ICU) for monitoring, until surgical resection of their HCC. The surgery was performed 4 days post H-FIRE treatment, immediately after the second CT scan. Tumor resection was performed using standard surgical technique. After surgery, the tumor was submitted for histopathology and immunohistochemistry. Dogs were recovered in the ICU and discharged to their owners 2 days later. Recheck exam and blood collection were performed 2 weeks after surgical removal (day 14). CBC, serum chemistry and serum analyses were performed on blood collected at each time point.

Histopathology and Immunohistochemistry.

Pre- and post-H-FIRE biopsy samples were processed within 20 minutes of excision. Biopsy samples were evaluated by a board-certified pathologist (SLC) to confirm a definitive diagnosis and assess completeness of excision. Post-HFIRE samples were grossly examined to identify regions of electroporation, non-treated tumor, and normal, non-neoplastic liver. Foci of electroporation were grossly identified in the majority of samples as well-demarcated foci of hemorrhage and necrosis. Sections were taken through these areas for examination of the treated/un-treated interface. Sections were routinely processed and stained with H&E. Immunohistochemistry for CD3, CD4, CD8, and CD79a was performed to evaluate the local immune response to treatment Gene Expression Analysis.

Figure 22:
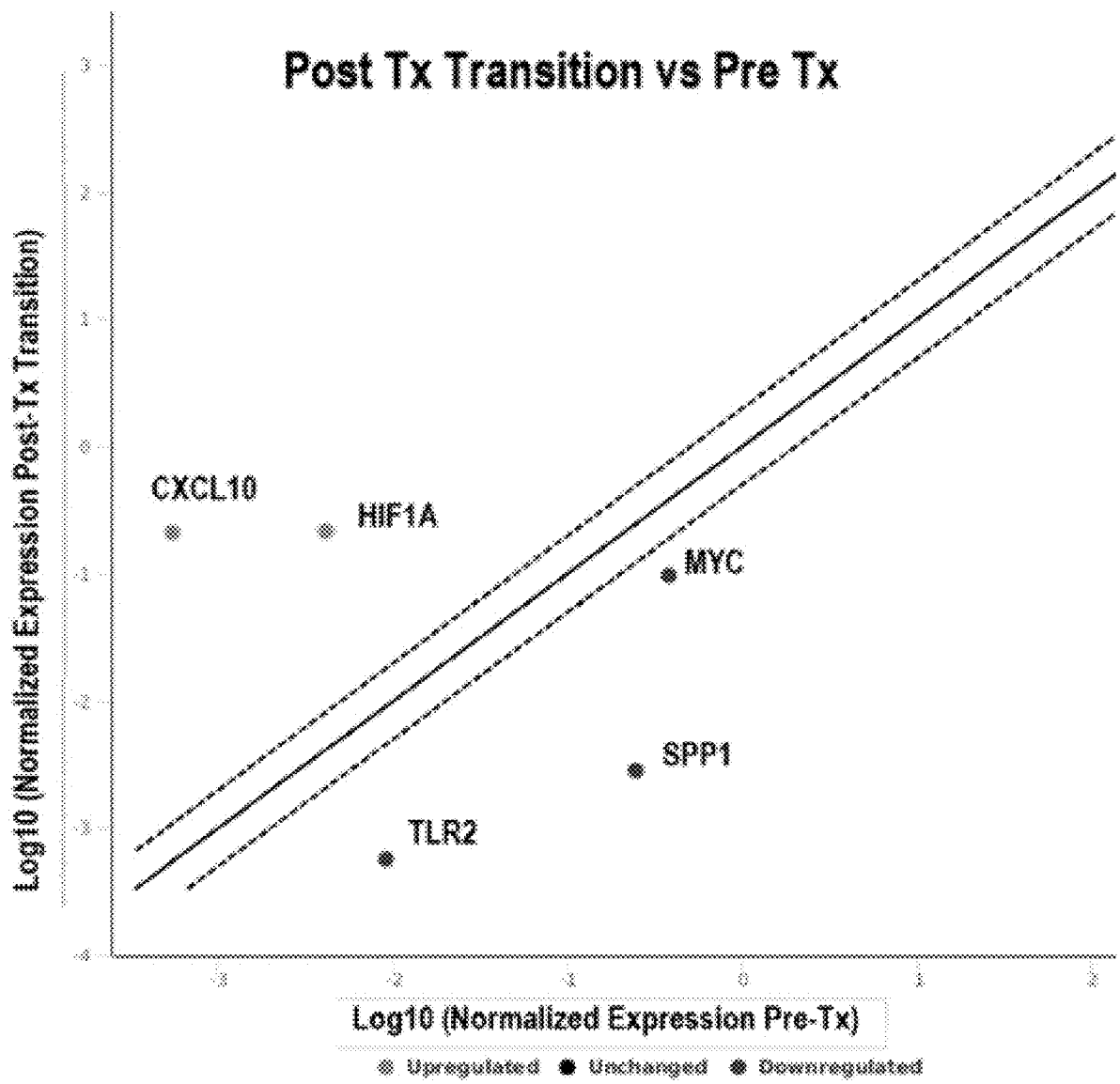
FIG. 22 shows a scatter plot of gene expression array data illustrating the results from FIG. 34. CXCL10 and HIF1A expression is significantly up-regulated and TLR2, SPP1 and MYC are significantly down-regulated following H-FIRE treatment in all 3 patients compared to baseline. Change in expression of all other genes was less than 2-fold (unchanged) and represented by the solid black line FIG. 23 show results an Ingenuity Pathway Analysis (IPA) of global changes in gene expression patterns following H-FIRE in 3 patients. Results revealed diverse, but functionally related predications in canonical pathways significantly increased by H-FIRE for Patients 1 and 2. Conversely, the gene expression profile for Patient 3 showed either no change or down-regulation of functionally similar canonical pathways.

Formalin-fixed paraffin embedded (FFPE) pre- and post-H-FIRE treatment tumor tissue was used in a SuperArray to compare specific gene expression between pre-treatment and post-treatment. Sections of the transition zone, at the ablated/non-ablated tumor of the post-treatment tumor were selected for RNA extraction. Total RNA was extracted from 10 um thick slices of each of pre-treatment tumor biopsies, and post-treatment FFPE tissues. RNA extraction was performed using an RNA isolation kit (Zymo Research Corporation, Irvine, Calif., USA), according to manufacturer's directions. The extracted RNA was quantified and assessed through standard QA/QC. The resulting RNA samples went through 1st strand synthesis and qPCR amplification in an ABI 7500 FAST thermocycler, according to the Qiagen RT2 profiler protocol. A custom, canine specific, superarray developed and validated in our Lab was used, based on the Qiagen RT2 profiler platform. Our array design contains 89 genes of interest, associated with inflammation and cancer, 3 positive controls (actin, HPRT1, GAPDH), genomic DNA control, no-template control, no-RT control, and no-amplification control. The RT-qPCR data were analyzed H-FIRE treatment can significantly increase cell death and innate immune system signaling. FIG. 22 shows a scatter plot of gene expression array data illustrating the results from FIG. 34. CXCL10 and HIF1 A expression is significantly up-regulated and TLR2, SPP1 and MYC are significantly down-regulated following H-FIRE treatment in all 3 patients compared to baseline. Change in expression of all other genes was less than 2-fold (unchanged) and represented by the solid black line using the 2(−Delta Delta C(2)) methodology. We compared the pre-treatment gene expression profile to the post-treatment groups samples, normalized to Normal Liver tissue archived from previous dogs. The superarray results were be analyzed using Qiagen's GeneGlobe Data Analysis software suite for individual gene expression differences and Ingenuity's IPA pathway analysis software for pathway analysis. FIG. 35 shows gene expression results following HFIRE treatment from genes with significant changes in expression.

Results.

Figures 28A, 28B:
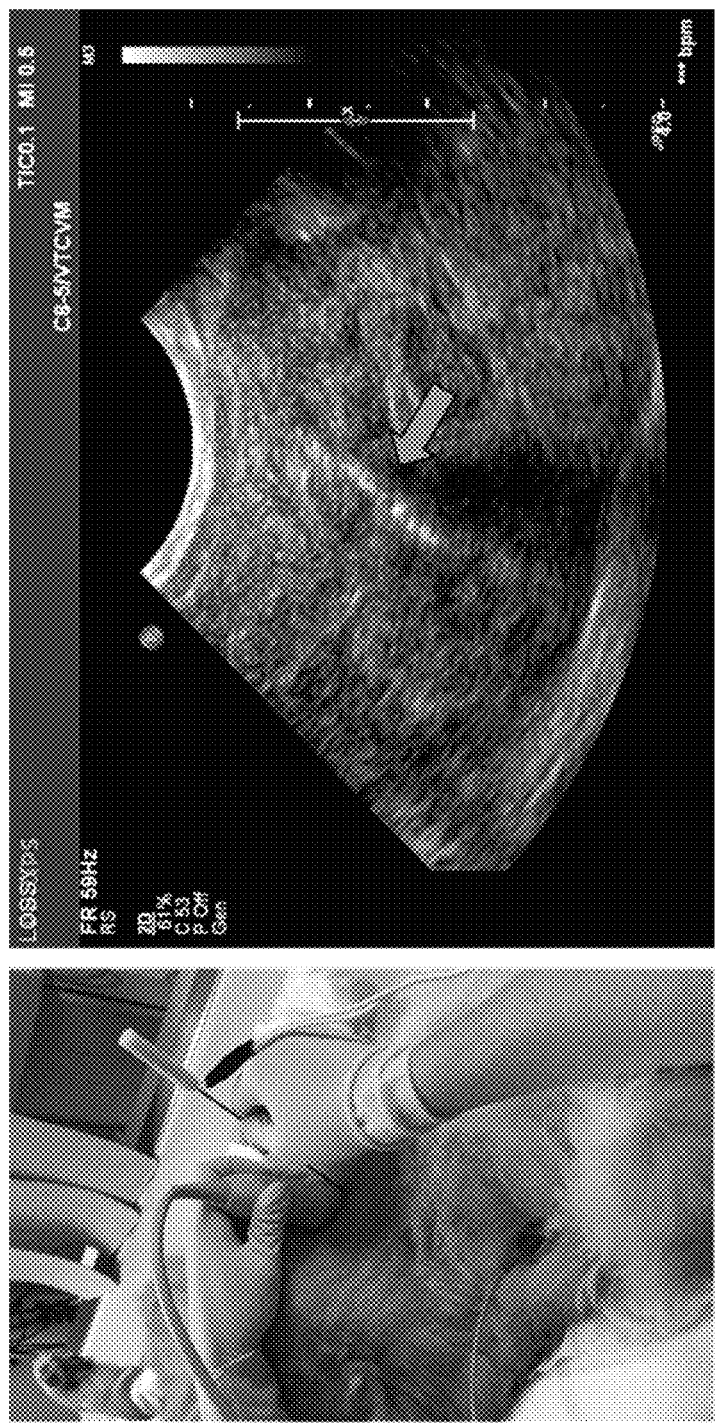
FIGS. 28A-28B show placement of the bipolar treatment probe into the tumor under ultrasound guidance (FIG. 28A). Ultrasound image of the bipolar treatment probe inserted into the tumor during treatment delivery (FIG. 28B); arrow—HFIRE bipolar electrode).

Three dogs met the inclusion criteria and were enrolled in the study. Patient 1 was a 15-year-old male castrated toy poodle with concurrent diabetes mellitus (controlled), hyperadrenocorticism (untreated) and seizures (controlled) that initially presented for general malaise and subsequent bloodwork revealed elevated liver enzymes. An MRI performed after his initial diagnosis of HCC revealed a primary brain tumor in the left frontal lobe most consistent with a meningioma and probably cerebral hemorrhages. Patient 2 was a 13-year-old female spayed mixed breed dog with concurrent hypothyroidism (medically controlled) that was asymptomatic on presentation but routine bloodwork revealed significant increases in liver enzymes, which initiated a thorough work-up. Patient 3 was a 14-year-old male castrated toy poodle with no significant concurrent medical conditions that presented with clinical signs of anorexia and weight loss. All patients had elevations in ALT and ALP at presentation. FIGS. 28A-28B show administration of HFIRE using ultrasound guided imaging. The arrow in FIG. 28B shows the bipolar treatment probe inserted into the tumor during treatment delivery.

Feasibility and Toxicity

H-FIRE Ablation

Figure 29:
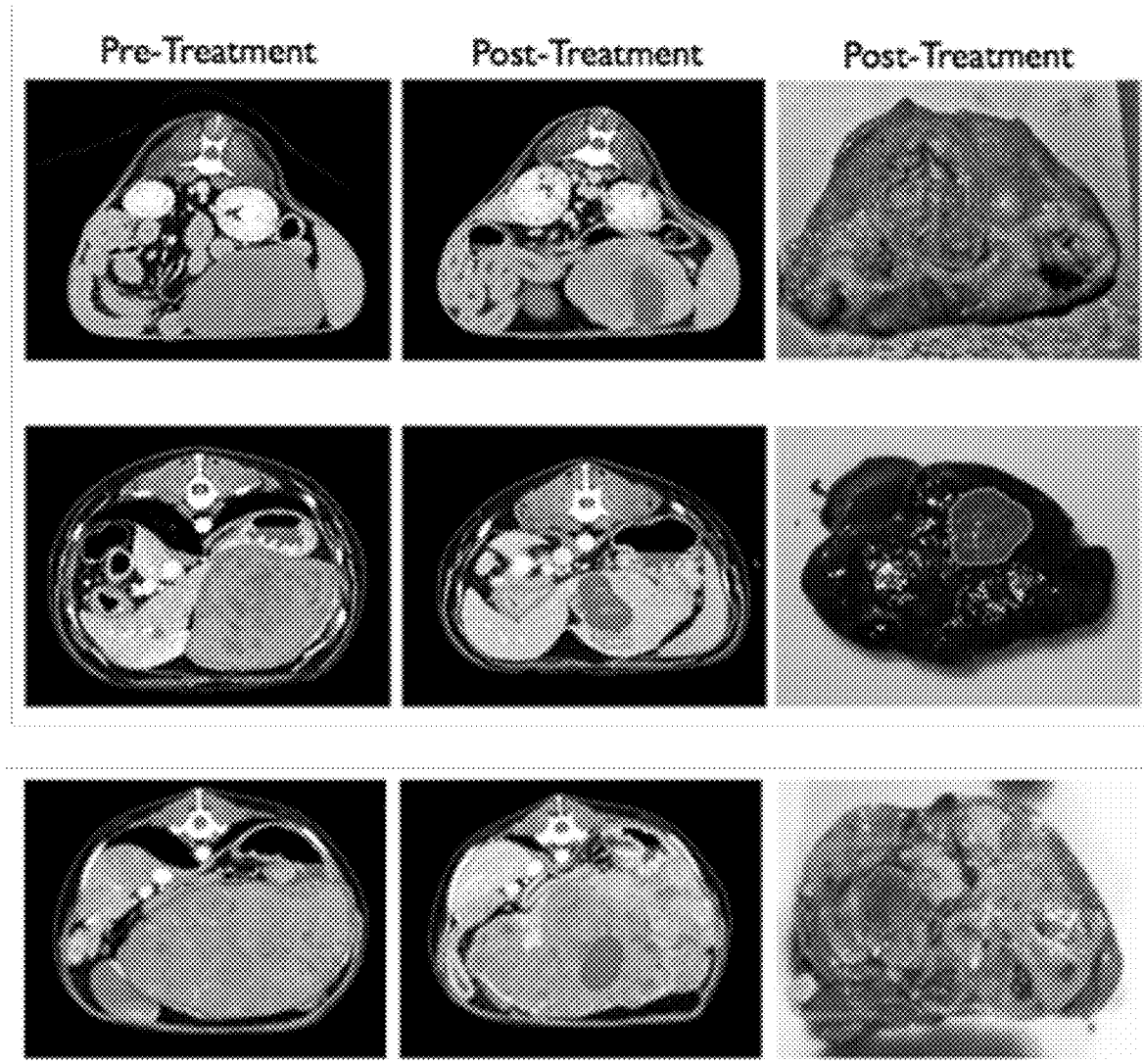
FIG. 29 shows a panel of CT images Pre- (left) and post-treatment (center) and images of gross tumor samples (right). CT images from all three patients showing predictable ablation volume (outlined) resulting from H-FIRE treatment. This correlated with the ablation volume noted in gross tumor samples (right).
Figure 30:
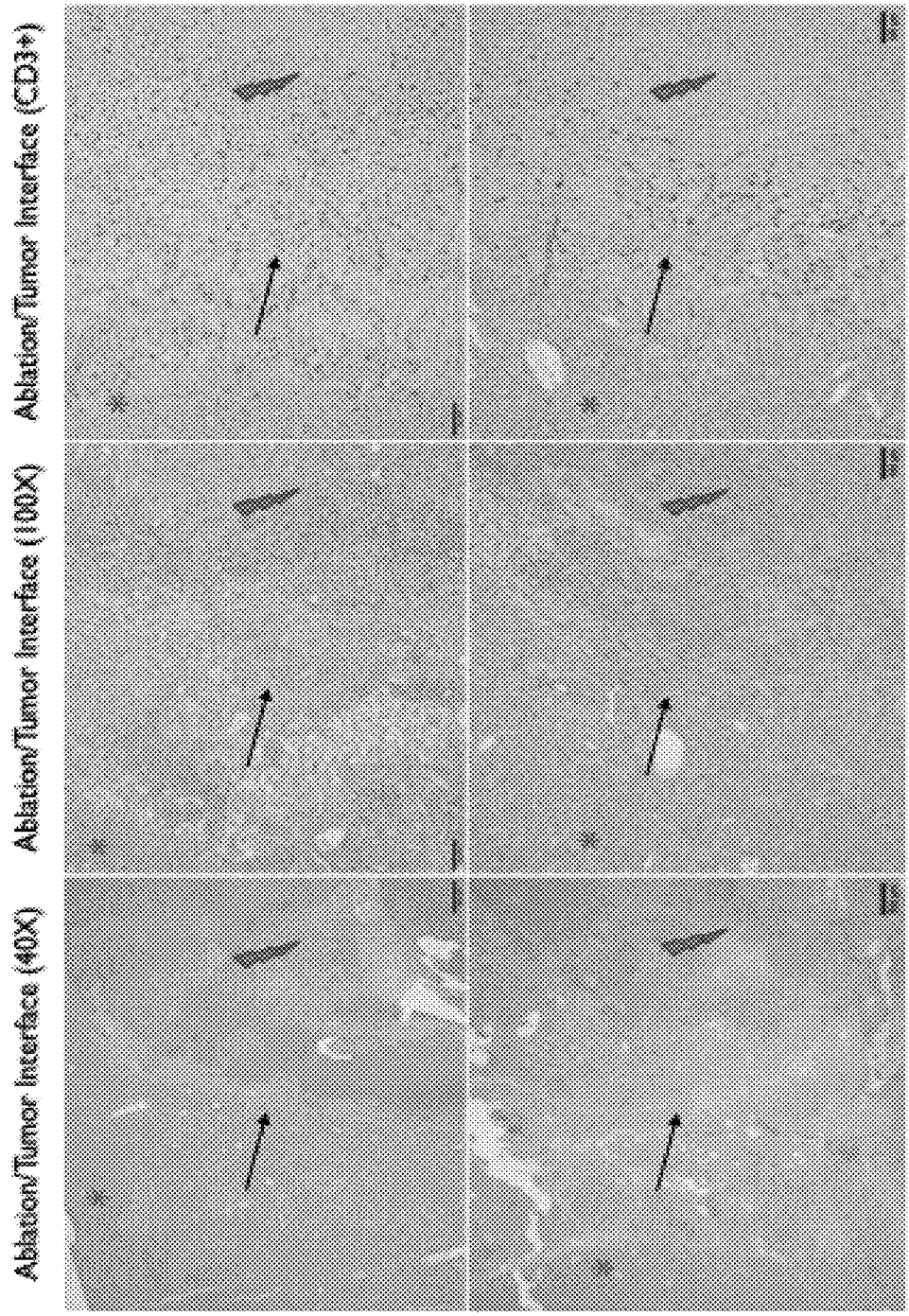
FIG. 30 shows a panel of images of tumor histopathology from patient 1 (top) and patient 2 (bottom) showing the well-defined ablation/tumor interface (arrows) with H&E at 40× (left) and 100× (center). IHC for CD3 revealed positive staining cells infiltrating the tumor-ablation interface. Untreated HCC is denoted by (*) and the ablation zone by the bolt.

No clinically significant adverse events were associated with H-FIRE treatment. No detectable cardiac interference occurred during H-FIRE delivery and only minimal muscle contraction was noted despite the absence of paralytics. H-FIRE resulted in a predictable ablation volume visible on CT prior to surgical resection (day 4) and in gross tumor samples following tumor excision in all three dogs (FIG. 29). Histopathology (H&E) revealed a well-defined ablation/tumor interface following H-FIRE in 2 patients (FIG. 30). In 1 patient, the ablation/tumor interface was poorly defined (FIG. 30).

Immunologic Reaction to the Ablation.

Figure 31:
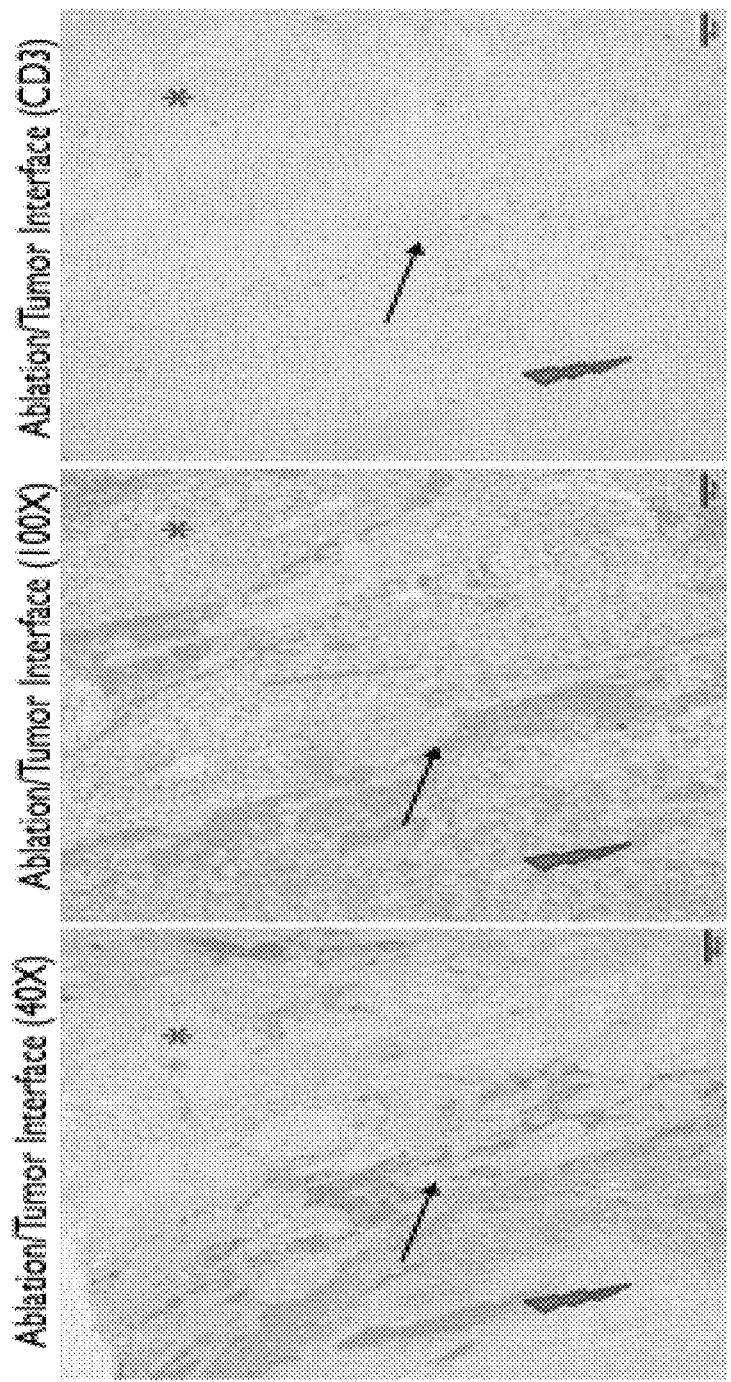
FIG. 31 shows a panel of images of tumor histopathology from patient 3 showing absence of a well-defined ablation/tumor interface (arrows) with H&E at 40× (left) and 100× (center). IHC for CD3 (right) shows the lack of CD3+ cells within the ablation/tumor interface. Untreated HCC is denoted by (*) and the ablation zone by the bolt.
Figure 32:
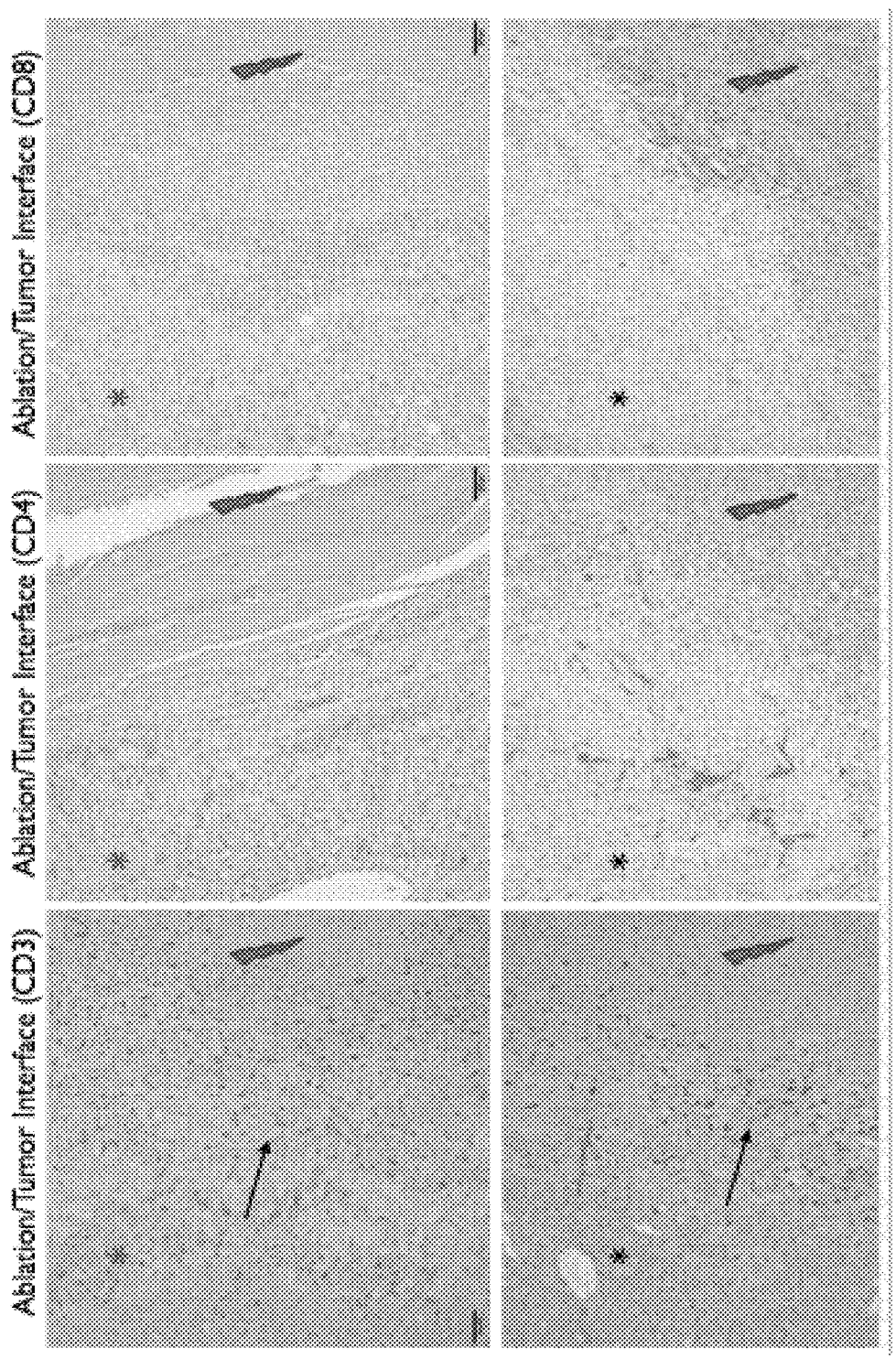
FIG. 32 shows a pane of images showing IHC results for CD3 (left), CD4 (center) and CD8 (right) on tumor samples from patient 1 (top) and patient 2 (bottom) showing infiltration of the ablation/tumor interface (arrows) with CD3+/CD4−/CD8− lymphocytes. Untreated HCC is denoted by (*) and the ablation zone by the bolt.

Immunohistochemistry on the tumor/ablation interface revealed infiltration with CD3+ lymphocytes following H-FIRE treatment in 2 patients (FIG. 31) Infiltrating T-cells were negative for both CD4 and CD8, suggesting they had a unique CD3+/CD4−/CD8− phenotype (FIG. 32) CD3+ lymphocyte infiltration was absent in the patient with a poorly defined ablation/tumor interface (FIG. 30-31) In all patients, the tumor/ablation interface was negative for CD79a+ lymphocytes.

Figure 33A:
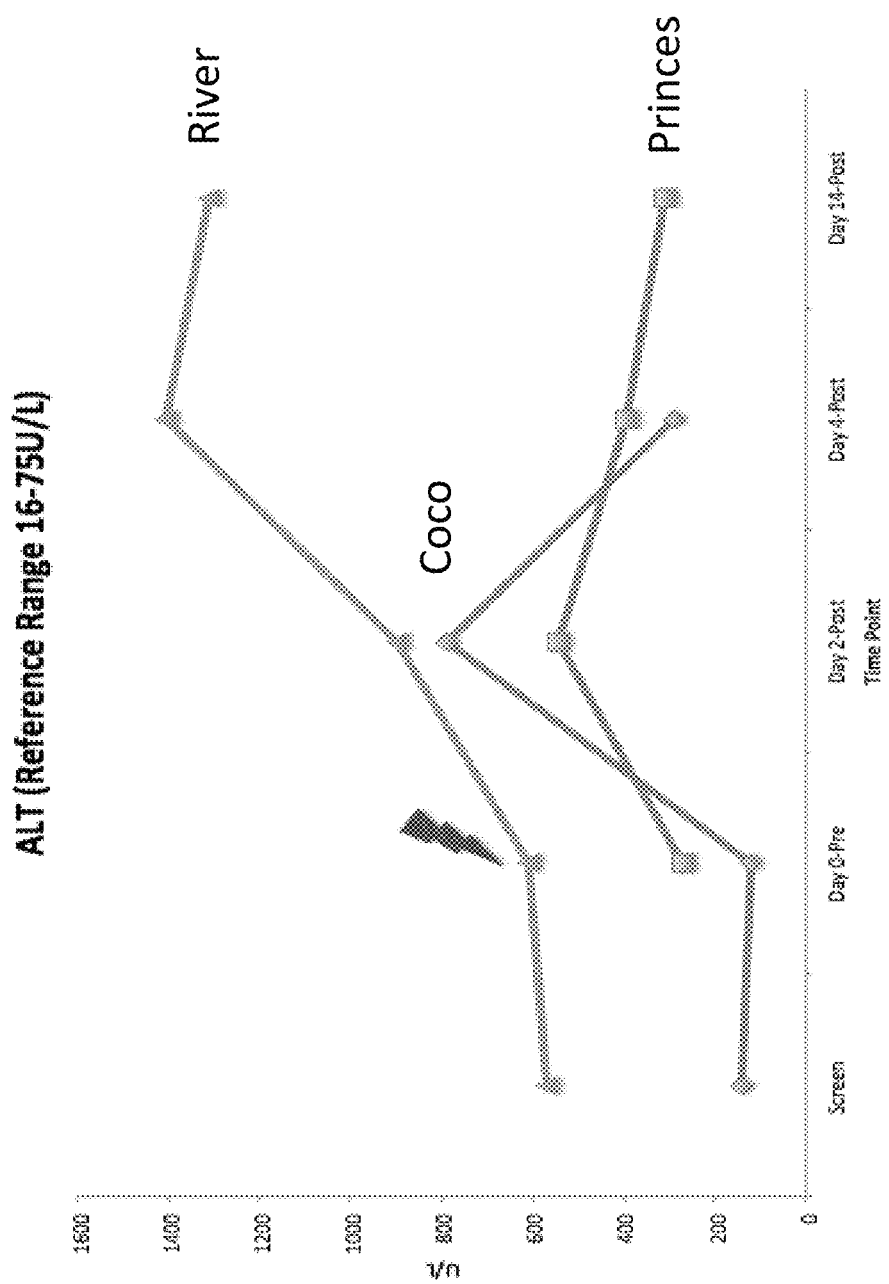
FIGS. 33A-33B show graphs that can demonstrate that ALT (FIG. 33A) and ALP (FIG. 33B) increased following H-FIRE treatment (bolt), but resolved over time following tumor removal (day 4).
Figure 33B:
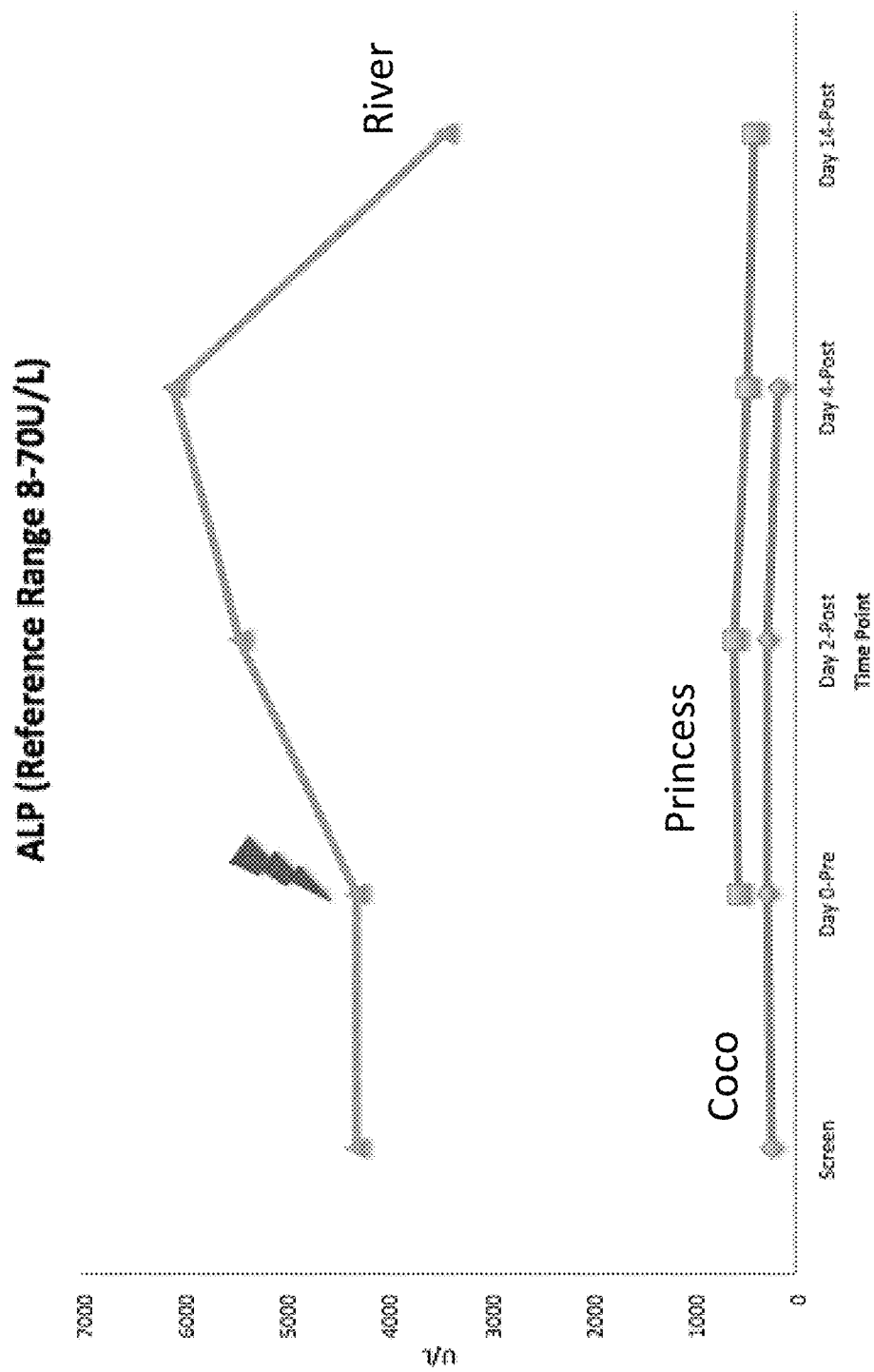

Alanine transaminase (ALT) and alkaline phosphatase (ALP) both increased compared to baseline following H-FIRE treatment (day 0) but resolved over time following tumor removal on day 4 (FIGS. 33A-33B). Liver enzyme elevations were most severe in patient 3 at all time points. Baseline liver values for patient 2 were obtained from the referring veterinarian so reference ranges varied significantly from serum chemistry analyzers at the VTH, thus it was excluded from the data set. Patient 1 was euthanized 8 days after surgery due to uncontrolled seizures thus recheck liver values were not available. Patients 2 and 3 are currently alive and undergo chest x-rays and an abdominal ultrasound every 3 months for re-staging. Neither recurrence nor metastasis has been identified in either patient to date.

Gene expression analysis (SuperArray) revealed up-regulation of CXCL10 and HIF1A expression following H-FIRE treatment in all 3 patients. In contrast, TLR2, SPP1 and MYC expression was down-regulated following H-FIRE treatment in all 3 patients compared to baseline (FIG. 22). Change in expression of all other genes was less than 2-fold, thus considered unchanged.

FIG. 23 show results an Ingenuity Pathway Analysis (IPA) of global changes in gene expression patterns following H-FIRE in 3 patients. Results revealed diverse, but functionally related predications in canonical pathways significantly increased by H-FIRE for Patients 1 and 2. Conversely, the gene expression profile for Patient 3 showed either no change or down-regulation of functionally similar canonical pathways.

FIGS. 24A-24F show graphs show results from the top 6 canonical pathways impacted by H-FIRE, comparing pre-treatment to post-treatment, ranked by z-score. Patient 1 and 2 are highly consistent, with patient 3 demonstrating opposing results.

Figure 25A:
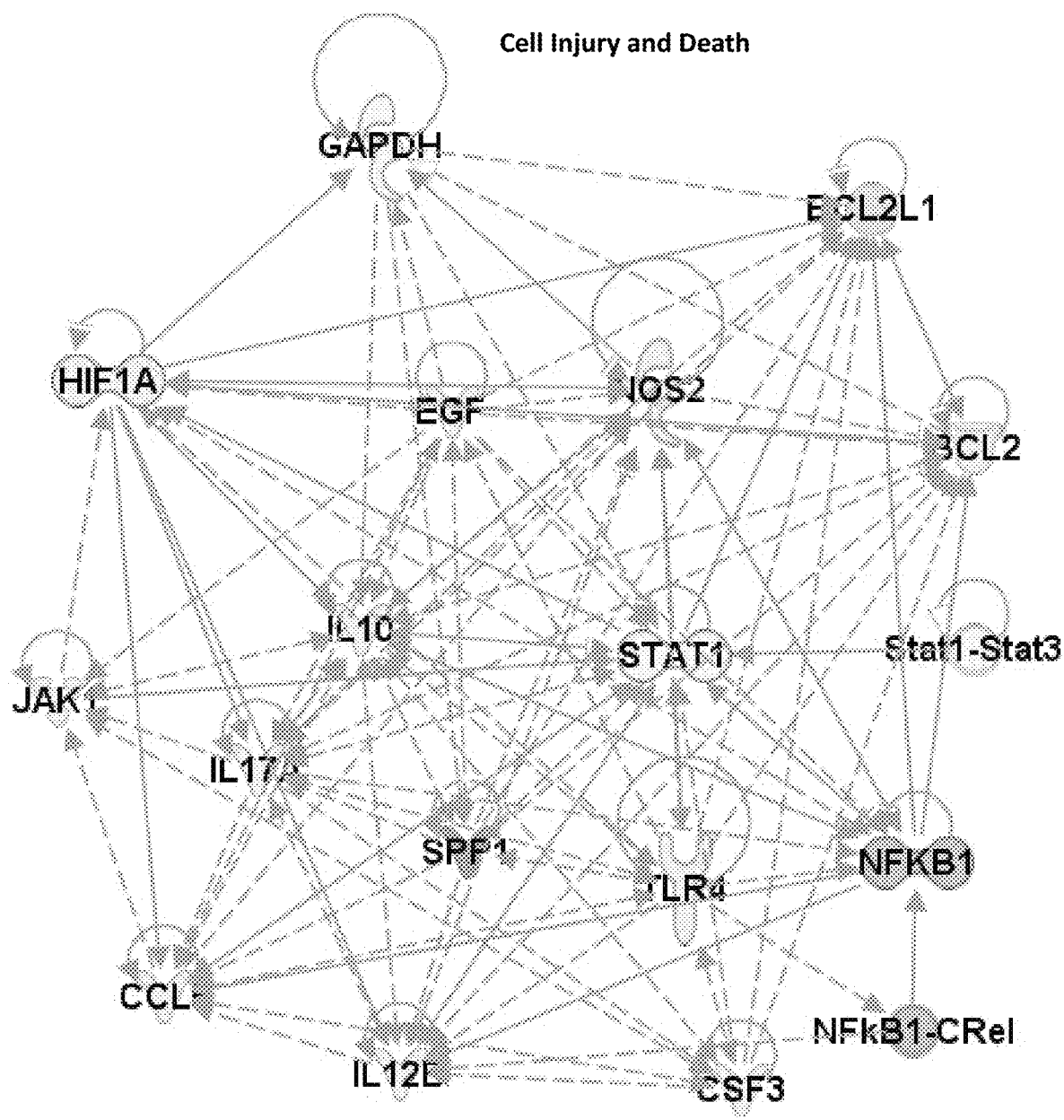
FIGS. 25A-25C show pathways associated with the activation of cellular immunity (FIG. 25B) and cell death (FIG. 25A) were significantly up-regulated following H-FIRE treatment.
Figure 25B:
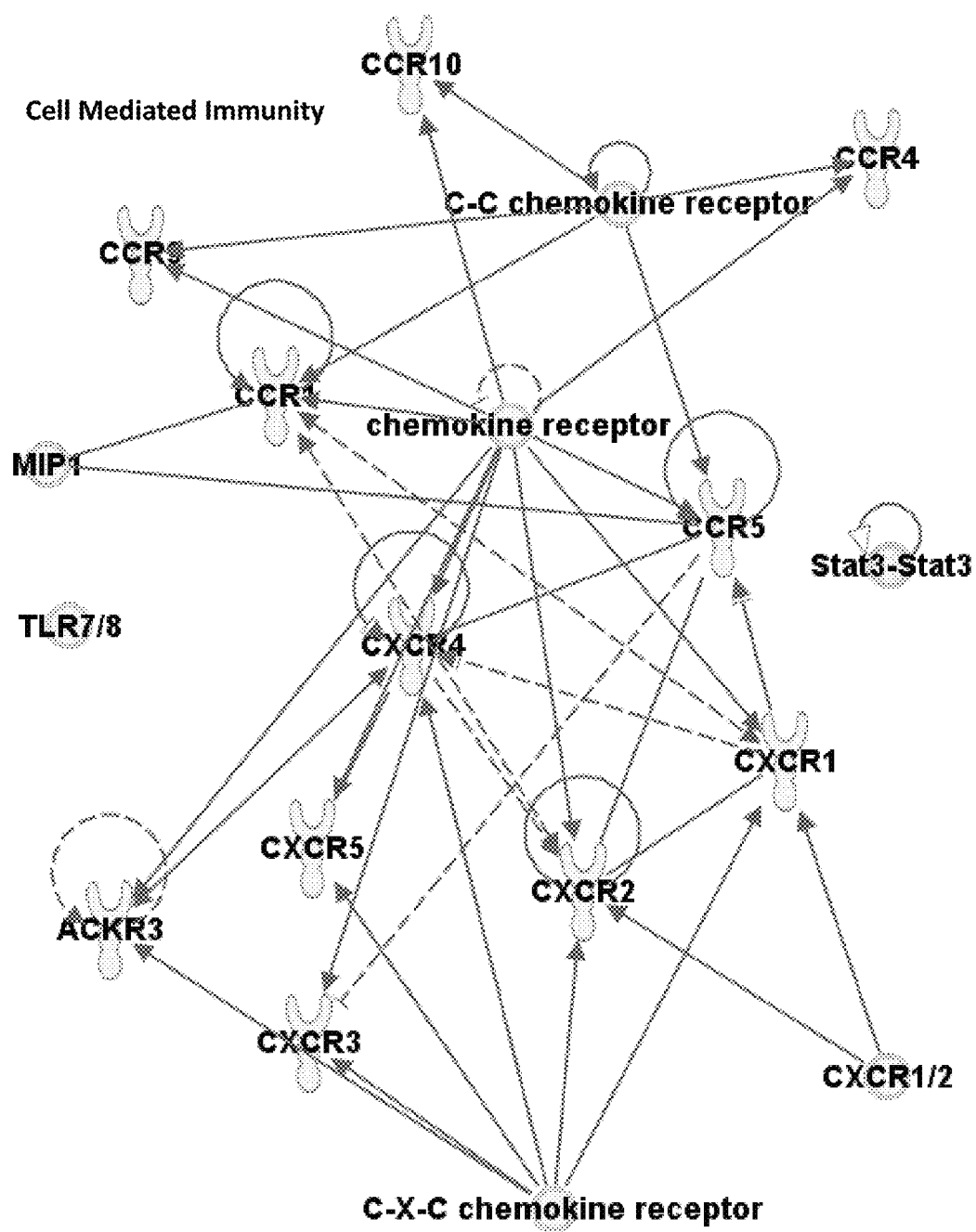
Figure 25C:
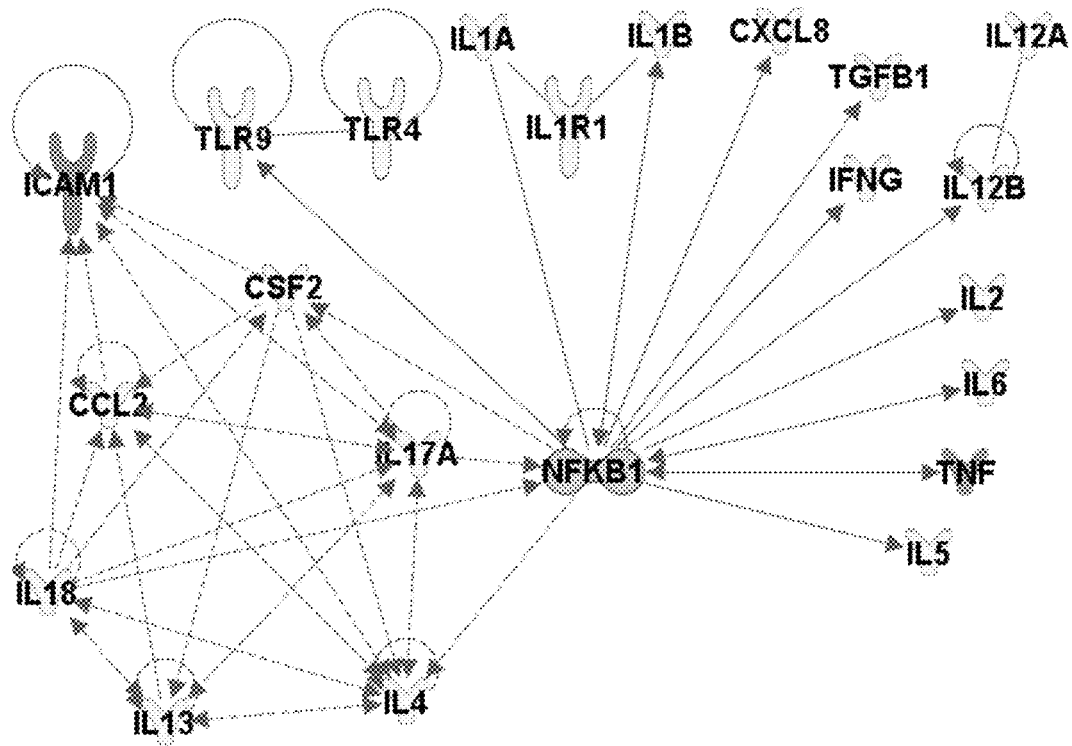
Figure 26A:
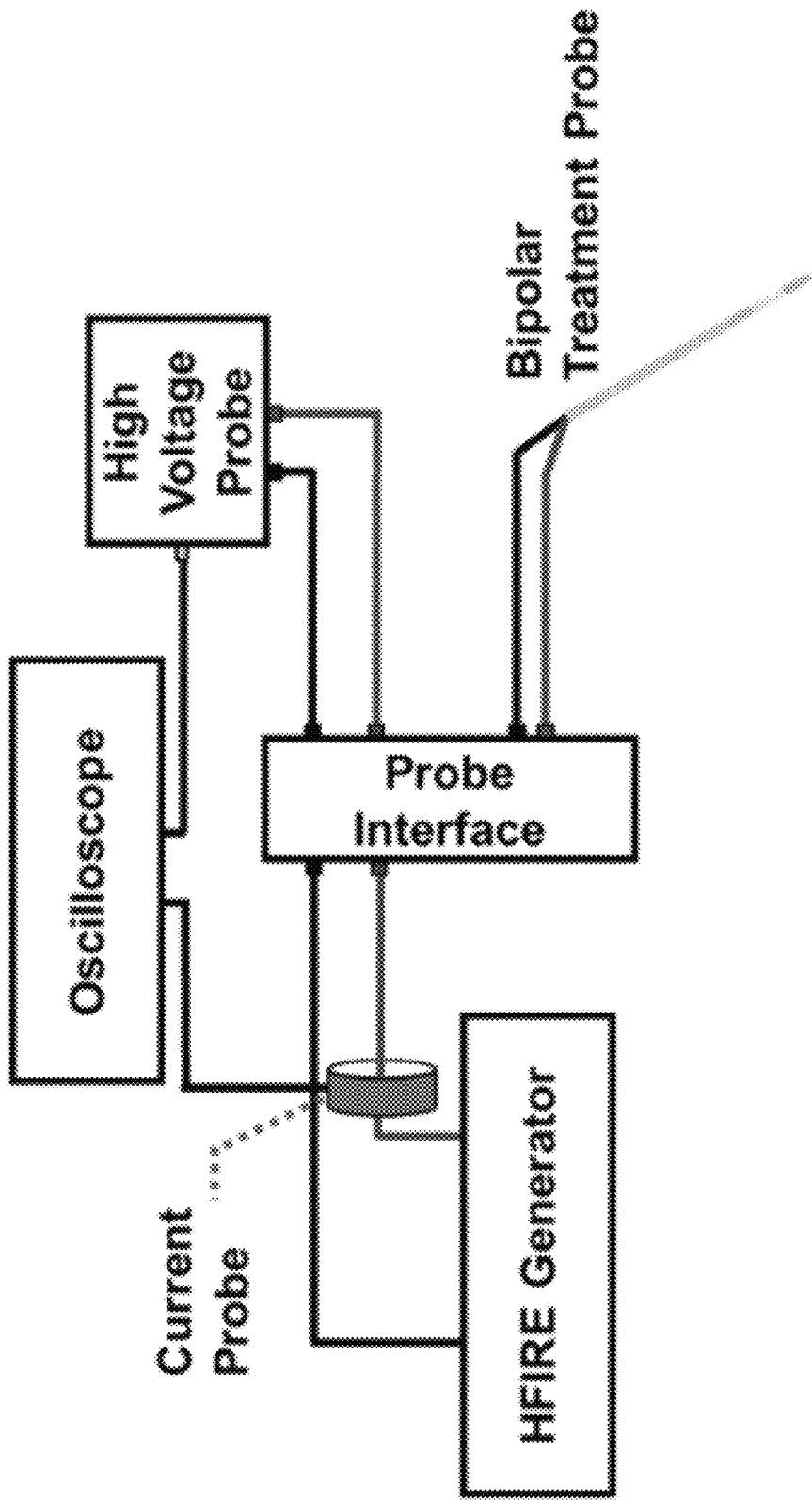
FIGS. 26A-26D a (FIG. 26A) Schematic of HFIRE experimental set-up and (FIG. 26C) 18-gauge, bipolar electrode.
Figure 26B:
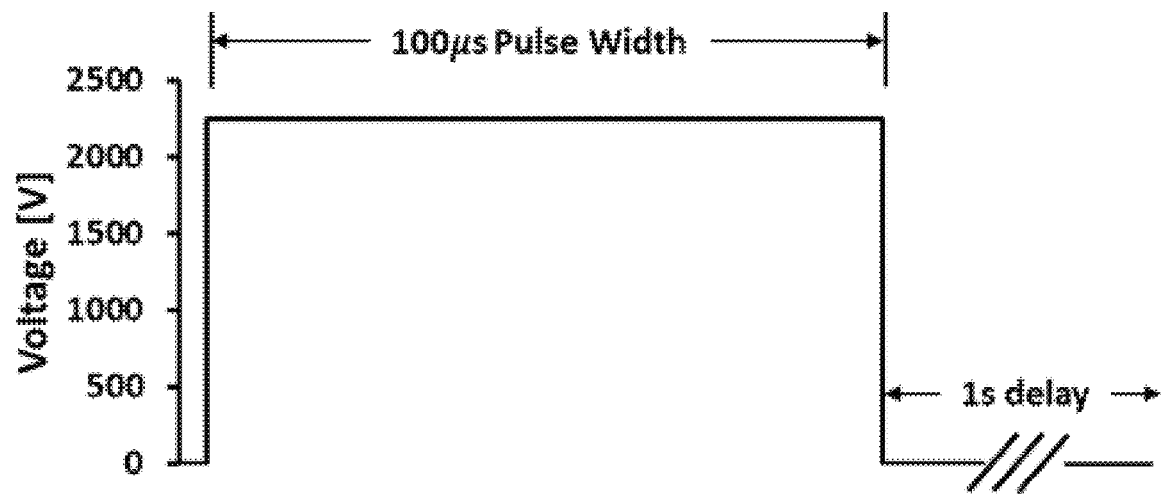
Figure 26C:
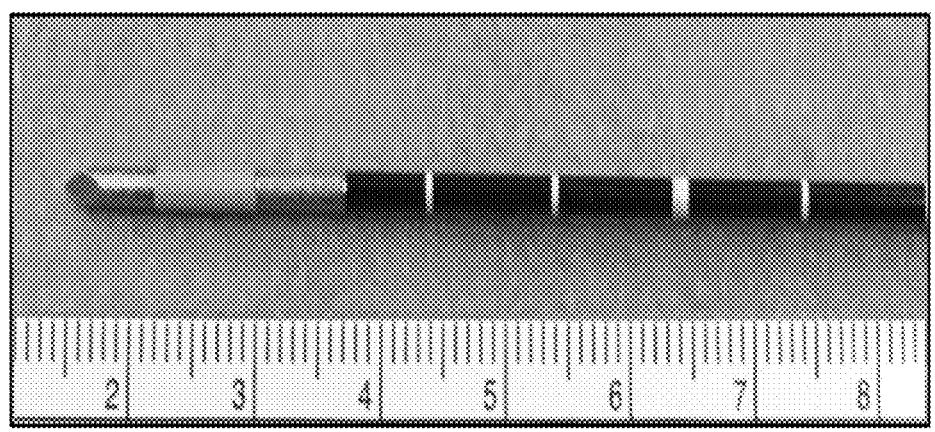
Figure 26D:
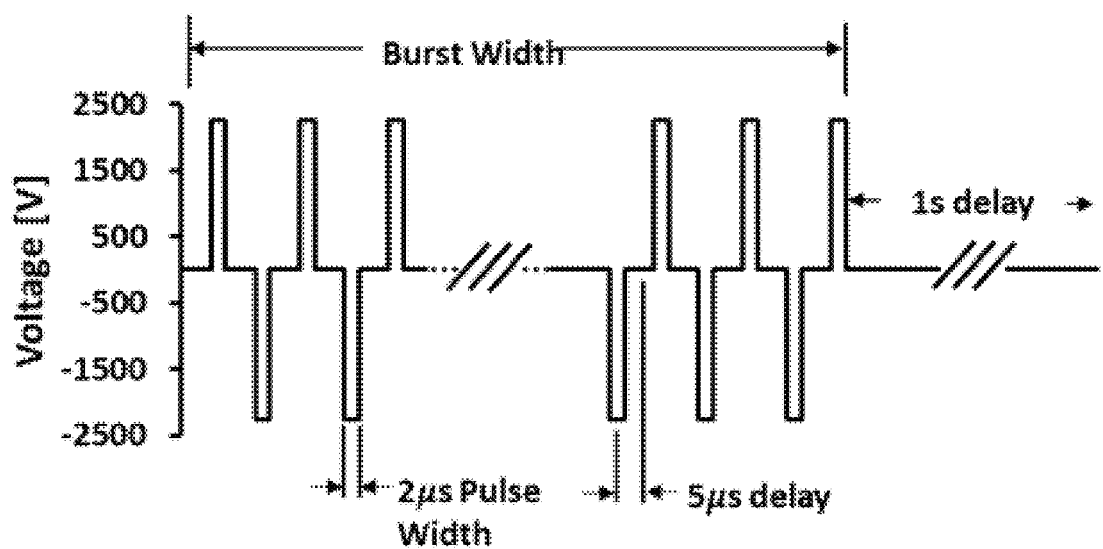

FIGS. 25A-25C show pathways associated with the activation/promotion of cellular Immunity (FIG. 25B) and cell death (FIG. 25A) were significantly up-regulated following H-FIRE treatment. FIG. 25A. IPA network analysis identified 2 functional networks that fit the canonical pathways identified above, cell injury/death and cell mediated immunity. Both of these networks were significantly upregulated in all patients following H-FIRE treatment FIG. 25C. NF-κB signaling was one of the most dominate pathways impacted by H-FIRE treatment. Gene expression patterns revealed a significant global up-regulation in NF-κB signaling. While patient 3's data was significant up-regulated, it was a down-regulation in the network going to a less down-regulation in the network.

Discussion

High Frequency irreversible electroporation (H-FIRE) appears to be an effective minimally invasive method for HCC ablation in our spontaneous canine liver tumor model. In our proof of principle study, we did not need to use paralytics or cardiac synchronization, without any adverse events observed. The ablated tumor volume was in close agreement with previous work from our team in normal liver, and was characterized by a unique change in the tumor microenvironment. H-FIRE represents the next step in ablative technology that negates the need for paralytics and cardiac synchronization required during traditional IRE. H-FIRE resulted in a predictable ablation volume in all three dogs. This allows for more precise treatment planning prior to ablation of entire tumors to minimize damage to surrounding normal structures. Additionally, critical structures, such as vascular/biliary structures appear to be preserved following H-FIRE treatment, thus it could be superior to alternative ablation methods for treatment of tumors adjacent to these structures. This ablation technique was evaluated in resectable tumors to allow for thorough evaluation of the loco-regional that would otherwise be limited without removal of the entire tumor.

The unique CD3+/CD4−/CD8− phenotype of lymphocytes infiltrating the ablation/tumor interface was unexpected as terminally differentiated T-cells typically express either CD4 or CD8. Double negative T-lymphocytes appear to be involved in immune regulation and tolerance, as well as host defense and inflammation. Since the liver is an immunologically rich but tolerogenic organ, the presence of these cells may serve to prevent development of auto-immune reactions upon exposure to foreign substances entering the liver.

One explanation for the absence of T-cell infiltration within the ablation/tumor interface of patient 3 is as follows. Cell death secondary to tumor necrosis typically triggers an adaptive immune response. Despite the abundant necrosis contained within this patient's tumor, adaptive immune cell infiltration was not detected. Additionally, due to the amount of necrosis associated with this tumor, it was difficult to appreciate the ablation zone grossly, thus it is possible that sections submitted for histopathology did not represent the ablation/tumor interface.

Liver enzymes (ALT and ALP) increased above baseline in all patients following H-FIRE treatment and resolved following tumor removal. This increase was anticipated since tumor cells and normal hepatocytes likely contain similar enzymes that are released upon cell death. Patient 3 had the most severe liver enzyme elevations and took the longest for these elevations to resolve, likely secondary to the relative increase in tumor size compared to patients 1 and 2.

CXCL10 (C-X-C motif chemokine ligand 10) encodes the ligand for CXCR3. Binding of the ligand to its receptor results in stimulation of monocytes, natural killer and T-cell migration and modulation of adhesion molecule expression. HIF-1alpha (hypoxia inducible factor 1 subunit alpha) encodes for the alpha subunit of the transcription factor HIF-1, which regulates cellular and systemic homeostatic response to hypoxia, plays a role in tumor angiogenesis and may contribute to cell autophagy. Increased expression of these genes can suggest that autophagy may play a role in the mechanism of cell death.

TLR2 (toll like receptor 2) encodes a protein that functions in pathogen recognition and activation/promotion of the innate immunity and may promote apoptosis. SPP1 (secreted phosphoprotein 1) encodes a cytokine that upregulates expression of IFN-y and IL-12, which are important for activation/promotion of innate and adaptive immunity. MYC is a proto-oncogene that codes for a protein involved in cell cycle progression, apoptosis and cellular transformation. Given this information, decreased expression of TLR2, SPP1 and MYC were not expected. This may be because by post-treatment measurements represent a single point in time, so initial increases in gene expression may have been missed.

Regulatory T-cells play an important role in immunosurveillance within the tumor microenvironment. Initial attempts at performing flow cytometry on peripheral blood for FOXP3 were compromised by sample handing during shipment, and since cells need to be alive for evaluation, repeat analysis on blood/serum is not possible. We plan to develop a method to extract lymphocytes from the ablation/tumor interface of persevered samples to definitively characterize their phenotype. Additionally, immunohistochemistry for FOXP3 will be performed on existing tumor samples, specifically evaluating the ablation/tumor interface. Beyond evaluation of H-FIRE in non-resectable tumors, future studies should aim to evaluate the effect of local therapy on distant metastatic lesions (abscopal effect). Additionally, combination therapy with checkpoint inhibitors may enhance the initial immune response induced by H-FIRE delivery, and should therefore be evaluated.

We claim:

1. A method of treating a tissue in a subject comprising:
ablating the tissue using a non-thermal ablation technique;
measuring a change in a treatment parameter during the step of ablating; and
administering an additional treatment to the subject in response to the measured change in the treatment parameter, wherein the additional treatment comprises is measuring the amount of a pro-inflammatory immune molecule or cell, a suppressive immune molecule or cell, or both in a bodily fluid or a biopsied tissue of the subject.

2. The method of claim 1, wherein the step of administering the additional treatment occurs 4-30 days after the ablating.

3. The method of claim 1, wherein the additional treatment further comprises a treatment selected from the group consisting of: tissue resection, thermal ablation, non-thermal ablation, chemotherapy, radiation therapy, immunotherapy, biologic therapy, genetic therapy, and combinations thereof.

4. The method of claim 1, where the non-thermal ablation technique is irreversible electroporation.

5. The method of claim 4, wherein the non-thermal ablation technique, is high-frequency irreversible electroporation.

6. The method of claim 1, wherein the treatment parameter is bulk tissue conductivity.

7. The method of claim 6, wherein the change in bulk tissue conductivity is measured by measuring current during the step of ablating.

8. The method of claim 1, wherein the treatment parameter is measured by measuring current during the step of ablating.

9. A method of treating a tissue in a subject comprising:
ablating the tissue using a non-thermal ablation technique;
measuring a change in a treatment parameter during the step of ablating; and
administering an additional treatment to the subject in response to the measured change in the treatment parameter;
wherein the treatment parameter is measured by measuring current during the ablating; and
wherein the administering of the additional treatment occurs 4 to 30 days after the ablating when the current measured is between 25 A and 100 A.

10. The method of claim 9, wherein the additional treatment is selected from the group consisting of: tissue resection, thermal ablation, non-thermal ablation, chemotherapy, radiation therapy, immunotherapy, biologic therapy, genetic therapy, and combinations thereof.

11. The method of claim 9, wherein the additional treatment is measuring the amount of a pro-inflammatory immune molecule or cell, a suppressive immune molecule or cell, or both in a bodily fluid or a biopsied tissue of the subject.

12. The method of claim 9, wherein the non-thermal ablation technique is configured to cause non-thermal irreversible electroporation of the tissue.

13. The method of claim 9, wherein the treatment parameter is bulk tissue conductivity.

14. The method of claim 9, wherein the step of administering occurs 0 to 5 days after the non-thermal ablation technique when the current is less than 25 A.

15. A method of treating a tissue in a subject comprising:
applying a plurality of electrical pulses to tissue of a subject, wherein the electrical pulses are configured to cause non-thermal ablation of the tissue;
measuring a current of the applied plurality of electrical pulses;
administering an additional treatment to the subject in response to and based on the measured current, wherein the step of administering occurs 0 to 5 days after the non-thermal ablation when the current is less than 25 A; and
wherein the step of administering occurs 4-30 days after the non-thermal ablation when the current is between 25 A and 100 A.

16. The method of claim 15, wherein the additional treatment is selected from the group consisting of: tissue resection, thermal ablation, non-thermal ablation, chemotherapy, radiation therapy, immunotherapy, biologic therapy, genetic therapy, and combinations thereof.

17. The method of claim 15, wherein the additional treatment is measuring the amount of a pro-inflammatory immune molecule or cell, a suppressive immune molecule or cell, or both in a bodily fluid or a biopsied tissue of the patient.

18. The method of claim 15, wherein the plurality of electrical pulses are configured to cause non-thermal irreversible electroporation of the tissue.

19. The method of claim 15, wherein in the plurality of electrical pulses are applied through a plurality of electrodes inserted into the tissue.

* * * * *